United States Patent
Fiebig et al.

(10) Patent No.: US 11,891,598 B2
(45) Date of Patent: Feb. 6, 2024

(54) MEANS AND METHODS FOR PRODUCING PHOSPHATE CONTAINING CAPSULAR POLYSACCHARIDES

(71) Applicant: MEDIZINISCHE HOCHSCHULE HANNOVER (MHH), Hannover (DE)

(72) Inventors: Timm Fiebig, Hannover (DE); Christa Litschko, Isernhagen (DE); Rita Gerardy-Schahn, Hiddenhausen (DE); Andrea Bethe, Hildesheim (DE); Monika Berger, Sehnde (DE)

(73) Assignee: MEDIZINISCHE HOCHSCHULE HANNOVER (MHH), Hannover (DE)

( * ) Notice: Subject to any disclaimer, the term of this patent is extended or adjusted under 35 U.S.C. 154(b) by 585 days.

(21) Appl. No.: 16/632,998

(22) PCT Filed: Jul. 26, 2018

(86) PCT No.: PCT/EP2018/070271
§ 371 (c)(1),
(2) Date: Jan. 22, 2020

(87) PCT Pub. No.: WO2019/020735
PCT Pub. Date: Jan. 31, 2019

(65) Prior Publication Data
US 2020/0208134 A1    Jul. 2, 2020

(30) Foreign Application Priority Data

Jul. 26, 2017 (LU) .................................. LU100349

(51) Int. Cl.
| | |
|---|---|
| C12N 15/03 | (2006.01) |
| A61K 39/02 | (2006.01) |
| C12N 15/113 | (2010.01) |
| A61K 39/00 | (2006.01) |

(52) U.S. Cl.
CPC .............. *C12N 15/03* (2013.01); *A61K 39/02* (2013.01); *C12N 15/113* (2013.01); *A61K 2039/55583* (2013.01); *C12N 2310/3517* (2013.01)

(58) Field of Classification Search
None
See application file for complete search history.

(56) References Cited

PUBLICATIONS

UNIPROT:H6T5X6, dated Apr. 18, 2012; http://ibis.internal.epo.org/exam/dbfetch.jsp?id=UNIPROT:H6T5X6.
UNIPROT: M4R713, dated May 29, 2013; http://ibis.internal.epo.org/exam/dbfetch.jsp?id=UNIPROT:M4R713.
UNIPROT:E0F019, dated Nov. 2, 2010; http://ibis.internal.epo.org/exam/dbfetch.jsp?id=UNIPROT:E0F019.
UNIPROT:E0FCQ3, dated Nov. 2, 2010; http://ibis.internal.epo.org/exam/dbfetch.jsp?id=UNIPROT:E0FCQ3.
UNIPROT:D7Z7G4, dated Oct. 5, 2010; http://ibis.internal.epo.org/exam/dbfetch.jsp?id=UNIPROT:D7Z7G4.
UNIPROT:A0A1L1LWS3, dated Feb. 15, 2017; http:/ibis.internal.epo.org/exam/dbfetch.jsp?id=UNIPROT:A0A1L1LWS3.
UNIPROT:Q5QRV6, dated Jan. 4, 2005; http:/ibis.internal.epo.org/exam/dbfetch.jsp?id=UNIPROT:Q5QRV6.
UNIPROT:Q5QH16, dated Jan. 4, 2005; http://ibis.internal.epo.org/exam/dbfetch.jsp?id=UNIPROT:Q5QH16.
UNIPROT:Q6UYC4, dated Jul. 5, 2004; http://ibis.internal.epo.org/exam/dbfetch.jsp?id=UNIPROT:Q6UYC4.
UNIPROT:D9P7M2, dated Oct. 5, 2010; http://ibis.internal.epo.org/exam/dbfetch.jsp?id=UNIPROT:D9P7M2.
UNIPROT:Q714U8, dated Jul. 5, 2004; http://ibis.internal.epo.org/exam/dbfetch.jsp?id=UNIPROT:Q714U8.
UNIPROT:E0EA77, dated Nov. 2, 2010; http://ibis.internal.epo.org/exam/dbfetch.jsp?id=UNIPROT:E0EA77.
UNIPROT:A0A179CWH5, dated Sep. 7, 2016; http://ibis.internal.epo.org/exam/dbfetch.jsp?id=UNIPROT:A0A179CWH5.
UNIPROT:F6KWE2, dated Jul. 27, 2011; http://ibis.internal.epo.org/exam/dbfetch.jsp?id=UNIPROT:F6KWE2.
UNIPROT:F4YBG0, dated Jun. 28, 2011; http://ibis.internal.epo.org/exam/dbfetch.jsp?id=UNIPROT:F4YBG0.

*Primary Examiner* — Oluwatosin A Ogunbiyi
(74) *Attorney, Agent, or Firm* — Riverside Law LLP

(57) ABSTRACT

The present invention relates to a host cell, which comprises under the control of a heterologous promoter a polynucleotide comprising a nucleotide sequence encoding a polypeptide capable of synthesizing a polysaccharide consisting of a dimeric repeating unit as well as to a vaccine composition comprising such host cell. Furthermore, either such host cell or a polypeptide expressed by such host cell is used for the production of a polysaccharide consisting of a dimeric repeating unit which may be used as a glycoconjugate vaccine.

15 Claims, 51 Drawing Sheets
Specification includes a Sequence Listing.

| protein | DxD motif from CslB |
|---|---|
| CslB | EWVTFIDPDDFLD |
| Cps1B | EWVTFIDPDDFLS |
| Cps12B | EWVTFIDPDDFLD |
| Ccs2 | EWVTFIDPDDFVS |

| protein | Conserved H444 and H584 from TagF | |
|---|---|---|
| TagF | QTWHGTP | LRMHYLI |
| CslB | FLQHGVI | FVPHPNF |
| Cps1B | FLQHGIT | FAPHPNI |
| Cps12B | FLQHGII | FLPHQNF |
| Ccs2 | FLQHGIT | FAPHPNM |
| Cps3D | NTWHGT | FRGHHLV |
| Cps7D | STWHGTP | FRGHSLL |

| protein | Conserved residues from TarM R326 and K331 | |
|---|---|---|
| TarM | HISRMVPTKRID | |
| Cps3D | NIGRMSHEKDQL | |
| Cps7D | TIGRLSIEKDHA | |

F

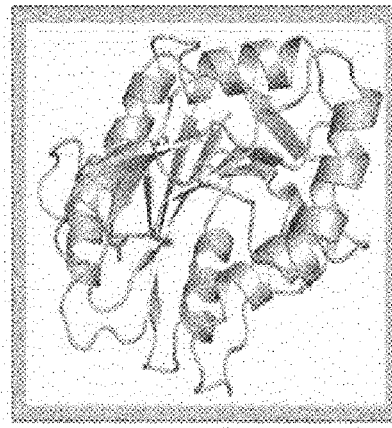

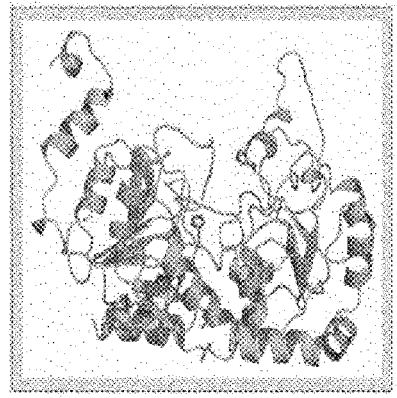

Figure 7
GT-A/TagF
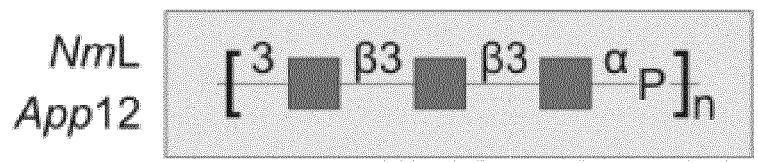
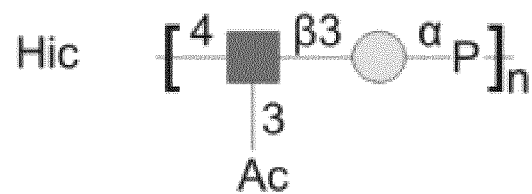
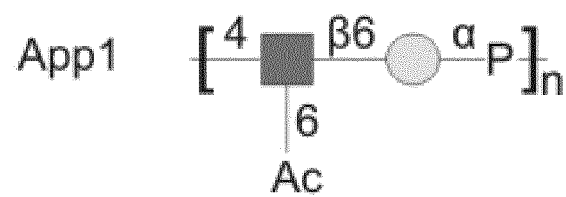
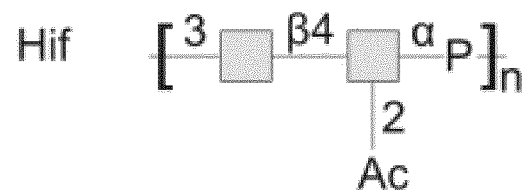

Figure 10

```
K4CP     ---------------KKEKIE---SATLKRVPLVSIYIPAKNCSKYIVRCVES
CslB     --------------------PKLKATSKKYTIISAIYNVAPYLDDYFKS
Cps1B    --------------IKKHLP---VK-YEGKHQFTIVSAVYNVEKYLDDFFDS
Ccs2     ---------------LKKYIP---SS-HKGNNKFTIISAIYNTEKYLDEYFSS
Fcs2     ----------------------MKTNFIFSIIMPIYNVDQWLEEAILS
Cps4B    -----------SIKLEKFLS---IK-HYGNNEFTIVSAIYNVEKYLDQYFNS
Cps12B   -----------RLLQLRNFIYLNSRKKLNSKKFTIISAVYNVSEVLDDYLES
BtY31    YTVVNNMTQISLLKLRKYLP---IKKRQGNHQFTVVTAVYNVSKYLPDFFES

K4CP     ALNQTIT----DLEVCICDDGSTQDTLRILQEHYANHPR-VRFISQ-KNKGI
CslB     LEKQ-RLDFQSNINVLLVDDGSPQNSREIIMKWVNKYFNNIFYIYK-KNGGQ
Cps1B    IVKQ-NLSKKHIQILLVDDGSKDSSANIIKKWQKKYFNNIHYYYK-ENGGQ
Ccs2     ITTQ-LLNFKNNIFIICVDDGSVDDAKIIKKWQRKYFKNITVIYK-ENGGQ
Fcs2     IINQKKINFEENVQLLLVNDCSPQNSEEICLKFRKKYFNNILYKNEKNLGL
Cps4B    IFKQ-TLLFKNNINIICVDDGSTQKSAEIIEKYRKKYFQNIKYIYK-ENGGQ
Cps12B   LVNQ-RLDFETSIDVILVNDGSPQDSEILIKKWIKKYFNNIHYIKK-KNGGQ
BtY31    IVNQ-SLDFEKHIHIICVDDGSTQNSSEVIKNWQRKYFNNITYLYK-ENGGI

K4CP     GSASNTAVRLCRGFYIGQLDSDFLEPDAVELCLDEFRKDL--SLACVYTTN
CslB     SSARNLGLKYVSTEWVTFIDPDDFLDSNYFYLIDKTIKDQK--NIGGVITKF
Cps1B    ASARNLGLKYVQTEWVTFIDPDDFLSLNYFLEVDKKLSEHK--NIAMIVCNL
Ccs2     ASARNVGIEHVQTEWVTFIDPDDFVSKNYFSEVDKQISESE--NVSLIACPL
Fcs2     SGTRNKGLTLAEGKYINFFDPDDTLSPSVLYEVNKFFTQNSSQNLAHISIPL
Cps4B    ASARNLGIKYVTTKWVTFIDPDDFISRNYFELVDDFIEKNT--NLSLVSCPF
Cps12B   SSARNLGLKFVKTEWVTFIDPDDFLDLNYFYLLNDTLEKYD--HIGAFVTKF
BtY31    SSARNLGLQYVETEWVTFIDSDDFVHYDYFRVVDNAVSKNN--DIKLAVGNL

K4CP     RNIDREGNLISNGYNWPIY----SREKLTSAMICHHFRMFTARAWNLTE---
CslB     KLFKEKLGTYHDGFQTDFCFNK-PVRIVTTSNFEDCVQFSSSSSIYQTKIIK
Cps1B    LFFMEKKEIITDKHPLKFRFEK-DVNCLSIKDLNNNLNLSVATSFFRTSVIQ
Ccs2     VFYFEDKDMFKDTHPLKYRFNK-GNVTLPISDLKDKIQLSASTAFFKSSDIG
Fcs2     VFFEAASG-----LHPKYRLLGNKNRIIDLDKEQHNFILSSASSFYPRDNIK
Cps4B    IFYFEDKNIYKDRHPLNFRFKN-GEYISPIKSLDKHIQLSVNSAFFRTAVIK
Cps12B   KLFKEKFGTYHDGFQTDFCFTK-PIRVLKANDMEDCVQFSSSSSVYRTDVIH
BtY31    RFYFEENKLVKDGHSLRYRFTQKEVNIVPIDNLDKNINLFVTVSFFKTKLLH

K4CP     ----GFNESISN------AVDYDMYLKL--SEVGPFKHINKICNRVLHGENT
CslB     DNNILFDEKLTASFEDTKFFYEYLFYLDSSKNTNIAYVRDALYYVRLRA---
Cps1B    GNQLLFDNRVKPNFEDGKFISDYLFELQ---HYNALFLKKPVYFYRKREDGT
Ccs2     NVRF--DEKMKPSFEDAKFVIDYLLSN---KNKYASFVSNISYYYRKRADGS
Fcs2     KNKFD--TSL-FGEEDTLFNFNIYSNIN---KFGYVCENGVQYNYRRRQEGG
Cps4B    KNNIQ-FGEIRPNFEDAKFVGDYLLSVN--QENLIGFMKDVSIFYRKRSDQS
Cps12B   KNKILFDEKLTASFEDTKFFYDYLYNI---KESNILYIKDAIYNYRLRSNES
BtY31    DNKIIFNDKIKPNFEDGKFLADYFLCVE---TGNVAYLQKAIFFYRKRG---

K4CP     SIKKLDIQKENHFKVVNESLSRLGIKKYKYSPLTNLNECRKYTWEKI
CslB     ---------------------------------
Cps1B    STLDTSWQKPEKYKNVLEYGFIPMLQKYHNKL--------------
Ccs2     STLDGAWFNTNLFTRVL-----------------
Fcs2     SQVDLSRVKPQAFITPIQI--------LEN-------------
Cps4B    STLDTAWKNPLLYSQVLEN----------------
Cps12B   SSSNSQWTKKAKYQEFFQFGLLSVIKKYNE---------------
BtY31    ---------------------------------
```

| Name | Start | Sequence | End |
|---|---|---|---|
| Cps10C/1-191 | | ------------------------- | |
| Cps8D/1-472 | 145 | Y----------RITDTNKWVSVWHGIPYKKMFVD | 168 |
| cps6D/1-505 | 79 | Y----------RITDTNKWVSVWHGIPYKKMFVD | 102 |
| TagF/1-409 | 119 | L----------NKKENQTYIQTWHGTPLKRLAND | 142 |
| CshC/1-388 | 112 | F----------IRKEGQVYLNTWHGTPMKTLGKD | 135 |
| Bt189/1-382 | 108 | F----------IRKAEQIYLNTWHGTPMKTLGKD | 131 |
| Bt188/1-378 | 109 | F----------IRKAEQIYLNTWHGTPMKTLGKD | 132 |
| Bt192/1-383 | 109 | F----------IRKAEQIYLNTWHGTPMKTLGKD | 132 |
| Cps3D/1-378 | 108 | F----------IRKEGQVYLNTWHGTPMKTLGKD | 131 |
| Cps9D/1-381 | 106 | F----------IRKEGQIYLNTWHGTPMKTLGKD | 129 |
| Cps11D/1-384 | 109 | F----------IRKEGQIYLNTWHGTPMKTLGKD | 132 |
| c3694/1-383 | 109 | F----------IRKKGQRYLNTWHGTPIKFLGKD | 132 |
| CszC/1-372 | 99 | F----------IRKPEQKYLSAWHGTPFKTLGRD | 122 |
| Cps7D/1-384 | 111 | F----------IRKPEQKFLSTWHGTPFKTLGRD | 134 |
| Cps2D/1-377 | 105 | F----------IRKPEQKFLSTWHGTPFKTLGRD | 128 |
| Csw/1-188 | | ------------------------- | |
| Cps5B/1-150 | | ------------------------- | |
| Fcs2/1-404 | 117 | FKPISFKHLKYYNDLIETKIIWLQHGITMNNIEIA | 151 |
| Cps1B/1-395 | 111 | NNYFGD------NYDFSKKFIFLQHGITKDDLSQW | 139 |
| BfY31/1-400 | 114 | YNYFGD------HYENSKKFIFLQHGVIQNNLSRW | 142 |
| Ccs2/1-379 | 97 | THYFKD------NSLMDKDYVFLQHGITKDDLSSW | 125 |
| Cps4B/1-401 | 120 | INPFKD------HFEFTKKFIFLQHGVTHNDLSDW | 148 |
| CslB/1-417 | 117 | GEWVTG------HNFKFQKFIFLQHGVISSNLSKP | 145 |
| Cps12B/1-414 | 115 | NEWATH------HSFKFQKFIFLQHGIITSNLSKP | 143 |

B

| Name | Start | Sequence | End |
|---|---|---|---|
| Cps10C/1-191 | 65 | DDVIFVVRPHPEEDVETLSN---------------L | 85 |
| Cps8D/1-472 | 436 | D-YVLITKMHYLNY--LANT-------------- | 452 |
| cps6D/1-505 | 370 | D-YVLITKMHYLNY--LANT-------------- | 386 |
| TagF/1-409 | 264 | D-YVILLRMHYLIS--NALD-------------L | 281 |
| CshC/1-388 | 247 | K-YQLIFRGHHLVE--NILK-------------D | 264 |
| Bt189/1-382 | 242 | K-YNLVFRGHHLVE--SLLS-------------E | 259 |
| Bt188/1-378 | 243 | K-YNLVFRGHHLVE--SLLS-------------E | 260 |
| Bt192/1-383 | 243 | K-YNLVFRGHHLVE--SLLS-------------E | 260 |
| Cps3D/1-378 | 243 | K-YNLIFRGHHLVE--QLLE-------------T | 260 |
| Cps9D/1-381 | 241 | K-YNLIFRGHHLVE--QLLE-------------T | 258 |
| Cps11D/1-384 | 244 | K-YNLIFRGHHLVE--QLLE-------------T | 261 |
| c3694/1-383 | 244 | D-CHIVFRGHMIE--KLVS-------------E | 261 |
| CszC/1-372 | 235 | G-AKLVFRGHALLQ--AALA-------------D | 252 |
| Cps7D/1-384 | 247 | G-AKVVFRGHSLLQ--EALS-------------K | 264 |
| Cps2D/1-377 | 241 | G-AKVIFRGHSLLQ--EALS-------------K | 258 |
| Csw/1-188 | 97 | PQLQLLESKHPDENIDLKNR-----I--------I | 118 |
| Cps5B/1-150 | 43 | NGFNVVLKTHPWEEKKNNIRTSLTKNIIEEFLKNL | 77 |
| Fcs2/1-404 | 257 | NNVIIKFVLHPGFKQYAKYF-----KQLE------ | 280 |
| Cps1B/1-395 | 249 | LGYKVIFAPHPNIEPYLNEF-----N--------I | 270 |
| BfY31/1-400 | 253 | YGYQIIFAPHANIEPYLPMF-----K--------V | 274 |
| Ccs2/1-379 | 233 | YGYKFIFAPHPNMQEYLKEF-----D--------I | 254 |
| Cps4B/1-401 | 256 | YDFEVIFAPHKNIEPYLDLF-----N--------I | 277 |
| CslB/1-417 | 264 | GNLEITFVPHPNFYSILEEY-----ELLDIVFKNL | 293 |
| Cps12B/1-414 | 253 | GKIEISFLPHQNFHQLLEEN-----SLNEKLFFDI | 282 |

Figure 12

```
Cps10D/1-403   228 QRPVGRPIYFGF GGSM-SANVIALRYV EHWWPV 261
Cps5A/1-266     90 ---SSTDKITLG ASRRYGRRVKG---DAYL-FEL 117
Csw/1-396      220 QK----FKRISIVGSIQPRKNQLD---A KI-INK 246
Cps6D/1-292    121 KKY---QLNTAV SRLDADKNIFA---I DL-GKT 148
Cps8D/1-291    121 KKH---QLNTAV SRLDADKNIFA---M DL-GKE 148
TarM/1-493     312 PKHFQTEKIVGH SRMVPTKRIDL---L EV-AEL 342
CshC/1-424     253 --TQFTGTKFIN GRMSHEKDQIK---L KA-FNI 281
Cps3D/1-390    222 --TLFNGQKFIN GRMSHEKDQLK---L EA-FYE 250
Cps9D/1-392    225 --TSFNGQKFIN GRMSHEKDQLK---L EA-FCE 253
Cps11D/1-389   222 --TSFNGQKFIN GRMSHEKDQLK---L EA-FCE 250
Bt189/1-389    222 --ANFAGTKFIN GRMSHEKDQLK---L EA-FAE 250
Bt188/1-390    222 --DNFAGTKFIN GRMSHEKDQLK---L EA-FAE 250
Bt192/1-387    221 --DNFTGTKFIN GRMSHEKDQLK---L EA-FAE 249
c3694/1-388    226 --FENDKIYFIT LGRLSVEKDQQK---L NA-FCR 254
CszC/1-442     275 --FQGTGKVFIT GRLSMEKDHAK---L NS-FAQ 303
Cps7D/1-391    225 --FKTPGKVFLT GRLSIEKDHAK---L NS-FAK 253
Cps2D/1-439    273 --FNTEDKVFLT GRLSIEKDHAK---L NS-FAN 301
```

Figure 14

```
Cps10C/1-191    ------------------------------------
Cps8D/1-472   84 D I S S F - - - - - - I Q Y Y K - D K F D V Y I I L - - R E L P E D I 109
cps6D/1-505   18 D I S S F - - - - - - I Q Y Y K - D K F D V Y I I L - - R E L P E D I  43
TagF/1-409    56 S P K Y I Y E Y M - - Q K Y Y P - N Y R Y I W S F K N P D K N V - - -  84
CshC/1-388    45 N P Y A I L S Y M L E H Q Y - - - N Y I Y I V V I K E G T L I P N N L  76
Bt189/1-382   41 N P Y A I L L Y M L D H N Y - - - D F T Y I V V V K P E T V I P D S L  72
Bt188/1-378   42 N P Y A I L L Y M L D H N Y - - - D F T Y I V V V K P E T V I P D S L  73
Bt192/1-383   42 N P Y A I L L Y M L D H N Y - - - D F T Y I V V V K P E T I I P D S L  73
Cps3D/1-378   41 N P Y A I L S Y M L E N N Y - - - D Y T Y V V V I K D G T V I P D N L  72
Cps9D/1-381   39 N P Y A I L S Y M L G N N Y - - - D Y T Y V V V I K D G T V I P D N L  70
Cps11D/1-384  42 N P Y A I L S Y M L G N N Y - - - D Y T Y V V V I K D G T V I P D N L  73
c3694/1-383   40 N P Y A L F L D I I D D Q R F D - N F R H I W V I N N E K K I P E Q L  73
CszC/1-372    30 S P Y A L F L Y M F N H P D Y Q - D W T H I W V I N D P A K I P E E Y  63
Cps7D/1-384   42 N P L A L F L Y L F N H N E Y K - N W T H I W V I N D T S N I P E E Y  75
Cps2D/1-377   36 N P Y A L F L Y L L N H Q E Y K - S W T H I W V V N N I D N I S S E Y  69
Csw/1-188       ------------------------------------
Cps5B/1-150     ------------------------------------
Fcs2/1-404    50 N A E A F F T Y I N K S V P H - - I A K N S Y F V L D K N S P D I S R  82
Cps1B/1-395   45 N A E H F Y R Y M Q T H H P E - - - - Q R C Y F V L N K S S I D W Q R  75
BtY31/1-400   48 N A E H F Y R Y M M K N H P E - - - - Q C C Y F A L N E D S H D W K R  78
Ccs2/1-379    31 N A E H L Y C Y V M K N N P S - - - - Q S I Y F V L N R D S H D W E R  61
Cps4B/1-401   54 N G E H F Y R Y M M N N H P E - - - - Q K I Y F A I N R N S N D W G R  84
CslB/1-417    48 N A E H L Y R S W F I S T D N S P D - I T P Y Y L L D K K S S H W P K  81
Cps12B/1-414  42 N A E H L Y E K L L K N K N L D N F I D D H Y Y L L D K E S E H W N R  79
```

| | | |
|---|---|---|
| Cps10C/1-191 | - - - - - - - - - - - - - - - - - - - - - - - - - - - - - - - - - - | |
| Cps8D/1-472 | 297 Y Y I S D L D N K D A L L I A D L L I S D Y H E L I Y T F D R Y N K P | 331 |
| cps6D/1-505 | 231 Y Y I S D L D N K D A L L I A D L L I S D Y H E L I Y T F D R Y N K P | 265 |
| TagF/1-409 | - - - - - - - - - - - - - - - - - - - - - - - - - - - - - - - - - - | |
| CshC/1-388 | - - - - - - - - - - - - - - - - - - - - - - - - - - - - - - - - - - | |
| Bt189/1-382 | - - - - - - - - - - - - - - - - - - - - - - - - - - - - - - - - - - | |
| Bt188/1-378 | - - - - - - - - - - - - - - - - - - - - - - - - - - - - - - - - - - | |
| Bt192/1-383 | - - - - - - - - - - - - - - - - - - - - - - - - - - - - - - - - - - | |
| Cps3D/1-378 | - - - - - - - - - - - - - - - - - - - - - - - - - - - - - - - - - - | |
| Cps9D/1-381 | - - - - - - - - - - - - - - - - - - - - - - - - - - - - - - - - - - | |
| Cps11D/1-384 | - - - - - - - - - - - - - - - - - - - - - - - - - - - - - - - - - - | |
| c3694/1-383 | - - - - - - - - - - - - - - - - - - - - - - - - - - - - - - - - - - | |
| CszC/1-372 | - - - - - - - - - - - - - - - - - - - - - - - - - - - - - - - - - - | |
| Cps7D/1-384 | - - - - - - - - - - - - - - - - - - - - - - - - - - - - - - - - - - | |
| Cps2D/1-377 | - - - - - - - - - - - - - - - - - - - - - - - - - - - - - - - - - - | |
| Csw/1-188 | 55 A Y W Y A L - - - D D V R F S E K L N Y D - - - - - - - - - - - - - - - | 72 |
| Cps5B/1-150 | 16 - - - - - - - - - - - - - - D F S V L E - - - - - - - - - - - - - - | 21 |
| Fcs2/1-404 | 227 A E L E - - - - - - - - - - I F K E S D - - - - - - - - - - - - - - | 236 |
| Cps1B/1-395 | 219 E L N K - - - - - - - - - - A F M T T N - - - - - - - - - - - - - - | 228 |
| BtY31/1-400 | 223 E F N P - - - - - - - - - - D F M N T N - - - - - - - - - - - - - - | 232 |
| Ccs2/1-379 | 203 A Y N S - - - - - - - - - - Q F M E T E - - - - - - - - - - - - - - | 212 |
| Cps4B/1-401 | 226 S I N S - - - - - - - - - - E F M N T Q - - - - - - - - - - - - - - | 235 |
| CslB/1-417 | 234 T Q L V - - - - - - - - - - N F L D S D - - - - - - - - - - - - - - | 243 |
| Cps12B/1-414 | 223 D A I S - - - - - - - - - - S F K E T S - - - - - - - - - - - - - - | 232 |
| | | |
| Cps10C/1-191 | - - - - - - - - - - - - - - - - - - - - - - - - - - - - - - - - - - | |
| Cps8D/1-472 | 332 A V L I Q Y D Y E S F V K Q H T S R K Q E L E I L A S R K Y V A K E A | 366 |
| cps6D/1-505 | 266 A V L I Q Y D Y E S F V K Q H T S R K Q E L E I L A S R K Y V A Q E A | 300 |
| TagF/1-409 | - - - - - - - - - - - - - - - - - - - - - - - - - - - - - - - - - - | |
| CshC/1-388 | - - - - - - - - - - - - - - - - - - - - - - - - - - - - - - - - - - | |
| Bt189/1-382 | - - - - - - - - - - - - - - - - - - - - - - - - - - - - - - - - - - | |
| Bt188/1-378 | - - - - - - - - - - - - - - - - - - - - - - - - - - - - - - - - - - | |
| Bt192/1-383 | - - - - - - - - - - - - - - - - - - - - - - - - - - - - - - - - - - | |
| Cps3D/1-378 | - - - - - - - - - - - - - - - - - - - - - - - - - - - - - - - - - - | |
| Cps9D/1-381 | - - - - - - - - - - - - - - - - - - - - - - - - - - - - - - - - - - | |
| Cps11D/1-384 | - - - - - - - - - - - - - - - - - - - - - - - - - - - - - - - - - - | |
| c3694/1-383 | - - - - - - - - - - - - - - - - - - - - - - - - - - - - - - - - - - | |
| CszC/1-372 | - - - - - - - - - - - - - - - - - - - - - - - - - - - - - - - - - - | |
| Cps7D/1-384 | - - - - - - - - - - - - - - - - - - - - - - - - - - - - - - - - - - | |
| Cps2D/1-377 | - - - - - - - - - - - - - - - - - - - - - - - - - - - - - - - - - - | |
| Csw/1-188 | - - - - - - - - - - - - - - - - - - - - - - - - - - - - - - - - - - | |
| Cps5B/1-150 | - - - - - - - - - - - - - - - - - - - - - - - - - - - - - - - - - - | |
| Fcs2/1-404 | - - - - - - - - - - - - - - - - - - - - - - - - - - - - - - - - - - | |
| Cps1B/1-395 | - - - - - - - - - - - - - - - - - - - - - - - - - - - - - - - - - - | |
| BtY31/1-400 | - - - - - - - - - - - - - - - - - - - - - - - - - - - - - - - - - - | |
| Ccs2/1-379 | - - - - - - - - - - - - - - - - - - - - - - - - - - - - - - - - - - | |
| Cps4B/1-401 | - - - - - - - - - - - - - - - - - - - - - - - - - - - - - - - - - - | |
| CslB/1-417 | - - - - - - - - - - - - - - - - - - - - - - - - - - - - - - - - - - | |

```
Cps12B/1-414      - - - - - - - - - - - - - - - - - - - - - - - - - - - - -

Cps10C/1-191   15 - - - - - - - - - - - - - - S D K S L L P E N I K G K R V I F F P L Q  35
Cps8D/1-472   367 N E L Y Q F N W N L L K R Y S K Q S T L P E Y L D S S - Y I K H K L G  400
cps6D/1-505   301 E E L Y Q F N W N L L K R Y S T H A T L P E Y L D S S - Y I K H K L G  334
TagF/1-409        - - - - - - - - - - - - - - - - - - - - - - - - - - - - -
CshC/1-388        - - - - - - - - - - - - - - - - - - - - - - - - - - - - -
Bt189/1-382       - - - - - - - - - - - - - - - - - - - - - - - - - - - - -
Bt188/1-378       - - - - - - - - - - - - - - - - - - - - - - - - - - - - -
Bt192/1-383       - - - - - - - - - - - - - - - - - - - - - - - - - - - - -
Cps3D/1-378       - - - - - - - - - - - - - - - - - - - - - - - - - - - - -
Cps9D/1-381       - - - - - - - - - - - - - - - - - - - - - - - - - - - - -
Cps11D/1-384      - - - - - - - - - - - - - - - - - - - - - - - - - - - - -
c3694/1-383       - - - - - - - - - - - - - - - - - - - - - - - - - - - - -
CazC/1-372        - - - - - - - - - - - - - - - - - - - - - - - - - - - - -
Cps7D/1-384       - - - - - - - - - - - - - - - - - - - - - - - - - - - - -
Cps2D/1-377       - - - - - - - - - - - - - - - - - - - - - - - - - - - - -
Csw/1-188      73 - - - - - - - - - - - - - - - - - - - - - - - Y I F L S Q -  78
Cps5B/1-150    22 - - - - - - - - - - - - - - - - - - - - - - - - - Y K G R - - -  25
Fcs2/1-404    237 - - - - - - - - - - - - - - - - - - - - - - - - - Y Y K N - - -  240
Cps1B/1-395   229 - - - - - - - - - - - - - - - - - - - - - - - - - Y A K A - - -  232
BtY31/1-400   233 - - - - - - - - - - - - - - - - - - - - - - - - - Y A Q H - - -  236
Ccs2/1-379    213 - - - - - - - - - - - - - - - - - - - - - - - - - Y A I H - - -  216
Cps4B/1-401   236 - - - - - - - - - - - - - - - - - - - - - - - - - Y A K A - - -  239
CslB/1-417    244 - - - - - - - - - - - - - - - - - - - - - - - - - Y L K N - - -  247
Cps12B/1-414  233 - - - - - - - - - - - - - - - - - - - - - - - - - Y I K N - - -  236
```

Figure 16

```
Cps10C/1-191    182  I - K S I F K F - - - N - - - - - - - - - - - - - - - - - D K - - - -   191
Cps8D/1-472          - - - - - - - - - - - - - - - - - - - - - - - - - - - - - - - -
cps6D/1-505     475  N S K I I N E F Y P L E D G K S T Q R I V D K I N F N A D L R - -   505
TagF/1-409      379  I D A F Y D R F C S V D N G K A S Q Y I G D L I H K D I K E Q - -   409
CshC/1-388      357  S S N E I E K Y A A F D D G S A T K R T I D F M F Y N D R S N L -   388
Bt189/1-382     351  L E R D I E K Y S Y L D D G R A T Q R T I D F I F D N D R S S I -   382
Bt188/1-378     352  L E R D I E K Y S Y L D D G R A T Q R T V D F I F K N - - - - - -   378
Bt192/1-383     352  L E R D I E K Y S Y L D D G R A T Q R T V D F I F K N D N R Y V -   383
Cps3D/1-378     352  S E Q D I Q K Y S Y L D D G Q A T K R T V E F M L D K - - - - - -   378
Cps9D/1-381     350  S E Q D I N K Y S Y L D D G K A T K R T V E F M F D R D D S C V -   381
Cps11D/1-384    353  S E Q D I N K Y S Y L D D G K A T K R T V E F M F D R D D S C V -   384
c3694/1-383     354  A S K G I D K F C K N D D G S V C G K V I E W F F F E E K S - - -   383
CszC/1-372      346  E E H Q L S R F A P Y D D G H V S E R V M N A I L Y D - - - - - -   372
Cps7D/1-384     358  E D S K V A Q F A P H D D G N V S E K V I N A L F L D - - - - - -   384
Cps2D/1-377     352  E D N K V A E F A P H D D G N V S E K V I N A L F S - - - - - - -   377
Csw/1-188            - - - - - - - - - - - - - - - - - - - - - - - - - - - - - - - -
Cps5B/1-150          - - - - - - - - - - - - - - - - - - - - - - - - - - - - - - - -
Fcs2/1-404      377  Y L Y R I R N M Y K Y N D N K N C E R L L N E V L K N E - - - - -   404
Cps1B/1-395     371  Y Q S R I Q K T F K Y R D T N N C Q R V Y E A I I - - - - - - - -   395
BtY31/1-400     375  Y K T R I E N T F P F R D G K N C E R I Y Q S I Q A - - - - - - -   400
Ccs2/1-379      354  Y L K R I N D T F P F R D G K N C Q R V Y E A I T N - - - - - - -   379
Cps4B/1-401     376  Y K S R I A Q T F P F Q D G K C C E R V Y F A I Q N - - - - - - -   401
CslB/1-417      392  Y K K R V D E I F P T L H Q K S S E I I K L E L F K - - - - - - -   417
Cps12B/1-414    382  Y K K R I S N V F L P S L G D S C N Y I L K N V F T N P K R N I N   414
```

```
Cps10D/1-403    1   -----------------------------NTLFIF         6
Cps5A/1-266         -----------------------------------
Csw/1-396      11   --RAVNGLVKSSINTA----NAFAEEGLDVHLINF         39
Cps6D/1-292         -----------------------------------
Cps8D/1-291         -----------------------------------
TarM/1-493    101   EIEESKGISRYFDITTGTYIAYIRKSKSE-----K        130
CshC/1-424     41   ---IPNGISRSFI----NLMSSLKGSSAHSVLLIN         68
Cps3D/1-390    10   ---IPNGISRSFL----NLMASIKDSGKNITLLIN         37
Cps9D/1-392    13   ---IPNGISRSFL----NLMASIKDSEKNITLLIN         40
Cps11D/1-389   10   ---IPNGISRSFL----NLMASIKDSEKNITLLIN         37
Bt189/1-389    10   ---IPNGISRSFL----NLMSSLNNHKNNITLLIN         37
Bt188/1-390    11   ---LQNGITRSFL----NLMSTIGREK-NILVLIN         37
Bt192/1-387    10   ---LQNGITRSFL----NLMSTIGREK-NILVLIN         36
c3694/1-388    12   ---IPNGILSSWL----NLISVIDRDKYNISLVVD         39
CszC/1-442     61   ---MGNGITTATI----NLIANIDRSKYTVTLVID         88
Cps7D/1-391    12   ---MGNGITTSVI----NLISNIDRSKYTVTLVID         39
Cps2D/1-439    60   ---MGNGITTSVI----NLIANIDRSKYTITLVID         87
```

B

```
Cps10D/1-403    28   LSMKGVIFDVLIPSNNKLDKVALKSALKSVASNVY   62
Cps5A/1-266          -----------------------------------
Csw/1-396       75   VSC--------------------------------   77
Cps6D/1-292          -----------------------------------
Cps8D/1-291          -----------------------------------
TarM/1-493     151   VHMK--------------------------ETF    157
CshC/1-424      89   ISVLSRVGRTPM----TLEEL----WVRNKFENIF   115
Cps3D/1-390     58   ITVLSRVGRTPM----TLEEL----WVRNKFEETY    84
Cps9D/1-392     61   VTVLSRVGRTPM----TLEEL----WVRNKFEETY    87
Cps11D/1-389    58   VTVLSRVGRTPM----TLEEL----WVRNKFEETY    84
Bt189/1-389     58   VTVLSRVGRTPM----TLEEL----WVKTKFEETY    84
Bt188/1-390     58   ISVFSRSGRMLM----TLEEL----WVRNKFDENF    84
Bt192/1-387     57   ISVFSRSGRMLM----TLEEL----WVRNKFDENF    83
c3694/1-388     60   IQVIGTCGNMLY----NIEEK----WLNDKLNNQF    86
CszC/1-442     109   INVIARVGRMDM----TLEDR----YIHGLMNQRY   135
Cps7D/1-391     60   INVVARVGRMNM----DLEER----YIHGLNNQHY    86
Cps2D/1-439    108   INVVARVGRMDM----DLEER----YIHGLNNQHY   134
```

| | | |
|---|---|---|
| Cps10D/1-403 | 63 FYRNKPKKFTKLNTLKRGIEKRVRT-------LIN | 90 |
| Cps5A/1-266 | -------------------------- | |
| Csw/1-396 | 78 --RNTPFYSIHQQFFKAEYSAHYKHVLMKIESLLS | 110 |
| Cps6D/1-292 | -------------------------- | |
| Cps8D/1-291 | -------------------------- | |
| TarM/1-493 | 158 NVDNKVCYQVFY------------------ | 169 |
| CshC/1-424 | 116 KFPSEAFKTTLIRIYKREARRLLGE-------- | 140 |
| Cps3D/1-390 | 85 QIYSESFTNTLLKVYKREVRRLLGN--------- | 109 |
| Cps9D/1-392 | 88 QMYSESFTETLLKVYKREVRRLLGD--------- | 112 |
| Cps11D/1-389 | 85 QMYSESFTETLLKVYKREVRRLLGD--------- | 109 |
| Bt189/1-389 | 85 QFYSKEFEETLIRIYKRESRRLLGD--------- | 109 |
| Bt188/1-390 | 85 KFYSEEFKRVIEKIYKREARRLFGD--------- | 109 |
| Bt192/1-387 | 84 KFYSEEFKRVIEKIYKREARRLFGD--------- | 108 |
| c3694/1-388 | 87 TLASKEMYDILDHAYQREFLRLFGY--------- | 111 |
| CszC/1-442 | 136 ELDSPAAKKILKDSWKQEYDRVFGQ--------- | 160 |
| Cps7D/1-391 | 87 ELQSSVARGILQDSWEKEYQRIFGN--------- | 111 |
| Cps2D/1-439 | 135 ELQSSVAQDILWNSWEKEYQRIFGN--------- | 159 |

```
Fcs2/1-245    10  IMPIYNVDQWLEEAILSIINQKKINFEENVQLILV  44
CsIB/1-229    13  ISAIYNVAPYLDDYFKSLEKQ-RLDFQSNINVILV  46
Cps12B/1-272  26  ISAVYNVSEYLDDYLESLVNQ-RLDFETSIDVILV  59
BtY31/1-247   33  VTAVYNVSKYLPDFFESIVNQ-SLDFEKHIHIICV  66
Cps1B/1-266   18  VSAVYNVEKYLDDFFDSIVKQ-NLSFKKHIQILV  51
Ccs2/1-249    18  ISAIYNTEKYLDEYFSSITTQ-LLNFKNNIFIICV  51
Cps4B/1-256   21  VSAIYNVEKYLDQYFNSIFKQ-TLLFKNNINIICV  54
```

B

```
Fcs2/1-245    115 FTQNSSQNLAHISIPLVFFEAASG-----LHPKYR  144
CsIB/1-229    116 IKDQK--NIGGVITKFKLFKEKLGTYHDGFQTDFC  148
Cps12B/1-272  129 LEKYD--HIGAFVTKFKLFKEKFGTYHDGFQTDFC  161
BtY31/1-247   136 VSKNN--DIKLAVGNLRFYFEENKLVKDGHSLRYR  168
Cps1B/1-266   121 LSEHK--NIAMIVCNLLFFMEKKEIITDKHPLKFR  153
Ccs2/1-249    121 ISESE--NVSLIACPLVFYFEDKDMFKDTHPLKYR  153
Cps4B/1-256   124 IEKNT--NLSLVSCPFIFYFEDKNIYKDRHPLNFR  156
```

C

```
Fcs2/1-245    145 LLGNKNRIIDLDKEQHNFILSSASSFYPRDNIKKN  179
CsIB/1-229    149 FNK-PVRIVTTSNFEDCVQFSSSSSIYQTKIIKDN  182
Cps12B/1-272  162 FTK-PIRVLKANDMEDCVQFSSSSSVYRTDVIHKN  195
BtY31/1-247   169 FTQKEVNIVPIDNLDKNINLFVTVSFFKTKLLHDN  203
Cps1B/1-266   154 FEK-DVNCLSIKDLNNNLNLSVATSFFRTSVIQGN  187
Ccs2/1-249    154 FNK-GNVTLPISDLKDKIQLSASTAFFKSSDIGNV  187
Cps4B/1-256   157 FKN-GEYISPIKSLDKHIQLSVNSAFFRTAVIKKN  190
```

| | Cps10C | Cps8D | Cps6D | TagF | CshC | Bt189 | Bt188 | Bt192 | Cps3D | Cps9D | Cps11D | c3694 |
|---|---|---|---|---|---|---|---|---|---|---|---|---|
| 1: Cps10C | 100.00 | 21.43 | 18.86 | 20.55 | 19.29 | 20.29 | 20.59 | 20.29 | 18.98 | 21.58 | 21.58 | 22.14 |
| 2: Cps8D | 21.43 | 100.00 | 96.06 | 21.45 | 19.92 | 22.87 | 22.87 | 22.87 | 22.01 | 21.24 | 21.24 | 20.31 |
| 3: Cps6D | 18.86 | 96.06 | 100.00 | 24.49 | 23.67 | 27.38 | 28.01 | 27.68 | 25.23 | 25.52 | 25.52 | 23.67 |
| 4: TagF | 20.55 | 21.45 | 24.49 | 100.00 | 28.57 | 27.96 | 28.46 | 28.15 | 27.64 | 28.30 | 28.61 | 29.14 |
| 5: CshC | 19.29 | 19.92 | 23.67 | 28.57 | 100.00 | 68.32 | 68.78 | 67.89 | 71.16 | 70.87 | 70.57 | 47.23 |
| 6: Bt189 | 20.29 | 22.87 | 27.38 | 27.96 | 68.32 | 100.00 | 98.67 | 97.91 | 77.45 | 77.37 | 77.23 | 48.54 |
| 7: Bt188 | 20.59 | 22.87 | 28.01 | 28.46 | 68.78 | 98.67 | 100.00 | 99.21 | 77.45 | 77.87 | 77.78 | 48.40 |
| 8: Bt192 | 20.29 | 22.87 | 27.68 | 28.15 | 67.89 | 97.91 | 99.21 | 100.00 | 77.45 | 77.37 | 77.28 | 47.75 |
| 9: Cps3D | 18.98 | 22.01 | 25.23 | 27.64 | 71.16 | 77.45 | 77.87 | 77.45 | 100.00 | 92.29 | 92.06 | 44.27 |
| 10: Cps9D | 21.58 | 21.24 | 25.52 | 28.30 | 70.87 | 77.37 | 77.87 | 77.37 | 92.29 | 100.00 | 100.00 | 44.83 |
| 11: Cps11D | 21.58 | 21.24 | 25.52 | 28.61 | 70.57 | 77.23 | 77.78 | 77.28 | 92.06 | 100.00 | 100.00 | 44.71 |
| 12: c3694 | 22.14 | 20.31 | 23.67 | 29.14 | 47.23 | 48.54 | 48.40 | 47.75 | 44.27 | 44.83 | 44.71 | 100.00 |
| 13: C3zC | 17.14 | 18.75 | 22.19 | 28.93 | 44.29 | 44.81 | 45.08 | 45.08 | 44.14 | 43.05 | 43.05 | 44.99 |
| 14: Cps7D | 17.14 | 18.70 | 22.19 | 27.73 | 41.58 | 44.83 | 44.71 | 44.71 | 42.86 | 42.55 | 42.22 | 48.55 |
| 15: Cps2D | 16.43 | 18.70 | 22.85 | 28.53 | 44.77 | 46.90 | 46.36 | 46.36 | 44.35 | 43.82 | 43.82 | 48.40 |
| 16: Csw | 20.69 | 14.84 | 16.38 | 9.40 | 14.08 | 12.77 | 12.77 | 12.77 | 11.97 | 11.27 | 11.27 | 12.59 |
| 17: Cps5B | 16.50 | 16.46 | 17.07 | 17.54 | 14.95 | 13.08 | 13.08 | 13.08 | 12.15 | 13.08 | 13.08 | 11.11 |
| 18: Fcs2 | 17.24 | 15.97 | 19.28 | 16.62 | 16.06 | 17.68 | 18.04 | 17.99 | 17.07 | 17.33 | 17.33 | 17.82 |
| 19: Cps1B | 16.89 | 18.50 | 20.12 | 18.10 | 18.77 | 21.98 | 21.98 | 21.98 | 20.99 | 20.99 | 20.99 | 19.63 |
| 20: BtY31 | 12.75 | 16.99 | 20.60 | 19.51 | 17.13 | 17.85 | 18.15 | 17.85 | 16.87 | 16.87 | 16.87 | 17.38 |
| 21: Cc2 | 13.61 | 17.01 | 20.91 | 17.59 | 17.90 | 19.57 | 19.88 | 19.57 | 18.27 | 18.89 | 18.89 | 20.00 |
| 22: Cps4B | 15.07 | 14.67 | 17.27 | 18.60 | 17.68 | 18.40 | 18.71 | 18.40 | 16.51 | 16.82 | 16.82 | 17.33 |
| 23: Cs1B | 12.08 | 14.50 | 18.66 | 18.45 | 15.52 | 14.71 | 15.32 | 15.02 | 14.67 | 15.27 | 15.27 | 18.99 |
| 24: Cps12B | 15.33 | 17.83 | 22.06 | 17.42 | 17.72 | 17.22 | 17.18 | 17.22 | 18.65 | 18.67 | 18.67 | 18.92 |

| | C8zC | Cps7D | Cps2D | C3w | Cps5B | Fcs2 | Cps1B | BtY31 | Ccs2 | Cps4B | C31B | Cps12B |
|---|---|---|---|---|---|---|---|---|---|---|---|---|
| 1: Cps10C | 17.14 | 17.14 | 16.43 | 20.69 | 16.50 | 17.24 | 16.83 | 12.75 | 13.61 | 15.07 | 12.08 | 15.33 |
| 2: Cps8D | 18.75 | 18.70 | 18.70 | 14.84 | 16.46 | 15.97 | 18.50 | 16.99 | 17.01 | 14.67 | 14.50 | 17.83 |
| 3: Cps6D | 22.19 | 22.19 | 22.85 | 16.38 | 17.07 | 19.28 | 20.12 | 20.60 | 20.91 | 17.27 | 18.66 | 22.06 |
| 4: TagF | 28.93 | 27.73 | 28.53 | 9.40 | 17.54 | 16.62 | 18.10 | 19.51 | 17.59 | 18.60 | 18.45 | 17.42 |
| 5: CshC | 44.29 | 41.58 | 44.77 | 14.08 | 14.95 | 16.06 | 18.77 | 17.13 | 17.90 | 17.68 | 15.52 | 17.72 |
| 6: Bt183 | 44.81 | 44.83 | 46.90 | 12.77 | 13.08 | 17.68 | 21.98 | 17.85 | 19.57 | 18.40 | 14.71 | 17.22 |
| 7: Bt188 | 45.08 | 44.71 | 46.36 | 12.77 | 13.08 | 18.04 | 21.98 | 18.15 | 19.88 | 18.71 | 15.32 | 17.18 |
| 8: Bt192 | 45.08 | 44.71 | 46.36 | 11.97 | 13.08 | 17.99 | 21.98 | 17.85 | 19.57 | 18.40 | 15.02 | 17.22 |
| 9: Cps3D | 44.14 | 42.86 | 44.35 | 11.27 | 12.15 | 17.07 | 20.99 | 16.87 | 18.27 | 16.51 | 14.67 | 18.65 |
| 10: Cps9D | 43.05 | 42.55 | 43.82 | 11.27 | 13.08 | 17.33 | 20.99 | 16.87 | 18.89 | 16.82 | 15.27 | 18.67 |
| 11: Cps11D | 43.05 | 42.22 | 43.82 | 12.59 | 13.08 | 17.33 | 20.99 | 16.87 | 18.89 | 16.82 | 15.27 | 18.67 |
| 12: C3694 | 44.99 | 48.55 | 48.40 | 13.29 | 11.11 | 17.82 | 19.63 | 17.38 | 20.00 | 17.33 | 14.99 | 18.92 |
| 13: C8zC | 100.00 | 69.89 | 70.62 | 12.59 | 11.11 | 16.27 | 17.99 | 16.67 | 18.35 | 16.92 | 16.52 | 18.47 |
| 14: Cps7D | 69.89 | 100.00 | 87.53 | 12.59 | 13.89 | 17.77 | 18.60 | 16.36 | 17.13 | 20.24 | 17.99 | 18.67 |
| 15: Cps2D | 70.62 | 87.53 | 100.00 | 12.59 | 12.96 | 16.92 | 19.82 | 17.88 | 19.27 | 19.94 | 18.71 | 19.34 |
| 16: C3w | 13.29 | 12.59 | 12.59 | 100.00 | 16.10 | 17.96 | 21.39 | 21.26 | 19.41 | 21.18 | 18.57 | 18.71 |
| 17: Cps5B | 11.11 | 13.89 | 12.96 | 16.10 | 100.00 | 18.32 | 25.56 | 22.39 | 18.32 | 21.37 | 30.18 | 17.14 |
| 18: Fcs2 | 16.27 | 17.77 | 16.92 | 17.96 | 18.32 | 100.00 | 30.13 | 26.91 | 30.58 | 26.77 | 31.17 | 32.55 |
| 19: Cps1B | 17.99 | 18.60 | 19.82 | 21.39 | 25.56 | 30.13 | 100.00 | 51.91 | 50.66 | 50.13 | 31.12 | 31.61 |
| 20: BtY31 | 16.67 | 16.36 | 17.88 | 21.26 | 22.39 | 26.91 | 51.91 | 100.00 | 50.53 | 54.43 | 30.67 | 31.63 |
| 21: Ccs2 | 18.35 | 17.13 | 19.27 | 19.41 | 18.32 | 30.58 | 50.66 | 50.53 | 100.00 | 52.91 | 30.36 | 32.71 |
| 22: Cps4B | 16.92 | 20.24 | 19.94 | 21.18 | 21.37 | 26.77 | 50.13 | 54.43 | 52.91 | 100.00 | 30.36 | 29.74 |
| 23: C31B | 16.52 | 17.99 | 18.71 | 18.74 | 18.57 | 30.18 | 31.12 | 31.12 | 30.67 | 30.36 | 100.00 | 51.36 |
| 24: Cps12B | 17.47 | 18.67 | 19.34 | 18.71 | 17.14 | 32.55 | 31.61 | 31.63 | 32.71 | 29.74 | 51.36 | 100.00 |

|    | | Fcs2 | CsIB | Cps12B | BtY31 | Cps1B | Ccs2 | Cps4B |
|----|---|------|------|--------|-------|-------|------|-------|
| 1: | Fcs2   | 100.00 | 32.09  | 32.22  | 27.31  | 31.25  | 30.04  | 30.38 |
| 2: | CsIB   | 32.09  | 100.00 | 69.47  | 41.59  | 47.11  | 45.29  | 46.22 |
| 3: | Cps12B | 32.22  | 69.47  | 100.00 | 42.55  | 44.87  | 38.96  | 41.57 |
| 4: | BtY31  | 27.31  | 41.59  | 42.55  | 100.00 | 54.11  | 47.37  | 49.79 |
| 5: | Cps1B  | 31.25  | 47.11  | 44.87  | 54.11  | 100.00 | 54.84  | 54.37 |
| 6: | Ccs2   | 30.04  | 45.29  | 38.96  | 47.37  | 54.84  | 100.00 | 58.63 |
| 7: | Cps4B  | 30.38  | 46.22  | 41.57  | 49.79  | 54.37  | 58.63  | 100.00 |

MEANS AND METHODS FOR PRODUCING PHOSPHATE CONTAINING CAPSULAR POLYSACCHARIDES

This application contains a Sequence Listing in computer readable form, which is incorporated herein by reference.

CROSS-REFERENCE TO RELATED APPLICATIONS

This application is the U.S. national phase application filed under 35 U.S.C. § 371 claiming benefit to International Patent Application No. PCT/EP2018/070271, filed on Jul. 26, 2018, which claims priority to Luxembourg Patent Application No. LU100349, filed Jul. 26, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "206119_0033_00US_SequenceListing.TXT", created on Jan. 9, 2020, file size of 161,218 bytes. This Sequence Listing is identical to an ASCII formatted sequence listing filed in the International Patent Application No. PCT/EP2018/070271. The sequence listing submitted via EFS-Web is part of the Specification and is herein incorporated by reference in its entirety.

TECHNICAL FIELD OF THE INVENTION

The present invention relates to a host cell, which comprises under the control of a heterologous promoter a polynucleotide comprising a nucleotide sequence encoding a polypeptide capable of synthesizing a polysaccharide consisting of a dimeric repeating unit as well as to a vaccine composition comprising such host cell. Furthermore, either such host cell or a polypeptide expressed by such host cell is used for the production of a polysaccharide consisting of a dimeric repeating unit, which may be used as a glycoconjugate vaccine.

BACKGROUND ART

Bacterial pathogens developed a variety of strategies to invade and ensure its survival in the host (1). The extracellular capsule polysaccharides (CPSs) represent a major virulence determinant of encapsulated pathogenic bacteria. They form a highly hydrated physical barrier representing an extensive protective cell layer (1, 2). CPSs are widely distributed and found in diverse bacterial pathogens such as *Escherichia coli* (*E. coli*), *Neisseria meningitidis* (Nm), *Haemophilus influenzae* (Hi), *Actinobacillus pleuropneumoniae* (App), *Staphylococcus aureus* and *Streptococcus pneumoniae* (1, 3).

Based on the genetic and chemical properties of different *E. coli* strains, CPSs are divided into four groups (group I-IV). Group II capsules are characterized by a high negative charge density that is introduced by either negatively charged sugar positions (sialic acid or glucuronic acid) or phosphate groups (1). Genes responsible for biosynthesis and export of group II capsules are located in the so-called capsule gene cluster that has been found in many disease-causing strains (1, 4-9). This gene cluster is structured into three regions (regions 1-3), of which region 1 and 3 are conserved and encode for proteins involved in capsule assembly and transport to the cell surface. Region 2 is serogroup-specific and encodes for proteins that are required for capsule polysaccharide synthesis.

The enzymes that synthesize the CPS are so called capsule polymerases (CPs). Capsule polymerases generating a linkage between two sugar positions—a so-called glycosidic linkage—belong to a group of enzymes called glycosyltransferases (GT). It is important at this point to highlight that structural data obtained for glycosyltransferases of all domains of life revealed only three protein folds termed GT-A, GT-B, and GT-C (10). While GT-C folded enzymes represent a minor group of multi-membrane spanning proteins, enzymes with GT-A and GT-B folds are abundant and can be monotopic or soluble (11). Another group of capsule polymerases display hexose-1-phosphate transferase activity. These enzymes are able to generate a phosphodiester linkage when transferring a sugar-phosphate and display sequence motifs that are characteristic for a protein family called Stealth (13).

While the above described capsule polymerases either generate a CPS with glycosidic or a phosphodiester linkage or bond, the prior art lacks capsule polymerases that are able to generate both linkage types in a polymer and further synthesize a polysaccharide consisting of a dimeric repeating unit, since the prior art only teaches capsule polymerases having both linkage types in a polymer being able to synthesize a polysaccharide consisting of a trimeric repeating unit (14).

Thus, the objective of the present invention is the provision of a capsule polymerase family being able to synthesize a polysaccharide consisting of a dimeric repeating unit.

SUMMARY OF THE INVENTION

The capsule polymerases characterized so far in the prior art are either glycosyltransferases or hexose-phosphate transferases. The TagF-like capsule polymerase family of the present invention, a new family of polymerases, combines glycosyltransferase and hexose-/alditol-phosphate transferase activity. All TagF-like capsule polymerases contain a domain modeled onto the crystal structure of the teichoic acid polymerase TagF. This TagF-like domain acts in concert with a second domain adopting either a GT-A or a GT-B fold. The polypeptide of the present invention, either having a TagF-like domain and a GT-B fold or a TagF-like domain and a GT-A fold, may be capable of synthesizing a polysaccharide consisting of a dimeric repeating unit.

The present invention relates to a host cell, which comprises under the control of a heterologous promoter a polynucleotide comprising a nucleotide sequence encoding a polypeptide, wherein the nucleotide sequence is selected from the group consisting of:

a) a nucleotide sequence encoding a polypeptide comprising a TagF-like domain and a GT-B domain having the amino acid sequences shown in SEQ ID NO. 1 and 17, SEQ ID NO. 2 and 18, SEQ ID NO. 3 and 19, SEQ ID NO. 4 and 20, SEQ ID NO. 5 and 21, SEQ ID NO. 6 and 22, SEQ ID NO. 7 and 23, SEQ ID NO. 8 and 24, SEQ ID NO. 9 and 25, SEQ ID NO. 10 and 26, SEQ ID NO. 11 and 27, wherein the polypeptide synthesizes a polysaccharide consisting of a dimeric repeating unit;

b) a nucleotide sequence encoding a polypeptide comprising a TagF-like domain and a GT-A domain having the amino acid sequences shown in SEQ ID NO. 12 and 28, SEQ ID NO. 13 and 29, SEQ ID NO. 14 and 30, SEQ ID NO. 15 and 31, SEQ ID NO. 16 and 32, wherein the polypeptide synthesizes a polysaccharide consisting of a dimeric repeating unit;

c) a nucleotide sequence encoding a pair of fragments of the polypeptide as defined in (a) and in (b), wherein each fragment is at least 15 amino acid residues in length and wherein the pair of fragments synthesizes a polysaccharide consisting of a dimeric repeating unit;

d) a nucleotide sequence encoding a polypeptide having an amino acid sequence that is at least 18% identical to the amino acid sequence of residues 1 to 378 of SEQ ID NO. 3 and that is at least 40% identical to the amino acid sequence of residues 1 to 389 of SEQ ID NO. 23, wherein the polypeptide synthesizes a polysaccharide consisting of a dimeric repeating unit;

e) a nucleotide sequence encoding a polypeptide having an amino acid sequence that is at least 18% identical to the amino acid sequence of residues 1 to 378 of SEQ ID NO. 3 and that is at least 30% identical to the amino acid sequence of residues 1 to 256 of SEQ ID NO. 32, wherein the polypeptide synthesizes a polysaccharide consisting of a dimeric repeating unit, and wherein the nucleotide sequence of (a) to (e) encodes a polypeptide having a conserved tyrosine at a position corresponding to position 49 of SEQ ID NO. 3 or having a conserved aspartic acid at a position corresponding to position 49 of SEQ ID NO. 3.

Further contemplated by the present invention may be a method of producing a host cell of the present invention, the method comprising: a) cloning a nucleotide sequence encoding a polypeptide expressed by the host cell of the present invention into a vector; b) transforming cells with said vector of (a) and growing the cells in medium.

Additionally, the present invention may comprise a method of expressing a polypeptide in a host cell comprising: a) culturing the host cell of the present invention; b) expressing the polypeptide in the host cell.

The present invention may encompass a vaccine composition comprising the host cell of the present invention.

Further, a composition comprising a polypeptide expressed by the host cell of the present invention may also be envisaged by the present invention.

The given capsule structures assemble the typical CPS structure synthesized by TagF-like capsule polymerases consisting of oligosaccharides connected through phosphodiester bonds or monosaccharides connected through glycerol-phosphate units. Identical structures are highlighted with colored boxes. The occurrence of the typical CPS structures and genes that encode putative TagF-like capsule polymerases demonstrates the conservation and abundance of the TagF-like polymerases among a variety of group II capsule expressing bacteria.

Figure 8:
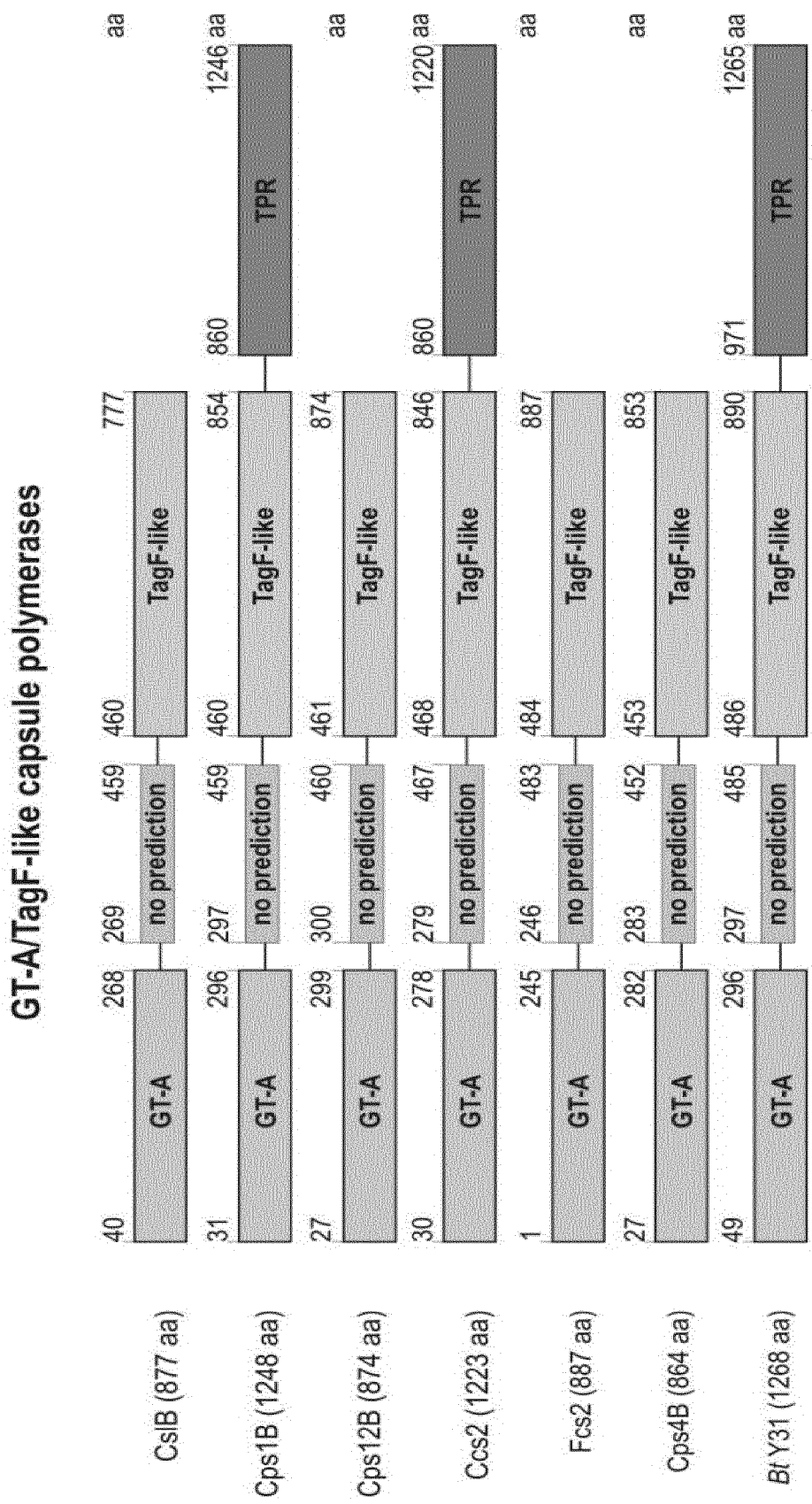
Figure 8:
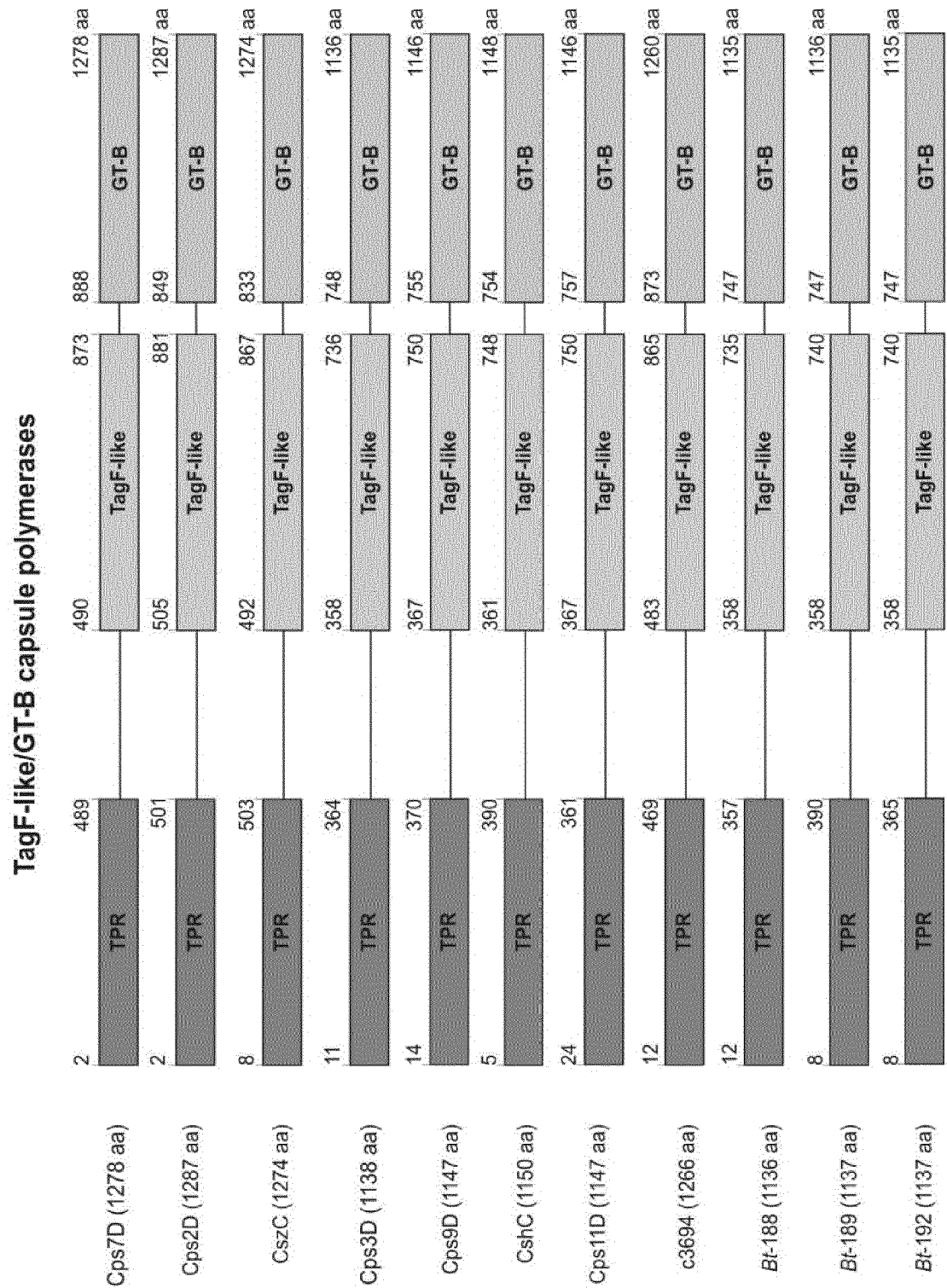

FIG. 8: Overview of the predicted domain architecture of all TagF-like polymerases. Homology modeling was performed using the structure prediction tool PHYRE2. Protein denominations with complete amino acid lengths indicated in brackets are displayed in the left panel. The first and last amino acids of each domain as predicted by PHYRE2 are indicated. It is of note that the absolute value for the first and last amino acid might slightly vary if consecutive predictions, performed over a period of several months, are compared. The following protein sequences were used for PHYRE2 modeling: CslB of NmL (uniprot: Q9RGQ9), Cps1B of App1 (GenBank: KY798410), Cps12B of App12 (uniprot: Q69AA8), Ccs2 of Hic (GenBank: AEC50903.1), Fcs2 of Hif (GenBank: AAQ12660.1), Cps4B of App4 (uniprot: F4YBG0), BtY31 of the non-serotyped *Bibersteinia trehalosi* strain Y31 (GenBank: OAQ14264.1), Cps7D of App7 (GenBank: ACE62291.1), Cps2D of App2 (uniprot: Q6UYC4), CszC of NmZ (uniprot: Q5QRV6), Cps3D of App3 (GenBank: KY807157), Cps9D of App9 (uniprot: E0F019), CshC of NmH (uniprot: H6T5X6), Cps11D of App11 (uniprot: EOFCQ3), Bt188 of the non-serotyped *Bibersteinia trehalosi* strain USDA-ARS-USMARC-188 (GenBank: AHG82487.1), Bt189 of the non-serotyped *Bibersteinia trehalosi* strain USDA-ARSUSMARC-189 (GenBank: AHG84818.1), Bt192 of the non-serotyped *Bibersteinia trehalosi* strain USDA-ARS-USMARC-192 (GenBank: AGH37704.1) and c3694 of *E. coli* K2 strain CFT073 (GenBank: AAN82142.1).

Figure 9:
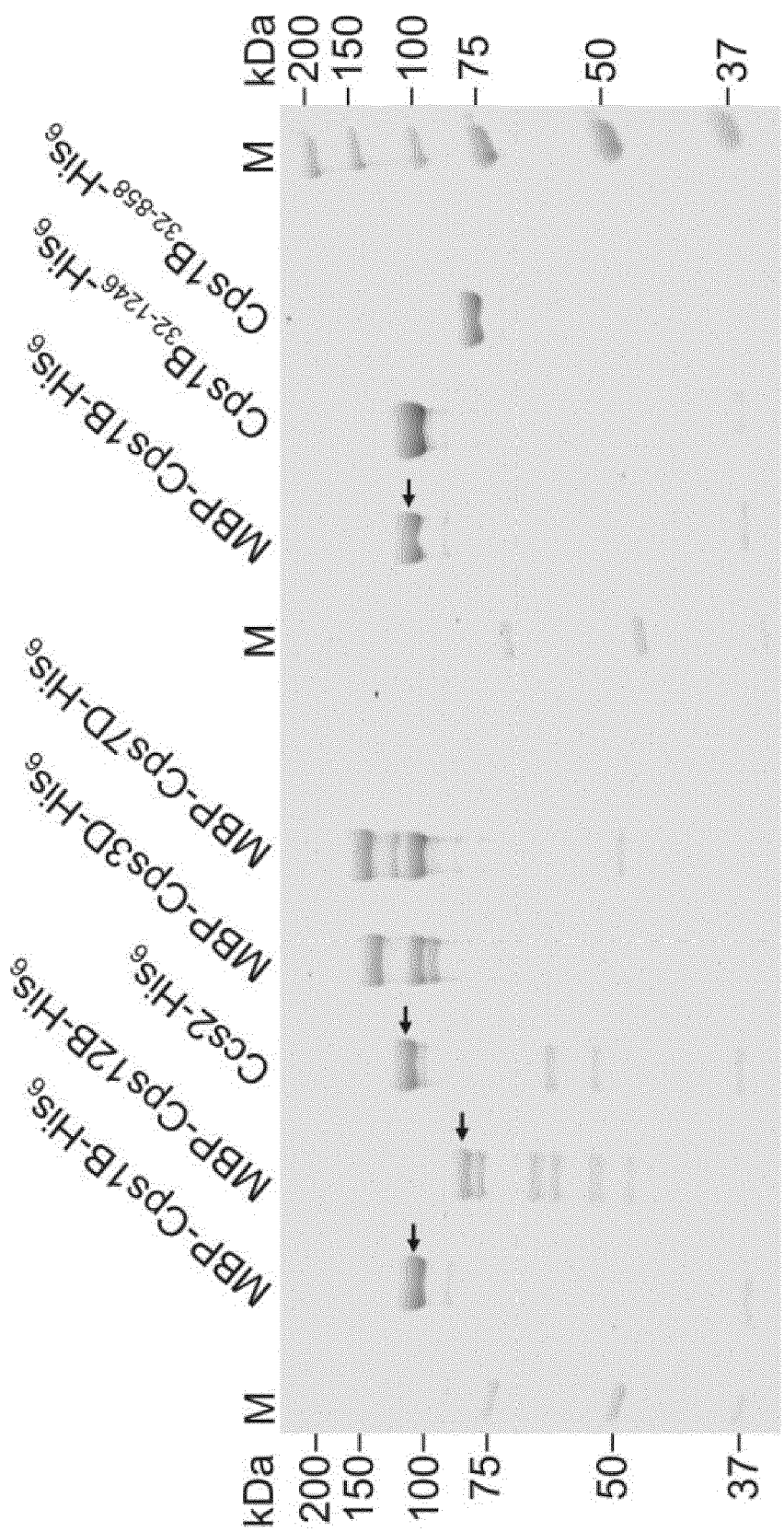

FIG. 9: Coomassie-stained SDS-polyacrylamide gel of the polymerases.

Separated samples contain the protein fractions that were obtained after the purification of each construct. 1.5 to 3 μg protein were loaded per lane. Expression cultures were transformed with the constructs indicated on top of each lane. Only full-length proteins of MBP-Cps3D-His6 (177 kDa) and MBP-Cps7D-His6 (192 kDa) could be enriched additionally to degradation products. However, for the constructs MBP-Cps1B-His6 (190 kDa), MBP-Cps12B-His6 (146 kDa) and Ccs2-His6 (144 kDa) only soluble degradation products (indicated by arrows) could be purified. This phenomenon has also been shown for CslB (10). The full-length proteins are generally insoluble. The degradation constructs seem to lack the MBP-tag and an N-terminal part of the protein sequence. The main protein band resulting from the MBP-Cps1BHis6 purification was sequenced N-terminally and could be identified as a ΔN31 truncation (MBP-Cps1B32-1246-His6) with a theoretical molar masse of 144 kDa. The N-terminal and C-terminal truncation construct that lacking the TPR domain (MBP-Cps1B32-858-His6) has a theoretical molar mass of 99 kDa.

FIG. 10: Sequence alignment of all predicted N-terminal CTA domains.

Database references for all TagF-like polymerase sequences are indicated in the figure legend of FIG. 8.

Similar amino acids are shown in grey boxes and the conserved aspartate positions of the DxD motif are highlighted in red. The sequence alignment was performed with Clustal Omega (ebi.ac.uk/Tools/msa/clustalo/) and annotated with the Jalview software. It also includes the sequence of K4CP of *E. coli* K4 (uniprot Q8L0V4) that was used as template for PHYRE$^2$ modeling.

FIG. 11: Sequence alignment of all predicted TagF-like domains.

A) Conserved histidine (H) at a position corresponding to position 122 of SEQ ID NO. 3. B) Conserved histidine (H) at a position corresponding to position 251 of SEQ ID NO. 3. Database references for all TagF-like polymerase sequences are indicated in the figure legend of FIG. 8. The sequence alignment was performed with Clustal Omega (ebi.ac.uk/Tools/msa/clustalo/) and annotated with the Jalview software. It also includes the sequence of Tagg of *Staphylococcus epidermidis* (uniprot: Q5HLM5) that was used as template for the PHYRE$^2$ modeling.

FIG. 12: Sequence alignment of all predicted C-terminal GT-B domains.

Conserved arginine (R) at a position corresponding to position 234 of SEQ ID NO. 23 and a conserved lysine (K) at a position corresponding to position 239 of SEQ ID NO. 23. Database references for all TagF-like polymerase sequences are indicated in the figure legend of FIG. 8. The sequence alignment was performed with Clustal Omega (ebi.ac.uk/Tools/msa/clustalo/) and annotated the Jalview software. It also includes the sequence of TarM of *Staphylococcus aureus* (uniprot A0A0J9X257) that was used as template for PHYRE$^2$ modeling.

Figure 13:
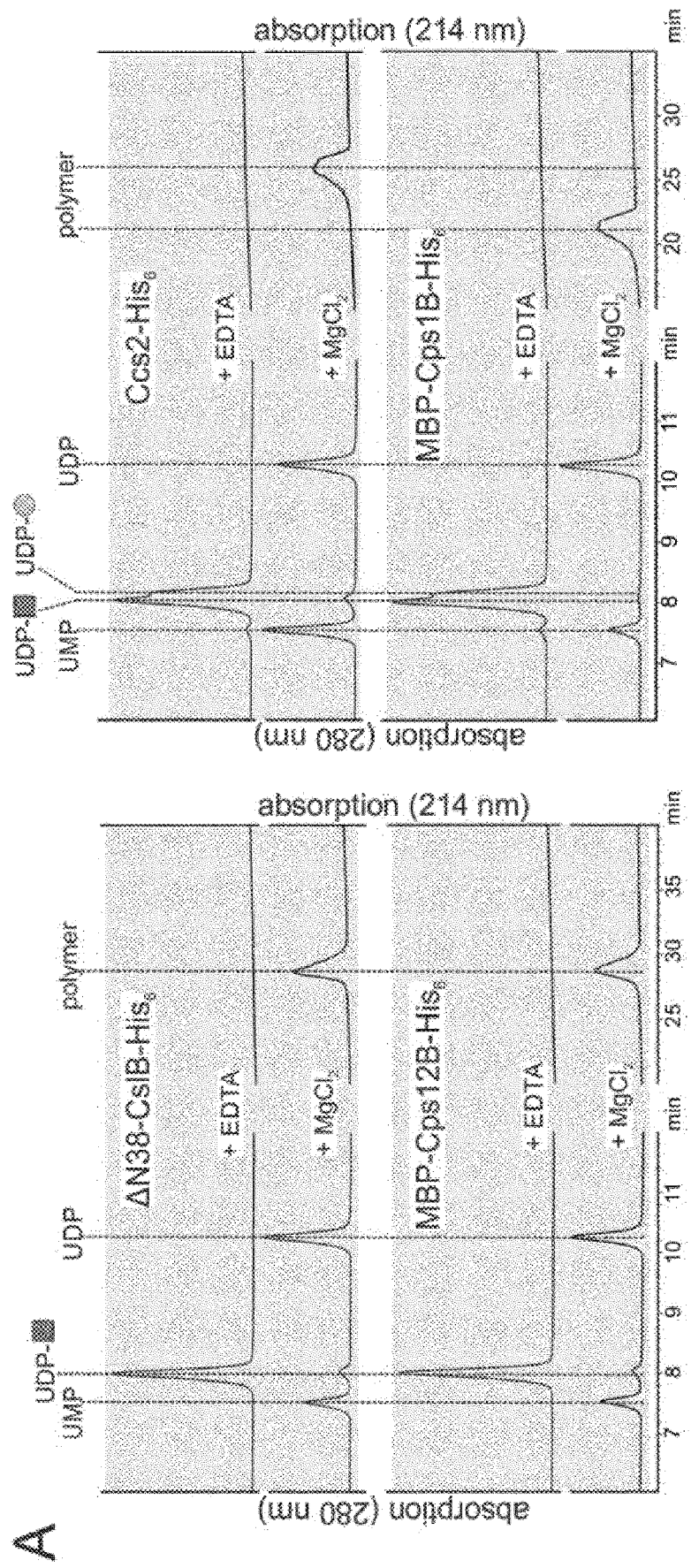
Figure 13:
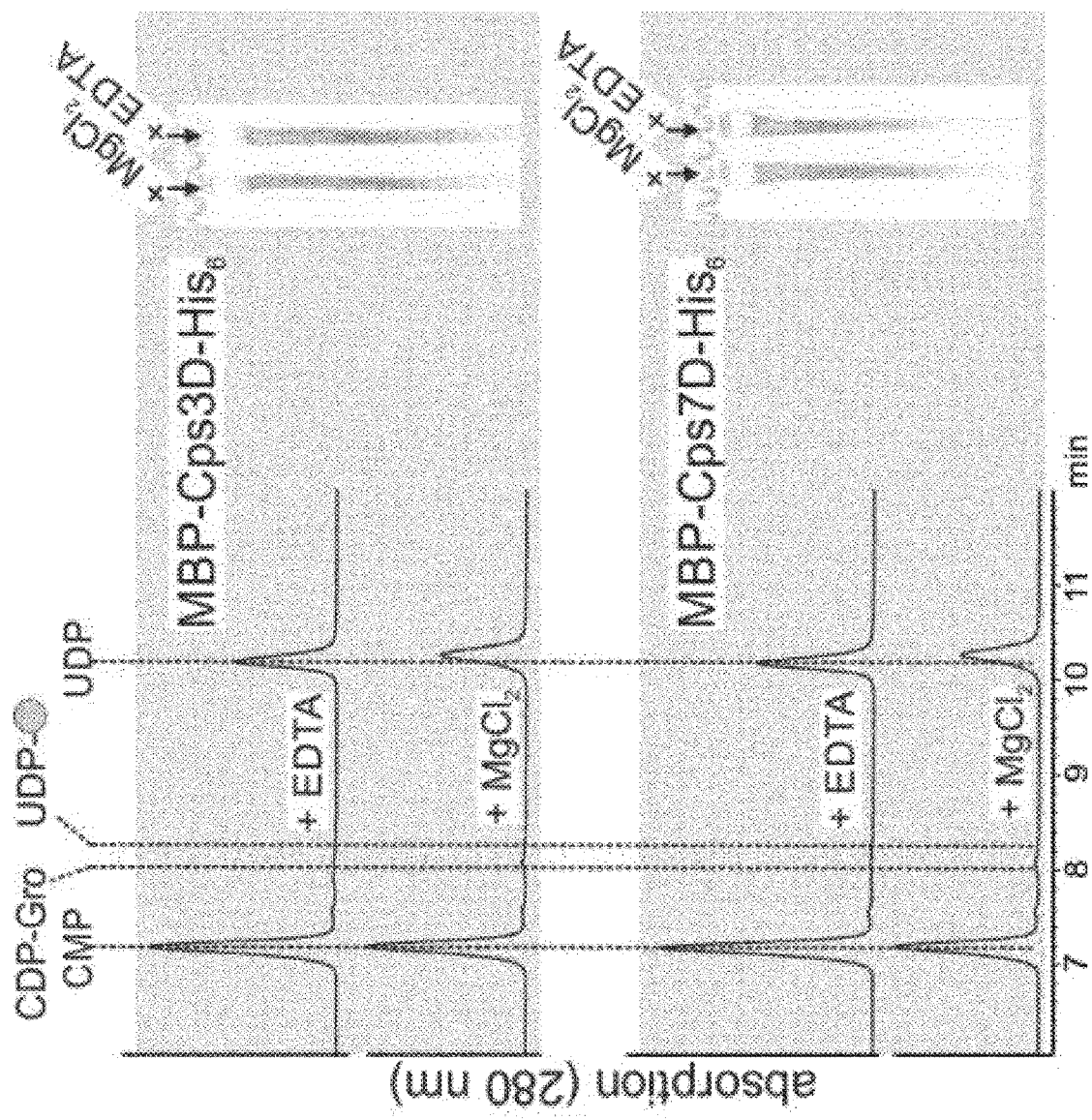

FIG. 13: HPLC-AEC assay in the presence (+MgCl$_2$) and absence (+EDTA) of magnesium chloride.

A) Polymerases adopting GT-A/TagF-like architecture depend on magnesium chloride to catalyze the conversion of their nucleotide activated substrates into the polymer. This finding corroborates the PHRYE2 prediction since GT-A folded proteins are known to require a divalent cation for activity. B) Consistent with the fact that there is no evidence of a bound metal ion associated with catalysis in GT-B folded enzymes, the polymerases adopting the TagF-like/GT-B architecture also work in the presence of the chelate reagent EDTA.

FIG. 14: Sequence alignment of all predicted TagF-like domains including conserved amino acid motif I.

Conserved tyrosine (Y) at a position corresponding to position 49 in SEQ ID NO. 3 in SEQ ID NO. 1 (CshC), SEQ ID NO. 2 (Bt189), SEQ ID NO. 4 (Bt192), SEQ ID NO. 5 (Cps3D), SEQ ID NO. 6 (Cps9D), SEQ ID NO. 7 (Cps11D), SEQ ID NO. 9 (CszC), SEQ ID NO. 10 (Cps7D), SEQ ID NO. 11 (Cps2D), SEQ ID NO. 12 (Fcs2), SEQ ID NO. 13 (Cps1B), SEQ ID NO. 14 (BtY31), SEQ ID NO. 15 (Ccs2), SEQ ID NO. 16 (Cps4B), or conserved aspartic acid (D) at a position corresponding to position 49 of SEQ ID NO. 3 for SEQ ID NO. 8 (c3694).

FIG. 15: Sequence alignment of all predicted TagF-like domains including a stretch in the TagF-like domain of Cps6D (SEQ ID NO. 35) and Cps8D (SEQ ID NO. 36).

A) Amino acid stretch in TagF-like domain from positions 231 to 300 in SEQ ID NO. 35 (Cps6D) and from positions 297 to 366 in SEQ ID NO. 36 (Cps8D). (B) Amino acid stretch in TagF-like domain from positions 301 to 334 in SEQ ID NO. 35 (Cps6D) and from positions 367 to 400 in SEQ ID NO. 36 (Cps8D).

FIG. 16: Sequence alignment of all predicted TagF-like domains including conserved amino acid motif II.

Conserved aspartic acid (D) at a position corresponding to position 364 of SEQ ID NO. 3 in SEQ ID NO. 1 (CshC), SEQ ID NO. 2 (Bt189), SEQ ID NO. 4 (Bt192), SEQ ID NO. 5 (Cps3D), SEQ ID NO. 6 (Cps9D), SEQ ID NO. 7 (Cps11D), SEQ ID NO. 8 (c3694). SEQ ID NO. 9 (CszC), SEQ ID NO. 10 (Cps7D), SEQ ID NO. 11 (Cps2D), SEQ ID No. 12 (Fcs2), SEQ ID NO. 13 (Cps1B), SEQ ID NO. 14 (BtY31), SEQ ID NO. 15 (Ccs2) and SEQ ID NO. 16 (Cps4B).

FIG. 17: Sequence alignment of all predicted GT-B domains including conserved amino acid motifs I, II and III.

A) Conserved asparagine (N) and leucine (L) at positions corresponding to positions 20 and 21 of SEQ ID NO. 23 in SEQ ID NO. 17 (CshC), SEQ ID NO. 18 (Bt189), SEQ ID NO. 19 (Bt188), SEQ ID NO. 20 (Bt192), SEQ ID NO. 21 (Cps3D), SEQ ID NO. 22 (Cps9D), SEQ ID NO. 24 (c3694), SEQ ID NO. 25 (CszC), SEQ ID NO. 26 (Cps7D), SEQ ID NO. 27 (Cps2D). B) Conserved valine (V) at a position corresponding to position 60 of SEQ ID NO. 23 in SEQ ID NO. 17 (CshC), SEQ ID NO. 18 (Bt189), SEQ ID NO. 19 (Bt188), SEQ ID NO. 20 (Bt192), SEQ ID NO. 21 (Cps3D), SEQ ID NO. 22 (Cps9D), SEQ ID NO. 24 (c3694), SEQ ID NO. 25 (CszC), SEQ ID NO. 26 (Cps7D), SEQ ID NO. 27 (Cps2D). C) Conserved serine (S) at a position corresponding to position 88 of SEQ ID NO. 23 in SEQ ID NO. 17 (CshC), SEQ ID NO. 18 (Bt189), SEQ ID NO. 19 (Bt188), SEQ ID NO. 20 (Bt192), SEQ ID NO. 21 (Cps3D), SEQ ID NO. 22 (Cps9D), SEQ ID NO. 24 (c3694), SEQ ID NO. 25 (CszC), SEQ ID NO. 26 (Cps7D), SEQ ID NO. 27 (Cps2D).

FIG. 18: Sequence alignment of all predicted GT-A domains including conserved amino acid motifs I, II and III.

A) Conserved isoleucine (I) at a position corresponding to position 38 of SEQ ID NO. 32 in SEQ ID NO. 28 (Fcs2), SEQ ID NO. 29 (Cps1B), SEQ ID NO. 30 (BtY31), SEQ ID NO. 31 (Ccs2). B) Conserved arginine (R) at a position corresponding to position 156 of SEQ ID NO. 32 in SEQ ID NO. 28 (Fcs2), SEQ ID NO. 29 (Cps1B), SEQ ID NO. 30 (BtY31), SEQ ID NO. 31 (Ccs2). C) Conserved phenylalanine (F) at a position corresponding to position 181 of SEQ ID NO. 32 in SEQ ID NO. 28 (Fcs2), SEQ ID NO. 29 (Cps1B), SEQ ID NO. 30 (BtY31), SEQ ID NO. 31 (Ccs2).

FIG. 19: Matrix showing sequence identities of all predicted TagF-like domains.

Sequence identity of at least 18% choosing SEQ ID NO. 3 (TagF domain of Bt188) as the reference sequence.

FIG. 20: Matrix showing sequence identities of all predicted GTB domains.

Sequence identity of at least 40% choosing SEQ ID NO. 23 (GT-B domain of Cps11D) as the reference sequence.

FIG. 21: Matrix showing sequence identities of all predicted GTA domains.

Sequence identity of at least 30% choosing SEQ ID NO. 32 (GT-A domain of Cps4B) as the reference sequence.

Figure 22:
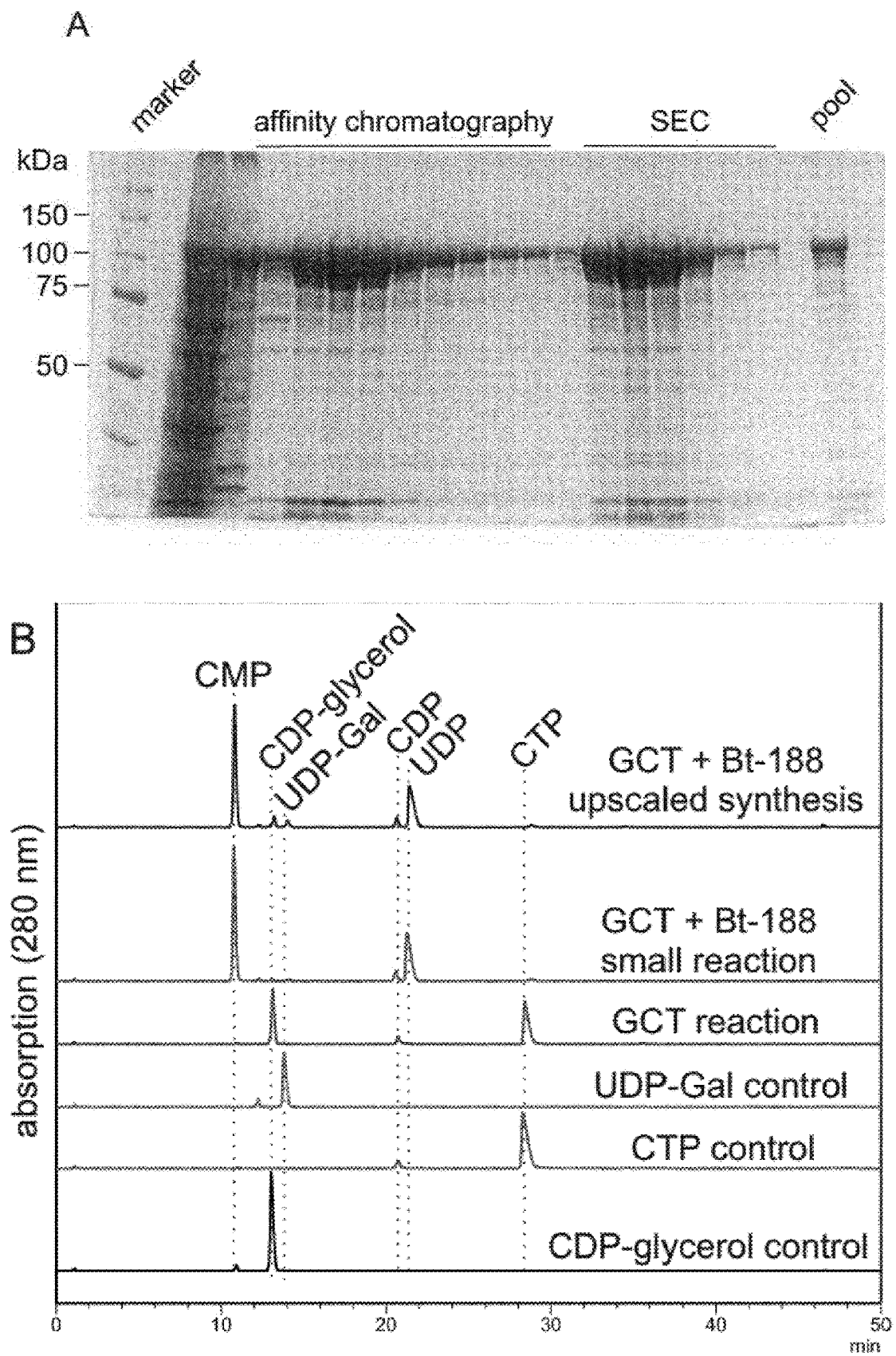
Figure 22:
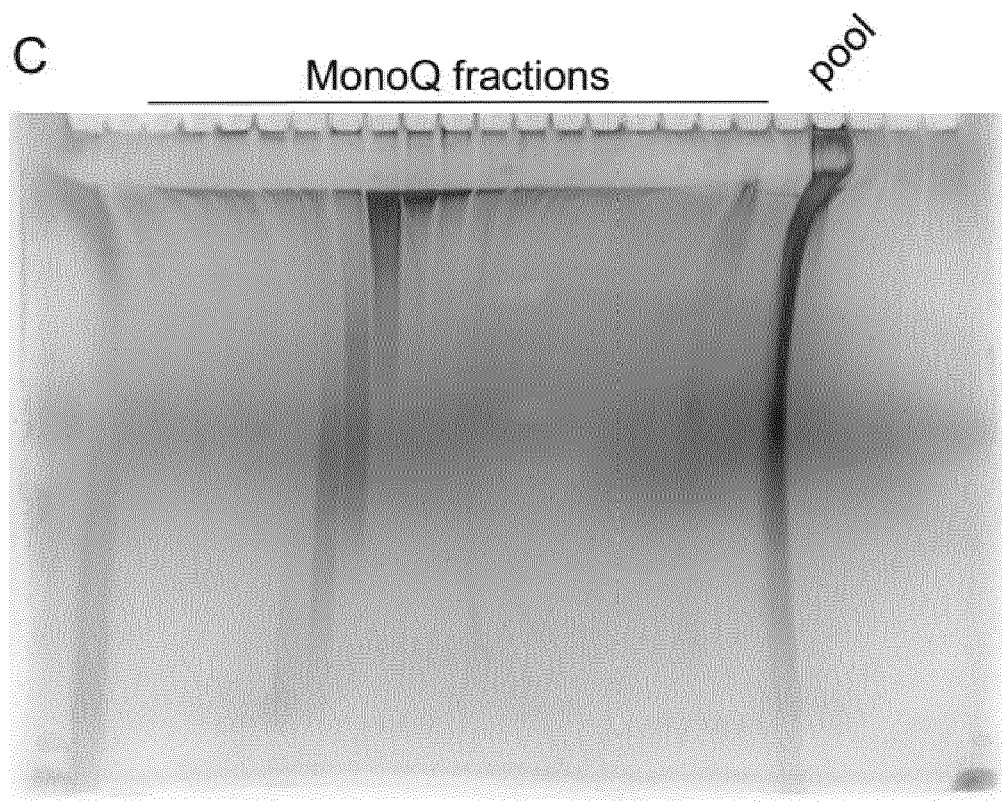
Figure 22:
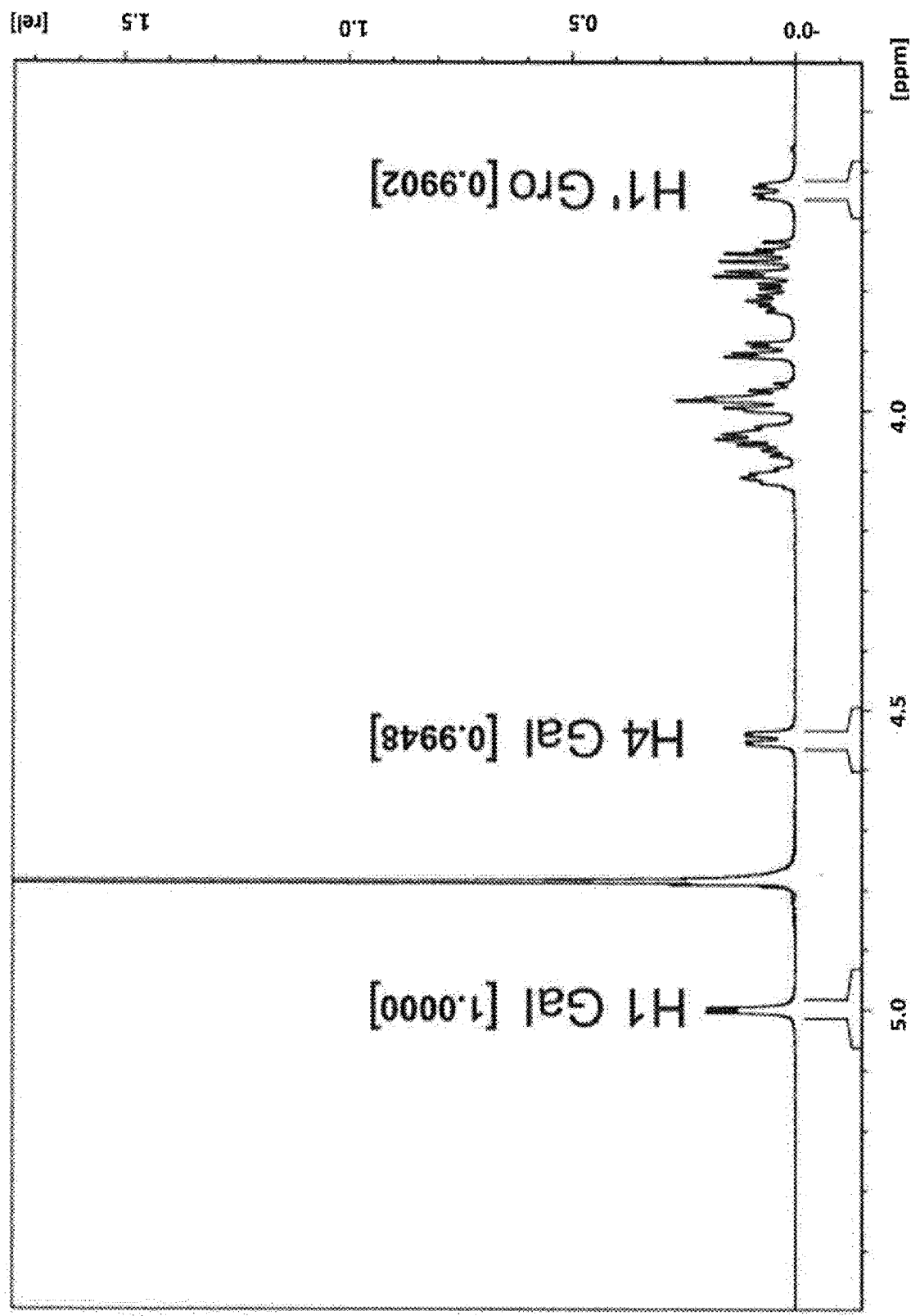
Figure 22:
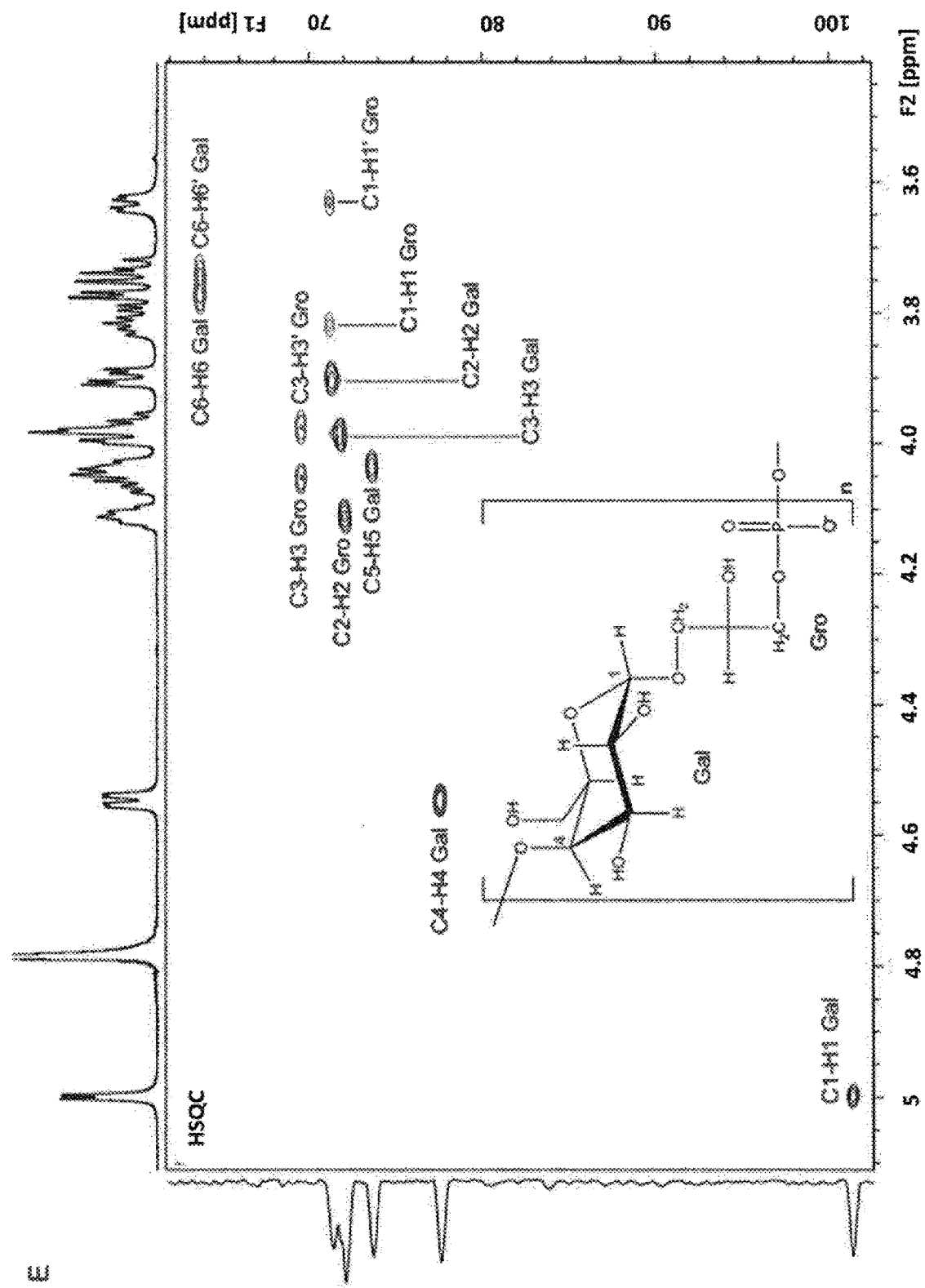

FIG. 22: Purification and characterization of Bt-188.

A) Coomassie-stained SDS-polyacrylamide gel showing the fractions collected during the purification of Bt-188-His6 by affinity chromatography (via its C-terminal His$_6$-tag) and size exclusion chromatography (SEC). The pooled fraction contains the full-length construct (134.1 kDa) together with two smaller bands most likely resulting from N-terminal degradation. B) HPLC-AEC analysis of the Cps7B (GCT) and Bt-188 reaction. C) The polymer produced in the upscaled synthesis (see also B) being purified by AEC using a MonoQ column and a combination of linear NaCl gradients. D) $^1$H NMR analysis of the polymer produced in the upscaled synthesis after purification. The integrals (enclosed in square brackets) of isolated proton signals from the Gal and glycerol (Gro) moieties are consistent with a dimeric repeating unit. E) Corresponding $^1$H, $^{13}$C HSQC NMR analysis demonstrating a dimeric repeating unit.

Figure 23:
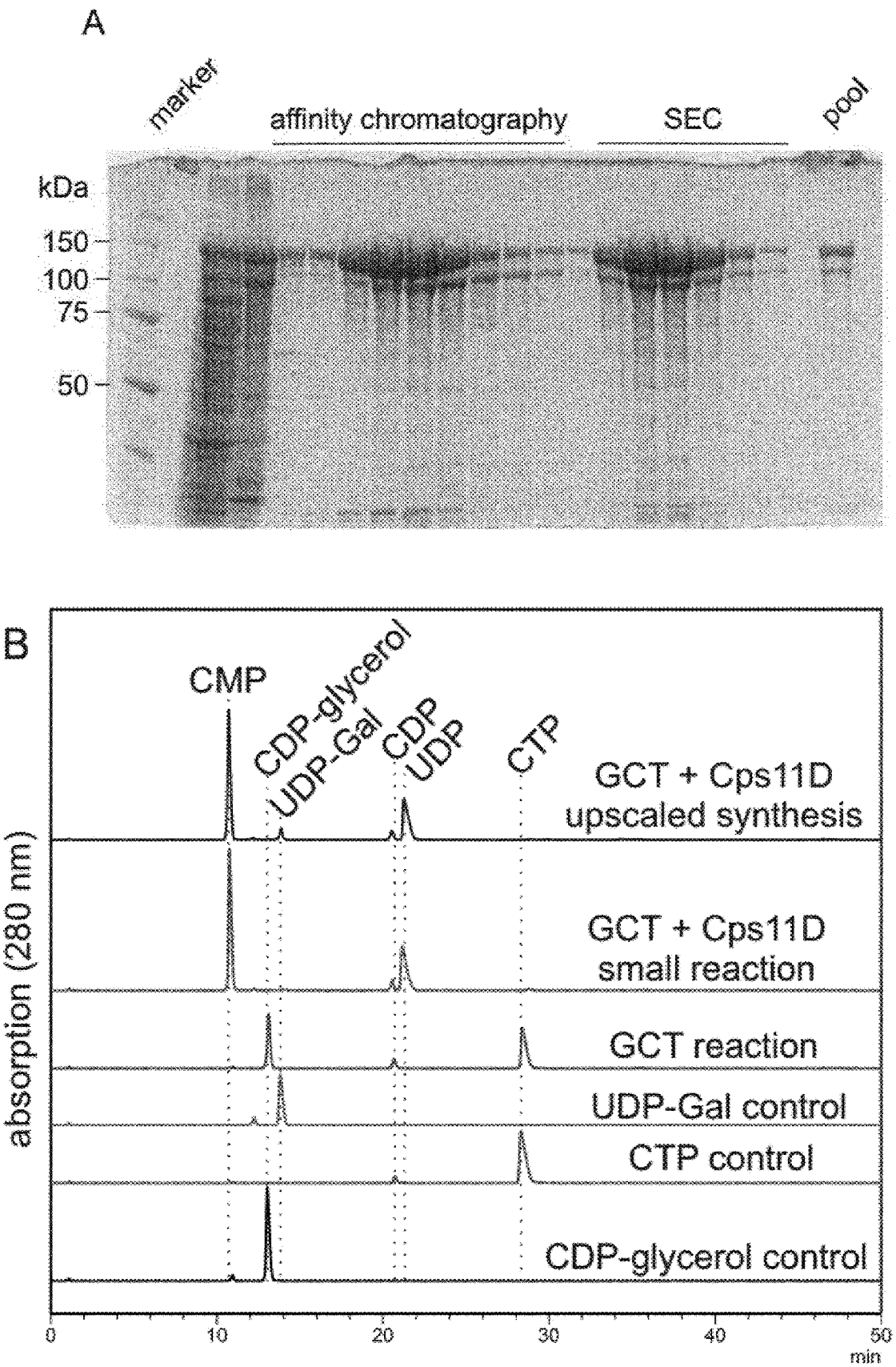
Figure 23:
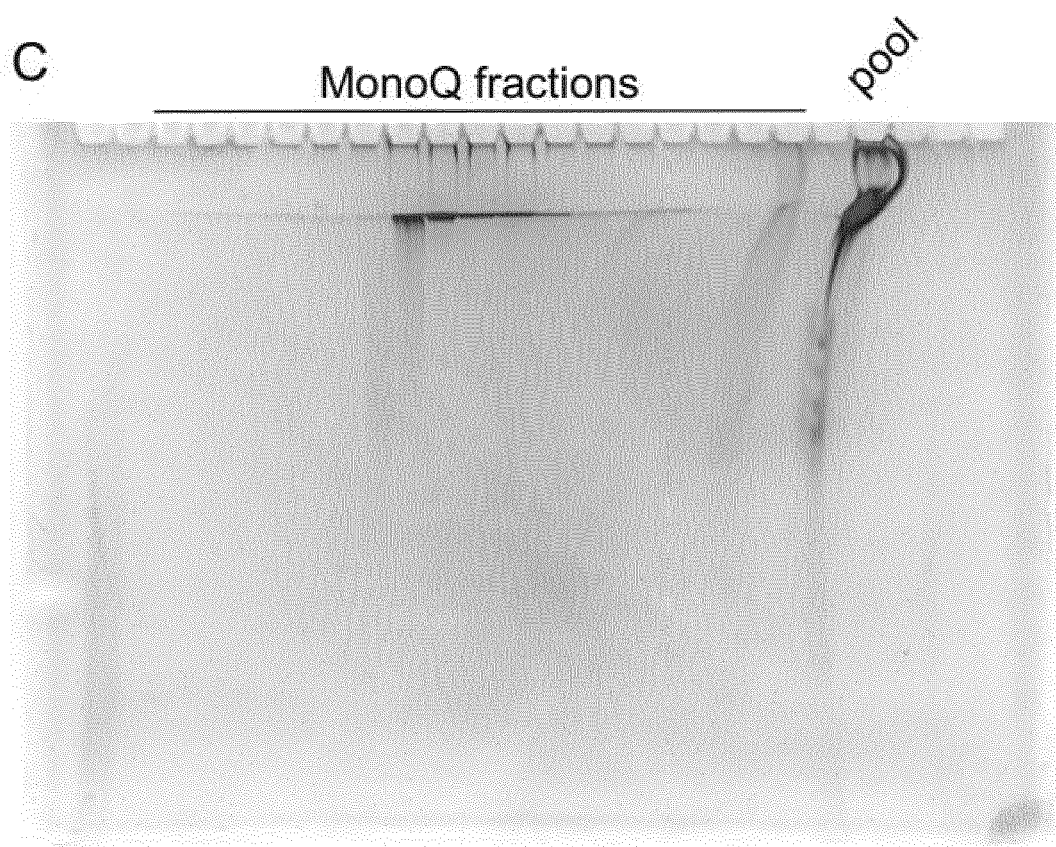
Figure 23:
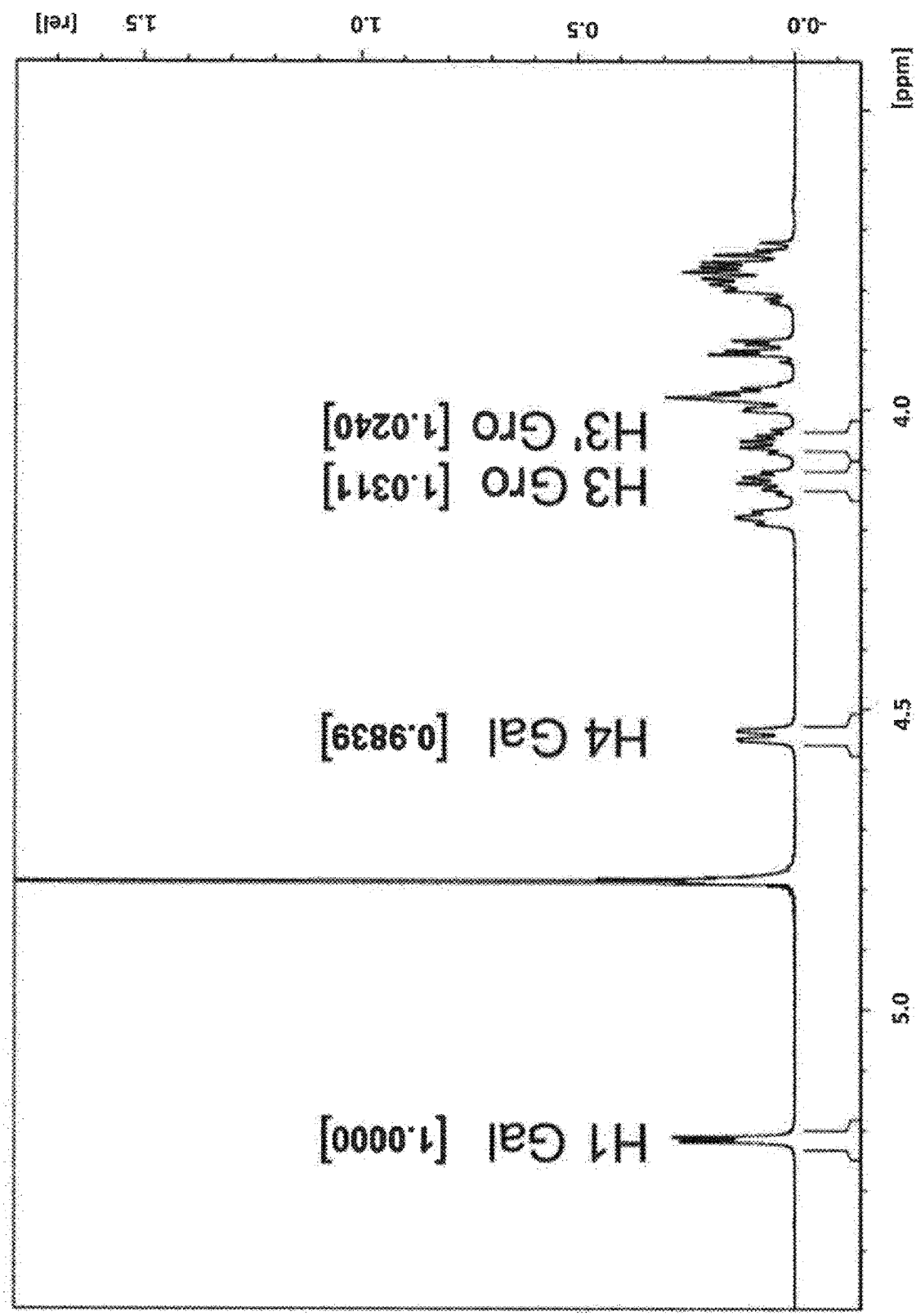
Figure 23:
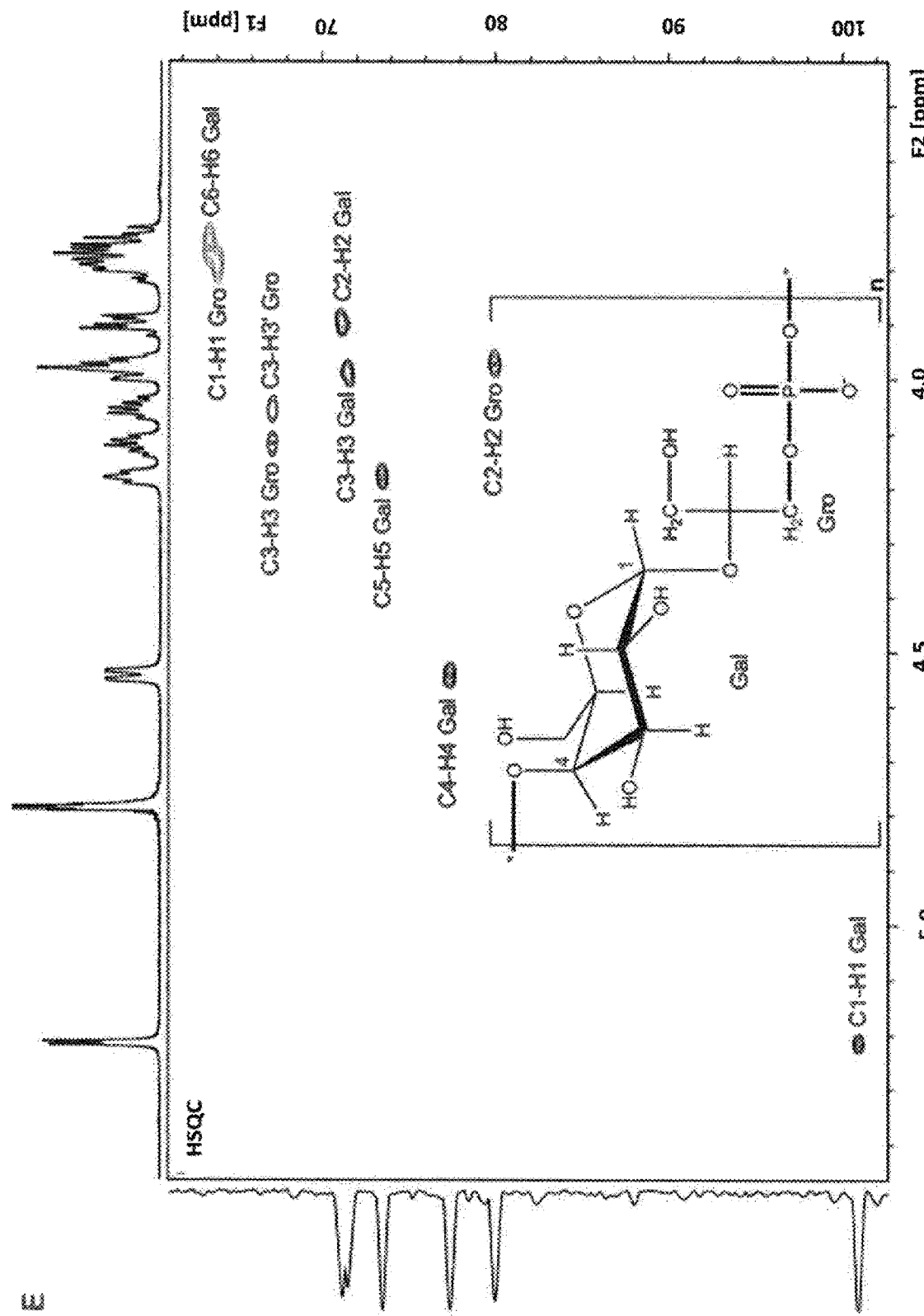

FIG. 23: Purification and characterization of Cps11D.

A) Coomassie-stained SDS-polyacrylamide gel showing the fractions collected during the purification of MBP-Cps11D-His6 by affinity chromatography (via its C-terminal His$_6$-tag) and size exclusion chromatography (SEC). The pooled fractions contain the full-length construct (176.4 kDa) together with one smaller band most likely resulting from N-terminal degradation. B) HPLC-AEC analysis of the Cps7B (GCT) and Cps11D reaction. C) The polymer produced in the upscaled synthesis (see also B) was purified by AEC using a MonoQ column and a combination of linear NaCl gradients. D) $^1$H NMR analysis of the polymer produced in the upscaled synthesis after purification. The integrals (enclosed in square brackets) of isolated proton signals from the Gal and glycerol (Gro) moieties are consistent with a dimeric repeating unit. E) Corresponding $^1$H, $^{13}$C HSQC NMR analysis demonstrating a dimeric repeating unit.

Figure 24:
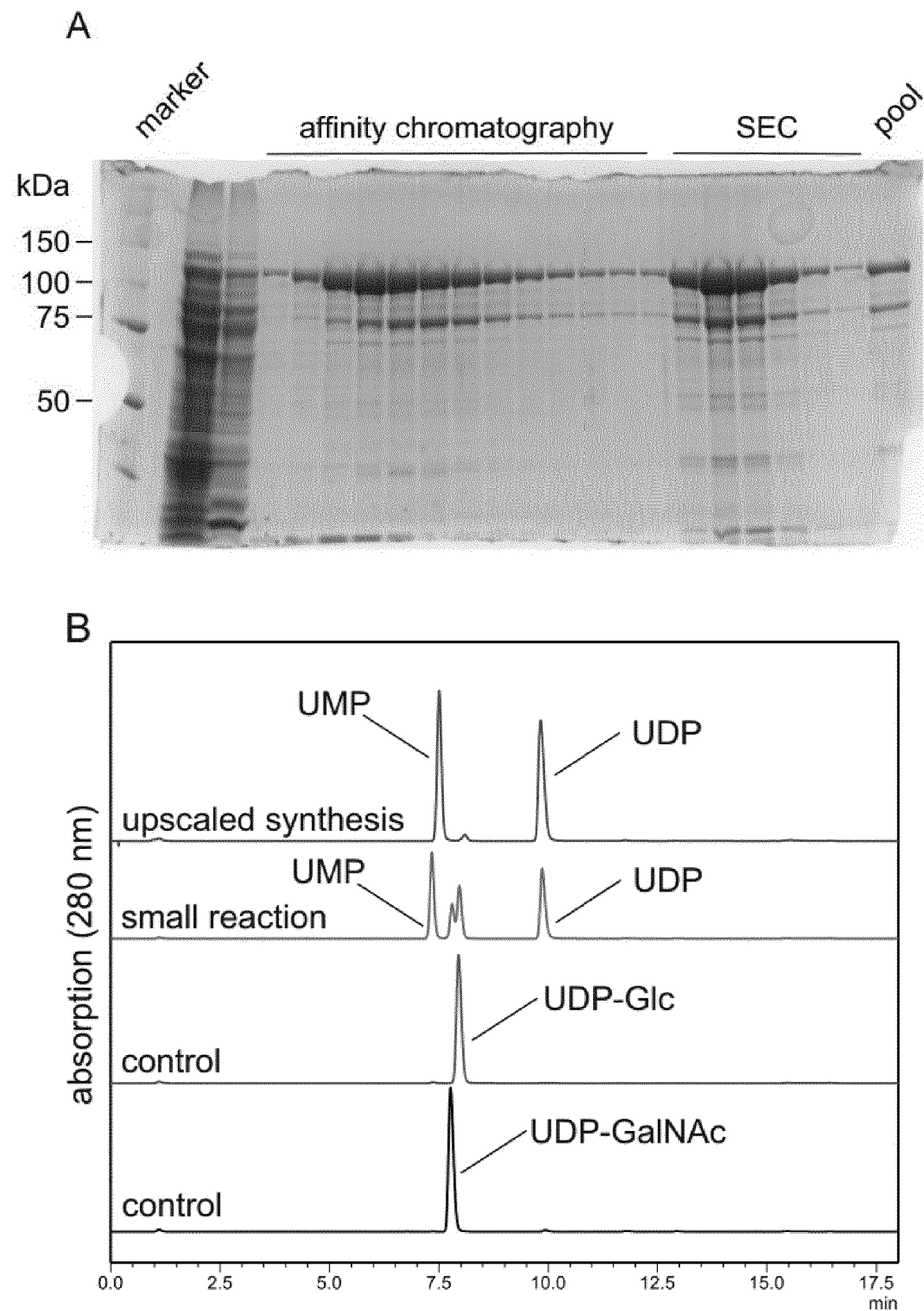
Figure 24:
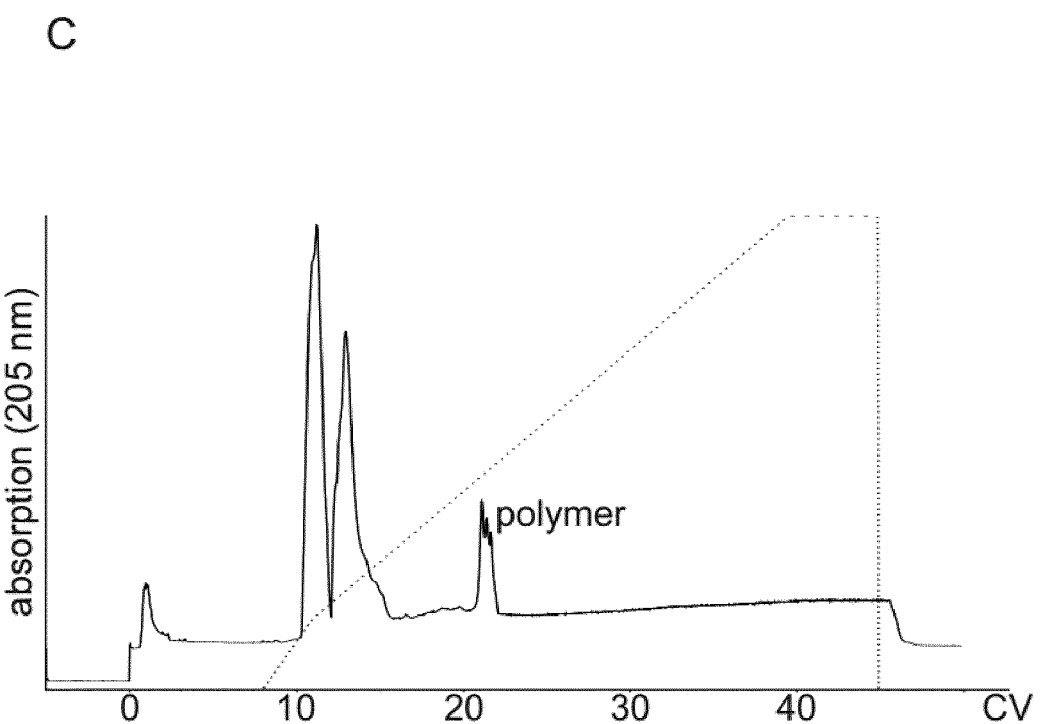
Figure 24:
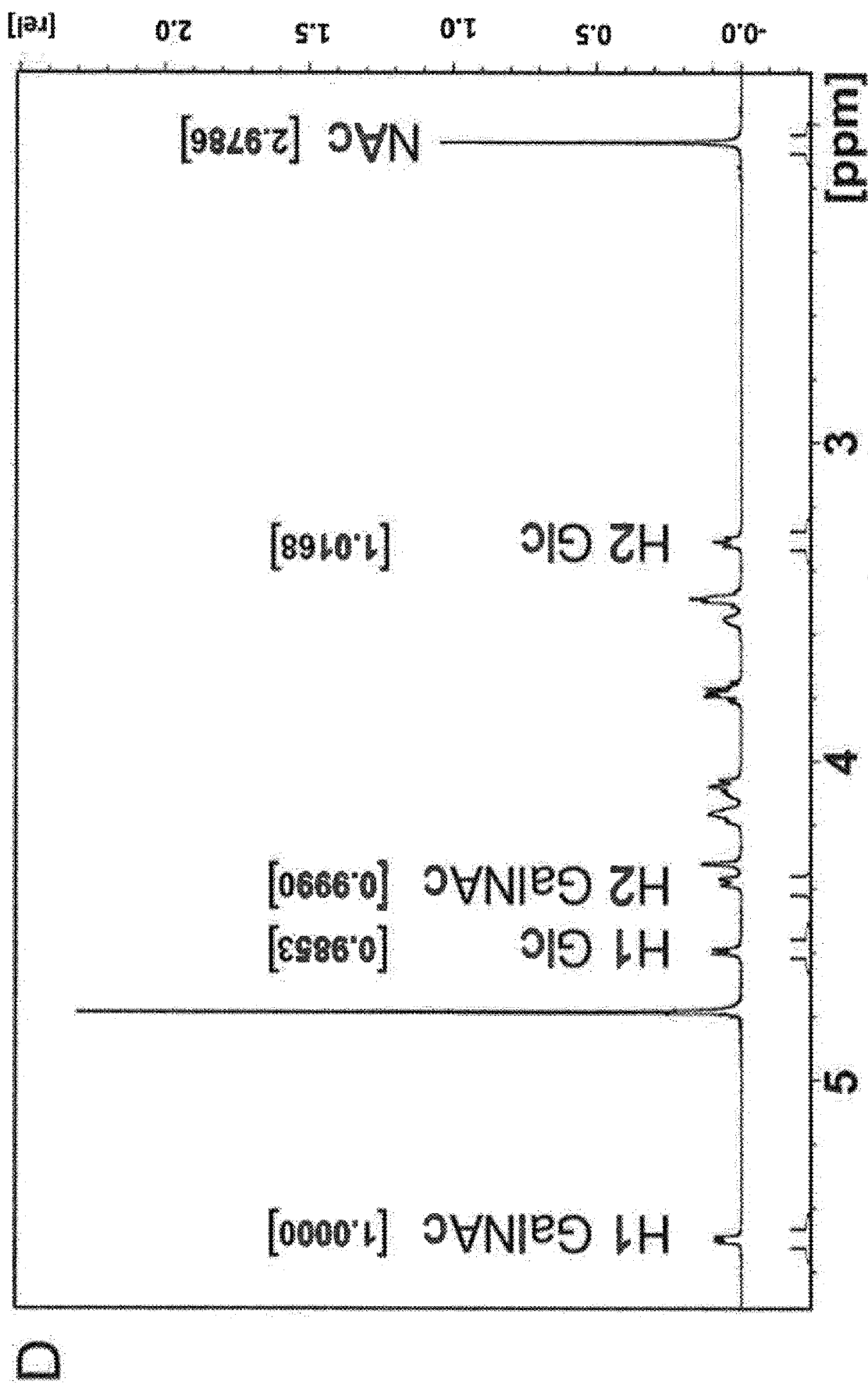
Figure 24:
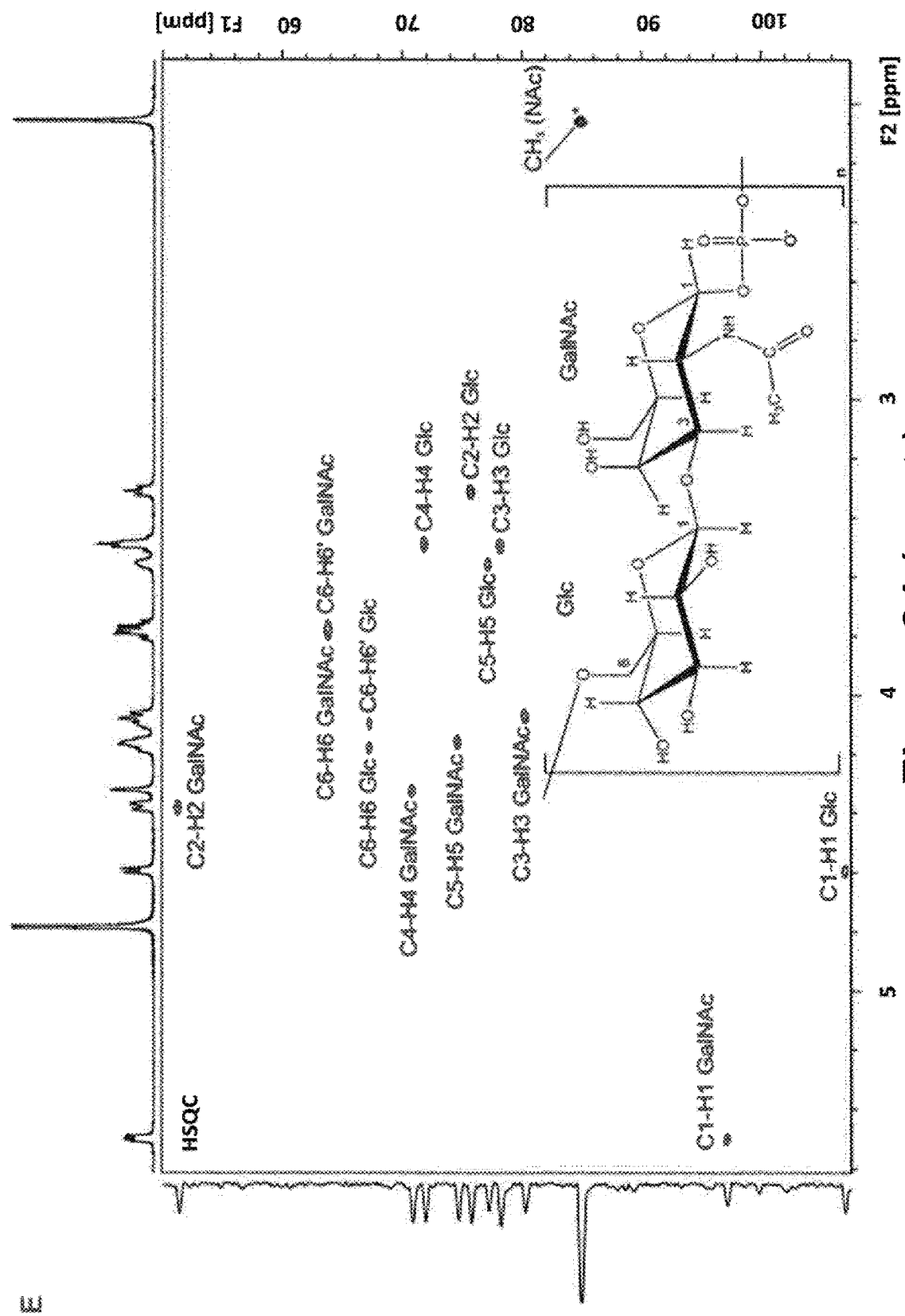

FIG. 24: Purification and characterization of Cps4B.

A) Coomassie-stained SDS-polyacrylamide gel showing the fractions collected during the purification of MBP-Cps4B-His6 by affinity chromatography (via its C-terminal His$_6$-tag) and size exclusion chromatography (SEC). The pooled fractions (pool) contain the full-length construct (145.7 kDa) and one additional prominent band most likely resulting from N-terminal degradation. B) HPLC-AEC analysis of the Cps4B reaction. C) The polymer produced in the upscaled synthesis (see also B) was purified by AEC using a MonoQ column and a combination of linear NaCl gradients (dotted line). The material eluting from the column is consisted with long, negatively charged polymer. D) $^1$H NMR analysis of the polymer produced by Cps4B after purification. The integrals (enclosed in square brackets) of isolated proton signals inform the GalNAc and Glc moieties are consistent with a dimeric repeating unit. E) Corresponding $^1$H, $^{13}$C HSQC NMR analysis demonstrating a dimeric repeating unit.

Figure 25:
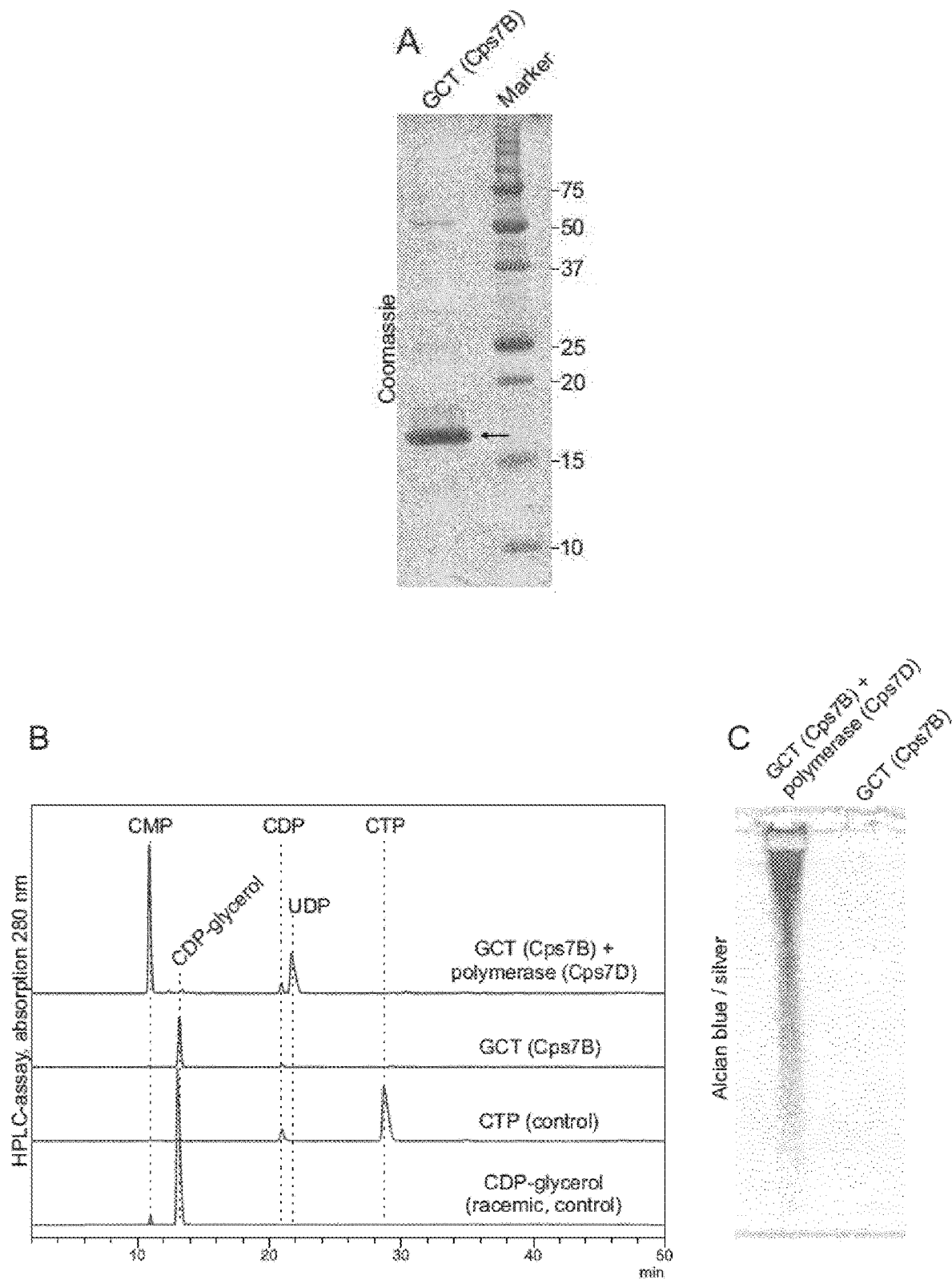

FIG. 25: Purification and characterization of Cps7B (GCT)

To allow the synthesis of enantiopure polymer, we used the CTP:glycerol-3-phosphate cytidylyltransferase (GCT) from *Actinobacillus pleuropneumoniae* serotype 7 strain AP76 (encoded in gene cps7B) for the production of enantiopure CDP-glycerol from CTP and commercially available enantiopure sn-glycerol-3-phosphate.

A) Cps7B-His6 (subsequently referred to as Cps7B or GCT) was cloned, expressed in *E. coli* and purified using affinity and size exclusion chromatography. B) An HPLC-AEC assay was developed to confirm the CTP:glycerol-3-phosphate cytidylyltransferase activity of Cps7B. As expected, Cps7B converts its substrates CTP and sn-glycerol-3-phosphate (not UV-active at 280 nm) into enantiopure CDP-glycerol (brown chromatogram labeled 'GOT (Cps7B)'). Small amounts of CDP in the reaction mixture can also be detected in the CTP control and are consequently not a side product of the GCT reaction. In the combined one-pot synthesis (green chromatogram labeled 'GCT (Cps7B)+polymerase (Cps7D)'), Cps7B consumes CTP to generate CDP-glycerol, which, together with UDP-Gal, is in turn used up by the polymerase Cps7D to synthesize polymer. The nucleotide products of this reaction are UDP (resulting from the galactose transfer) and CMP (resulting from the sn-glycerol-3-phosphate transfer). C) Corresponding Alcian blue/silver stained PAGE used to visualize the polymer generated in the one-pot reaction.

DETAILED DESCRIPTION OF THE INVENTION

The solution of the present invention is described in the following, exemplified in the appended examples, illustrated in the figures and reflected in the claims.

The present invention provides a host cell, which comprises under the control of a heterologous promoter a polynucleotide comprising a nucleotide sequence encoding a polypeptide, wherein the nucleotide sequence is selected from the group consisting of:
  a) a nucleotide sequence encoding a polypeptide comprising a TagF-like domain and a GT-B domain having the amino acid sequences shown in SEQ ID NO. 1 and 17, SEQ ID NO. 2 and 18, SEQ ID NO. 3 and 19, SEQ ID NO. 4 and 20, SEQ ID NO. 5 and 21, SEQ ID NO. 6 and 22, SEQ ID NO. 7 and 23, SEQ ID NO. 8 and 24, SEQ ID NO. 9 and 25, SEQ ID NO. 10 and 26, SEQ ID NO. 11 and 27, wherein the polypeptide synthesizes a polysaccharide consisting of a dimeric repeating unit;
  b) a nucleotide sequence encoding a polypeptide comprising a TagF-like domain and a GT-A domain having the amino acid sequences shown in SEQ ID NO. 12 and 28, SEQ ID NO. 13 and 29, SEQ ID NO. 14 and 30, SEQ ID NO. 15 and 31, SEQ ID NO. 16 and 32, wherein the polypeptide synthesizes a polysaccharide consisting of a dimeric repeating unit;
  c) a nucleotide sequence encoding a pair of fragments of the polypeptide as defined in (a) and in (b), wherein each fragment is at least 15 amino acid residues in length and wherein the pair of fragments synthesizes a polysaccharide consisting of a dimeric repeating unit;
  d) a nucleotide sequence encoding a polypeptide having an amino acid sequence that is at least 18% identical to the amino acid sequence of residues 1 to 378 of SEQ ID NO. 3 and that is at least 40% identical to the amino acid sequence of residues 1 to 389 of SEQ ID NO. 23, wherein the polypeptide synthesizes a polysaccharide consisting of a dimeric repeating unit;
  e) a nucleotide sequence encoding a polypeptide having an amino acid sequence that is at least 18% identical to the amino acid sequence of residues 1 to 378 of SEQ ID NO. 3 and that is at least 30% identical to the amino acid sequence of residues 1 to 256 of SEQ ID NO. 32, wherein the polypeptide synthesizes a polysaccharide consisting of a dimeric repeating unit, and wherein the nucleotide sequence of (a) to (e) encodes a polypeptide having a conserved tyrosine at a position corresponding to position 49 of SEQ ID NO. 3 or having a conserved aspartic acid at a position corresponding to position 49 of SEQ ID NO. 3.

The term "host cell" refers to a cell in which DNA (or RNA) e.g. a polynucleotide is introduced, which is not per se DNA (or RNA) from the host cell itself. Further, the host cell may also refer to a cell in which an expression vector may be propagated and which supports the replication or expression of the expression vector.

The term "heterologous" means derived from a cell or organism with a different genomic background. Thus, a "heterologous" nucleic acid or protein is one that originates from a foreign source (or species) or, if from the same source, is modified from its original form.

The term "promoter" refers to a region of DNA upstream from the translational start codon and which is involved in recognition and binding of RNA polymerase and other proteins to initiate transcription. Promoters contain specific DNA sequences called response elements that make sure a secure initial binding site for RNA polymerase as well as for proteins called transcription factors recruiting RNA polymerase is provided.

A promoter may be located on an expression vector adjacent a restriction site such that a heterologous nucleotide sequence may be located downstream of the promoter and in correct reading frame in relation to a translational start codon. The start codon may be provided on the vector (e.g. immediately 3' to the promoter) or it may be inserted as a 5' end of the heterologous nucleotide sequence. A linker may be provided between the promoter and the start codon, if desired. 3'-Regulatory regions may similarly be provided on the vector or inserted with the heterologous nucleotide sequence.

In this context, a heterologous promoter sequence is from a source different from that the encoding sequence was derived from, or, if from the same source, is modified from its original form. Modification may occur, e.g., by treating the DNA with a restriction enzyme to generate a promoter element that is capable of conferring tissue-specific expression on the expression cassette which includes the promoter.

Thus, the term "under the control of a heterologous promoter" means that the expression of the polynucleotide comprising a nucleotide sequence encoding a polypeptide is monitored/supervised/controlled by a heterologous promoter in a host cell of the present invention.

A polynucleotide refers to nucleotides, either ribonucleotides or deoxyribonucleotides or a combination of both, in a polymeric unbranched form of any length. Preferably, a polynucleotide refers to deoxyribonucleotides in a polymeric unbranched form of any length. Here, nucleotides consist of a pentose sugar (deoxyribose), a nitrogenous base (adenine, guanine, cytosine or thymine) and a phosphate group. The terms "polynucleotide(s)", "nucleic acid sequence(s)" are used interchangeably herein.

By "nucleotide sequence" of a polynucleotide is intended, for a DNA molecule or polynucleotide, a sequence of deoxyribonucleotides (succession of letters that indicate the order of nucleotides within a DNA molecule) and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). By convention, sequences are usually presented from the 5' end to the 3' end. For DNA, the sense strand is used.

The term "polypeptide", when used herein, means a peptide, a protein or a polypeptide, which are used interchangeable and which encompasses amino acid chains of a given length, wherein the amino acid residues are linked by covalent peptide bonds. However, peptidomimetics of such proteins/polypeptides, wherein amino acid(s) and/or peptide bond(s) have been replaced by functional analogs are also encompassed by the invention as well as other than the 20 gene-encoded amino acids, such as selenocysteine. Peptides, oligopeptides and proteins may be termed polypeptides. As mentioned, the terms polypeptide and protein are often used interchangeably herein. The term polypeptide also refers to, and does not exclude, modifications of the polypeptide. Modifications include glycosylation, acetylation, acylation, phosphorylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (54).

The polypeptide of the present invention shares the common feature of being modeled onto the crystal structure of the teichoic acid polymerase TagF. While the TagF-like domain (SEQ ID NOs. 1, 2, 3, 4, 5, 6, 7, 8, 9, 10, 11, 12, 13, 14, 15 and 16) may generate the phosphodiester linkage in the CPS, a GT-A folded domain (SEQ ID NOs. 28, 29, 30, 31 and 32) located N-terminally or a GT-B folded domain (SEQ ID NOs. 17, 18, 19, 20, 21, 22, 23, 24, 25, 26 and 27) located C-terminally of the TagF-like domain may generate the glycosidic linkage. The GT-A folded domain of the polypeptide of the present invention may be located N-terminally or C-terminally of the TagF-like domain, preferably N-terminally of the TagF-like domain. The GT-B folded domain of the polypeptide of the present invention may be located N-terminally or C-terminally of the TagF-like domain, preferably C-terminally of the TagF-like domain.

In the following Table 1 an overview of the polypeptides of the present invention with both of their domains, either a TagF-like domain and a GT-B domain or a TagF-like domain and a GT-A domain is depicted.

TABLE 1

Overview of the polypeptides of the present invention and their corresponding SEQ ID NOs., which encode a TagF-like domain, a GT-B or a GT-A domain.

| SEQ ID NO. | Domain | Polymerase |
|---|---|---|
| 1 | TagF | CshC |
| 2 | TagF | Bt189 |
| 3 | TagF | Bt188 |
| 4 | TagF | Bt192 |
| 5 | TagF | Cps3D |
| 6 | TagF | Cps9D |
| 7 | TagF | Cps11D |
| 8 | TagF | C3694 |
| 9 | TagF | CszC |
| 10 | TagF | Cps7D |
| 11 | TagF | Cps2D |
| 12 | TagF | Fcs2 |
| 13 | TagF | Cps1B |
| 14 | TagF | BtY31 |
| 15 | TagF | Ccs2 |
| 16 | TagF | Cps4B |
| 17 | GT-B | CshC |
| 18 | GT-B | Bt189 |
| 19 | GT-B | Bt188 |
| 20 | GT-B | Bt192 |
| 21 | GT-B | Cps3D |
| 22 | GT-B | Cps9D |
| 23 | GT-B | Cps11D |
| 24 | GT-B | C3694 |
| 25 | GT-B | CszC |
| 26 | GT-B | Cps7D |
| 27 | GT-B | Cps2D |
| 28 | GT-A | Fcs2 |
| 29 | GT-A | Cps1B |
| 30 | GT-A | BtY31 |
| 31 | GT-A | Ccs2 |
| 32 | GT-A | Cps4B |

The polynucleotide comprising a nucleotide sequence encoding the polypeptide of the present invention further comprises a nucleotide sequence encoding a linker polypeptide. Preferably, the nucleotide sequence encoding said linker polypeptide is disposed in the polynucleotide of the present invention between the nucleotide sequence encoding the TagF-like domain (e.g. SEQ ID NO. 1) and the GT-B domain (e.g. SEQ ID NO. 17) or between the nucleotide sequence encoding the TagF-like domain (e.g. SEQ ID NO. 12) and the GT-A domain (e.g. SEQ ID NO. 28) such that it results in a fusion between said TagF-like domain, linker polypeptide and GT-B or GT-A domain. Thus, the polypeptide comprising a TagF-like domain and a GT-B domain or a TagF-like domain and a GT-A domain having the amino acid sequences shown in (a) or (b) (e.g. SEQ ID NO. 1 and 17 or SEQ ID NO. 12 and 28) is being expressed in frame. In this context, a "fusion" refers to a co-linear linkage of two or more proteins, domains of proteins or fragments (e.g. fragments of domains) thereof via their individual peptide backbones through genetic expression of a nucleotide sequence encoding those proteins or domains. Preferably, it refers to a co-linear linkage of the TagF-like domain and the GT-B domain of a polypeptide of the present invention or the TagF-like domain and the GT-A domain of a polypeptide of the present invention via a polypeptide linker.

Said polypeptide linker is preferably a flexible linker. Preferably, it comprises plural, hydrophilic, peptide-bonded amino acids and connects the C-terminal end of the TagF-like domain and the N-terminal end of the GTB domain or the C-terminal end of the GT-A domain and the N-terminal end of the TagF-like domain. Preferably, said polypeptide linker comprises a plurality of glycine, alanine, aspartate, glutamate, proline, isoleucine and/or arginine residues. It is further preferred that said polypeptide linker comprises a plurality of consecutive copies of an amino acid sequence. Usually, the polypeptide linker comprises 0, 5, 10, 15, 20, 25, 30, 35, 40, 45, 50 amino acids or 1 to 50, preferably 1 to 40, 1 to 30, 1 to 20, 1 to 15 or 1 to 10 amino acids although polypeptide linkers of more than 50 amino acids may work as well.

Additionally, the present invention comprises a nucleotide sequence encoding a polypeptide comprising a TagF-like domain and a nucleotide sequence encoding a polypeptide comprising a GT-B or GT-A domain, wherein the nucleotide sequences are being separated on two different vectors used in the present invention. Preferably, the nucleotide sequence encoding the polypeptide comprising the TagF-like domain (e.g. SEQ ID NO. 1 or 12) may be inserted in one vector, whereas the nucleotide sequence encoding the polypeptide comprising the GT-B domain (e.g. SEQ ID NO. 17) or GT-A domain (e.g. SEQ ID NO. 28) may be inserted in another vector, such that it results not in a fusion between said TagF-like domain and said GT-B or said GT-A domain, instead resulting in a pair of polypeptides (two polypeptides) one comprising the TagF-like domain, the other polypeptide comprising the GT-B or GT-A domain. No matter if the polypeptide is expressed as a fusion protein or if a pair of polypeptides is expressed, the polypeptide(s) may synthesize a polysaccharide consisting of a dimeric repeating unit. Thus, a polypeptide comprising both domains (TagF-like domain and GT-B or TagF-like domain and GT-A) is able to catalyze the reaction of a polysaccharide consisting of a dimeric repeating unit in trans (a pair of polypeptides, one comprising the TagF-like domain, the other comprising the GT-B or GT-A domain) as well. Hence, the term "a nucleotide sequence encoding a polypeptide comprising a TagF-like domain and a GT-B (or GT-A domain)" may also refer to a nucleotide sequence encoding a pair of polypeptides, one polypeptide comprising a TagF-like domain the other polypeptide comprising a GT-B or GT-A domain.

The term "synthesize" may be used interchangeably with the terms "generate" or "produce". In some embodiments, synthesizing as used through the present invention may also refer to produce an enantiomerically pure polysaccharide consisting of a dimeric repeating unit. Commercially available racemic mixture of CDP-glycerol may be used as substrate for the TagF-like/GT-B folded CPs, leading to polymers that were not enantiopure (see e.g. FIG. 5B). Commercially available CDP-glycerol in general is a racemic mixture containing sn-glycerol-1-phosphate (C2' of glycerol has S chirality) and sn-glycerol-3-phosphate (C2' has R chirality). To allow the synthesis of enantiopure polysaccharide, the CTP:glycerol-3-phosphate cytidylyltransferase (GCT) from *Actinobacillus pleuropneumoniae* serotype 7 strain AP76 (encoded in gene cps7B) or a polypeptide or enzyme with a similar function may be used for the production of enantiopure CDP-glycerol from CTP and commercially available enantiopure sn-glycerol-3-phosphate (see Example 11). This means, the production of enantiopure CDP-glycerol is not to be understood to be limited to the use of CTP:glycerol-3-phosphate cytidylyltransferase (GCT) from *Actinobacillus pleuropneumoniae* serotype 7 strain AP76 (encoded in gene cps7B), however, can be achieved by the use of any polypeptide or enzyme having a similar function. Such a polypeptide or enzyme could be any polypeptide or enzyme having nucleotidyltransferase activity, or preferably can be any polypeptide or enzyme having cytidylyltransferase activity, or more preferably can be any polypeptide or enzyme having CTP:glycerol-3-phosphate cytidylyltransferase activity or even more preferably can be the CTP:glycerol-3-phosphate cytidylyltransferases TarD and TagD from *Staphylococcus aureus* and *Bacillus subtilis* or even more preferably can be the homologs of cps7B, encoded in the genome of *Actinobacillus pleuropneumoniae* serotypes 2, 3, 6, 8, 9, 11, 13, 17 (referred to as 'cpsB' in Bossé, J. T. et al., *Vet. Microbiol.* 220, 83-89 (2018)).

When said term "to produce (an) enantiomerically pure polysaccharide(s)" is used in the present invention, the substrate CDP-glycerol is enantiopure being produced from CTP and commercially available enantiopure sn-glycerol-3-phosphate by the CTP:glycerol-3-phosphate cytidylyltransferase (GCT) from *Actinobacillus pleuropneumoniae* serotype 7 strain AP76 (encoded in gene cps7B) or a polypeptide or enzyme with a similar function, thus consisting exclusively of sn-glycerol-3-phosphate. Non-limiting examples of entiomerically pure synthesized polysaccharide consisting of a dimeric repeating unit and being produced with the substrate CDP-glycerol may refer to the polysaccharide of said polypeptides Bt188, Cps11D and Cps7D (FIG. 22, 23, 25).

The term "polysaccharide" refers to a polymeric carbohydrate molecule, which is composed of long chains of monosaccharides being bound together by glycosidic linkages. ≥3 monosaccharides built up a polysaccharide of the present invention. Preferably, ≥5 monosaccharides built up a polysaccharide of the present invention. More preferably, ≥10 monosaccharides built up a polysaccharide of the present invention.

Preferably, the polysaccharide of the present invention may be a capsule polysaccharide (CPS). Many pathogenic bacteria are surrounded by a thick layer of high-molecular weight polysaccharides referred to as capsule (4). The capsule can be up to 400 nm (1.50) thick and forms the outermost barrier of the bacterial cell. Due to the nature of the molecular building blocks (monosaccharides) capsules possess a high water binding capability and support bacterial survival by physical means (51). Moreover and of particular importance in the case of bacterial pathogenesis, capsules impair the efficiency of the hosts first line immune defense mechanisms (52). The grouping of capsular polysaccharides (CPSs) bases on molecular insight obtained by studying CPS biosynthesis in *E. coli*. 84 chemically distinct CPSs that have been identified in *E. coli*, which, based on chemical characteristics of the CPSs and based on genetic information, have been subdivided into four capsule groups (I-IV) (4).

The term "a dimeric repeating unit" refers to an assembly of two different building blocks, wherein building block 1 is a monosaccharide and building block 2 is a monosaccharide different from building block 1 or an alditol, whereas the monosaccharide or the alditol of building block 2 is connected to a phosphate.

In detail, Fcs2, Cps1B, BtY31, Ccs2 and Cps4B of the GT-A/TagF-like family as well as CshC, Bt189, Bt188, Bt192, Cps3D, Cps9D, Cps11D, c3694, CszC, Cps7D, Cps2D of the TagF-like/GT-B family (Tab. 1) synthesize a polysaccharide consisting of a dimeric repeating unit, whereas Cps12B and CslB as a member of the GT-A/TagF-like family synthesize a polysaccharide consisting of a trimeric repeating unit. In this context, a "trimeric repeating unit" refers to 3 building blocks, wherein either each building block comprises a monosaccharide, whereas building block 3 comprises a monosaccharide connected to a phosphate or wherein building block 1 and 2 comprise two monosaccharides and building block 3 comprises an alditol connected to a phosphate.

Further, a nucleotide sequence may encode a pair of fragments of a polypeptide being expressed by the host cell of the present invention, meaning that a nucleotide sequence encodes either one fragment of the TagF-like domain (e.g. SEQ ID NO. 1) of the polypeptide and another fragment of the GT-B domain (e.g. SEQ ID NO. 17) or one fragment of the TagF-like domain (e.g. SEQ ID NO. 12) of the polypeptide and another fragment of the GT-A domain (SEQ ID NO. 28), wherein the pair of fragments synthesizes a polysaccharide consisting of a dimeric repeating unit. Further, each fragment may be at least 15 amino acid residues in length. Preferably, each fragment may be at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 300, 400, or 500 amino acid residues in length or may have a length from 15-500, 30-500, 50-500, 100-500 or 200-500, or from 15-200, 30-200, 50-200, 100-200 amino acid residues, or may have a length from 15-100, 20-100, 25-100, 30-100, 35-100, 40-100, 45-100, 50-100 amino acid residues.

The present invention may also relate to a nucleotide sequence encoding a pair of fragments of a polypeptide being expressed by the host cell of the present invention, wherein the fragment of the TagF-like domain may be at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 300, 400, or 500 amino acid residues in length or may have a length from 15-500, 30-500, 50-500, 100-500 or 200-500, or a length from 15-200, 30-200, 50-200 or 100-200 amino acid residues, or a length from 15-100, 20-100, 25-100, 30-100, 35-100, 40-100, 45-100 or 50-100 amino acid residues, and may further comprise a conserved histidine at a position corresponding to the position 122 of SEQ ID NO. 3 (FIG. 11A) and a conserved histidine at a position corresponding to the position 251 of SEQ ID NO. 3 (FIG. 11B) and wherein the fragment of the GT-B domain may be at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 300, 400, or 500 amino acid residues in length or may have a length from 15-500, 30-500, 50-500, 100-500 or 200-500, or a length from 15-200, 30-200, 50-200 or 100-200 amino acid residues, or a length from 15-100, 20-100, 25-100, 30-100, 35-100, 40-100, 45-100 or 50-100 amino acid residues, and may further comprise a conserved arginine at a position corresponding to position 234 of SEQ ID NO. 23 and a conserved lysine at a position corresponding to position 239 of SEQ ID NO. 23 (FIG. 12). Additionally, the present invention may also relate to a nucleotide sequence encoding a pair of fragments of a polypeptide being expressed by the host cell of the present invention, wherein the fragment of the TagF-like domain may be at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 300, 400, or 500 amino acid residues in length or may have a length from 15-500, 30-500, 50-500, 100-500 or 200-500 amino acid residues, or a length from 15-200, 30-200, 50-200 or 100-200 amino acid residues, or a length from 15-100, 20-100, 25-100, 30-100, 35-100, 40-100, 45-100 or 50-100 amino acid residues, and may further comprise a conserved histidine at a position corresponding to the position 122 of SEQ ID NO. 3 (FIG. 11A) and a conserved histidine at a position corresponding to the position 251 of SEQ ID NO. 3 (FIG. 11A) and wherein the fragment of the GT-A domain may be at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 300, 400, or 500 amino acid residues in length or may have a length from 15-500, 30-500, 50-500, 100-500 or 200-500 amino acid residues, or a length from 15-200, 30-200, 50-200 or 100-200 amino acid residues, or a length from 15-100, 20-100, 25-100, 30-100, 35-100, 40-100, 45-100 or 50-100 amino acid residues, and may further comprise the conserved aspartate residues of the D×D motif at positions corresponding to positions 107-109 of SEQ ID NO. 32 (FIG. 10).

Preferably, the fragment of the TagF-like domain may be at least 130 amino acids in length and the fragment of the GT-B domain may be at least 100 amino acids in length. Preferably, the fragment of the TagF-like domain may be at least 130 amino acids in length and the fragment of the GT-A domain may be at least 100 amino acids in length.

Again, the nucleotide sequence encoding a linker polypeptide as mentioned above is disposed in the polynucleotide of the present invention between the nucleotide sequence encoding the fragment of the TagF-like domain (e.g. SEQ ID NO. 1) and the fragment of the GT-B domain (e.g. SEQ ID NO. 17) or between the nucleotide sequence encoding the fragment of the TagF-like domain (e.g. SEQ ID NO. 12) and the fragment of the GT-A domain (e.g. SEQ ID NO. 28) such that it results in a fusion between said fragment of the TagF-like domain, the linker polypeptide and the fragment of the GT-B or GT-A domain, which may synthesize a polysaccharide consisting of a dimeric repeating unit.

Additionally, the present invention comprises a nucleotide sequence encoding a fragment of a polypeptide comprising a TagF-like domain and a nucleotide sequence encoding a fragment of a polypeptide comprising a GT-B or GT-A domain, wherein the nucleotide sequences are being separated on two different vectors used in the present invention.

Preferably, the nucleotide sequence encoding a fragment of the TagF-like domain (e.g. SEQ ID NO. 1 or 12) may be inserted in one vector, whereas the nucleotide sequence encoding a fragment of the GT-B domain (e.g. SEQ ID NO. 17) or a fragment of the GT-A domain (e.g. SEQ ID NO. 28) may be inserted in another vector, such that it results not in a fusion between the fragment of the TagF-like domain and the fragment of the GT-B or GT-A domain, instead resulting in a pair of polypeptides (two polypeptides) one comprising the fragment of the TagF-like domain, the other polypeptide comprising the fragment of the GT-B or GT-A domain, wherein the pair of polypeptides each having only a fragment may synthesize a polysaccharide consisting of a dimeric repeating unit.

A nucleotide sequence encoding a polypeptide may have an amino acid sequence that is at least 15%, 16%, 16.5%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% identical to the amino acid sequence of residues 1 to 378 of SEQ ID NO. 3 and that is at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% identical to the amino acid sequence of residues 1 to 389 of SEQ ID NO. 23. Amino acid sequence of residues 1 to 378 of SEQ ID NO. 3 refers to the TagF-like domain of Bt188 and amino acid sequence of residues 1 to 389 of SEQ ID NO. 23 refers to the GT-B domain of Cps11D. Additionally, a nucleotide sequence encoding a polypeptide having an amino acid sequence that is from 30% to 99.5%, 35% to 99.5%, 40% to 99.5%, or 44% to 99.5% identical to the amino acid sequence of residues 1 to 378 of SEQ ID NO. 3 and that is from 25% to 100%, 30% to 100%, 35% to 100%, 40% to 100% identical to the amino acid sequence of residues 1 to 389 of SEQ ID NO. 23 may also be preferred by the present invention.

A nucleotide sequence encoding a polypeptide may have an amino acid sequence that is at least 15%, 16%, 16.5%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% identical to the amino acid sequence of residues 1 to 378 of SEQ ID NO. 3 and that is at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to the amino acid sequence of residues 1 to 256 of SEQ ID NO. 32. Again, amino acid sequence of residues 1 to 378 of SEQ ID NO. 3 refers to the TagF-like domain of Bt188 and amino acid sequence of residues 1 to 256 of SEQ ID NO. 32 refers to the GT-A domain of Cps4B. Additionally, a nucleotide sequence encoding a polypeptide having an amino acid sequence that is from 30% to 99.5%, 35% to 99.5%, 40% to 99.5%, or 44% to 99.5% identical to the amino acid sequence of residues 1 to 378 of SEQ ID NO. 3 and that is from 30% to 99%, 35% to 99%, 42% to 99%, 46.5% to 99%, 47% to 99% identical to the amino acid sequence of residues 1 to 256 of SEQ ID NO. 32 may also be preferred by the present invention.

"Percent (%) sequence identity" with respect to amino acid sequences disclosed herein is defined as the percentage of amino acid residues in a candidate sequence that are pair-wise identical with the amino acid residues in a reference sequence after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared. The overall sequence identity of the present invention is determined using the Clustal Omega program (20) (ebi.ac.uk/Tools/msa/clustalo/) and annotated with the Jalview software (13).

By a polynucleotide comprising a nucleotide sequence encoding a polypeptide expressed by the host cell of the present invention having an amino acid sequence at least, for example, 95% "identical" to a reference amino acid sequence is intended that the amino acid sequence of the polypeptide is identical to the reference sequence except that the amino acid sequence of the polypeptide may include up to five point mutations per each 100 nucleotides of the reference amino acid sequence. In other words, to obtain a polynucleotide comprising a nucleotide sequence encoding a polypeptide expressed by the host cell of the present invention having an amino acid sequence at least 95% identical to a reference amino acid sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference amino acid sequence or anywhere between those terminal positions, interspersed either individually among nucleotides in the reference sequence or in one or more contiguous groups within the reference sequence.

The nucleotide sequence further encodes a polypeptide having a conserved tyrosine at residue 52 of SEQ ID NO.1 (CshC) which corresponds to residue 49 of SEQ ID NO. 3, or at residue 48 of SEQ ID NO. 2 (Bt189) which corresponds to residue 49 of SEQ ID NO. 3, or at residue 49 of SEQ ID NO. 3 (Bt188) which corresponds to residue 49 of SEQ ID NO. 3, or at residue 49 of SEQ ID NO. 4 (Bt192) which corresponds to residue 49 of SEQ ID NO. 3, or at residue 48 of SEQ ID NO. 5 (Cps3D) which corresponds to residue 49 of SEQ ID NO. 3, or at residue 46 of SEQ ID NO. 6 (Cps9D) which corresponds to residue 49 of SEQ ID NO. 3, or at residue 49 of SEQ ID NO. 7 (Cps11D) which corresponds to residue 49 of SEQ ID NO. 3, or at residue 37 of SEQ ID NO. 9 (CszC) which corresponds to residue 49 of SEQ ID NO. 3, or at residue 49 of SEQ ID NO. 10 (Cps7D) which corresponds to residue 49 of SEQ ID NO. 3, or at residue 43 of SEQ ID NO. 11 (Cps2D) which corresponds to residue 49 of SEQ ID NO. 3, or at residue 57 of SEQ ID NO. 12 (Fcs2) which corresponds to residue 49 of SEQ ID NO. 3, or at residue 52 of SEQ ID NO. 13 (Cps1B) which corresponds to residue 49 of SEQ ID NO. 3, or at residue 55 of SEQ ID NO. 14 (BtY31) which corresponds to residue 49 of SEQ ID NO. 3, or at residue 38 of SEQ ID NO. 15 (Ccs2) which corresponds to residue 49 of SEQ ID NO. 3, or at residue 61 of SEQ ID NO. 16 (Cps4B) which corresponds to residue 49 of SEQ ID NO. 3, or having a conserved aspartic acid at residue 47 of SEQ ID NO. 8 (c3694) which corresponds to residue 49 of SEQ ID NO. 3 (FIG. 14).

As used herein, the term "conserved amino acid" refers to an amino acid (e.g. tyrosine, aspartic acid, histidine etc.) that is similar or identical at a specific position along an alignment of sequences (amino acid sequences) of evolutionarily related polypeptides. If a certain number of aligned amino acid sequences of evolutionarily related polypeptides may have an identical amino acid at a specific position, which corresponds to a certain position of the reference sequence, the sequences (amino acid sequences) have a higher sequence identity.

The present invention may further envisage a vector comprising under the control of a heterologous promoter a nucleotide sequence encoding a polypeptide of the present invention. Such a vector may be, e.g., a plasmid, cosmid, virus, bacteriophage or another vector used e.g. conventionally in genetic engineering, and may comprise further genes such as marker genes which allow for the selection and/or replication of said vector in a suitable host cell and under suitable conditions. In a preferred embodiment, said vector is an expression vector, in which the nucleotide sequence of the present invention is operatively linked to expression control sequence(s) allowing expression in prokaryotic or eukaryotic host cells as described herein. The term "operatively linked", as used in this context, refers to a linkage between one or more expression control sequences and the coding region in the polynucleotide to be expressed in such a way that expression is achieved under conditions compatible with the expression control sequence.

Suitable expression vectors for use in practicing the present invention include, for example, vectors such as pET, pMal-c, pGEX, pBAD, pQE, pACYC, pSC101, pASK-IBA, pLAFR1, pBBR1MCS-3. Preferably, by using pMal-c-based vectors, the encoded polypeptides are expressed under a tac promoter control as fusion proteins with an N-terminal maltose-binding protein (MBP) fused by a protease-resistant S3N10 linker. In addition, prokaryotic vectors such as pcDNA2; and yeast vectors such as pYes2, and mammalian vectors such as pcDNA3; and insect cell vectors such as pFastBac and pMT; and protozoan vector (e.g. for *Leishmania tarentolae*) such as pLEXSY-2, pLEXSY_I-3 and pLEXSY_IE-blecherry4 are non-limiting examples of other vectors suitable for use with the present invention.

The coding sequences inserted in the vector can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

Furthermore, the vectors may, in addition to the nucleotide sequence(s) of the invention, comprise expression control elements, allowing proper expression of the coding regions in suitable hosts. Such control elements are known to the artisan and may include a promoter, translation initiation codon, translation and insertion site or internal ribosomal entry sites (IRES) (55) for introducing an insert into the vector.

Thus, the present invention may also encompass a method of producing a recombinant vector comprising inserting the nucleotide sequence encoding a polypeptide of the present invention into a vector and further inserting a heterologous promoter being able to control the expression of the polypeptide of the present invention.

Additionally, the host cell of the present invention may be isolated. In this context, the terms "isolated" or "purified" as used herein refer to the state of being free of other, dissimilar compounds with which the host cell of the invention is normally associated in its natural state. In the present invention the host cell is harvested by centrifugation, before the cell pellet is resuspended in lysis buffer.

The present invention may also relate to a host cell, which comprises under the control of a heterologous promoter a polynucleotide comprising a nucleotide sequence encoding a polypeptide, wherein the nucleotide sequence is selected from the group consisting of:
  a) a nucleotide sequence encoding a polypeptide comprising a TagF-like domain and a GT-B domain having the amino acid sequences shown in SEQ ID NO. 1 and 17, SEQ ID NO. 2 and 18, SEQ ID NO. 3 and 19, SEQ ID NO. 4 and 20, SEQ ID NO. 5 and 21, SEQ ID NO. 6 and 22, SEQ ID NO. 7 and 23, SEQ ID NO. 8 and 24, SEQ ID NO. 9 and 25, SEQ ID NO. 10 and 26, SEQ ID NO. 11 and 27, wherein the polypeptide synthesizes a polysaccharide consisting of a dimeric repeating unit;
  b) a nucleotide sequence encoding a polypeptide comprising a TagF-like domain and a GT-A domain having the amino acid sequences shown in SEQ ID NO. 12 and 28, SEQ ID NO. 13 and 29, SEQ ID NO. 15 and 31, SEQ ID NO. 16 and 32, wherein the polypeptide synthesizes a polysaccharide consisting of a dimeric repeating unit;
  c) a nucleotide sequence encoding a pair of fragments of the polypeptide as defined in (a) and in (b), wherein each fragment is at least 15 amino acid residues in length and wherein the pair of fragments synthesizes a polysaccharide consisting of a dimeric repeating unit;
  d) a nucleotide sequence encoding a polypeptide having an amino acid sequence that is at least 18% identical to the amino acid sequence of residues 1 to 378 of SEQ ID NO. 3 and that is at least 40% identical to the amino acid sequence of residues 1 to 389 of SEQ ID NO. 23, wherein the polypeptide synthesizes a polysaccharide consisting of a dimeric repeating unit;
  e) a nucleotide sequence encoding a polypeptide having an amino acid sequence that is at least 18% identical to the amino acid sequence of residues 1 to 378 of SEQ ID NO. 3 and that is at least 30% identical to the amino acid sequence of residues 1 to 256 of SEQ ID NO. 32, wherein the polypeptide synthesizes a polysaccharide consisting of a dimeric repeating unit,
and wherein the nucleotide sequence of (a) to (e) encodes a polypeptide having a conserved tyrosine at a position corresponding to position 49 of SEQ ID NO. 3 or having a conserved aspartic acid at a position corresponding to position 49 of SEQ ID NO. 3.

Additionally, the present invention may relate to a host cell, which comprises under the control of a heterologous promoter a polynucleotide comprising a nucleotide sequence encoding a polypeptide, wherein the nucleotide sequence is selected from the group consisting of:
  a) a nucleotide sequence encoding a polypeptide comprising a TagF-like domain and a GT-B domain having the amino acid sequences shown in SEQ ID NO. 1 and 17, SEQ ID NO. 2 and 18, SEQ ID NO. 3 and 19, SEQ ID NO. 4 and 20, SEQ ID NO. 5 and 21, SEQ ID NO. 6 and 22, SEQ ID NO. 7 and 23, SEQ ID NO. 8 and 24, SEQ ID NO. 9 and 25, SEQ ID NO. 10 and 26, SEQ ID NO. 11 and 27, wherein the polypeptide synthesizes a polysaccharide consisting of a dimeric repeating unit;
  b) a nucleotide sequence encoding a polypeptide comprising a TagF-like domain and a GT-A domain having the amino acid sequences shown in SEQ ID NO. 12 and 28, SEQ ID NO. 13 and 29, SEQ ID NO. 14 and 30, SEQ ID NO. 15 and 31, SEQ ID NO. 16 and 32, wherein the polypeptide synthesizes a polysaccharide consisting of a dimeric repeating unit;
  c) a nucleotide sequence encoding a polypeptide having an amino acid sequence that is at least 18% identical to the amino acid sequence of residues 1 to 378 of SEQ ID NO. 3 and that is at least 40% identical to the amino acid sequence of residues 1 to 389 of SEQ ID NO. 23, wherein the polypeptide synthesizes a polysaccharide consisting of a dimeric repeating unit;
  d) a nucleotide sequence encoding a polypeptide having an amino acid sequence that is at least 18% identical to the amino acid sequence of residues 1 to 378 of SEQ ID NO. 3 and that is at least 30% identical to the amino acid sequence of residues 1 to 256 of SEQ ID NO. 32, wherein the polypeptide synthesizes a polysaccharide consisting of a dimeric repeating unit,
and wherein the nucleotide sequence of (a) to (e) encodes a polypeptide having a conserved tyrosine at a position corresponding to position 49 of SEQ ID NO. 3 or having a conserved aspartic acid at a position corresponding to position 49 of SEQ ID NO. 3.

The present invention may also comprise a host cell, which comprises under the control of a heterologous promoter a polynucleotide comprising a nucleotide sequence encoding a polypeptide, wherein the nucleotide sequence is selected from the group consisting of:
  a) a nucleotide sequence encoding a polypeptide comprising a TagF-like domain and a GT-B domain having the amino acid sequences shown in SEQ ID NO. 1 and 17, SEQ ID NO. 2 and 18, SEQ ID NO. 3 and 19, SEQ ID NO. 4 and 20, SEQ ID NO. 5 and 21, SEQ ID NO. 6 and 22, SEQ ID NO. 7 and 23, SEQ ID NO. 8 and 24, SEQ ID NO. 9 and 25, SEQ ID NO. 10 and 26, SEQ ID NO. 11 and 27, wherein the polypeptide synthesizes a polysaccharide consisting of a dimeric repeating unit;
  b) a nucleotide sequence encoding a polypeptide comprising a TagF-like domain and a GT-A domain having the amino acid sequences shown in SEQ ID NO. 12 and 28, SEQ ID NO. 13 and 29, SEQ ID NO. 15 and 31, SEQ ID NO. 16 and 32, wherein the polypeptide synthesizes a polysaccharide consisting of a dimeric repeating unit;
  c) a nucleotide sequence encoding a polypeptide having an amino acid sequence that is at least 18% identical to the amino acid sequence of residues 1 to 378 of SEQ ID NO. 3 and that is at least 40% identical to the amino acid sequence of residues 1 to 389 of SEQ ID NO. 23, wherein the polypeptide synthesizes a polysaccharide consisting of a dimeric repeating unit;
  d) a nucleotide sequence encoding a polypeptide having an amino acid sequence that is at least 18% identical to the amino acid sequence of residues 1 to 378 of SEQ ID NO. 3 and that is at least 30% identical to the amino acid sequence of residues 1 to 256 of SEQ ID NO. 32, wherein the polypeptide synthesizes a polysaccharide consisting of a dimeric repeating unit, and wherein the nucleotide sequence of (a) to (e) encodes a polypeptide having a conserved tyrosine at a position corresponding to position 49 of SEQ ID NO. 3 or having a conserved aspartic acid at a position corresponding to position 49 of SEQ ID NO. 3.

The host cell of the present invention may be a prokaryotic host cell or a eukaryotic host cell. Preferably, the host cell is a prokaryotic host cell, more preferably the prokaryotic host cell is a bacterium. The eukaryotic host cell may be a mammalian cell line such as HEK or CHO, and insect cell line such as Sf9 or S2 or a protozoan host cell such as *Leishmania tarentolae*. The prokaryotic host cell of the present invention may be selected from the group consisting of *Escherichia coli, Actinobacillus pleuropneumoniae, Bibersteinia trehalosi, Actinobacillus suis, Haemophilus influenzae, Campylobacter jejuni, Campylobacter coli, Neisseria meningitidis, Mannheimia varigena, Neisseria mucosa, Moraxella lacunata, Neisseria elongate, Klebsiella* sp G5, *Cronobacter universalis, Cronobacter turicensis, Aeromonas veronii, Cronobacter sakazakii, Yersinia enterocolitica, Helicobacter pullorum, Bacillus subtilis* and *Bacillus cereus*. Preferably, the prokaryotic host cell of the present invention may be selected from the group consisting of *Escherichia coli, Actinobacillus pleuropneumoniae, Bibersteinia trehalosi, Actinobacillus suis, Haemophilus influenzae, Campylobacter jejuni, Campylobacter coli, Neisseria meningitidis, Mannheimia varigena, Neisseria mucosa, Moraxella lacunata, Neisseria elongate, Klebsiella* sp G5, *Cronobacter universalis, Cronobacter turicensis, Aeromonas veronii, Cronobacter sakazakii, Yersinia enterocolitica, Helicobacter pullorum* and *Bacillus cereus*. More preferably, the prokaryotic host cell of the present invention may be selected from the group consisting of *Escherichia coli, Actinobacillus pleuropneumoniae, Bibersteinia trehalosi, Actinobacillus suis, Haemophilus influenzae, Campylobacter jejuni, Campylobacter coli* and *Neisseria meningitidis*. Even more preferably, the prokaryotic host cell is *Escherichia coli, Actinobacillus pleuropneumoniae* or *Bibersteinia trehalosi*.

Further, the host cell may be cultured and the polynucleotide comprising the nucleotide sequence encoding a polypeptide may be expressed. The host cell of the present invention is cultured under conditions that permit the expression of the polynucleotide comprising the nucleotide sequence to produce the encoded polypeptide. Preferably, the conditions refer to the use of colonies of transformed *E. coli* expression strains to inoculate an appropriate culture medium (e. g. LB or PowerBroth) while growing at 15-37° C., preferably at 37° C. At an $OD_{600}$ of 0.5-3.0 (preferably 1.0), the incubation temperature is changed to 4° C.-37° C. (preferably 15° C.) and protein expression is induced by addition of 0.1-1.0 mM (preferably 0.5) isopropyl-β-D-1-thiogalactopyranoside (IPTG). The cells are cultures for 3-48 h, preferably 20 h.

The present invention mal also comprise the host cell of the present invention, wherein the heterologous promoter is a prokaryotic promoter. The prokaryotic promoter used in the present invention may be recognized by RNA polymerase and an associated sigma factor, which in turn may be brought to the promoter DNA by an activator protein's binding to its own DNA binding site nearby. Further, the present invention may also envisage a eukaryotic promoter such as a CMV promoter for mammalian cells; metallothionein (MT), polyhedrin and p10 promoter for insect cells; or T7 Promoter for protozoan cells.

The prokaryotic promoter of the present invention may be a tac promoter, lacUV5 promoter, T4 promoter, T7 promoter, araBAD ($P_{BAD}$) promoter, tet promoter or a T5 promoter. Preferably, the prokaryotic promoter is a tac promoter. The term "tac promoter" refers to a synthetically produced DNA promoter, preferably used for protein production in *Escherichia coli*. The tac promoter is produced from the combination of promoters from the trp and lac operons.

Also encompassed by the present invention may be the host cell of the present invention, wherein the nucleotide sequence may encode a polypeptide having a conserved aspartic acid at a position corresponding to position 364 of SEQ ID NO. 3. The present invention may envisage the nucleotide sequence encoding a polypeptide of the present invention having a conserved tyrosine at a position corresponding to position 49 of SEQ ID NO. 3 or having a conserved aspartic acid at a position corresponding to position 49 of SEQ ID NO. 3 as previously described and further having a conserved aspartic acid at position 369 of SEQ ID NO.1 (CshC) which corresponds to position 364 of SEQ ID NO. 3, or at position 363 of SEQ ID NO. 2 (Bt189) which corresponds to position 364 of SEQ ID NO. 3, or at position 364 of SEQ ID NO. 3 (Bt188), or at position 364 of SEQ ID NO. 4 (Bt192) which corresponds to position 364 of SEQ ID NO. 3, or at position 364 of SEQ ID NO. 5 (Cps3D) which corresponds to position 364 of SEQ ID NO. 3, or at position 362 of SEQ ID NO. 6 (Cps9D) which corresponds to position 364 of SEQ ID NO. 3, or at position 365 of SEQ ID NO. 7 (Cps11D) which corresponds to position 364 of SEQ ID NO. 3, or at position 366 of SEQ ID NO. 8 (c3694) which corresponds to position 364 of SEQ ID NO. 3, or at position 358 of SEQ ID NO. 9 (CszC) which corresponds to position 364 of SEQ ID NO. 3, or at position 370 of SEQ ID NO. 10 (Cps7D) which corresponds to position 364 of SEQ ID NO. 3, or at position 364 of SEQ ID NO. 11 (Cps2D) which corresponds to position 364 of SEQ ID NO. 3, or at position 389 of SEQ ID NO. 12 (Fcs2) which corresponds to position 364 of SEQ ID NO. 3, or at position 383 of SEQ ID NO. 13 (Cps1B) which corresponds to position 364 of SEQ ID NO. 3, or at position 387 of SEQ ID NO. 14 (BtY31) which corresponds to position 364 of SEQ ID NO. 3, or at position 366 of SEQ ID NO. 15 (Ccs2) which corresponds to position 364 of SEQ ID NO. 3, or at position 388 of SEQ ID NO. 16 (Cps4B) which corresponds to position 364 of SEQ ID NO. 3 (FIG. 16).

The present invention may also encompass the host cell of the present invention, wherein the nucleotide sequence may encode a polypeptide having a conserved asparagine and a conserved leucine at positions corresponding to positions 20 and 21 of SEQ ID NO. 23 (FIG. 17A) and/or a conserved valine at a position corresponding to position 60 of SEQ ID NO. 23 (FIG. 17B) and/or a conserved serine at a position corresponding to position 88 of SEQ ID NO. 23 (FIG. 17C).

The present invention may also encompass the host cell of the present invention, wherein the nucleotide sequence may encode a polypeptide having a conserved isoleucine corresponding to position 38 of SEQ ID NO. 32 (FIG. 18A) and/or a conserved arginine at a position corresponding to position 156 of SEQ ID NO. 32 (FIG. 18B) and/or a conserved phenylalanine at a position corresponding to position 181 of SEQ ID NO. 32 (FIG. 18C).

Further, the present invention may envisage the nucleotide sequence encoding a polypeptide not comprising a glutamine tyrosine alanine (QYA) motif at positions corresponding to positions 160-162 of SEQ ID NO. 3. Also the nucleotide sequence encoding a polypeptide of the present invention does not have a glutamine histidine glycine (QHG) motif at positions corresponding to positions 160-162 of SEQ ID NO. 3.

Also contemplated by the present invention may be the nucleotide sequence encoding a polypeptide not comprising a serine tyrosine (ST) motif at positions corresponding to positions 289-290 of SEQ ID NO. 3.

Additionally, the present invention may encompass the nucleotide sequence encoding a polypeptide of the present invention not comprising a stretch in the TagF-like domain as can be seen at positions 297 to 366 and from positions 367 to 400 in SEQ ID NO. 36 (Cps8D) (FIGS. 15A and B). Further, the present invention may encompass the nucleotide sequence encoding a polypeptide of the present invention not comprising a stretch in the TagF-like domain as can be seen at positions 231 to 300 and from positions 301 to 334 in SEQ ID NO. 35 (Cps6D) (FIGS. 15A and B).

Additionally, the present invention may encompass the host cell of the present invention, wherein the polypeptide may be a polymerase, preferably a capsule polymerase (CPs), more preferably a glycosyltransferase and a hexose-phosphate transferase or glycosyltransferase and alditol-phosphate transferase As used herein, the term a "capsule polymerase (CP)" refers to an enzyme that assembles the CPS.

A "glycosyltransferase (GT)" refers to a CP generating a linkage between two sugar positions—a so-called glycosidic linkage. Glycosyltransferases identify only three protein folds termed GT-A, GT-B, and GT-C (10). While GT-C folded enzymes represent a minor group of multi-membrane spanning proteins, enzymes with GT-A and GT-B folds can be monotopic or soluble. In this context, "a GT-A fold (domain)" as well as "a GT-B fold (domain)", have as their characteristic element two Rossmann-like domains that are either tightly associated, forming a central, continuous β-sheet (GT-A), or opposed to each other, forming a deep cleft that contains the catalytic center (GT-B).

Another group of capsule polymerases display hexose-phosphate transferase or alditol-phosphate transferase activity. In this context, a hexose-phosphate transferase is able to generate a product containing a phosphodiester linkage when transferring a sugar-phosphate. An alditol-phosphate transferase is able to generate a product containing a phosphodiester linkage when transferring an alditol-phosphate.

The common feature of all members of this polymerase family is the domain catalyzing said phosphdiester linkage, called TagF-like domain. Since the crystal structure of the techoic acid polymerase TagF (15)—a glycerol-phosphate transferase—was used as template for homology modelling by the structure prediction tool PHYRE² (19), this domain was named TagF-like domain (FIGS. 1C, D and 8). Further, it displays no similarity to the hexose-1-phosphate transferases of the stealth protein family. Like TagF, the TagF-like domain adopts a GT-B-like fold. Said TagF-like domain can transfer hexose-phosphate, N-acteylhexosamine-phosphate, glycerol-phosphate and ribitol-phosphate moieties (FIG. 1A, green box).

A β-glycosidic linkage can be generated by a GT-A folded domain (FIGS. 1C and 8) located N-terminally from the TagF-like domain and a α-glycosidic linkage by a GT-B folded domain (FIGS. 1D and 8) C-terminally flanking the TagF-like domain.

The capsule polymerase of the present invention may be able to generate both linkage types (gylcosidic and phosphodiester) in a polymer (e.g. polysaccharide) with a dimeric repeating unit, whereas the prior art has described capsule polymerases generating polysaccharides with either a glycosidic or a phosphodiester linkage or polymerases also generating both linkage types in a polymer, but wherein the polymer consists of a trimeric repeating unit (14).

In the present invention the TagF-like domain, the GT-A and the GT-B domain refer to catalytically active domains having catalytically important positions (FIG. 1E). Said catalytically important positions that were identified based on the template structures used for modelling were changed to alanine, which led to inactive CPs. The catalytically active domains, TagF-like domain and GT-B domain or TagF-like domain and GT-A domain may also be located on two different polypeptides of the present invention.

In detail, the present invention may comprise the nucleotide sequence encoding a polypeptide of the present invention having the conserved aspartate position of the DxD motif at positions corresponding to positions 107-109 of SEQ ID NO. 32 (FIG. 10) and a conserved tyrosine at a position corresponding to position 49 of SEQ ID NO. 3 or a conserved aspartic acid at a position corresponding to position 49 of SEQ ID NO. 3 (FIG. 14). Further, the present invention comprises the nucleotide sequence encoding a polypeptide having conserved aspartate positions of the DxD motif at positions corresponding to positions 107-109 of SEQ ID NO. 32 (FIG. 10) and a conserved tyrosine at a position corresponding to position 49 of SEQ ID NO. 3 or a conserved aspartic acid at a position corresponding to position 49 of SEQ ID NO. 3 (FIG. 14) and a conserved aspartic acid at a position corresponding to position 364 of SEQ ID NO. 3. (FIG. 16).

Further, the present invention may envisage the nucleotide sequence encoding a polypeptide of the present invention having a conserved histidine at a position corresponding to position 122 of SEQ ID NO. 3 (FIG. 11A) and a conserved tyrosine at a position corresponding to position 49 of SEQ ID NO. 3 or a conserved aspartic acid at a position corresponding to position 49 of SEQ ID NO. 3 (FIG. 14). Further, the present invention may envisage the nucleotide sequence encoding a polypeptide having a conserved histidine at a position corresponding to position 122 of SEQ ID NO. 3 (FIG. 11A) and a conserved tyrosine at a position corresponding to position 49 of SEQ ID NO. 3 or a conserved aspartic acid at a position corresponding to position 49 of SEQ ID NO. 3 (FIG. 14) and a conserved aspartic acid at a position corresponding to position 364 of SEQ ID NO. 3. (FIG. 16).

Further, the present invention may encompass the nucleotide sequence encoding a polypeptide of the present invention having a conserved histidine at a position corresponding to position 251 of SEQ ID NO. 3 (FIG. 11B) and a conserved tyrosine at a position corresponding to position 49 of SEQ ID NO. 3 or a conserved aspartic acid at a position corresponding to position 49 of SEQ ID NO. 3 (FIG. 14). Further, the present invention may envisage the nucleotide sequence encoding a polypeptide having a conserved histidine at a position corresponding to position 251 of SEQ ID NO. 3 (FIG. 11B) and a conserved tyrosine at a position corresponding to position 49 of SEQ ID NO. 3 or a conserved aspartic acid at a position corresponding to position 49 of SEQ ID NO. 3 (FIG. 14) and a conserved aspartic acid at a position corresponding to position 364 of SEQ ID NO. 3 (FIG. 16).

Additionally, the present invention may envisage the nucleotide sequence encoding a polypeptide of the present invention having a conserved histidine at a position corresponding to position 251 of SEQ ID NO. 3 (FIG. 11B) and a conserved histidine at a position corresponding to position 122 of SEQ ID NO. 3 (FIG. 11A) and a conserved tyrosine at a position corresponding to position 49 of SEQ ID NO. 3 or a conserved aspartic acid at a position corresponding to position 49 of SEQ ID NO. 3 (FIG. 14) and a conserved aspartic acid at a position corresponding to position 364 of SEQ ID NO. 3 (FIG. 16).

Further, the present invention may comprise the nucleotide sequence encoding a polypeptide having conserved aspartate positions of the DxD motif at positions corresponding to positions 107-109 of SEQ ID NO. 32 (FIG. 10) and a conserved histidine at a position corresponding to position 251 of SEQ ID NO. 3 (FIG. 11B) and a conserved histidine at a position corresponding to position 122 of SEQ ID NO. 3 (FIG. 11A) and a conserved tyrosine at a position corresponding to position 49 of SEQ ID NO. 3 or a conserved aspartic acid at a position corresponding to position 49 of SEQ ID NO. 3 (FIG. 14).

The present invention may also comprise the nucleotide sequence encoding a polypeptide having conserved aspartate positions of the DxD motif at positions corresponding to positions 107-109 of SEQ ID NO. 32 (FIG. 10) and a conserved histidine at a position corresponding to position 251 of SEQ ID NO. 3 (FIG. 11B) and a conserved histidine at a position corresponding to position 122 of SEQ ID NO. 3 (FIG. 11A) and a conserved aspartic acid at a position corresponding to position 364 of SEQ ID NO. 3. (FIG. 16).

Also contemplated by the present invention may the nucleotide sequence encoding a polypeptide having conserved aspartate positions of the DxD motif at positions corresponding to positions 107-109 of SEQ ID NO. 32 (FIG. 10) and a conserved histidine at a position corresponding to position 251 of SEQ ID NO. 3 (FIG. 11B) and a conserved histidine at a position corresponding to position 122 of SEQ ID NO. 3 (FIG. 11A) and a conserved tyrosine at a position corresponding to position 49 of SEQ ID NO. 3 or a conserved aspartic acid at a position corresponding to position 49 of SEQ ID NO. 3 (FIG. 14) and a conserved aspartic acid at a position corresponding to position 364 of SEQ ID NO. 3. (FIG. 16).

Further, the present invention may comprise the nucleotide sequence encoding a polypeptide having the conserved arginine at a position corresponding to position 234 of SEQ ID NO. 23 and the conserved lysine at a position corresponding to position 239 of SEQ ID NO. 23 (FIG. 12) and a conserved tyrosine at a position corresponding to position 49 of SEQ ID NO. 3 or a conserved aspartic acid at a position corresponding to position 49 of SEQ ID NO. 3 (FIG. 14). Further, the present invention may comprise the nucleotide sequence encoding a polypeptide having the conserved arginine at a position corresponding to position 234 of SEQ ID NO. 23 and the conserved lysine at a position corresponding to position 239 of SEQ ID NO. 23 (FIG. 12) and a conserved tyrosine at a position corresponding to position 49 of SEQ ID NO. 3 or a conserved aspartic acid at a position corresponding to position 49 of SEQ ID NO. 3 (FIG. 14) and a conserved aspartic acid at a position corresponding to position 364 of SEQ ID NO. 3. (FIG. 16).

Additionally, the present invention may comprise the nucleotide sequence encoding a polypeptide of the present invention having the conserved arginine at a position corresponding to position 234 of SEQ ID NO. 23 and the conserved lysine at a position corresponding to position 239 of SEQ ID NO. 23 (FIG. 12) and a conserved histidine at a position corresponding to position 251 of SEQ ID NO. 3 (FIG. 11B) and a conserved histidine at a position corresponding to position 122 of SEQ ID NO. 3 (FIG. 11A) and a conserved tyrosine at a position corresponding to position 49 of SEQ ID NO. 3 or a conserved aspartic acid at a position corresponding to position 49 of SEQ ID NO. 3 (FIG. 14).

Additionally, the present invention may comprise the nucleotide sequence encoding a polypeptide of the present invention having the conserved arginine at a position corresponding to position 234 of SEQ ID NO. 23 and the conserved lysine at a position corresponding to position 239 of SEQ ID NO. 23 (FIG. 12) and a conserved histidine at a position corresponding to position 251 of SEQ ID NO. 3 (FIG. 11B) and a conserved histidine at a position corresponding to position 122 of SEQ ID NO. 3 (FIG. 11A) and a conserved tyrosine at a position corresponding to position 49 of SEQ ID NO. 3 or a conserved aspartic acid at a position corresponding to position 49 of SEQ ID NO. 3 (FIG. 14) and a conserved aspartic acid at a position corresponding to position 364 of SEQ ID NO. 3. (FIG. 16).

In addition to the catalytically active domains, all members of the CP family of the GT-A/TagF-like capsule polymerases (Cps1B, Ccs2, Fcs2, Cps4B, BtY31) and of the TagF-like/GT-B capsule polymerases (Cps7D, Cps2D, CszC, Cps3D, Cps9D, CshC, Cps11D, c3694, Bt188, Bt189 and Bt192) may comprise a third domain that is rich in tetratricopeptide repeats (TPR) (FIG. 8). TPRs are usually involved in protein-protein interactions and do not show enzymatic activity.

Also contemplated by the present invention may be the host cell of the present invention, wherein the polypeptide may be fused to a N- and/or C-terminal tag. A "tag" is an amino acid sequence which is homologous or heterologous to an amino acid sequence sequence to which it is fused. Said tag may, inter alia, facilitate purification of a protein or facilitate detection of said protein to which it is fused. If the polypeptide may be fused to a N-terminal tag, the tag may be a MBP tag. If the polypeptide may be fused to a C-terminal tag, the tag may be a His tag (in particular a hexa hisitidine ($His_6$) tag) or a Strepll tag. A polypeptide being just fused to a C-terminal tag without having a N-terminal tag, whereas the C-terminal tag may be a His tag (in particular a hexa hisitidine ($His_6$) tag) may also be preferred. Preferably, if the polypeptide of the present invention may be fused to a N- and C terminal tag, the N-terminal tag may be a MBP tag and the C-terminal tag may be a Strepll tag. More preferably, if the polypeptide of the present invention may be fused to a N- and C terminal tag, the N-terminal tag may be a MBP tag and the C-terminal tag may be a His tag (in particular a hexa hisitidine ($His_6$) tag).

The N- and/or C-terminal tag may be selected from the group consisting of a His tag, MBP tag, GFP tag, FLAG tag, Strep tag, Strepll tag, NusA tag, GST tag, thioredoxin and intein. Preferably, the N- and/or C-terminal tag is a MBP tag and/or Strepll tag. More preferably, the N- and/or C-terminal tag is a MBP tag and/or His tag (in particular hexa hisitidine ($His_6$) tag). If a MBP tag is preferred for the N-terminal tag, the MBP tag may be fused by a protease-resistant linker (in particular a S3N10 linker) to the polypeptide. In this context, the "MBP" refers to maltose binding protein (MBP) being a common protein expression tag. It is one of the most well-known and accomplished means of tagging proteins. Fusion of a target protein (e.g. polypeptide) to MBP permits its one-step purification using amylose resin. Additionally, in E. coli, MBP is known to have significantly enhanced the solubility of many proteins it has been fused to.

Additionally, the present invention may envisage the host cell of the present invention, wherein the polysaccharide may comprise a repeating unit of two different monosaccharides or one monosaccharide and one alditol. The polysaccharide consisting of a dimeric repeating unit of the present invention may comprise a repeating unit, which consists of two different building blocks (building block 1 and building block 2), wherein building block 2 also comprises a phosphate. In this context, the term "two different monosaccharides" refers to one monosaccharide (e.g. glucose) of building block 1 of the repeating unit and another monosaccharide of building block 2, which is either not identical to the monosaccharide of building block 1 (e.g. galactose) or identical to the monosaccharide of building block 1 (e.g. N-Acetylgalactosamine for the two different monosaccharides), but further modified by a glycosyltransferase and/or an O-acetyltransferase (preferably by an O-acetyltransferase) and which is always connected to a phosphate. Additionally, two identical monosaccharides, whereas the monosaccharide of building block 1 is further modified by a glycosyltransferase and/or an O-acetyltransferase may also be comprised by the present invention, when the term "two different monosaccharides" is used. In this context, the term "alditol" refers to an alditol being connected to a phosphate.

Building block 1 may be selected from N-acetyglucosamine (GlcNAc), galactose (Gal), N-acetylgalactosamine (GalNAc), glucose (Glc), galactofuranose, mannose (Man), N-acetylmannosamine (ManNAc), which are non-limiting examples of monosaccharides of the repeating unit and which may also be additionally modified by a glycosyltransferase and/or an O-acetyltransferase. In this context, the term "glycosyltransferase" refers to an enzyme, which catalyzes the transfer of a saccharide moiety to a nucleophilic glycosyl acceptor, preferably a hydroxyl group of a monosaccharide of building block 1 or a monosaccharide/alditol of building block 2. The term "glycosyltransferase" as used herein, may comprise glucosyltransferase, which catalyzes the transfer of glucose. It may also comprise galactosyltransferase, N-acetylglucosamintransferase, N-acetylgalactosamine transferase, mannosyltransferase, N-acetylmannosamine transferase or galactofuranosyltransferase. A glycosyltransferase may establish the natural glycosidic linkages known to a person skilled in the art. Thus, the present invention may comprise the host cell of the present invention, wherein the polysaccharide may comprise a repeating unit of two different monosaccharides or one monosaccharide and one alditol, wherein the first monosaccharide may have an additional modification such as glucose, galactose or N-acetylglucosamine and/or O-acetyl. Further, the polysaccharide of the present invention may also comprise a repeating unit of two different monosaccharides, wherein the first monosaccharide may have two additional modifications such as two glucose molecules, two galactose molecules or two N-acetylglucosamine molecules (in particular two glucose molecules) or two O-acetyl molecules.

Figure 7:
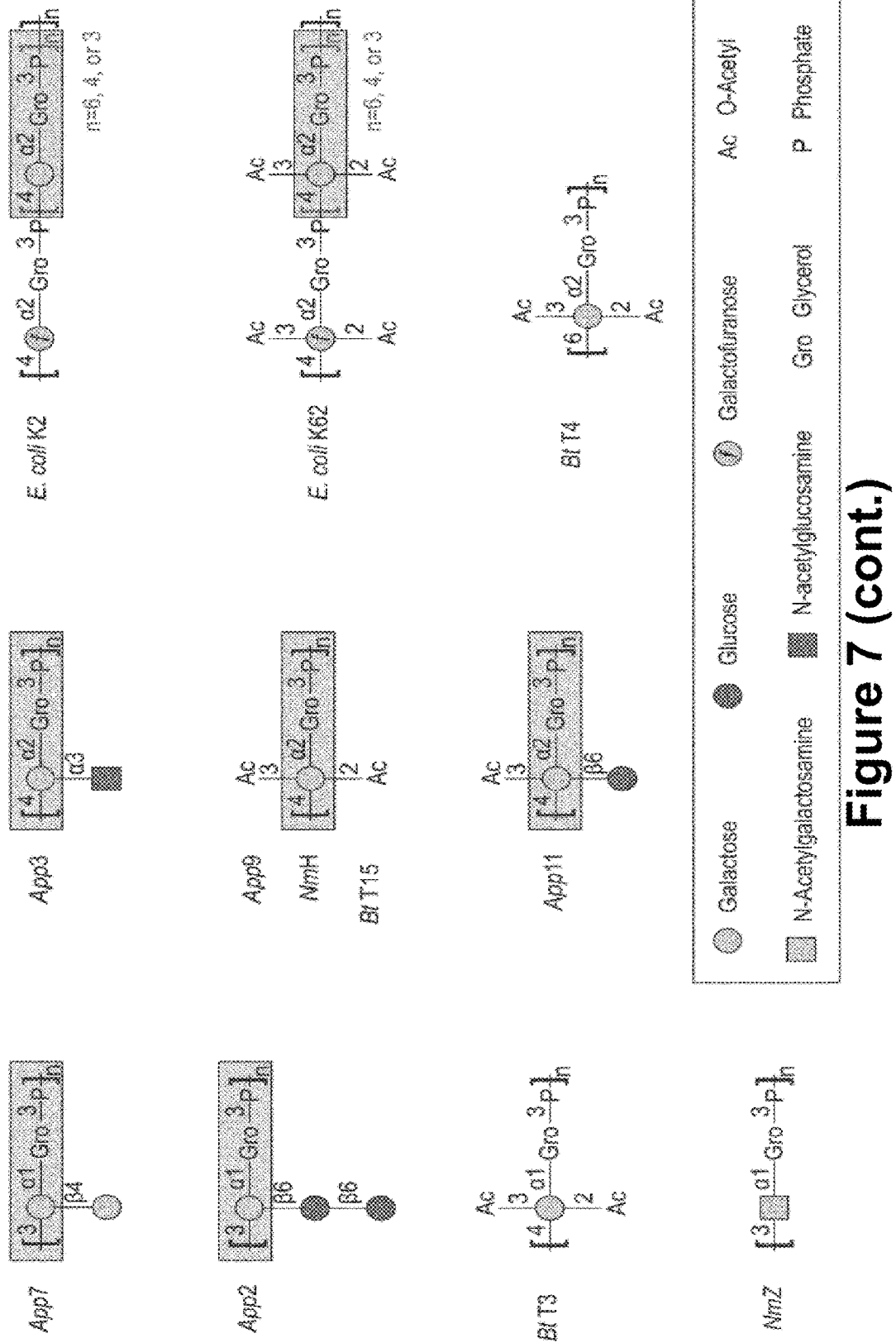
FIG. 7: The natural capsule structures of group II capsule expressing bacteria that encode TagF-like capsule polymerases.

Building block 2 may be selected from galactose-phosphate (Gal-P), N-acetylgalactosamine-phosphate (GalNAc-P) or glycerol-phosphate (Gro-P), the latter which refers to an alditol (FIG. 7). All of the above mentioned monosaccharides and alditols are non-limiting examples of monosaccharides and alditols of the repeating unit. The monosaccharide of building block 2, in particular galactose or N-acetylgalactosamine, is bonded to a phosphate, wherein building block 2 comprising a monosaccharide and phosphate is bonded to building block 1 of the following repeating unit via a phosphodiester linkage (bond). The alditol of building block 2, in particular glycerol, is also bonded to a phosphate, wherein building block 2 comprising an alditol and phosphate is bonded to building block 1 of the following repeating unit via a phosphodiester linkage (bond). Galactose-phosphate (Gal-P) or N-acetylgalactosamine-phosphate (GalNAc-P) of building block 2 may also be additionally modified by a glycosyltransferase and/or an O-acetyltransferase.

Thus, the present invention may comprise the host cell of the present invention, wherein the polysaccharide may comprise a repeating unit of two different monosaccharides, wherein the second monosaccharide may have an additional modification such as glucose, galactose or N-acetylglucosamine and/or O-acetyl. Further, the polysaccharide of the present invention may also comprise a repeating unit of two different monosaccharides, wherein the second monosaccharide may have two additional modifications such as two glucose molecules, two galactose molecules or two N-acetylglucosamine molecules or two O-acetyl molecules.

Thus, the repeating unit of the polysaccharide consisting of a dimeric repeating unit of the present invention comprises a building block 1 (monosaccharide) and a building block 2 (monosaccharide plus phosphate or alditol plus phosphate) and the modification(s) catalyzed by a glycosyltransferase and/or an O-acetyltransferase modifying building block 1. Further, the repeating unit of the polysaccharide consisting of a dimeric repeating unit of the present invention also comprises a building block 1 (monosaccharide) and a building block 2 (monosaccharide plus phosphate or alditol plus phosphate) and the modification(s) catalyzed by a glycosyltransferase and/or an O-acetyltransferase modifying building block 2.

Further, building block 1 and building block 2 build up the backbone chain of the repeating unit. In this context, the term "backbone chain" refers to the bonding of building block 1 (monosaccharide) to building block 2 (monosacchriade plus phosphate via phosphoester linkage or alditol plus phosphate via phosphoester linkage) in a chain, which is characterized as a glycosidic linkage. It further refers to the bonding of building block 2 (monosaccharide plus phosphate or alditol plus phosphate) to building block 1 (monosaccharide) of the following repeating unit in a chain, which is characterized as phosphodiester linkage.

The present invention may further comprise the host cell of the present invention, wherein the repeating unit may comprise one or more glycosidic and one or more phosphodiester linkage(s). Preferably, the repeating unit of the present invention comprises one, two or three glycosidic linkages (e.g. Cps2D of App2 in FIG. 7 having three glycosidic linkages) and one or more phosphodiester linkage(s). More preferably, the repeating unit of the present invention has one phosphodiester linkage, bonding the monosaccharide of building block 2, in particular galactose or N-acetylgalactosamine, to the phosphate of building block 2, and linking said phosphate to the monosaccharide of building block 1, or, bonding the alditol of building block 2, in particular glycerol, to the phosphate of building block 2, and linking said phosphate to the monosaccharide of building block 1. Thus, the repeating unit of the present invention may comprise one, two or three glycosidic linkages and one phosphodiester linkage. A polysaccharide consisting of a dimeric repeating unit of the present invention having two gylcosidic linkages comprises bonding building block 1 and building block 2 via the first glycosidic linkage and bonding the modification, in particular a glucose, galactose or N-acetylglucosamine molecule catalyzed by a glycosyltransferase via the second glycosidic linkage. A polysaccharide consisting of a dimeric repeating unit of the present invention having three gylcosidic linkages comprises bonding building block 1 and building block 2 via the first glycosidic linkage and bonding the first modification, in particular a glucose, galactose or N-acetylglucosamine molecule catalyzed by a glycosyltransferase via the second glycosidic linkage and bonding the second modification, in particular a glucose, galactose or N-acetylglucosamine molecule catalyzed by a glycosyltransferase via the third glycosidic linkage.

The glycosidic linkage connecting the modifications (such as glucose(s), galactose(s) or N-acetylglucosamine(s), which are non-limiting examples of monosaccharides of the repeating unit) to building block 1 may also be an α- or β-glycosidic linkage. The glycosidic linkage connecting the modifications (such as glucose(s), galactose(s) or N-acetylglucosamine(s), which are non-limiting examples of monosaccharides of the repeating unit) to building block 2 may also be an α- or β-glycosidic linkage.

Additionally, the present invention comprises the host cell of the present invention, wherein the two different monosaccharides of the repeating unit are connected by a β-glycosidic linkage or wherein the monosaccharide and the alditol of the repeating unit are connected by an α-glycosidic linkage. The repeating unit having two different monosaccharides in building block 1 and 2 being connected by a β-glycosidic linkage may also have a phosphodiester linkage connecting building block 2 of one repeating unit to building block 1 of the following repeating unit. The repeating unit having a monosaccharide in building block 1 and an alditol in building block 2 being connected by an α-glycosidic linkage may also have a phosphodiester linkage connecting building block 2 of one repeating unit to building block 1 of the following repeating unit.

Further, the present invention may also comprise the host cell of the present invention, wherein the polysaccharide is a phosphate containing polysaccharide.

As mentioned above, building block 2 of the repeating unit comprises a monosaccharide, in particular galactose or N-acetylgalactosamine, or an alditol, in particular glycerol, which are bonded to a phosphate via a phosphoester linkage.

The new CP family synthesizes phosphate containing CPS in pathogens expressing a group 2 capsule. Group II capsules are characterized by a high negative charge density. The negative charge may be introduced by either the integration of negatively charged sugar moieties (sialic acid or glucuronic acid) or by the integration of phosphodiester linkages generated by the TagF-like domain or CPs belonging to the stealth protein family. Thus, in the present invention the polysaccharide may be negatively charged, since it has a phosphodiester linkage, thus the polysaccharide refers to a phosphate containing polysaccharide.

The polysaccharide of the present invention does not comprise Kdo, also called 3-deoxy-D-manno-oct-2-ulosonic acid (OclA), which may introduce the negative charge and may be transferred/integrated by domains similar to the TagF-like domain.

The present invention may further envisage a method of producing the host cell of the present invention, the method comprising: a) cloning a nucleotide sequence encoding a polypeptide expressed by the host cell of the present invention into a vector, b) transforming cells with said vector of (a) and growing the cells in medium.

A nucleotide sequence encoding the polypeptide of the present invention may be cloned into a vector of the present invention, preferably a plasmid or cosmid, more preferably pET, pMal-c, pGEX, pBAD, pQE, pACYC, pSC101, pASK-IBA, pLAFR1, pBBR1MCS-3, using standard cloning techniques. Standard cloning techniques such as using restriction enzymes or recombinational cloning is known to the skilled person in the art. E. coli cells, preferably M15 (pREP4), BL21, BL21(DE3), W3110, are then transformed with said vector and grown in LB or PowerBroth medium. If necessary, antibiotics may also be added for plasmid selection, preferably streptomycin, actinomycin, blasticidin, neomycin, kanamycin, gentamicin or ampicillin. In this context, the term "transforming" refers to the process by which foreign DNA, preferably a vector comprising the nucleotide sequence encoding the polypeptide of the present invention, is introduced into a cell. The process transformation is known to the person skilled in the art and may be performed by e.g. standard heatshock.

Additionally, the present invention may comprise a method of expressing a polypeptide in a host cell comprising a) culturing the host cell of the present invention, b) expressing the polypeptide in the host cell. The host cell of the present invention may be cultured under conditions sufficient for the expression of the polypeptide. Those conditions, under which the host cell is cultured may refer using colonies of transformed E. coli expression strains to inoculate an appropriate culture medium (e. g. LB or PowerBroth) while growing at 15-37° C., preferably at 37° C. At an $OD_{600}$ of 0.5-3.0 (preferably 1.0), the incubation temperature is changed to 4° C.-37° C. (preferably 15° C.) and protein expression is induced by addition of 0.1-1.0 mM (preferably 0.5) isopropyl-β-D-1-thiogalactopyranoside (IPTG).

Also comprised by the invention is a vaccine composition comprising the host cell of the present invention.

The term "vaccine composition" refers to an attenuated vaccine or live vaccine, a subject is administered with, thus being vaccinated with. The vaccine composition is created by reducing the virulence of the host cell of the present invention, but still keeping the host cell viable (or "live"). Preferably, the vaccine composition may comprise the host cell of the present invention capable of eliciting an immune response against the host cell of the present invention. A particle of the host cell may be used in the vaccine composition or the whole host cell itself.

Accordingly said vaccine composition is administered to a subject in need thereof. Preferably, the subject is a vertebrate, even more preferred a mammal including rats, rabbits, pigs, mice, cats, dogs, sheep, horses, goats, cows and humans. Preferably, the subject being vaccinated may be an animal mentioned above. The term "administered" means administration of a therapeutically or diagnostically effective dose of the vaccine composition comprising the host cell of the present invention to a subject. By "therapeutically or diagnostically effective amount" is meant a dose that produces the effects for which it is administered. The exact dose will depend on the purpose of the treatment or diagnosis, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art. The methods are applicable to both human therapy and veterinary applications.

The vaccine composition may be administered alone or in combination with other treatments. The vaccine may further comprise auxiliary substances, such as wetting or emulsifying agents or pH buffering agents, to further enhance their effectiveness. The vaccine composition may also comprise a carrier. In this context, the term "carrier" refers to a diluent, adjuvant, or vehicle with which the vaccine composition is administered. Carriers may be sterile liquids, such as water and oils including those of petroleum, animal, vegetable or synthetic origin, such as peanut oil, soybean oil, mineral oil, sesame oil and the like. Water is a preferred carrier when the vaccine composition is administered orally or intravenously. Saline solutions and aqueous dextrose and glycerol solutions can also be employed as liquid carriers, particularly for injectable solutions. Where the composition is administered by injection, an ampoule of sterile water for injection or saline can be provided so that the ingredients may be mixed prior to administration.

The administration of the vaccine composition may be done in a variety of ways as discussed above, including, but not limited to intraperitoneally, intravenously, subcutaneously, intramuscularly or orally. Preferably, the administration of the vaccine composition is performed intramuscularly. More preferably, the administration of the vaccine composition is performed subcutaneously, if an animal, in particular small animals such as mice, rats, rabbits, cats or dogs are vaccinated. If pigs are vaccinated with a life vaccine, possible routes are systemic immunization (intradermal or intramuscular) and mucosal immunization (oral and intranasal routes), preferably mucosal immunization via intranasal route. If pigs are vaccinated with a glycoconjugate vaccine, systemic immunization is the preferred method.

The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently.

An optimal amount for a particular vaccine composition may be ascertained by standard studies involving observation of appropriate immune responses in subjects. The dosages are preferably given once a year, however, during progression of the treatment the dosages can be given in much longer time intervals and in need can be given in much shorter time intervals. In a preferred case, the immune response is monitored using herein described methods and further methods known to those skilled in the art and dosages are optimized, e.g., in time, amount and/or composition. Following an initial vaccination, subjects may receive one or several booster immunization adequately spaced.

Additionally, the present invention may comprise a composition comprising a polypeptide expressed by the host cell of the present invention. The term "composition", as used in accordance with the present invention, relates to a composition, which comprises at least a polypeptide expressed by the host cell of the present invention and a carrier.

It is envisaged that the composition of the present invention may comprise the polypeptide and the carrier in any combination. The composition comprising a polypeptide expressed by the host cell of the present invention, if desired, can also contain minor amounts of wetting or emulsifying agents, or pH buffering agents as a carrier. The pH of the buffering agent is preferably adjusted to lie between 5 and 10 by addition of an acid or a base, preferably pH 8.0. Preferably, the composition of the present invention may comprise 20 mM Tris pH 8.0, 1 mM DTT, 10 mM $MgCl_2$ as a carrier.

The composition may be in solid, liquid or gaseous form and may be, inter alia, in the form of (a) powder(s), (a) tablet(s), (a) solution(s), (an) aerosol(s), granules, pills, suspensions, emulsions, capsules, syrups, liquids, elixirs, extracts, tincture or fluid extracts or in a form, which is particularly suitable for oral or parental or topic administration.

The composition comprising a polypeptide of the present invention is, for example, suitable for use in immunoassays in which it may be utilized in liquid phase or bound to a solid phase carrier. Examples of well-known carriers include glass, polystyrene, polyvinyl ion, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Solid phase carriers are known to those in the art and may comprise polystyrene beads, latex beads, magnetic beads, colloid metal particles, glass and/or silicon chips and surfaces, nitrocellulose strips, membranes, sheets, duracytes and the walls of wells of a reaction tray, plastic tubes or other test tubes. Suitable methods of immobilizing a polypeptide expressed by the host cell of the present invention on solid phases include but are not limited to ionic, hydrophobic, covalent interactions or (chemical) crosslinking and the like. Examples of immunoassays, which can utilize a polypeptide expressed by the host cell of the present invention, are competitive and non-competitive immunoassays in either a direct or indirect format. Commonly used detection assays can comprise radioisotopic or non-radioisotopic methods. Examples of such immunoassays are the radioimmunoassay (RIA), the sandwich (immunometric assay) and the Northern or Southern blot assay. Furthermore, these detection methods comprise, inter alia, IRMA (Immune Radioimmunometric Assay), EIA (Enzyme Immuno Assay), ELISA (Enzyme Linked Immuno Assay), FIA (Fluorescent Immuno Assay), and CLIA (Chemioluminescent Immune Assay).

Further, the composition comprising a polypeptide of the present invention is, for example, suitable for use in enzymatic activity reactions. The amount of purified polypeptide may be 0.1-1 nmol, preferably 0.1-0.3 nmol. The amount may be in a total volume of at least 50 μL assay buffer, preferably 75 μL assay buffer. If the volume is increased, the amount of polypeptide is increased as well. The assay buffer may contain 20 mM Tris pH 8.0, 1 mM DTT, 10 mM $MgCl_2$ and 1-50 mM donor sugar, such as UDP-GlcNAc (Carbosynth), UDP-Gal (Carbosynth) and CDP-glycerol, or any other donor sugar known to the person skilled in the art. Preferably 6-10 mM donor sugar may be used for the enzymatic activity reaction.

Additionally, the composition comprising a polypeptide of the present invention is, for example, suitable for use in in vitro polysaccharide synthesis. For in vitro synthesis of 5-12 mg polysaccharide, 1-50 nmol polypeptides may be used for incubation with 1-50 mM (preferably 6-10 mM) donor sugars as mentioned above in a total volume of 5-10 mL. Preferably, 1-25 nmol polypeptide may be used.

Also contemplated by the present invention may be the composition further comprising one or more polypeptide(s) having an amino acid sequence selected from the group consisting of: a) SEQ ID NO. 33 and 41; b) SEQ ID NO. 34 and 42; c) SEQ ID NO. 35 and 43; d) SEQ ID NO. 36 and 44; e) SEQ ID NO. 37 and 45; f) SEQ ID NO. 38 and 46; g) SEQ ID NO. 39 and 47; h) SEQ ID NO. 40 and 48, or fragments thereof.

TABLE 2

Overview of the polypeptides additionally used in the composition of the present invention and their corresponding sequences, which encode a TagF-like domain or domains that are similar to TagF-like domains (SiaTF, KdoTF), a GTB or a GTA domain.

| SEQ ID NO. | Domain | Polymerase |
|---|---|---|
| 33 | TagF | CslB |
| 34 | TagF | Cps12B |
| 35 | TagF | Cps6D |
| 36 | TagF | Cps8D |
| 37 | KdoTF | Cps5B |

TABLE 2-continued

Overview of the polypeptides additionally used in the composition of the present invention and their corresponding sequences, which encode a TagF-like domain or domains that are similar to TagF-like domains (SiaTF, KdoTF), a GTB or a GTA domain.

| SEQ ID NO. | Domain | Polymerase |
|---|---|---|
| 38 | KdoTF | Cps10C |
| 39 | SiaTF | Csw |
| 40 | SiaTF | Csy |
| 41 | GTA | CslB |
| 42 | GTA | Cps12B |
| 43 | GTB | Cps6D |
| 44 | GTB | Cps8D |
| 45 | GTB | Cps5A |
| 46 | GTB | Cps10D |
| 47 | GTB | Csw |
| 48 | GTB | Csy |

The one or more polypeptide(s) having an amino acid sequence selected from the group consisting of: a), b), c), d), e), f), g), h) or fragments thereof may also comprise a linker as mentioned earlier, which connects the TagF-like domain (e.g. SEQ ID NO. 33) (or Sialyltransferase domain for Csw and Csy and KdoTF domain for Cps5B and Cps10C) and the GT-A domain (e.g. SEQ ID NO. 41) or the TagF-like domain (e.g. SEQ ID NO. 35) and the GT-B domain (e.g. SEQ ID NO. 43). Preferably, the nucleotide sequence encoding said linker polypeptide is disposed in the polynucleotide between the nucleotide sequence encoding the TagF-like domain (e.g. SEQ ID NO. 33) and the GT-A domain (e.g. SEQ ID NO. 41) or between the nucleotide sequence encoding the TagF-like domain (e.g. SEQ ID NO. 35) and the GT-B domain (e.g. SEQ ID NO. 43) such that it results in a fusion between said TagF-like domain, linker polypeptide and GT-B or GT-A domain. Also contemplated by the present invention may be a nucleotide sequence encoding the TagF-like domain (e.g. SEQ ID NO. 33 or 35) being inserted in one vector, whereas the nucleotide sequence encoding the GT-B domain (e.g. SEQ ID NO. 43) or GT-A domain (e.g. SEQ ID NO.41) may be inserted in another vector, such that it results not in a fusion between said TagF-like domain and said GT-B or GT-A domain, instead resulting in a pair of polypeptides one comprising the TagF-like domain, the other polypeptide comprising the GT-B or GT-A domain.

The composition of the present invention may comprise a polypeptide expressed by the host cell of the present invention and one polypeptide having an amino acid sequence selected from the group consisting of: a), b), c), d), e), f), g), h) or fragments thereof. The present invention may also comprise a polypeptide expressed by the host cell of the present invention and one, two, three, four, five, six, seven or even all eight polypeptides having an amino acid sequence selected from the group consisting of: a), b), c), d), e), f), g), h) or fragments thereof.

In this context, the term "fragments thereof" refers to a fragment of each domain (TagF-like and GTB domain or TagF-like and GTA domain) of a polypeptide having an amino acid sequence selected from the group consisting of: a), b), c), d), e), f), g), h), meaning either a fragment of the TagF-like domain (e.g. SEQ ID NO. 35) and a fragment of the GT-B domain (e.g. SEQ ID No. 43) or a fragment of the TagF-like domain (e.f. SEQ ID NO. 33) and a fragment of the GT-A domain (e.g. SEQ ID NO.41). Each fragment may be at least 15 amino acid residues in length. Preferably, each fragment may be at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 300, 400 or 500 amino acid residues in length or from 15-500, 30-500, 50-500, 100-500 or 200-500 amino acid residues in length, or each fragment may be 15-200, 30-200, 50-200 or 100-200 amino acid residues in length, or 15-100, 20-100, 25-100, 30-100, 35-100, 40-100, 45-100 or 50-100 amino acid residues in length.

The composition, if desired, can also contain minor amounts of wetting or emulsifying agents, or pH buffering agents as a carrier. The pH of the buffering agent is preferably adjusted to lie between 5 and 10 by addition of an acid or a base, preferably pH 8.0. Preferably, the composition may comprise 20 mM Tris pH 8.0, 1 mM DTT, 10 mM $MgCl_2$ as a carrier.

The present invention may also encompass a method for synthesizing a polysaccharide consisting of a dimeric repeating unit comprising bringing the composition of the present invention further comprising one or more polypeptide(s) having an amino acid sequence selected from the group consisting of: a), b), c), d), e), f), g) and h) into contact with two donor substrates. In this context, the term "bringing into contact" means reacting the (purified) polypeptide expressed by the host cell of the present invention and/or one or more polypeptide(s) having an amino acid sequence selected from the group of: a), b), c), d), e), f), g) and h) with two donor substrates or performing a reaction of the polypeptide expressed by the host cell of the present invention and/or one or more polypeptide(s) having an amino acid sequence selected from the group of: a), b), c), d), e), f), g) and h) with two donor substrates.

Figure 2:
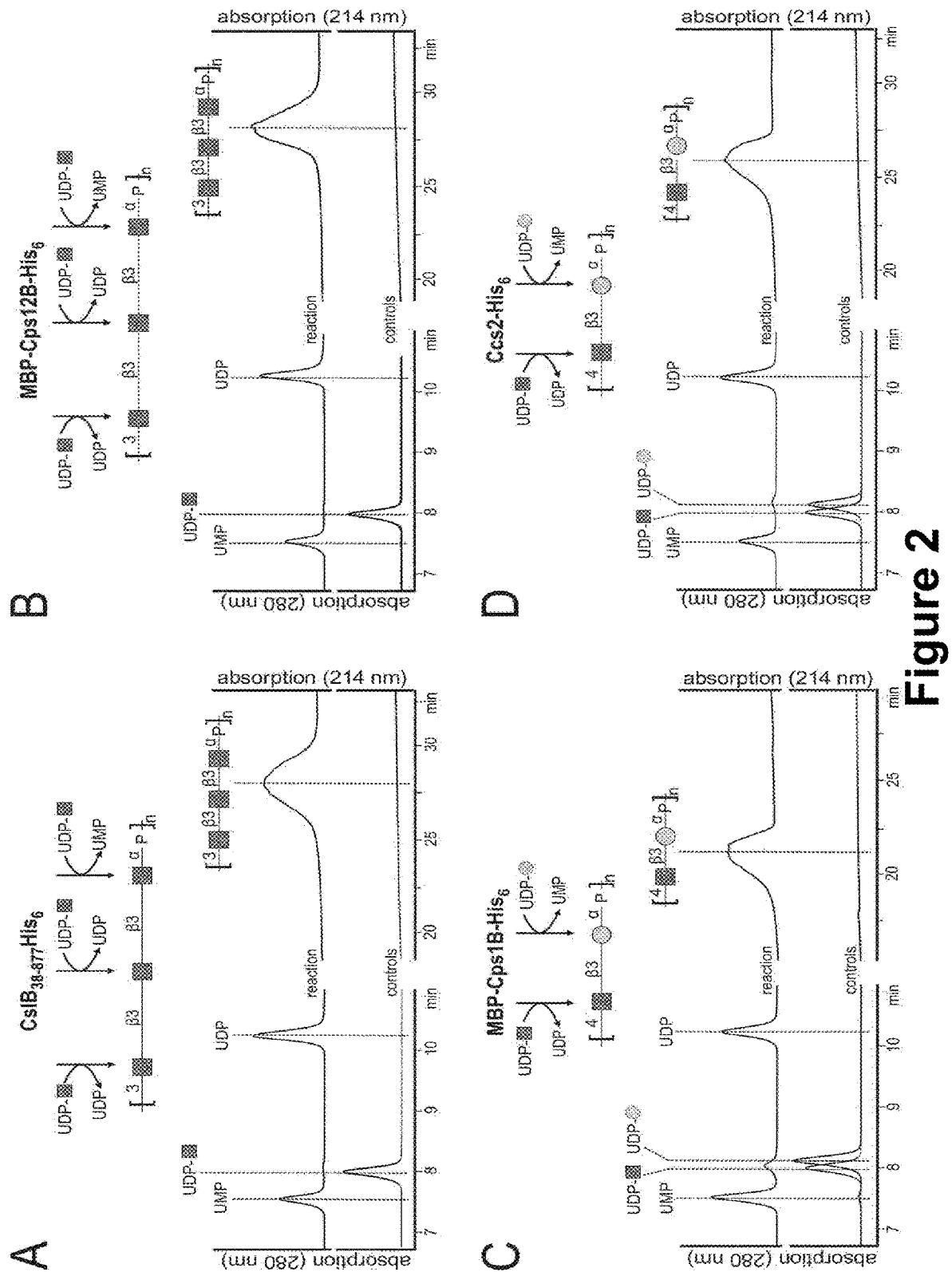
FIG. 2: HPLC-AEC and PAGE analyses of different capsule polymerase reactions.
A) CslB$_{38-87}$7-His$_6$ of NmL B) MBP-Cps12B-His$_6$ of App12 C) MBP-Cps1B-His$_6$ of App1 D) Ccs2-His$_6$ of Hic E) MBP-Cps3D-His$_6$ of App3 and F) MBP-Cps7D-His$_6$ of App7. The HPLC-AEC assay allows the separation and detection of nucleotide activated donor substrates and released nucleotide products in the 280 nm channel (left panels). UV-active polymers carrying GlcNAc moieties are detected in the 214 nm channel (see A, B, C, D). UV-inactive polymers are detected using an alcian blue/silver stained PAGE (see E, F).
Figure 2:
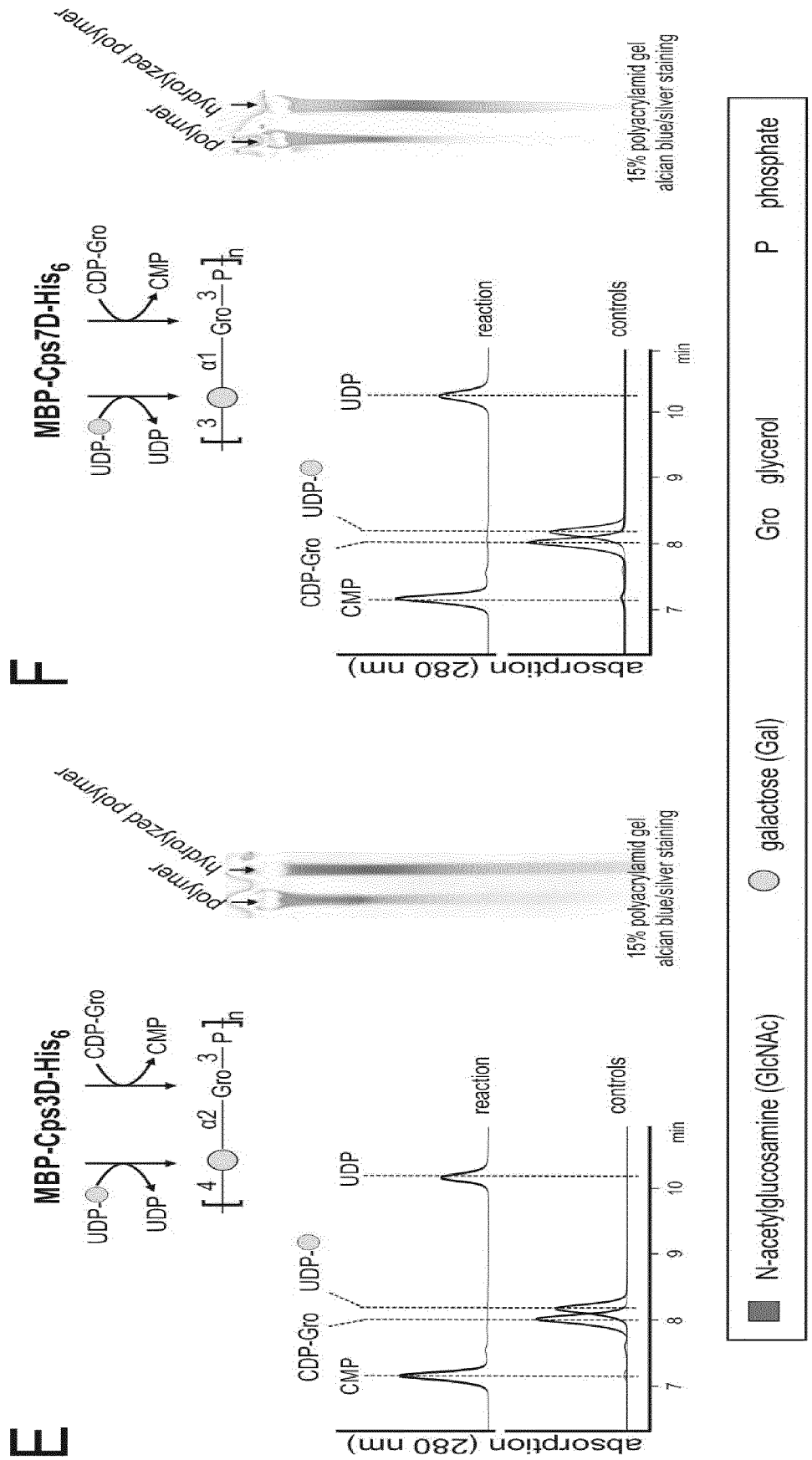

The polypeptides expressed by the host cell of the present invention were recombinantly expressed, in particular in *E. coli*, purified, preferably via their C-terminal histidine tag, and incubated with two donor substrates (nucleotide activated carbohydrates) and the reaction was analysed using a high performance liquid chromatography based anion exchange chromatography assay (HPLC-AEC). The HPLC-AEC assay allows monitoring the consumption of the donor substrates as well as the purification of all putative products of the reaction (FIG. 2). Preferably, the amount of purified polypeptide may be 1-25 nmol. The amount of the two donor substrates (donor sugars) may be 1-50 mM, preferably 6-10 mM. The CPS assembled in this reaction may elute at around 10-30 minutes from the column of the HPLC-AEC indicating a high negative charge density and thus considerable length.

The present invention may encompass the method as mentioned above, wherein the two donor substrates may be nucleotide monosaccharides or wherein the two donor substrates are a nucleotide monosaccharide and a nucleotide alditol.

The donor substrates may be selected from uridine diphosphate N-acetylglucosamine (UDP-GlcNAc), uridine diphosphate galactose (UDP-Gal), uridine diphosphate N-acetylgalactosamine (UDP-GalNAc), uridine diphosphate glucose (UDP-Glc), uridine diphosphate galactofuranose, uridine diphosphate N-acetylmannosamine (UDP-ManNAc), CMP-sialic acid, CMP-ketodeoxyoctonate (CMP-kdo) and uridine diphosphate mannose (UDP-Man), which refer to nucleotide monosaccharides (nucleotide sugars) or cytidine diphosphate glycerol (CDP-glycerol) and cytidine diphosphate ribitol (CDP-ribitol), which refer to nucleotide alditols. Here, the nucleotide may be an adenosine diphosphate (ADP), uridine diphosphate (UDP), cytidine diphosphate (CDP), guanosine disphosphate (GDP) or cytosine monophosphate (CMP), preferably UDP or CDP. The two donor substrates comprising two nucleotide monosaccharides may be selected from UDP-GlcNAc, UDP-Gal, UDP-GalNAc, UDP-Glu, uridine diphosphate galactofuranose, UDP-ManNAc, CMP-sialic acid, CMP-kdo and UDP-Man. The two donor substrates comprising one nucleotide monosaccharide and one nucleotide alditol may be selected from UDP-GlcNAc, UDP-Gal, UDP-GalNAc, UDP-Glu, uridine diphosphate galactofuranose, UDP-ManNAc, CMP-sialic acid, CMP-kdo and UDP-Man for the nucleotide monosaccharide and CDP-glycerol and CDP-ribitol for the nucleotide alditol. All of the above mentioned compounds are non-limiting examples of donor substrates.

The nucleotide monosaccharide(s) and the nucleotide alditol as mentioned above are characterized as being activated. In this context, the term "activated" means adding a NDP to (a) nucleotide monosaccharide(s) or to an alditol or adding a NMP to sialic acid or adding a NMP to Kdo, wherein NDP may be selected from adenosine diphosphate (ADP), uridine diphosphate (UDP), cytidine diphosphate (CDP), guanosine disphosphate (GDP). Thus, the two donor substrates may also refer to nucleotide activated monosaccharides or to a nucleotide activated monosaccharide and a nucleotide activated alditol or a nucleotide activated sialic acid or a nucleotide activated Kdo.

Also encompassed by the present invention may be a polysaccharide consisting of a dimeric repeating unit obtainable by the method mentioned above for use as a glycoconjugate vaccine.

The polysaccharide consisting of a dimeric repeating unit may also be used to make efficient vaccines, the so called glycoconjugate vaccines, in which polysaccharide-fragments are covalently coupled to adjuvant proteins to elicit T cell responses and immunological memory.

In this context, the term "glycoconjugate" refers to polysaccharide fragments being comprised of multiple-oligosaccharides covalently linked to a carrier protein. Such glycoconjugate may then be used as a vaccine being administered to a subject in need thereof.

The subject may be mammals, including rats, rabbits, pigs, mice, cats, dogs, sheep, horses, goats, cows and humans. Preferably, the glycoconjugate vaccine made by the polysaccharides generated by the polypeptides of the present invention is administered to animals mentioned above.

In general, polysaccharides, in particular capsular polysaccharide (CPSs) are isolated from large scale fermentation of pathogenic bacteria. This step essentially depends on the high-tech infrastructure of modern production plants and, as vaccines are applied to healthy individuals, requests extended control systems to guarantee product homogeneity and consistency (53). The isolation of polysaccharides, in particular CPSs from pathogen cultures is a major driver of costs, making glycoconjugate vaccines expensive and thus not sufficiently accessible to low-income countries or for their use in animal husbandry.

Immunogenic glycoconjugates may be formed between multifunctionalized CPS and proteins if the conditions are controlled very carefully. Most of the conjugates are today synthesized by coupling either CPS or oligosaccharides activated at hydroxyl groups or through their reducing end, respectively, to a protein or peptide with or without a linker group.

General glycoconjugation methods involve random activation of the capsular polysaccharide by periodate treatment or specific activation of fragments of the polysaccharide by reductive amination at their reducing ends. The former method for long CPS leads to a random oxidative cleavage of vicinal hydroxyl groups of the carbohydrates with the formation of reactive aldehyde groups. Coupling to a protein carrier for both methods is by reductive amination to the lysyl groups. A spacer group such as aminocaproic acid or adipic acid based derivatives can be reacted with the aldehydes by reductive amination and then coupled to the protein lysyl groups.

Thus, the present invention may also comprise an alternative, safe and economic way for glycoconjugate production by applying chemo-enzymatic synthesis of polysaccharides, in particular CPSs by use of recombinant capsule biosynthesis enzymes, e.g. the polypeptides of the present invention.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "less than" or in turn "more than" does not include the concrete number.

For example, "less than 20" means less than the number indicated. Similarly, "more than or greater than" means more than or greater than the indicated number, e.g. "more than 80%" means more than or greater than the indicated number of 80%.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified.

The term "including" means "including but not limited to". "Including" and "including but not limited to" are used interchangeably.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

A better understanding of the present invention and of its advantages will be gained from the following examples, offered for illustrative purposes only. The examples are not intended to limit the scope of the present invention in any way.

EXAMPLES OF THE INVENTION

Material and Methods

Example 1: General Cloning

The generation of plasmid pAN37-cslB-His6 (tac) encoding the capsule polymerase CslB38-874-His6 of NmL was described in (14). Plasmids encoding the polymerases of App1, App3, App7, App12 and Hic were cloned similarly. The genes encoding the polymerases Cps1B (Genbank: KY798410), Cps3D (Genbank: KY807157), Cps7D (uniprot: B3GYRO), Cps12B (uniprot: Q69AA8) and Ccs2 (uniprot: F6KWE2) were amplified by polymerase chain reaction (PCR) from heat-inactivated bacterial lysates as template and with primers given in Table 3 and Table 4. The *Actinobacillus pleuropneumoniae* lysates were kindly provided by Dr. Jochen Meens (University of Veterinary Medicine, Hannover, Germany) and *Haemophilus influenzae* serotype c lysate was kindly provided by Dr. Heike Claus (Institute for Hygiene and Microbiology, Wuerzburg, Germany).

TABLE 3

List of primers used.

Primers used for generating the listed plasmids.
Restriction sites are underlined.

| | | |
|---|---|---|
| CL57 | 5'-CCATAGGGATCCAATAAAGTAAAACGTAAATTTAG-3' (SEQ ID NO: 49) | |
| CL59 | 5'-CTTTTACCTAGGAACGCCCAACTTAATTAACATTAGTGGTGGTGGTGGTGGTGCTCGAG GATGAATTTTTCAAAAAAGATAG-3' (SEQ ID NO: 50) | |
| CL147 | 5'-CCATAGGGATCCTTAATAAACAACGAGAATG-3' (SEQ ID NO: 51) | |
| CL148 | 5'-GGTGCTCGAGTTTAGTATTTTCGTTAAATTC-3' (SEQ ID NO: 52) | |
| CL74 | 5'-CCATAGGGATCCAAGAAAAAATTTTATAAAGC-3' (SEQ ID NO: 53) | |
| CL94 | 5'-CTTTTACCTAGGAACGCCCAACTTAATTAACATTAGTGGTGGTGGTGGTGCTC GAGAATAACATTATAAAATCTATTAATTG-3' (SEQ ID NO: 54) | |
| CL33 | 5'-CCATAGGGATCCAATAAAATTAGTA-3' (SEQ ID NO: 55) | |
| CL56 | 5'-GGTGCTCGAGGTTTATATTTCTTTTTGG-3' (SEQ ID NO: 56) | |
| CL40 | 5'-GCATCTCATATGAGCAAAATCAATAGAAAACTTAAGAAAC-3' (SEQ ID NO: 57) | |
| CL39 | 5'-GGTGCTCGAGTGAAAGTAAATCGGCTAATTTTAATTG-3' (SEQ ID NO: 58) | |

Primers used for generating truncated Cps1B constructs.

| | |
|---|---|
| CL102 | 5'-AAACATTTACCTGTTAAATATGAAG-3' (SEQ ID NO: 59) |
| CL104 | 5'-CATGGACTATGGTCCTTG-3' (SEQ ID NO: 60) |
| CL128 | 5'-ATCCGGCATATCTAAGTTAATAATAG-3' (SEQ ID NO: 61) |
| CL129 | 5'-CTCGAGCACCACC-3' (SEQ ID NO: 62) |

Primer pairs used for generating following mutations in Cps1B. Altered
nucleotide positions compared to wildtype sequences are underlined.

| | | |
|---|---|---|
| D133A/ D135A | CL162 CL163 | 5'-TTACCTTTATTgcgCCAgcgGATTTTCTTAG-3' (SEQ ID NO: 63) 5'-CCCATTCTGTTTGTACGTATTTTAGTCC-3' (SEQ ID NO: 64) |
| H743A | CL137 CL136 | 5'-TAAAGATGATTTATCTCAATGGTTC-3' (SEQ ID NO: 65) 5'-GTTATACCcgcCTGTAAA-3' (SEQ ID NO: 66) |
| H717A | CL164 CL165 | 5'-CCATATTTAAATGAGTTTAACATCCCC-3' (SEQ ID NO: 67) 5'-TTCAATATTAGGcgcTGGTGCAAAAATAAC-3' (SEQ ID NO: 68) |

Primer pairs used for generating following mutations in Cps7D. Altered
nucleotide positions compared to wildtype sequences are underlined.

| | | |
|---|---|---|
| H612A | CL177 CL176 | 5'-TTAAAACATTAGGAAGAGATATGGAG-3' (SEQ ID NO: 69) 5'-ATGGAGTTCCcgcCCATGTAC-3' (SEQ ID NO: 70) |
| H743A | CL179 CL178 | 5'-AAGCATTATCCAAAATTAATCTAG-3' (SEQ ID NO: 71) 5'-CCTGAAGTAATGAcgcCCCTCTAA-3' (SEQ ID NO: 72) |

TABLE 3-continued

List of primers used.

| | | |
|---|---|---|
| R1123A | CL181 | 5'-GAGAAGGACCACGCTAAGT-3' (SEQ ID NO: 73) |
| | CL180 | 5'-TATTGATAGcgcACCTATTGTT-3' (SEQ ID NO: 74) |
| K1132A | CL160 | 5'-GCTAAGTTAATTAATAGTTTTGC-3' (SEQ ID NO: 75) |
| | CL159 | 5'-GTGGTCcgcCTCTATT-3' (SEQ ID NO: 76) |

Resulting PCR products were cloned via restriction sites given in Table 4 into modified pMal-c vectors (New England Biolabs). Amplified gene sequences of Cps1B, Cps3D, Cps7D and Cps12B were cloned into the modified pMal-c vector called pMBP-csxA-His6 (tac) (Table 4), thereby replacing the csxA sequence coding for the CP of NmX (16), resulting in plasmids pMBP-cps1B-His6, pMBP-cps3D-His6, pMBP-cps7D-His6 and pMBP-cps12B-His6, respectively (Table 4). In these plasmids the encoded proteins are expressed under tac promoter control as fusion proteins with an N-terminal maltose-binding protein (MBP) fused by a protease-resistant S3N10 linker (17) and a C-terminal 6×His tag (His6).

The amplified gene sequence of Ccs2 was cloned into the modified pMal-c vector pAN37-cslB-His6 (tac), which generation is described in (14), using the restriction sites given in Table 4. Plasmid pcps1B32-858-His6 (tac) for expression of the truncated Cps1B32-858-His6 protein was cloned in two steps. First plasmid pcps1B32-1246-His6 (tac) was generated with the Q5® site-directed mutagenesis kit (New England Biolabs) according to the manufacturer's guidelines. Primers CL102/CL104 and pMBP-cps1B-His6 were used as template. Subsequently, plasmid pcps1B32-858-His6 (tac) was generated with the Q5® site-directed mutagenesis kit using primers CL128/CL129 and pcps1B32-858-His6 as template.

Mutations at positions D133/D135, H587 and H717 to alanine in Cps1B were introduced in plasmid pcps1B32-858-His6 (tac). Cps7D mutations at positions H612, H743, R1123 and K1132 to alanine were introduced in plasmid pMBP-cps7D-His6. All mutants were generated with the Q5® site-directed mutagenesis kit (New England Biolabs) and the respective primers shown in Table 3.

Example 2: Expression and Purification of Recombinant Proteins

The expression and purification protocols were carried out as described in (14). Briefly, recombinant proteins were expressed in *Escherichia coli* M15[pREP4] in 500 mL expression cultures. Protein expression was induced at $OD_{600}$ of 0.6-1.0 and the culture was further incubated at 15° C. and 200 rpm for 21 h. After harvesting the cells by centrifugation, the cell pellet was resuspended in lysis buffer (50 mM Tris, pH 8.0, 500 mM NaCl, 2 mM DTT, 0.2 mg/mL DNase (Roche), 0.1 mg/mL RNaseA (Roche), 0.1 mg/mL lysozyme (Serva) and EDTA free protease inhibitor (complete EDTA-free, Roche) and the cell suspension was additionally sonified (Branson Digital Sonifier, 50% amplitude, 8×30 s, interrupted by cooling on ice). Recombinant $His_6$-tagged proteins were enriched by immobilized metal ion affinity chromatography and a subsequent elution of proteins using an imidazole gradient (25-500 mM imidazole over 20 min). Protein-containing fractions were pooled and applied to a size exclusion chromatography column (Superdex 10/300 GL, GE Healthcare) for further purification. Obtained protein solutions were stored at −80° C.

Example 3: Determination of the Oligomerization State

The oligomerization states of Cps1B wildtype and truncation constructs were determined via size exclusion chromatography (SEC). Protein standards (gel filtration markers kit, Sigma) used to calibrate the Superdex 200 10/300 GL column (GE Healthcare) were: Thyroglobulin (669 kDa), Apoferritin (443 kDa), R-Amylase (200 kDa), Alcohol Dehydrogenase (150 kDa), Albumin (66 kDa) and Carbonic

TABLE 4

Bacterial species, strains and proteins as well as plasmids and primers used.

| Bacterial species | Protein | Genebank/uniprot accession number | Heat-inactivated strain used for gene amplification |
|---|---|---|---|
| App | Cps1B | KY798410 | 4074 |
| App | Cps3D | KY807157 | S1421 |
| App | Cps7D | B3GYR0 | 7074 |
| App | Cps12B | Q69AA8 | 8329 |
| Hi | Ccs2 | F6KWE2 | ATC 9007 |

| Plasmid | Encoded recombinant protein | Molecular mass of the protein (in kDa) | Primer | Restriction sites |
|---|---|---|---|---|
| pMBP-cps1B-His | MBP-Cps1B-His | 190 | CL57/CL59 | BamHI/AvrII |
| pMBP-cps3D-His | MBP-Cps3D-His | 177 | CL147/CL148 | BamHI/XhoI |
| pMBP-cps7D-His | MBP-Cps7D-His | 192 | CL74/CL94 | BamHI/AvrII |
| pMBP-cps12B-His | MBP-Cps12B-His | 146 | CL33/CL56 | BamHI/XhoI |
| pccs2-His | Ccs2-His | 144 | CL40/CL39 | NdeI/XhoI |
| $pCps1B_32$-1246-$His_6$ | $Cps1B_{32}$-1246-$His_6$ | 144 | CL102/CL104 | — |
| $pCps1B_{32}$-858-$His_6$ | $pCpS1B_{32-858}$-$His_6$ | 99 | CL128/CL129 | — |

Anhydrase (29 kDa). Elution volumes of protein standards normalized to the column void volume were plotted against the logarithm of their molecular weights. The equation of the standard plot obtained by linear regression was used to determine the observed molecular weight values ($M_{obs}$) of the Cps1B constructs. The oligomerization states were obtained by division of the observed molecular weight by the theoretical molecular weights of the proteins.

Example 4: Activity Tests

Enzymatic activity reactions were carried out with 0.1-0.3 nmol of purified protein in a total volume of 75 pL assay buffer (20 mM Tris pH 8.0, 1 mM DTT, 10 mM $MgCl_2$, 5-10 mM donor sugar). Donor sugars used were UDP-GlcNAc (Carbosynth), UDP-Gal (Carbosynth) and CDP-glycerol (racemic, from Sigma Aldrich). Reactions containing wild-type proteins were incubated for 24 h at 37° C. Activity tests of mutant constructs were incubated for only 3 h at 37° C. to minimize the spontaneous hydrolysis of donor-sugar.

Example 5: SDS Polyacrylamide Gel Electrophoresis (SDS-PAGE)

SDS polyacrylamide gel electrophoresis (SDS-PAGE) was performed as described in (14).

Example 6: Analysis of Enzymatic Reactions Via HPLC and Polyacrylamide Gel Electrophoresis (PAGE)

HPLC-based anion exchange chromatography (HPLC-AEC) was performed on a Prominence UFLC-XR (Shimadzu) equipped with a CarboPac PA-100 column (2×250 mm, Dionex). Samples were separated as described in (14), with the adjustment that 20 mM Tris pH 8.0 and 1 M NaCl, 20 mM Tris pH 8.0 were used as mobile phases M1 and M2, respectively. 6 µL of the samples were loaded for the detection of nucleotides at 280 nm and 50 µL for the detection of capsular polysaccharide at 214 nm. Nucleotides were separated using a linear elution gradient from 0 to 30% M2 over 11 min. Polysaccharides were separated using an elution gradient consisting of a −2 curved gradient from 0 to 30% M2 over 4 min followed by a linear gradient from 30 to 84% M2 over 33 min. Chromatography was conducted at 0.6 mL/min with a column temperature of 50° C. 4 µL of Cps3D and Cps7D reaction samples mixed with 4 µL of a 2 M sucrose solution were used for separation on high percentage (15%) PAGE and visualized by a combined alcian blue/silver staining procedure described in (18).

Example 7: Upscaling of the In Vitro Polysaccharide Synthesis and Subsequent Purification For in vitro synthesis of 5-12 mg polysaccharide, 1-25 nmol protein were incubated over night at 37° C. in reaction buffer (20 mM Tris pH 8.0, 10 mM $MgCl_2$, 1 mM DTT) with 6-10 mM of the activated sugars in a total volume of 5-10 mL. In vitro synthesized polysaccharide was purified by anion exchange chromatography (AEC) using a MonoQ HR10/100 GL column (GE Healthcare) and a linear NaCl gradient starting from 0 to 1 M NaCl at a flow rate of 1 mL/min. Polysaccharide containing fractions were pooled, dialyzed against water (ZelluTrans, Roth, 1 kDa MWCO) and freeze-dried before further analysis.

Example 8: NMR Analysis

All $^1H$, $^{13}C$ and $^{31}P$ NMR experiments were recorded as previously described (14, 16). NMR experiments were recorded on a BrukerAvance III 400 MHz spectrometer equipped with a 5-mm broadband probe (Bruker). To specify the structures and to detect the $^{13}C$ chemical shifts, $^1H$, $^{13}C$ heteronuclear single quantum coherence (HSQC), $^1H$, $^1H$ correlated spectroscopy (COSY), $^1H$, $^{31}P$ heteronuclear multiple bond correlation (HMBC), $^1H$, $^1H$ nuclear overhauser enhancement spectroscopy (NOESY) and $^1H$, $^1H$ total correlated spectroscopy (TOCSY) experiments were performed. The Bruker TopSpin 3.5p16 program was used to process NMR data.

Example 9: Bioinformatics

Homologs of CslB were identified by protein blast searches using the CslB sequence and the blastp algorithm on ncbi website (blast.ncbi.nlm.nih.gov/Blast.cgi). The given structure prediction results for the TagF-like capsule polymerase family were obtained using the intensive mode of the structure prediction tool PHYRE$^2$ (19). Sequence Alignments were performed with the Clustal Omega program (uniprot.org/align/ (21) or ebi.ac.uk/Tools/msa/clustalo/(20)).

In detail, protein structure prediction was performed for each polypeptide sequence using the structure prediction software PHYRE$^2$. Alignment of all GTA domains from SEQ ID NO. 28 (Fcs2), SEQ ID NO. 29 (Cps1B), SEQ ID NO. 30 (BtY31), SEQ ID NO. 31 (Ccs2), SEQ ID NO. 32 (Cps4B), SEQ ID NO. 41 (CslB) and SEQ ID NO. 42 (Cps12B) was performed with Clustal Omega (see above) and annotated with the Jalview software (FIGS. 10 and 18). Alignment of all TagF-like domains from SEQ ID NO. 1 (CshC), SEQ ID NO. 2 (Bt189), SEQ ID NO. 3 (Bt188), SEQ ID NO. 4 (Bt192), SEQ ID NO. 5 (Cps3D), SEQ ID NO. 6 (Cps9D), SEQ ID NO. 7 (Cps11D), SEQ ID NO. 8 (c3694), SEQ ID NO. 9 (CszC), SEQ ID NO. 10 (Cps7D), SEQ ID NO. 11 (Cps2D), SEQ ID No. 12 (Fcs2), SEQ ID No. 13 (Cps1B), SEQ ID NO. 14 (BtY31), SEQ ID NO. 15 (Ccs2), SEQ ID NO. 16 (Cps4B), SEQ ID NO. 33 (CslB), SEQ ID NO. 34 (Cps12B), SEQ ID NO. 35 (Cps6D), SEQ ID NO. 36 (Cps8D), SEQ ID NO. 37 (Cps5B), SEQ ID NO. 38 (Cps10C), SEQ ID NO. 39 (Csw), SEQ ID NO. 40 (Csy) was performed with Clustal Omega (see above) and annotated with the Jalview software (FIGS. 11, 14, 15 and 16). Alignment of all GT-B domains from SEQ ID NO. 17 (CshC), SEQ ID NO. 18 (Bt189), SEQ ID NO. 19 (Bt188), SEQ ID NO. 20 (Bt192), SEQ ID NO. 21 (Cps3D), SEQ ID NO. 22 (Cps9D), SEQ ID NO. 23 (Cps11D), SEQ ID NO. 24 (c3694), SEQ ID NO. 25 (CszC), SEQ ID NO. 26 (Cps7D), SEQ ID NO. 27 (Cps2D), SEQ ID NO. 43 (Cps6D), SEQ ID NO. 44 (Cps8), SEQ ID NO.45 (Cps5A), SEQ ID NO. 46 (Cps10D), SEQ ID NO. 47 (Csw), SEQ ID NO. 48 (Csy) was performed with Clustal Omega (see above) and annotated with the Jalview software (FIGS. 12 and 17).

Example 10: Generation of Bt-188, Cps11D and Cps4B

The gene encoding the polymerase Cps11D (uniprot: EOFCQ3) was amplified by polymerase chain reaction (PCR) from heat-inactivated bacterial lysates of *Actinobacillus pleuropneumoniae* serotype 11 strain 56153 (Frey and Nicolet 1990, *J. Clin. Microbiol.* 28, 232-6) using the primers TF156 (GCATCTGGATCCTTAT-TAAAAAGCGAGAACTTTAAAATGAAACATAATG, SEQ ID NO. 78) and TF157 (GCATCTCTCGAGATTTGT-TAATAATGAATAAAACTTCGCCATAGC, SEQ ID NO. 79) and subsequently cloned via BamHI/XhoI into the modified pMal-c vector pMBP-csxA-His6 mentioned in paragraph [00170], resulting in the plasmid pMBP-cps11D-His6.

The gene encoding the polymerase Cps4B (uniprot: F4YBG0) was amplified by PCR from heat-inactivated bacterial lysates of *Actinobacillus pleuropneumoniae* serotype 4 strain M62 (Frey and Nicolet 1990, J. Clin. Microbiol. 28, 232-6) using the primers IB 46 (GCTC-CAATAACAATAACAACAACAATAACAATAACG-GATCCAATAAAGTAAAACGTAAATTTA GAAAAT-TACTACGAGATCC, SEQ ID NO. 80) and IB 47 (GGTGGTGGTGGTGGTGCTCGAGGGCTTTCTCCGT-GTATGAATAAAGTGTG, SEQ ID NO. 81) and cloned according to the restriction free protocol described in Bond and Naus 2012 (Nucleic Acids Res. 40, W209-13) into the modified pMal-c vector pMBP-csxA-His6 mentioned in paragraph [00170], resulting in the plasmid pMBP-cps4B-His6. Sanger sequencing demonstrated that the amplified cps4B gene contained two point mutations if compared to the sequence from the uniprot database (uniprot: F4YBG0). The mutations led to the amino acid exchanges A635T and R176S.

The protein sequence of Bt-188 was reverse translated into DNA (SEQ ID NO. 77) from the sequence deposited in the database (Genbank: AHG82487.1), synthesized and cloned into the expression vector pET-22b(+) via NdeI/XhoI, resulting in the plasmid pBt-188-His6.

The gene cps7B encoding the CTP:glycerol-3-phosphate cytidylyltransferase (GCT) from *Actinobacillus pleuropneumoniae* serotype 7 strain AP76 was amplified by PCR from heat-inactivated bacterial lysates using the primers TF116 (GCATCTCTCGAGCTCTTTTTCGTGAATTTGTTTTTGTC, SEQ ID NO. 82) and TF117 (GCATCTCATATGAAAAAAGTATTAACCTATGGAACC, SEQ ID NO. 83) and cloned into p1N37-cslB-$His_6$ (Litschko et al. 2015, *J. Biol. Chem.* 290, 24355-56), replacing the cslB gene and resulting in the construct pcps7B-His6.

Expression and purification of all enzymes was performed as described in paragraph [00174], with the adjustment that the buffer for the Cps7B-His purification was changed to 10 mM Tris pH 8.0, 300 mM NaCl, 10% glycerol, 1 mM DTT.

Activity tests were performed as described in [00177]. 5 mM UDP-GalNAc (Sigma) and 5 mM UDP-Glc (Roche) were used as donor substrate in the Cps4B reaction. 5 mM CTP (Sigma) and 5 mM sn-glycerol-3-phosphate (Sigma) were used as substrates for the GCT reaction.

HPLC analysis was performed as described in paragraph [00178]. However, separation of nucleotides in the Cps11D and Bt-188 reaction was performed using a linear gradient from 0 to 25% M2 over 41 min.

The upscaled polymer synthesis was performed as described in [00180] with the adjustments that the reaction volume was 2.2-3.5 ml, the concentration of sugar donors, CTP and sn-glycerol-3-phosphate was 5 mM each. The polymer was purified by anion exchange chromatography (AEC) using a MonoQ HR10/100 GL column (GE Healthcare) at a flow rate of 6 ml/min using a combination of linear gradients: from 0 mM to 150 mM NaCl over 3 column volumes (CV) and from 150 mM to 1000 mM NaCl over 28.5 CV. NMR analysis was performed as previously described (Litschko et al. 2018, *MBio.* 9, e00641-18).

Example 11: Synthesis of an Enantiopure Polysaccharide

Cps7B-His6 (subsequently referred to as Cps7B or GCT) was cloned, expressed in *E. coli* and purified using affinity and size exclusion chromatography (FIG. 25A).

An HPLC-AEC assay was developed to confirm the CTP:glycerol-3-phosphate cytidylyltransferase activity of Cps7B. As expected, Cps7B converts its substrates CTP and sn-glycerol-3-phosphate (not UV-active at 280 nm) into enantiopure CDP-glycerol (brown chromatogram labeled 'GCT (Cps7B)'). Small amounts of CDP in the reaction mixture can also be detected in the CTP control and are consequently not a side product of the GCT reaction. In the combined one-pot synthesis (green chromatogram labeled 'GCT (Cps7B)+polymerase (Cps7D)'), Cps7B consumes CTP to generate CDP-glycerol, which, together with UDP-Gal, is in turn used up by the polymerase Cps7D to synthesize polymer. The nucleotide products of this reaction are UDP (resulting from the galactose transfer) and CMP (resulting from the sn-glycerol-3-phosphate transfer) (FIG. 25B).

Corresponding Alcian blue/silver stained PAGE was then used to visualize the polymer generated in the one-pot reaction (FIG. 25C).

Results

Example 12: Definition of the TagF-Like Capsule Polymerase Family

With the aim to analyze the conservation and to identify homologs of CslB, (i) protein blast searches using the CslB amino acid sequence (AEQ62070.1) was performed and (ii) the literature for linear CPS consisting of oligosaccharides connected through phosphodiesters was manually searched. The best score (99% query cover, 58% sequence identity) in the protein blast search was obtained for the putative glycosyltransferase Cps12B (AAS7749.1) from *Actinobacillus pleuropneumoniae* serotype 12 (App12). App12 expresses a CPS identical to the NmL-CPS consisting of a GlcNAc-trimer linked by a phosphodiester bond (22) (FIG. 1A and FIG. 7).

Another hit was Ccs2 (AEC50903.1, 97% query cover, 33% sequence identity) from *Haemophilus influenzae* serotype c (Hic), which has been reported to express a CPS consisting of a disaccharide repeating unit composed of GlcNAc and Gal connected by a phosphodiester bond (23) (FIG. 1A and FIG. 7). Literature searches revealed that similar CPS structures were found on App1 (24) (FIG. 1A), App4 (25) and Hif (26, 27) (FIG. 7).

Moreover, a multitude of strains were found that express a group II CPS in which the hexoses are not linked by phosphodiesters alone but through glycerol-phosphate moieties instead. Among them are NmH (28) and NmZ (29), *E. coli* K2 (30), App2 (31), App3 (32), App7 (33), App9 (34), App11 (35) as well as *Bibersteinia trehalosi* (Bt) T3 (36), T4 (37) and T15 (38) (former *Mannheimia* (*Pasteurella*) *haemolytica*) (39). Although some of these CPS are modified by glycosylation or O-acetylation, they appear to have highly similar polymer backbones (FIG. 7).

Following the hypothesis that all of these CPS backbones are generated by homologs of CslB, it was analyzed the DNA sequence information of the above mentioned strains and identified putative capsule polymerases by their conserved location in the capsule gene cluster and their unusual length of more than 2500 bp per open reading frame (ORF) (FIG. 1B). Homology modelling was performed for each polypeptide sequence using the structure prediction software PHYRE$^2$ (19).

As a characteristic feature, all putative CPs contained a domain adopting a GT-B-like fold that was modeled with 100% confidence in each case onto the crystal structure of TagF, a teichoic acid polymerase from *Staphylococcus epidermidis* (15) (FIG. 8). Thus, this domain was called TagF-like domain and the herein described polymerases form the TagF-like capsule polymerase family. TagF adopts a GT-B like fold and uses CDP-glycerol as donor substrate for the consecutive transfer of glycerol-phosphate units (15).

Consequently, it was hypothesized that the TagF-like domain transfers the hexose-phosphate, N-acetylhexosamine-phosphate and glycerol-phosphate moieties of the polymers shown in FIG. 1A and FIG. 7. In addition to the TagF-like domain, all models were predicted to have either a GT-A folded domain at the N-terminus or a GT-B folded domain C-terminally flanking the TagF-like domain.

The GT-A fold was modeled (among others) onto the glucuronic acid transferase domain of the polymerase K4CP of *E. coli* K4, an enzyme synthesizing a chondroitin-like CPS (40). Consistent with the template being an inverting GT, the GT-A fold was only found in polymerases from strains expressing a capsular polymer in which a β-glycosidic linkage is present (FIG. 1; FIG. 7 and FIG. 8).

In contrast, the GT-B fold, modeled (among others) onto the α-glycosyltransferase TarM from *Staphylococcus aureus*, an enzyme modifying the glycerol moieties of teichoic acid (41), that is only present in strains expressing a CPS in which an α-glycosidic linkage is present (FIGS. 1A and D; FIG. 7 and FIG. 8). The two resulting archetypal architectures will hereafter be referred to as GT-A/TagF-like and TagF-like/GT-B. In addition to the two putative catalytic domains, some of the GT-A/TagF-like and TagF-like/GT-B variants were predicted to have a third domain at either the far N- or C-terminus, respectively, that was modeled onto proteins rich in tetratricopeptide repeats (TPRs). TPRs are usually involved in protein-protein interactions and do not show enzymatic activity (42).

Example 13: Functional Testing of Recombinant Capsule Polymerases

Besides CslB, five representative of the TagF-like capsule polymerase family were selected for further analyses. Cps12B (App12) was chosen due to its GT-A/TagF-like architecture and high similarity to the already described CslB polymerase. Cps1B (App1) and Ccs2 (Hic) were selected as candidates generating a dimeric repeating unit and carrying a C-terminal TPR domain. Cps3D (App3) and Cps7D (App7) linking the glycerol at position 2 or 1, respectively, were chosen as TagF-like/GT-B folded variants (FIG. 1D; FIG. 8). The ORFs coding for the putative polymerases were amplified from bacterial lysates, cloned with different N- and C-terminal tags (maltose binding protein (MBP) and/or hexa hisitidine (His6)) and expressed in *E. coli*. The protein construct of each polymerase resulting in the best expression level, namely MBP-Cps1B-His6, MBP-Cps3D-His6, MBP-Cps7D-His6 and Ccs2-His6 was purified by affinity chromatography and size exclusion chromatography. For activity testing, the enzymes were incubated with their donor substrates (nucleotide activated carbohydrates or alditols, e.g. UDP-GlcNAc (uridine diphosphate N-acetylglucosamine) or CDP-glycerol (cytidine diphosphate glycerol) and after 3 h the reaction was analyzed using HPLC-AEC. The HPLC-AEC assay allows the detection and separation of the donor substrates as well as all reaction products (FIG. 2), with the exception of the App3- and App7-polymers that lack the UV active N-acetyl-group. These polymers were detected using an alcian blue/silver stained PAGE (FIGS. 2E and F).

In all reactions, the consumption of the activated donor substrates and the formation of the by-products (UMP or CMP and UDP) in the 280 nm channel (compare controls and reaction in FIG. 2) was observed, as well as the formation of polymer in the 214 nm channel (for Cps12B (App12), Cps1B (App1) and Ccs2 (Hic)) and in the alcian blue/silver stained PAGE (for App3 and App7). The fact that all polymerases consume their putative donor substrates corroborates the correctness of the predicted enzyme function and the PHYRE2 homology modelings. It is of note that all enzymatic reactions take place in the absence of an acceptor. Thus, all polymerases are able to catalyze the polymer synthesis de novo.

Example 14: Confirming the Identity of In Vitro Synthesized Polymers with the Natural Bacterial Capsules To confirm the identity and to determine the detailed structure of the in vitro synthesized polymers by NMR spectroscopy, the in vitro polysaccharide production was scaled up. The resulting products were purified by preparative anion exchange chromatography (AEC) using a NaCl-gradient which enables the separation from other reaction components. The structure of the synthesized polysaccharide was determined by high resolution one- and two-dimensional $^1$H, $^{13}$C and $^{31}$P NMR techniques.

The polymers synthesized in vitro by Cps1B (App1), Ccs2 (Hic), Cps3D (App3) and Cps7D (App7) were analyzed more extensively by $^1$H-NMR, $^{31}$P-NMR, $^1$H, $^{13}$C-HSQC, $^1$H, $^{31}$P-HMBC, 2D-COSY and selective NOESY and TOCSY experiments. To provide a clear and concise display of the findings, only the $^{13}$C chemical shifts are presented in comparison to published reference spectra of the natural CPS (Table 5 and 6).

The backbone structures of the App1- and Hic-CPSs only differ by their position of the glycosidic linkages (FIG. 1A). The NMR results of the polysaccharide synthesized by MBP-Cps1B-His6 and Ccs2-His are in perfect congruence with the published data of the de-O-acetylated bacterial capsules of App1 and Hic described by Altman et al. (24) and Branefors-Helander et al. (23), respectively (Table 5).

Table 5: Comparison of $^{13}$C-chemical shifts of natural (n) and in vitro (iv) synthesized App1 and Hic polysaccharides. The chemical shift values of the natural App1 polymer (App1 n) and of the natural Hic polymer (Hic n) were taken from Altman et al. (24) and Branefors-Helander et al. (23), respectively. $^{13}$C-chemical shifts of in vitro synthesized polymers were obtained from $^1$H, $^{13}$C-HSQC experiments.

TABLE 5

Comparison of $^{13}$C-chemical shifts of natural (n) and in vitro (iv) synthesized App1 and Hic polysaccharides. The chemical shift values of the natural App1 polymer (App1 n) and of the natural Hic polymer (Hic n) were taken from Altman et al. (24) and Branefors-Helander et al. (23), respectively. $^{13}$C-chemical shifts of in vitro synthesized polymers were obtained from $^1$H, $^{13}$C-HSQC experiments.

| | $^{13}$C chemical shifts | | | | | | | | | | | |
|---|---|---|---|---|---|---|---|---|---|---|---|---|
| | glucosamine | | | | | | galactose | | | | | |
| | $C_1$ | $C_2$ | $C_3$ | $C_4$ | $C_5$ | $C_6$ | $C_1'$ | $C_2'$ | $C_2'$ | $C_4'$ | $C_5'$ | $C_6'$ |
| | | | | | | ppm | | | | | | |
| Comparison of natural (n) and in vitro (iv) synthesized App1 polymer | | | | | | | | | | | | |
| App1 n (24) | 101.8 | 56.2 | 73.9 | 74.9 | 75.9 | 61.3 | 96.7 | 69.1 | 69.6 | 69.7 | 71 | 67.9 |
| App1 iv | 101.7 | 56.3 | 73.9 | 74.8 | 75.9 | 61.3 | 96.8 | 69.1 | 69.4 | 70.0 | 71.0 | 67.8 |
| Comparison of natural (n) and in vitro (iv) synthesized Hic polymer | | | | | | | | | | | | |
| Hic n (23) | 104.3 | 57 | 74.1 | 75.1 | 76.2 | 61.5 | 97.6 | 68.7 | 80.1 | 70.3 | 72.9 | 62.2 |
| Hic iv | 104.3 | 57.1 | 74.1 | 75.0 | 76.2 | 61.6 | 97.7 | 69.0 | 79.9 | 70.3 | 73.0 | 62.2 |

Due to the fact that the natural App3-capsule polymer is modified by glycosylation (FIG. 1A), the $^{13}$C-chemical shifts of the in vitro synthesized App3-polymer were additionally compared to the *N. meningitidis* serogroup H (NmH) CPS consisting of the repeating unit [-4)-a-Gal-(1-2)-Gro-(3-PO4] (45), which is identical to the unmodified backbone of the App3-CPS (FIG. 7). The chemical shifts of the in vitro synthesized App3-polymer and the natural NmH polymer are in perfect congruence (Table 6). Unfortunately, there is no reference spectrum of the unmodified App7-CPS backbone structure available. Thus, the in vitro synthesized polymer was only compared to the natural App7 polymer, which is additionally decorated with a galactose position at position 4 ($C_4$) of the galactose moiety within the chain (33) (FIG. 1A). The $^{13}$C-chemical shifts coincide perfectly, only differing for $C_4$ of the galactose position, which is shifted upfield due to the lacking modification (Table 6).

Table 6: Comparison of $^{13}$C-chemical shifts of in vitro (iv) synthesized App3 and App7 polysaccharides and reference spectra (NmH, App7 n). The chemical shift values of natural NmH and App7 polymers were taken from van der Kaaden et al. (45) and Beynon et al. (33), respectively. $^{13}$C-chemical shifts of in vitro synthesized polymers were obtained from $^1$H, $^{13}$C-HSQC experiments.

Example 15: Truncational Studies of Cps1B and Relevance of the Tetratricopeptide Domain Many TagF-like polymerases were predicted to contain a domain modeled on templates rich in tetratricopeptide repeats (TPRs) (FIG. 1C,D and FIG. 8). Since TPRs are known for mediating protein-protein interactions (42, 46), it was hypothesized that the predicted TPR domains do not participate in the catalytic activity of the TagF-like polymerases. To proof this hypothesis, it was aimed to truncate the TPR domain in Cps1B and Cps7D as representative candidates for the GT-A/TagF-like and the TagF-like/GT-B architecture, respectively. MBP-Cps1B-His6 was initially purified using a combination of metal ion affinity chromatography and size exclusion chromatography. No full-length protein (189 kDa) could be detected in the resulting protein fraction, but the preparation was dominated by an N-terminal degradation product of app. 100-150 kDa (FIG. 9, black arrow).

With the aim to obtain homogeneity prior to the truncation of the TPR domain, N-terminal sequencing of the major degradation product was performed and revealed a fragment truncated N-terminally by 31 amino acids. Thus, the N-terminal truncation construct Cps1B32.i246-His6 was first generated. Cps1B32_1246-His6 was still active and dis-

TABLE 6

Comparison of $^{13}$C-chemical shifts of in vitro (iv) synthesized App3 and App7 polysaccharides and reference spectra (NmH, App7 n). The chemical shift values of natural NmH and App7 polymers were taken from van der Kaaden et al. (45) and Beynon et al. (33), respectively. $^{13}$C-chemical shifts of in vitro synthesized polymers were obtained from $^1$H, $^{13}$C-HSQC experiments.

Figure 3:
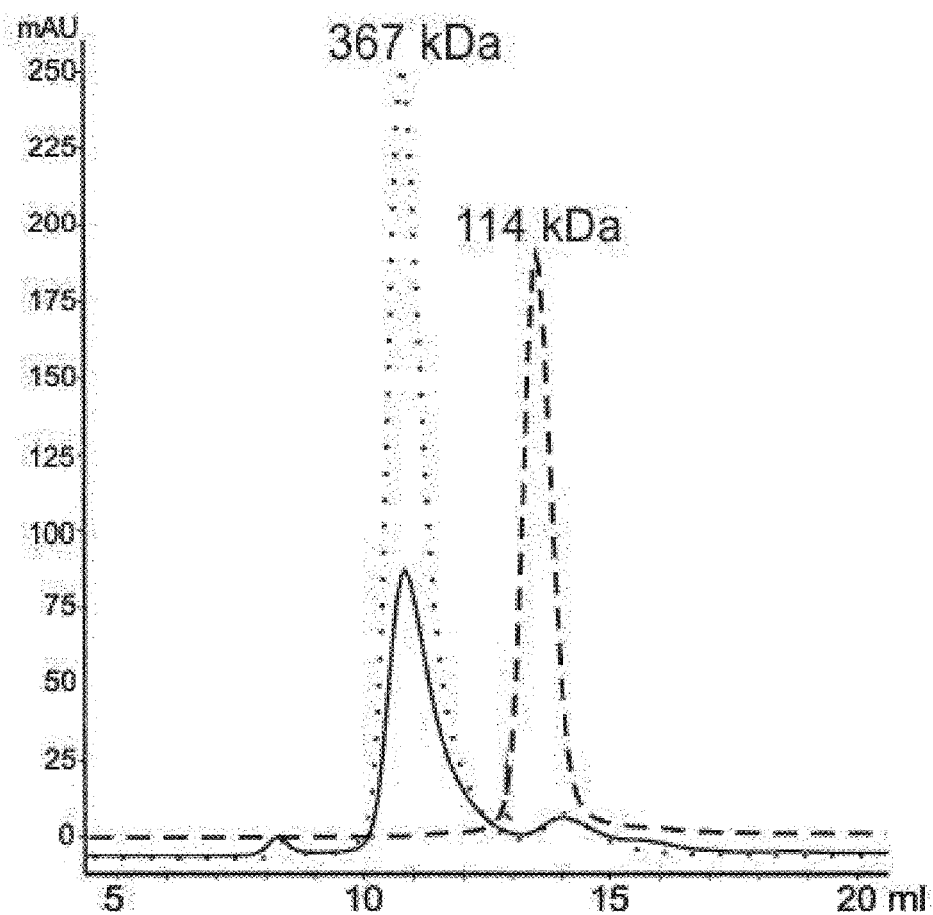
FIG. 3: Truncation studies of Cps1B.
A) Elution profiles of preparative size exclusion chromatography experiments of full-length and truncated Cps1B constructs. $M_W$ represents the theoretical molecular weight of the proteins in a monomeric state. $M_{obs}$ represents the observed molecular weight obtained from the elution profile in preparative SEC based on the calibration of the column with standard proteins. The oligomerization states were determined by subdividing $M_W$ by $M_{obs}$. B) Chemical composition of the unmodified repeating unit of the App1 capsule polysaccharide characterized by Altman et al. (1986) (24). C) Identical $^1$H-NMR spectra of both polysaccharides synthesized by full-length (MBP-Cps1B-His$_6$) and truncated Cps1B (Cps1B$_{32-858}$-HiS$_6$) demonstrating that the absence of the TPR domain in Cps1B32-858-His does not alter the chemical composition of the synthesized polysaccharide structure.
Figure 3:
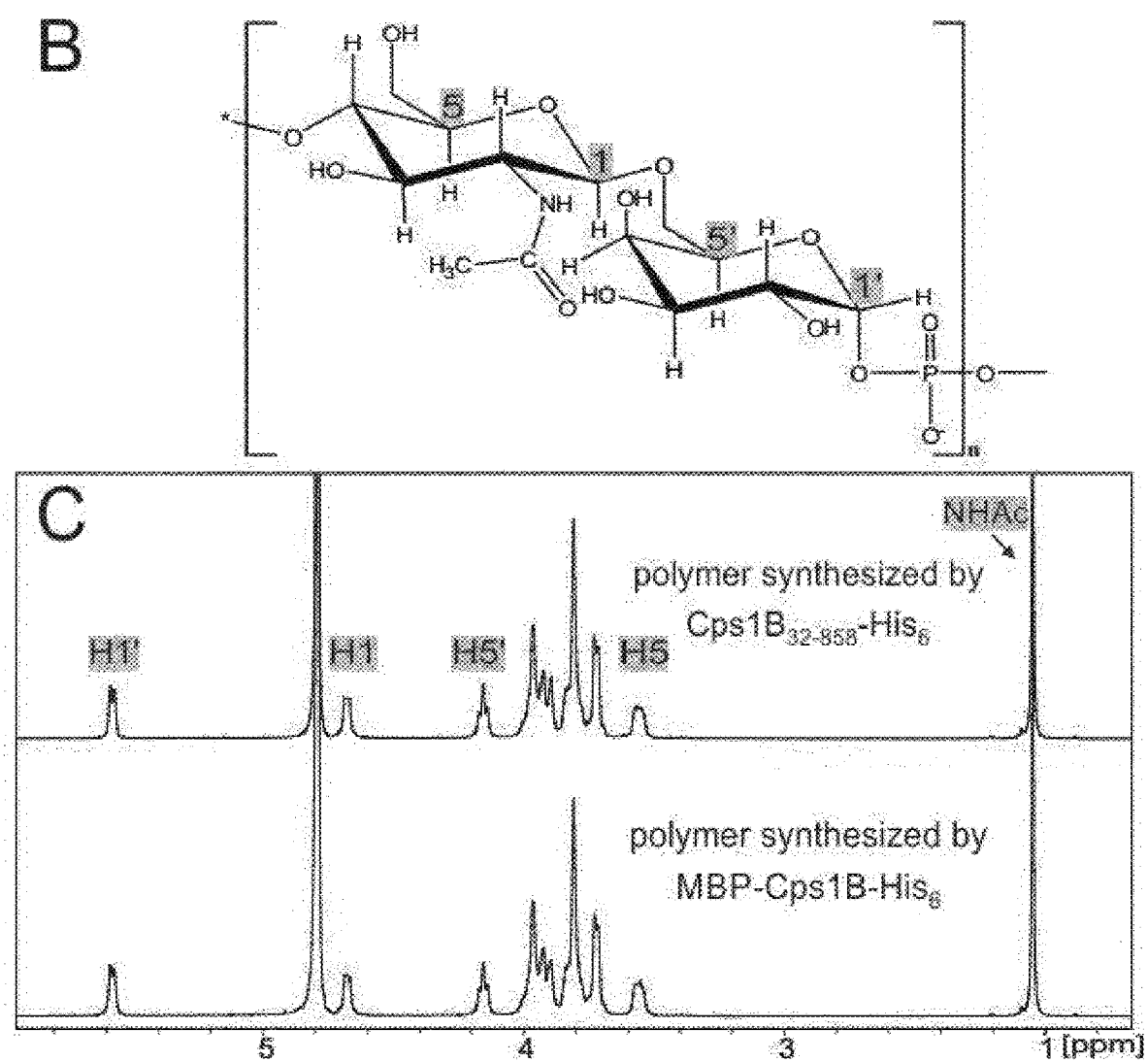

| | $^{13}$C chemical shifts | | | | | | | | |
|---|---|---|---|---|---|---|---|---|---|
| | Galactose | | | | | | Glycerol | | |
| | $C_1$ | $C_2$ | $C_3$ | $C_4$ | $C_5$ | $C_6$ | $C_1'$ | $C_2'$ | $C_3'$ |
| | | | | | ppm | | | | |
| Comparison of in vitro (iv) synthesized App3 and chemically identical NmH polymer | | | | | | | | | |
| NmH (45) | 99.3 | 69.6 | 70 | 75.8 | 71.9 | 62.0 | 62.5 | 78.3 | 65.8 |
| App3 iv | 99.1 | 69.8 | 69.9 | 75.9 | 72.1 | 62.1 | 62.4 | 78.4 | 65.9 |
| Comparison of natural (n) and in vitro (iv) synthesized App7 polymer | | | | | | | | | |
| App7 n (33) | 99.3 | 68.5 | 75.6 | 75.8 | 71.2 | 61.6 | 69.5 | 70 | 67.5 |
| App7 iv | 99.1 | 68.1 | 75.7 | 69.1 | 71.5 | 61.8 | 69.1 | 70.0 | 67.2 | played increased homogeneity in SDS PAGE analysis (FIG. 9). In size exclusion chromatography (SEC) experiments the construct eluted as single peak with an apparent molecular weight ($M_w$) of a di- to trimer (FIG. 3A).

To investigate if the TPR domain is necessary for enzymatic activity, the N-terminally and C-terminally truncated construct Cps1B32_858-His6 was subsequently generated. As expected, Cps1B32-858-His6 maintained its activity in the HPLC-AEC assay, but eluted as a monomer during SEC (FIG. 3A). To ensure that the lack of the TPR domain and the change in oligomeric state did not alter the identity of the produced polymer, the reaction was up-scaled and the polysaccharide was analyzed by $^1$H NMR. FIG. 3C shows that the $^1$H-NMR spectra obtained for the polysaccharide synthesized either in the presence of MBP-Cps1B-His or Cps1B32-858-His6 are in perfect congruence. It was surprisingly that attempts to truncate the N-terminal TPR domain of Cps7D failed. The construct showed low expression levels and could not be purified.

Example 16: Mutational Studies of TagF-Like Capsule Polymerase Family Members

Figure 1:
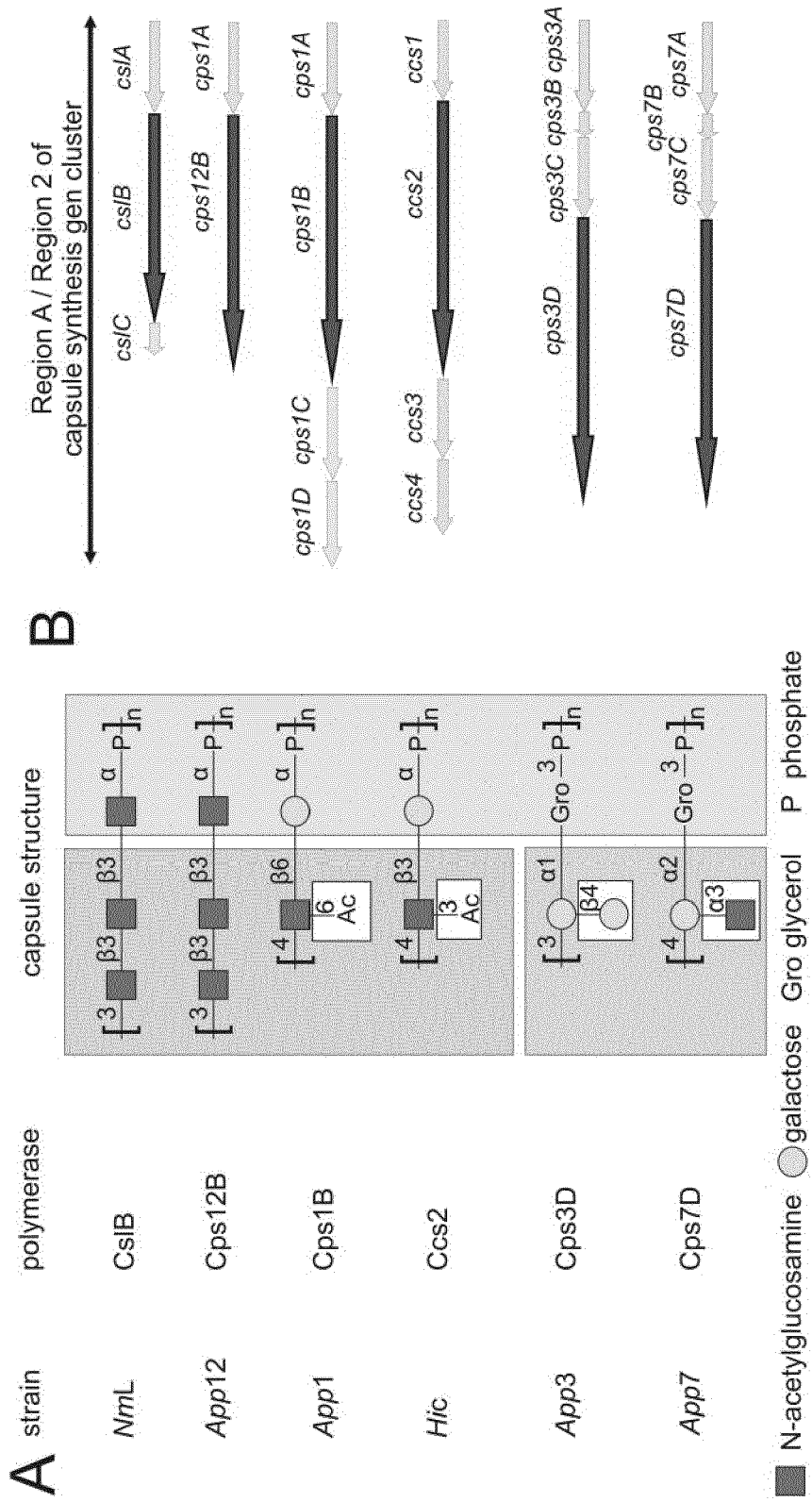
FIG. 1: Overview of the TagF-like capsule polymerases.
A) List of the characterized capsule polymerases that generate CPS backbones consisting of hexoses (red, violet) and hexose-phosphate or glycerol-phosphate units (green). Some capsules are additionally modified by O-acetylation or glycosylation (white boxes). B) Scheme of the serogroup-specific regions of the capsule gene clusters that are associated with the capsule synthesis. Genes encoding capsule polymerases are colored in red. Schematic domain organization of C) GT-A/TagF-like and D) TagF-like/GT-B-folded CPs. The coloring of each domain refers to the coloring of the moiety it putatively transfers during CPS assembly (see A). E) Excerpt of multiple sequence alignments highlighting conserved positions from each domain. F) Red: Homology model of the GT-A domain of Cps1B modeled on K4CP showing the aspartates of the DxD motif. Green: Homology model of the TagF-like domain of Cps7D modelled on TagF of S. epidermidis depicting the two catalytically important histidines. Violet: Homology model of the GT-B domain modeled on TarM of S. aureus showing the conserved lysine and arginine positions. All protein models were generated by PHYRE$^2$.
Figure 1:
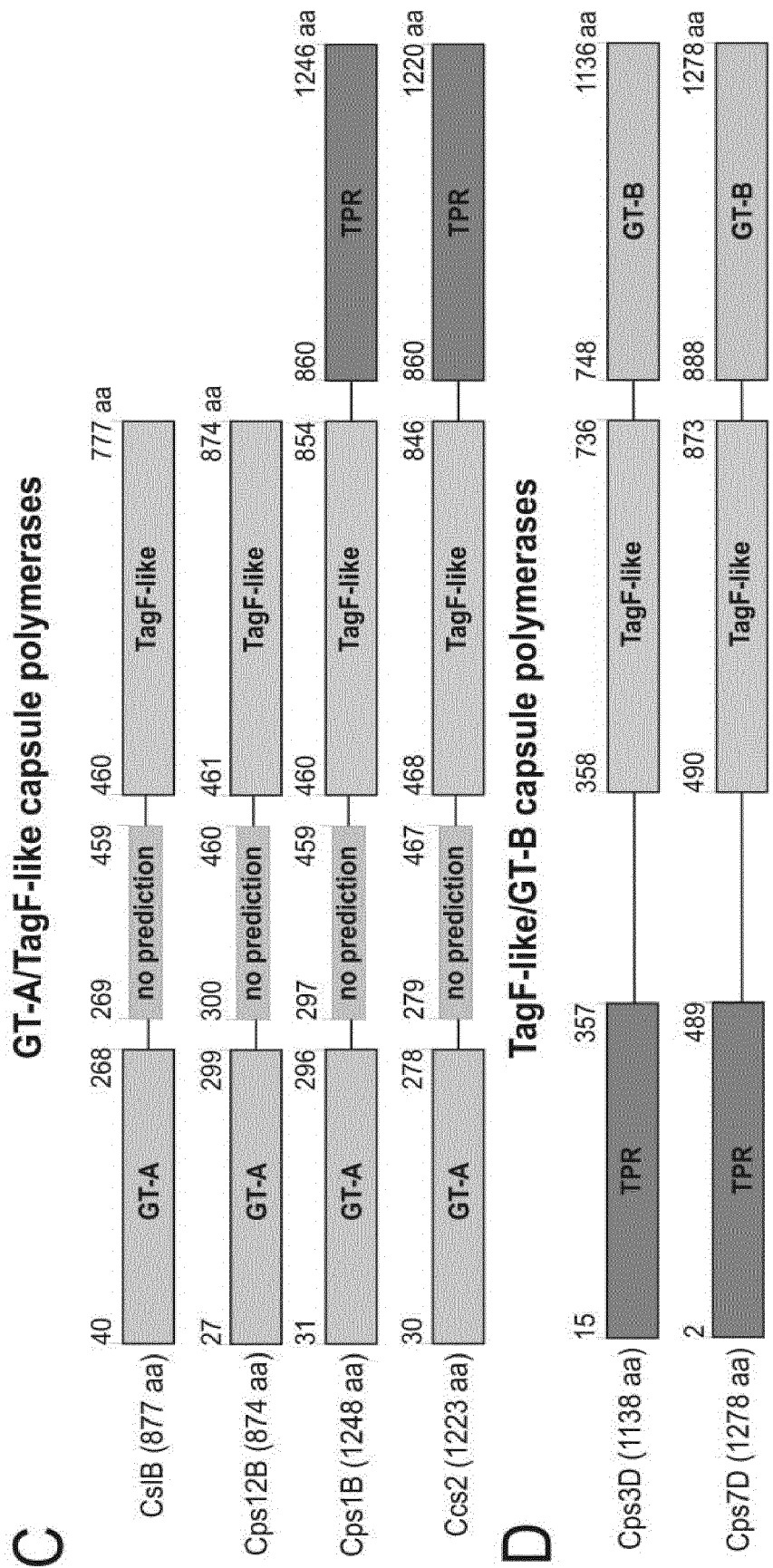

The alignments in FIG. 1E and the alignments in FIGS. 10 and 11 show that the DxD motif could be identified in the GT-A domain of all GT-A/TagF-like capsule polymerases and that the two histidine positions align in the TagF-like domain of all polymerases analyzed. Positions K331 and R326 in TarM, the template for modeling the N-terminal GT-B fold in TagF-like/GT-B folded polymerases (FIG. 1 and FIG. 8), were shown to be crucial for the activity of TarM (41). Both positions aligned perfectly with identical motifs in all GT-B folded domains of the polymerases displaying the TagF-like/GT-B architecture (FIG. 1 and FIG. 12).

Figure 4:
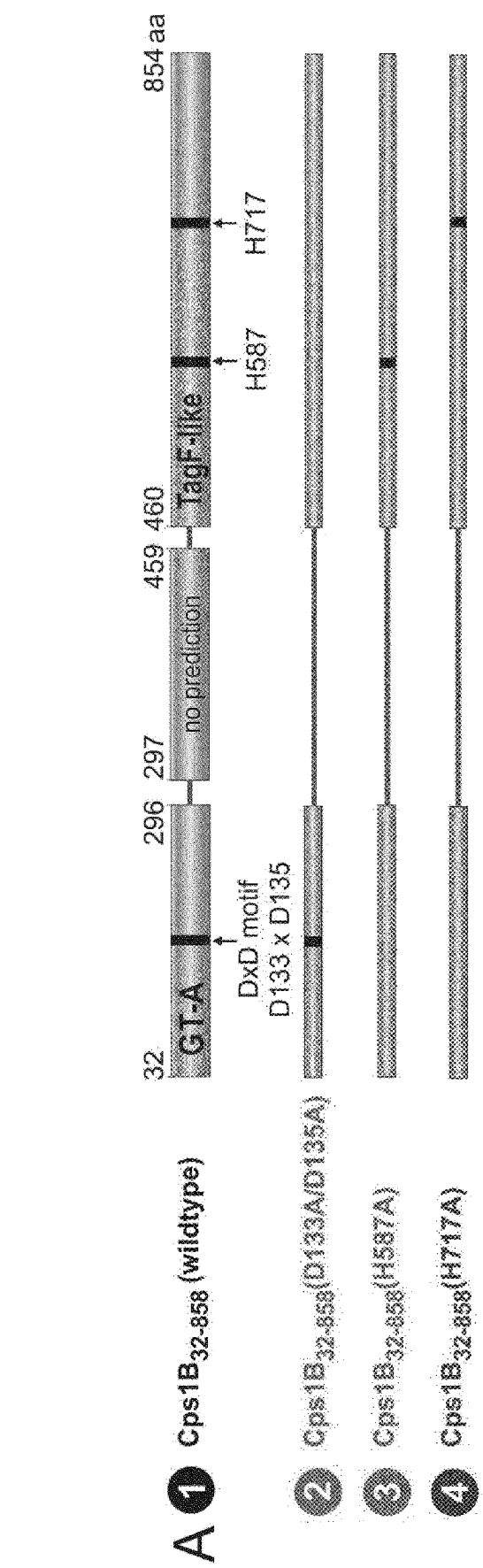
FIG. 4: Site-directed mutagenesis studies of Cps1B as representative of the polymerases of the GT-A/TagF-like architecture.
A) Schematic representation of Cps1B$_{32\_858}$-His6 showing conserved positions in each domain and the single domain mutants. B) Cps1B reaction scheme. C) HPLC-AEC analyses (left panel: 280 nm and right panel: 214 nm) show that all single domain mutants (2-4) are unable to produce polymer. Small amounts of UMP detected in the reactions are found in the controls as well, indicating that they result from spontaneous, enzyme-independent hydrolysis. However, combining two single domain mutants in trans restores donor sugar uptake and polymer synthesis, as documented by HPLC-AEC and D) alcian blue/silver stained PAGE.
Figure 4:
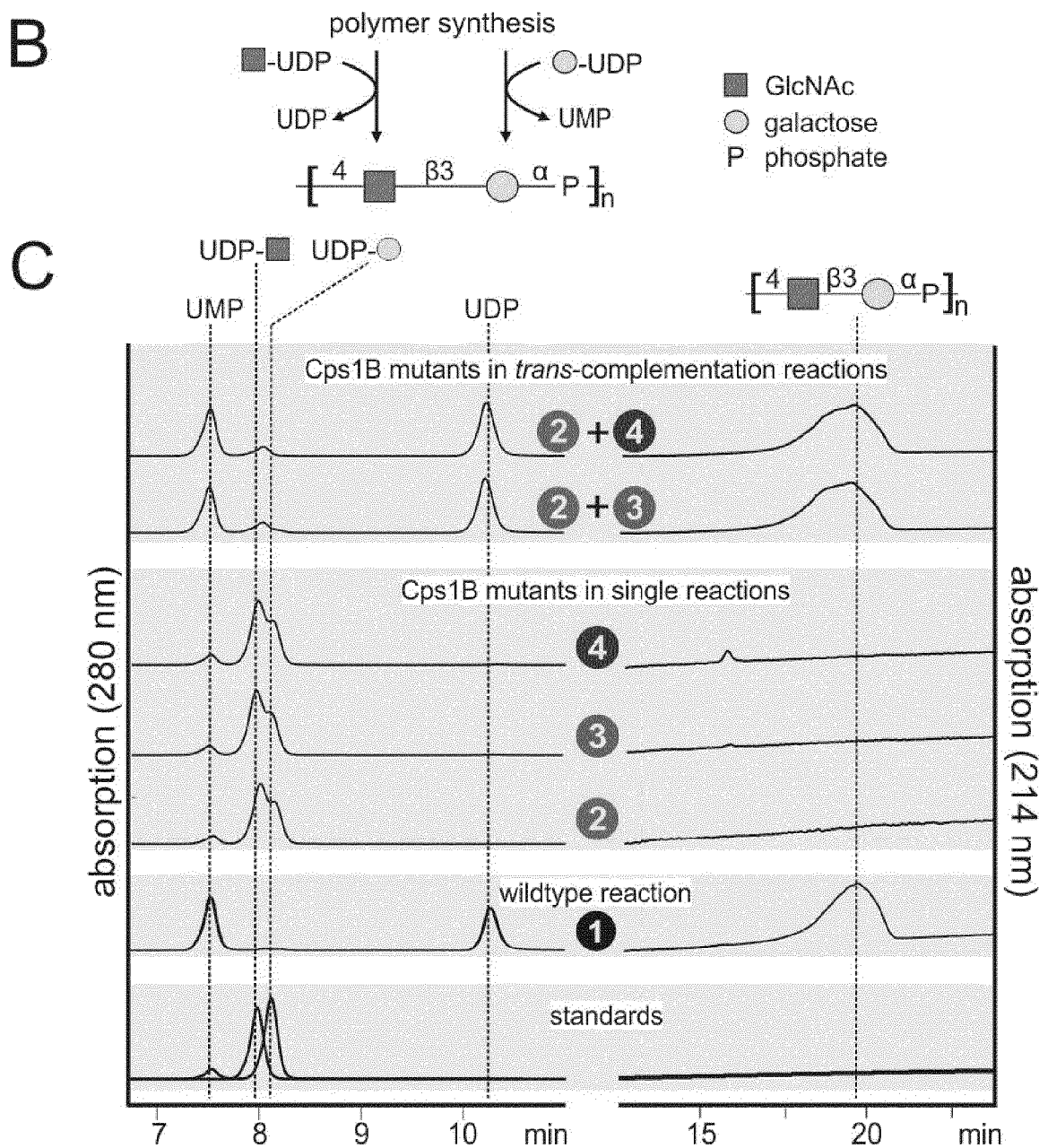
Figure 4:
Figure 5:
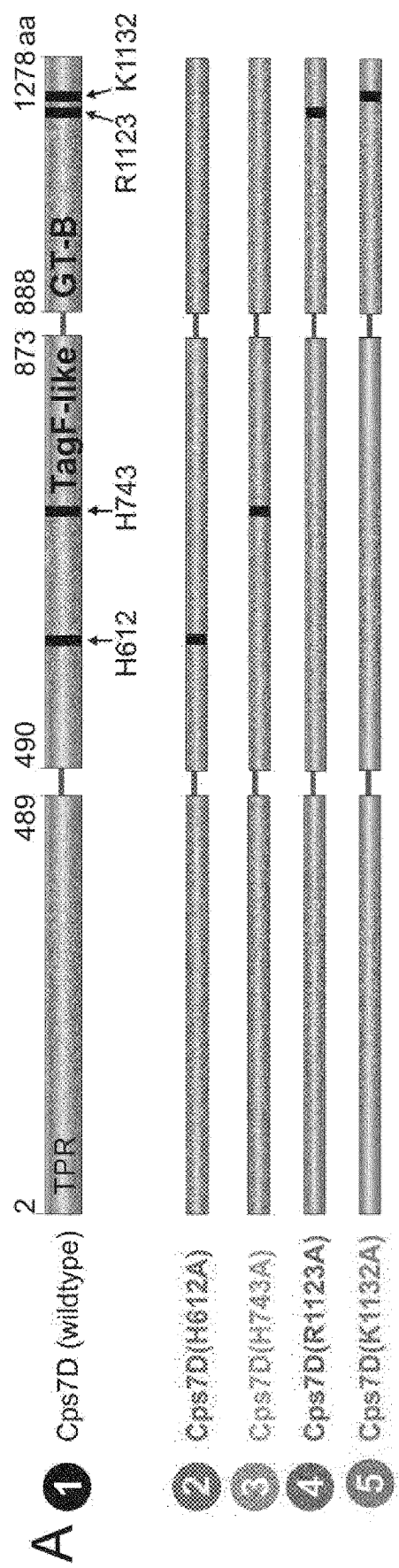
FIG. 5: Site-directed mutagenesis studies of Csp7D as representative of the polymerases of the TagF-like/GT-B architecture.
A) Schematic representation of Csp7D demonstrating conserved positions in each domain and the single domain mutants. B) Cps7D reaction scheme. C) HPLC-AEC analysis (left panel: 280 nm and right panel: 214 nm) show that all single domain mutants (2-5) are unable to produce polymer. Small amounts of CMP and UMP detected in the reactions are found in the controls as well, indicating that they result from spontaneous, enzyme-independent hydrolysis. Combining two single domain mutants in trans restores donor sugar uptake and polymer synthesis, depicted by HPLC-AEC and D) alcian blue/silver stained PAGE.
Figure 5:
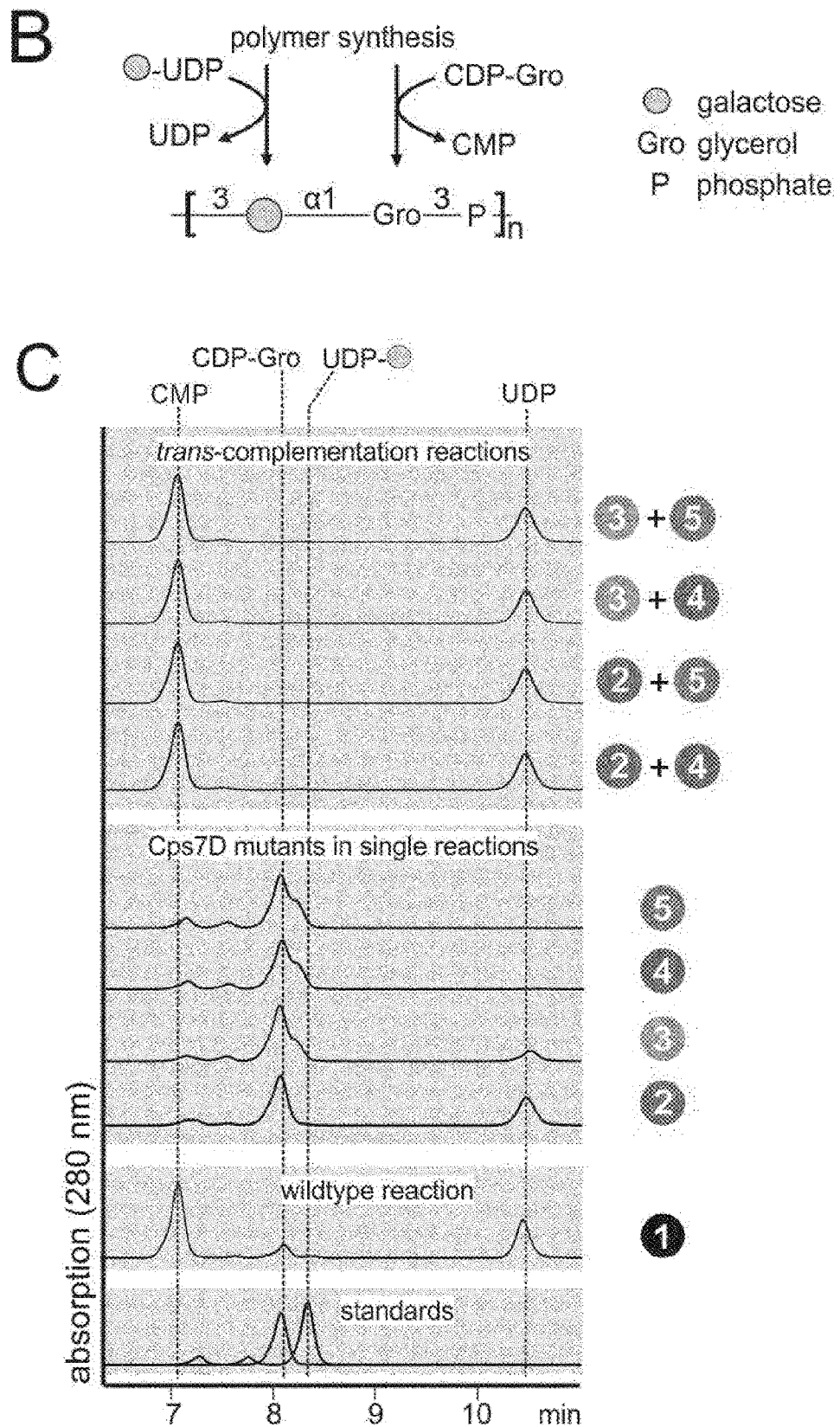
Figure 5:
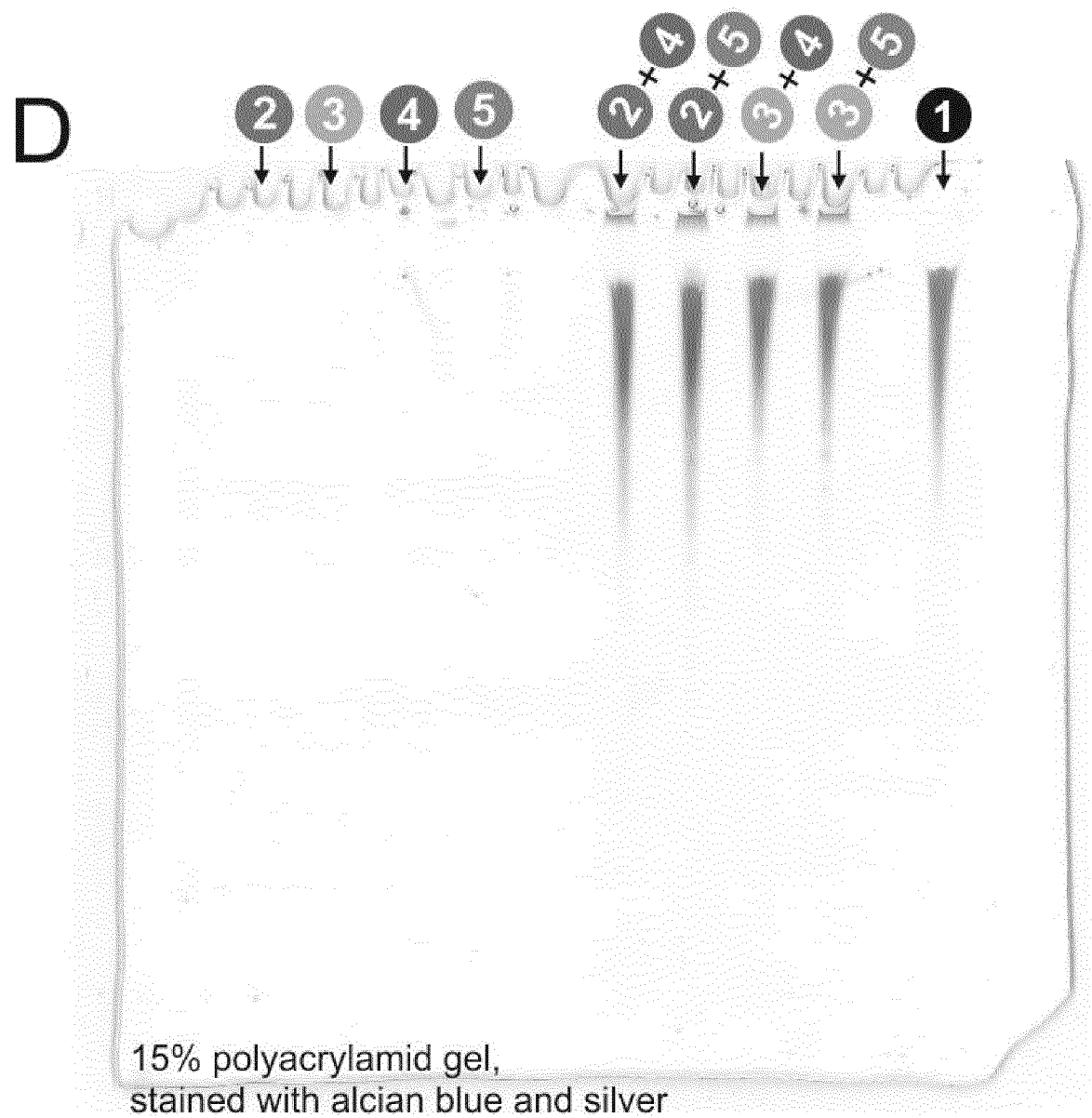
Figure 6:
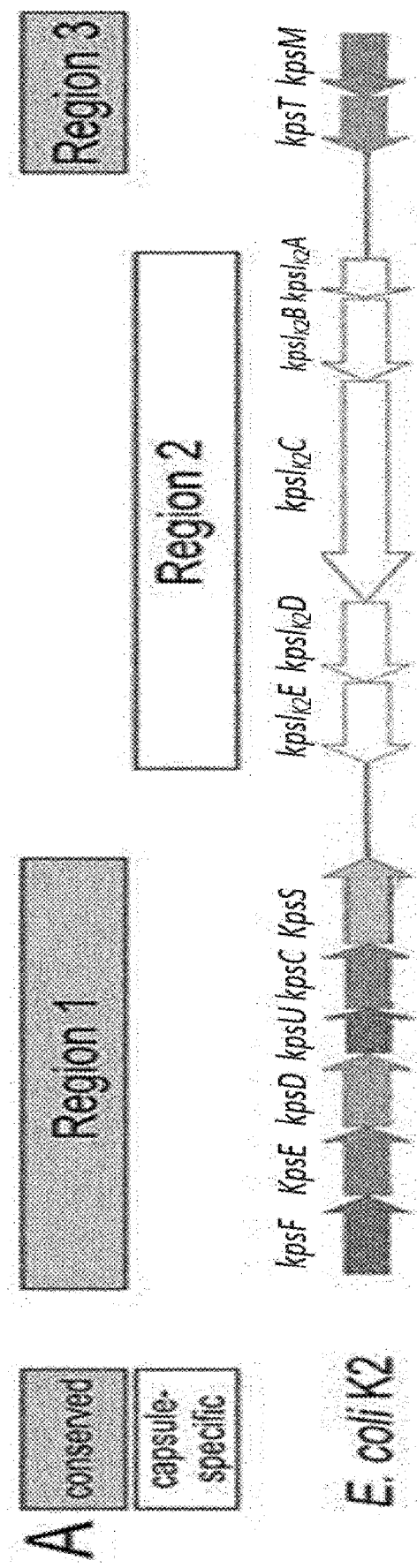
FIG. 6: Schematic overview of the capsule gene clusters of A) E. coli K2 B) NmL C) App serotypes 1, 3, 7 and 12 and D) Hi serotype c. The gene clusters are divided into conserved regions (grey boxes) and capsule-specific regions (white boxes). The conserved regions encode proteins necessary for translocation and export of the polysaccharide to the cell surface. The identified polymerases of each strain are highlighted in red and localized in the capsule specific region. Genes and interspaces in this scheme are not drawn to scale.
Figure 6:
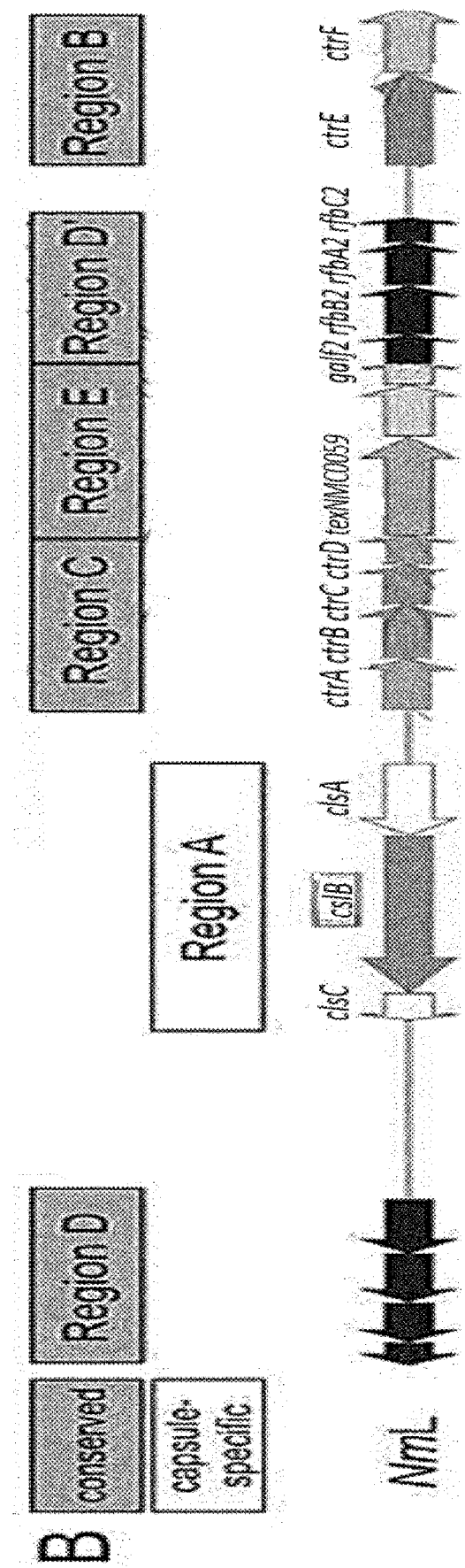
Figure 6:
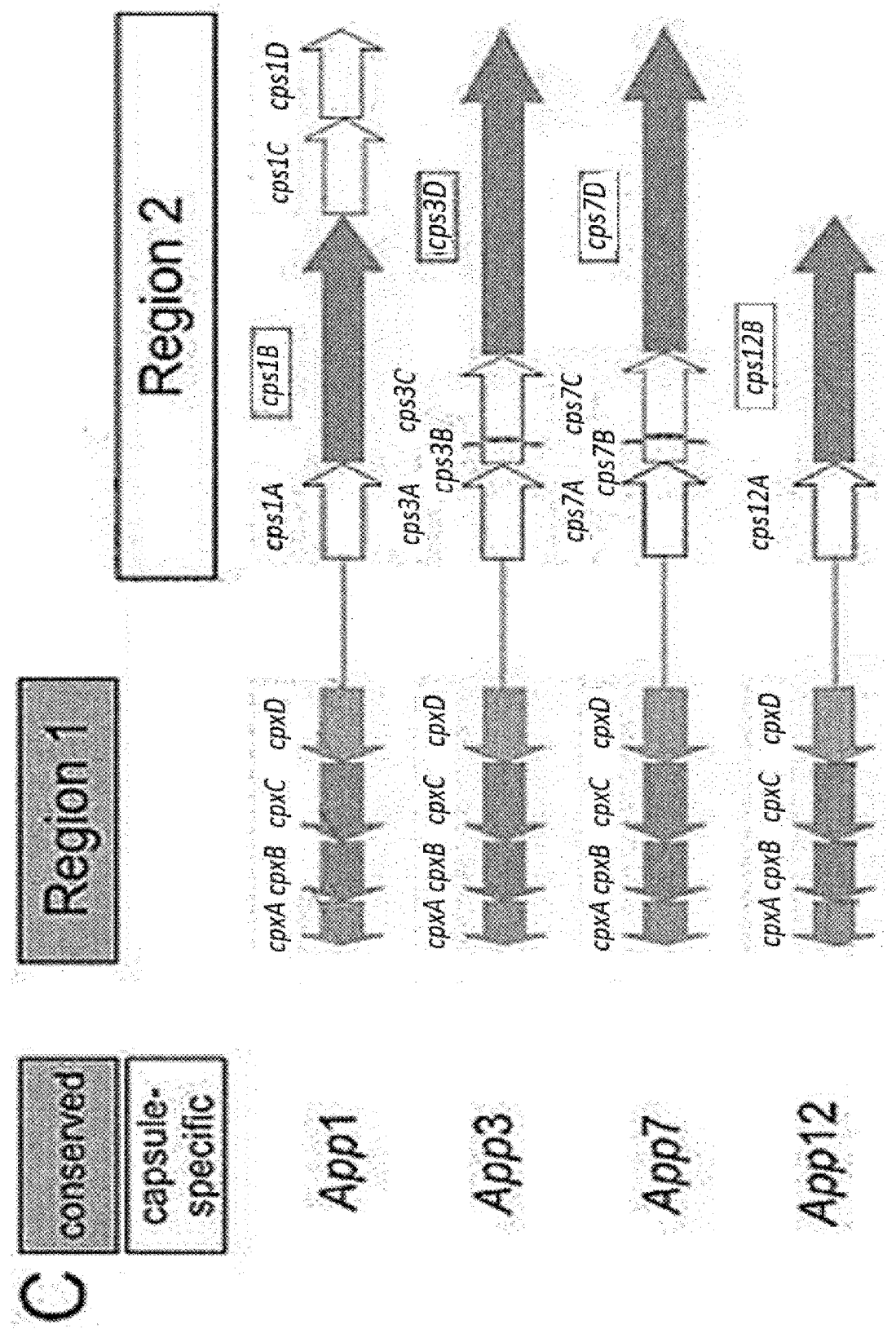
Figure 6:
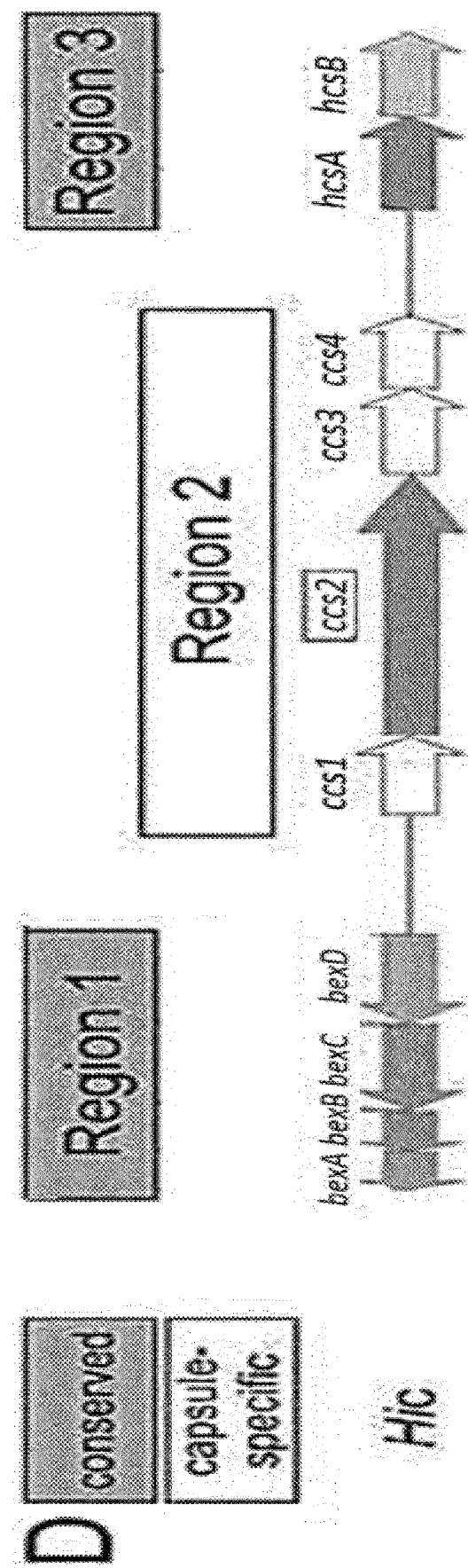

Focusing on Cps1B (expressed as Cps1B32_858-His6) as representative of the polymerases that possess the GT-A/TagF-like architecture and on Cps7D (expressed as MBP-Cps7D-His6) as representative of the polymerases that possess the TagF-like/GT-B architecture, all conserved positions were mutated to alanine to give the single domain mutants Cps1B32-858(D133A/D135A), Cps1B32-858 (H587A) and Cps1B32-85s(H717A) for Cps1B (FIG. 4) and Cps7D(H612A), Cps7D(H743A), Cps7D(R1123A) and Cps7D(K1132A) for Cps7D (FIG. 5). Mutant constructs were expressed in E. coli and subsequently purified at levels comparable with wildtype. However, when activity was controlled in the HPLC-based system, all mutant proteins were found to be inactive (FIGS. 4C and 5C). No polymer synthesis could be observed after 3 h of incubation and the level of UMP/CMP detected in the reactions was comparable to the controls and can thus be attributed to spontaneous hydrolysis of the donor substrates. Interestingly, considerable levels of UDP could be detected in the presence of the TagF-like domain mutants Cps7D(H612A) and Cps7D (H743A), indicating that the unmodified GT-B folded domain present in these constructs is still able to hydrolyze UDP-Gal.

With the aim to verify the two-domain architecture of the TagF-like polymerase family and assuming that each single domain mutant should still contain one remaining functional domain, trans-complementation reactions were performed, combining the GT-A domain mutant and the TagF-like domain mutants of Cps1B as well as the TagF-like domain mutants and the GT-B domain mutants of Cps7D. FIGS. 4 and 5 show that donor substrate uptake and polysaccharide synthesis is restored to wildtype levels for all trans-complementation reactions, indicating that the two remaining unmodified domains are able to catalyze the reaction in trans.

Example 17: Purification and Characterization of Bt-188

Coomassie-stained SDS-polyacrylamide gel showing the fractions collected during the purification of Bt-188-His6 by affinity chromatography (via its C-terminal $His_6$-tag) and size exclusion chromatography (SEC) is depicted in FIG. 22A. The pooled fraction contains the full-length construct (134.1 kDa) together with two smaller bands most likely resulting from N-terminal degradation, a phenomenon that has been observed for other TagF-like polymerases as well (see FIG. 9).

HPLC-AEC analysis of the Cps7B (GCT) and Bt-188 reaction is shown in FIG. 22B. As expected, Cps7B converts its substrates CTP and sn-glycerol-3-phosphate (not UV-active at 280 nm) into enantiopure CDP-glycerol (brown chromatogram labeled 'GCT reaction'). Small amounts of CDP in the reaction mixture can also be detected in the CTP control and are consequently not a side product of the GCT reaction. In the combined one-pot synthesis (green chromatogram labeled 'GCT+Bt-188 small reaction'), GCT consumes CTP to generate CDP-glycerol, which, together with UDP-Gal, is in turn used up by the polymerase Bt-188 to synthesize polymer. The nucleotide products of this reaction are UDP (resulting from the galactose transfer) and CMP (resulting from the sn-glycerol-3-phosphate transfer). The same enzyme cascade is exploited in the upscaled reaction (blue chromatogram labeled 'GCT+Bt-188 upscaled synthesis'), in which residual amounts of the nucleotide products UDP-Gal and CDP-glycerol can still be detected.

The polymer produced in the upscaled synthesis (see also B) was purified by AEC using a MonoQ column and a combination of linear NaCl gradients. Since the generated polymer is not UV-active, an Alcian blue/silver stained PAGE was used for visualization and to identify polymer containing fractions. The material eluting from the column is consistent with long, negatively charged polymer (FIG. 22C).

$^1$H NMR analysis of the polymer produced in the upscaled synthesis after purification is shown in FIG. 22D. The integrals (enclosed in square brackets) of isolated proton signals from the Gal and glycerol (Gro) moieties are consistent with a dimeric repeating unit.

Corresponding $^1$H, $^{13}$C HSQC NMR analysis is depicted in FIG. 22E and the $^1$H and $^{13}$C chemical shifts derived from the experiment are shown in Table 7. The observed correlations clearly demonstrate a dimeric repeating unit and are in perfect agreement with the previously characterized, de-O-acetylated capsule polymer isolated from *Bibersteinia trehalosi* serotype T3 (36).

TABLE 7

$^{13}$C and $^1$H chemical shifts (ppm) obtain from the $^1$H, $^{13}$C HSQC experiment.

|  | C1 | C2 | C3 | C4 | C5 | C6 |
|---|---|---|---|---|---|---|
| Gal | 101.30 | 71.29 | 71.71 | 77.52 | 73.58 | 63.72 |
|  | H1 | H2 | H3 | H4 | H5 | H6 | H6' |
| Gal | 5.00 | 3.90 | 3.98 | 4.55 | 4.04 | 3.77 | 3.73 |

TABLE 7-continued $^{13}$C and $^1$H chemical shifts (ppm) obtain from the $^1$H, $^{13}$C HSQC experiment.

|  | C1 | C2 | C3 |  |  |
|---|---|---|---|---|---|
| Gro |  | 71.16 | 72.00 | 69.48 |  |

|  | H1a | H1b | H2 | H3a | H3b |
|---|---|---|---|---|---|
| Gro | 3.82 | 3.63 | 4.11 | 4.05 | 3.98 |

Example 18: Purification and Characterization of Cps11D

Coomassie-stained SDS-polyacrylamide gel showing the fractions collected during the purification of MBP-Cps11D-His6 by affinity chromatography (via its C-terminal His$_6$-tag) and size exclusion chromatography (SEC) is depicted in FIG. 23A. The pooled fractions contain the full-length construct (176.4 kDa) together with one smaller band most likely resulting from N-terminal degradation, a phenomenon that has been observed for other TagF-like polymerases as well (see FIG. 9).

HPLC-AEC analysis of the Cps7B (GCT) and Cps11D reaction is shown in FIG. 23B. As expected, Cps7B converts its substrates CTP and sn-glycerol-3-phosphate (not UV-active at 280 nm) into enantiopure CDP-glycerol (brown chromatogram labeled GCT reaction). Small amounts of CDP in the reaction mixture can also be detected in the CTP control and are consequently not a side product of the GCT reaction. In the combined one-pot synthesis (green chromatogram labeled 'GCT+Cps11D small reaction'), GCT consumes CTP to generate CDP-glycerol, which, together with UDP-Gal, is in turn used up by the polymerase Cps11D to synthesize polymer. The nucleotide products of this reaction are UDP (resulting from the galactose transfer) and CMP (resulting from the sn-glycerol-3-phosphate transfer). The same enzyme cascade is exploited in the upscaled reaction (blue chromatogram labeled 'GCT+Cps11D upscaled synthesis'), in which residual amounts of the nucleotide product UDP-Gal can still be detected.

The polymer produced in the upscaled synthesis (see also B) was purified by AEC using a MonoQ column and a combination of linear NaCl gradients. Since the generated polymer is not UV-active, an Alcian blue/silver stained PAGE was used for visualization and to identify polymer containing fractions. The material eluting from the column is consisted with long, negatively charged polymer (FIG. 23C).

$^1$H NMR analysis of the polymer produced in the upscaled synthesis after purification is shown in FIG. 23D. The integrals (enclosed in square brackets) of isolated proton signals from the Gal and glycerol (Gro) moieties are consistent with a dimeric repeating unit.

Corresponding $^1$H, $^{13}$C HSQC NMR analysis is depicted in FIG. 23E and the $^1$H and $^{13}$C chemical shifts derived from the experiment are shown in Table 8. The observed correlations clearly demonstrate a dimeric repeating unit and are in perfect agreement with the backbone of the previously characterized polymers isolated from *Actinobacillus pleuropneumoniae* serotype 3, 9, 11 and *Neisseria meningitidis* serogroup H (28, 32, 34, 35).

TABLE 8

$^{13}$C and $^1$H chemical shifts (ppm) obtain from the $^1$H, $^{13}$C HSQC experiment.

|  | C1 | C2 | C3 | C4 | C5 | C6 |
|---|---|---|---|---|---|---|
| Gal | 100.92 | 71.21 | 71.53 | 77.41 | 73.51 | 63.56 |

|  | H1 | H2 | H3 | H4 | H5 | H6 | H6' |
|---|---|---|---|---|---|---|---|
| Gal | 5.22 | 3.90 | 3.98 | 4.54 | 4.18 | 3.76 | 3.76 |

|  | C1 | C2 | C3 |
|---|---|---|---|
| Gro | 64.00 | 79.95 | 67.18 |

|  | H1a | H1b | H2 | H3a | H3b |
|---|---|---|---|---|---|
| Gro | 3.79 | 3.79 | 3.97 | 4.12 | 4.06 |

Example 19: Purification and Characterization of Cps4B

Coomassie-stained SDS-polyacrylamide gel showing the fractions collected during the purification of MBP-Cps4B-His6 by affinity chromatography (via its C-terminal His$_6$-tag) and size exclusion chromatography (SEC) is depicted in FIG. 24A. The pooled fractions (pool) contain the full-length construct (145.7 kDa) and one additional prominent band most likely resulting from N-terminal degradation, a phenomenon that has been observed for other TagF-like polymerase fusion constructs as well (see FIG. 9).

HPLC-AEC analysis of the Cps4B reaction is shown in FIG. 24B. In both, the test reaction (small reaction) and the upscaled synthesis, the donor substrates UDP-GalNAc and UDP-Glc were consumed and converted to the nucleotide products UMP (resulting from the GalNAc-1-phosphate transfer) and UDP (resulting from the Glc transfer).

The polymer produced in the upscaled synthesis (see also B) was purified by AEC using a MonoQ column and a combination of linear NaCl gradients (dotted line). The material eluting from the column is consisted with long, negatively charged polymer (FIG. 24C).

$^1$H NMR analysis of the polymer produced by Cps4B after purification. The integrals (enclosed in square brackets) of isolated proton signals from the GalNAc and Glc moieties are consistent with a dimeric repeating unit (FIG. 24D).

Corresponding $^1$H, $^{13}$C HSQC NMR analysis is depicted in FIG. 24E and the $^1$H and $^{13}$C chemical shifts derived from the experiment are shown in Table 9. The observed correlations clearly demonstrate a dimeric repeating unit and are in perfect agreement with the previously characterized capsule polymer isolated from *Actinobacillus pleuropneumoniae* serotype 4 (24). *aliased

TABLE 9

$^{13}$C and $^1$H chemical shifts (ppm) obtain from the $^1$H, $^{13}$C HSQC experiment.

|  | C1 | C2 | C3 | C4 | C5 | C6 | CH3 |
|---|---|---|---|---|---|---|---|
| GalNAc | 97.09 | 51.36 | 80.24 | 70.84 | 74.64 | 63.59 | 24.90 |
| Glc | 107.05 | 75.70 | 78.15 | 71.90 | 77.15 | 67.29 |  |

|  | H1 | H2 | H3 | H4 | H5 | H6 | H6' | CH3 |
|---|---|---|---|---|---|---|---|---|
| GalNAc | 5.50 | 4.38 | 4.07 | 4.32 | 4.16 | 3.80 | 3.76 | 2.06 |
| Glc | 4.60 | 3.31 | 3.50 | 3.49 | 3.55 | 4.18 | 4.10 |  |

DISCUSSION

These findings present the identification of a novel family of capsule polymerases, designated the TagF-like capsule polymerase family. Members of this family are abundant among pathogenic group II capsule expressing bacteria with human and animal hosts, e.g. *Neisseria meningitidis* (Nm), *Actinobacillus pleuropneumoniae* (App), *Haemophilus influenzae* (Hi), *Bibersteinia trehalosi* (Bt) and *Escherichia coli* (*E. coli*). Based on the recently characterized bifunctional and so far unprecedented protein CslB (14), homologs with similar protein architectures and enzymatic functions were found, some of them even having a new function of generating polysaccharides consisting of a dimeric repeating unit instead of synthesizing polysaccharides consisting of a trimeric repeating unit such as CslB and CPs12B.

By characterization of five further family members, the conserved functionality and architecture of TagF-like polymerases was proofed. After gene amplification, protein expression and purification of the selected candidates Cps1B of App1, Cps3D of App3, Cps7D of App7, Cps12B of App12 and Ccs2 of Hic, their capsule polymerase activities were analyzed (FIG. 2) and the chemical properties of the products were determined via NMR (Table 5 and 6). All candidates represent capsule polymerases synthesizing polymers identical to the unmodified capsule backbones of the corresponding native CPS. In detail, Fcs2, Cps1B, BtY31, Ccs2 and Cps4B of the GT-A/TagF-like family as well as CshC, Bt189, Bt188, Bt192, Cps3D, Cps9D, Cps11D, c3694, CszC, Cps7D, Cps2D of the TagF-like/GT-B family synthesize a polysaccharides consisting of a dimeric repeating unit, whereas Cps12B as a member of the GT-A/TagF-like family synthesizes polysaccharides consisting of a trimeric repeating unit such as CslB. Remarkably, TagF-like polymerases combine the enzymatic functions to synthesize glycosidic and phosphodiester linkages within one protein. So far, both enzymatic functions among known group II capsule polymerases were exclusively catalyzed either by glycosyltransferases (11, 12) or hexose-phosphate transferases (Stealth proteins) (13) that were expressed as separate proteins.

To determine the bifunctionality and bipartite architecture of TagF-like polymerases, mutational studies were performed using representative candidates of the novel family. It was focused on Cps1B as representative of the polymerases possessing the GT-A/TagF-like architecture and on Cps7D as representative of the polymerases possessing the TagF-like/GT-B architecture (FIG. 1).

The positions of mutations were selected based on the already identified catalytic positions of the template proteins, TagF (15), K4CP (40) and TarM (41), that were used for modeling the predicted protein structures. The TagF-like domain present in all TagF-like polymerases (FIG. 1 and FIG. 8) was modeled on TagF, a teichoic acid polymerase from the Gram-positive bacterium *S. epidermidis* that adopts a GT-B fold (15). In TagF, two histidine positions were shown to be critical for the catalytic activity. Position H444 is an active base deprotonating the hydroxyl group of the glycerol acceptor at C1, and a second position, H584, takes part in coordination of the pyrophosphate of the donor substrate (15, 47). The introduction of alanine mutants in the corresponding histidine positions of Cps1B and Cps7D abolished the polymerase activity in both proteins (FIGS. 4 and 5).

The GT-A fold of GT-A/TagF-like polymerases were modeled onto the glucuronic acid transferase domain of the polymerase K4CP from *E. coli* K4 (40). The DxD motif that is highly conserved among GT-A folded proteins, interacts with the phosphate groups of the nucleotide donor sugars through the coordination of divalent cations (10, 40). As expected, mutating the DxD motif in Cps1B resulted in an inactive enzyme (FIG. 4). The template protein for modeling of the C-terminal GT-B fold in TagF-like/GT-B folded polymerases is TarM from *S. aureus* catalyzing the GlcNAcylation of teichoic acid (41). Positions K331 and R326 in TarM were shown to be essential for enzymatic activity. Both positions participate in the stabilization of the negative charges of UDP-phosphate of the donor substrates. R326 additionally bridges the resulting glycerol-GlcNAc moiety (41). The introduction of corresponding mutations in the C-terminal GT-B domain of Cps7D abolished its polymerase activity as well (FIG. 5).

Importantly, testing the mutants in trans-complementation reactions restored capsule polymerase activity (FIGS. 4 and 5). In trans-complementation reactions of CslB (14) and other two-domain polymerases of e.g. Nm serogroup W (48), the restored polymerase activity is significantly lower compared to wildtype reactions. In contrast, substrate uptake and the amount of synthesized polymer by Cps1B and Cps7D mutants complemented in trans is comparable to the wildtype reactions (FIGS. 4 and 5). The fact that all investigated mutants were inactive with regard to polymer synthesis, but active if combined in trans-complementation reactions, clearly confirms that mutations in one domain have no impact on the function of the second domain.

In addition, the mutational studies corroborate the predicted GT-A/TagF-like and TagF-like/GT-B architecture of the polymerases and highlight the importance of the catalytic positions. GT-A folded proteins are dependent on divalent cations for the coordination of the negatively charged donor substrates (11). In contrast, conserved amino acids stabilize the negative charges of donor substrates in GT-B folded proteins and enable a cation-independent reaction mechanism (10). The cation-dependency and -independency of TagF-like capsule polymerases was analyzed using the HPLC-AEC assay. Again in agreement with the predicted folds, it could be demonstrated that polymerases with the TagF-like/GT-B architecture are active even in the absence of divalent cations, while the activity of polymerases adopting the GT-A/TagF-like architecture depend on the presence of magnesium ions (FIG. 13).

The bioinformatics analyses indicate that the TagF-like domain catalyzes the transfer of the hexose-phosphate and glycerol-phosphate positions of the repeating units, whereas GT-A folds transfer hexose positions with inverted stereochemistry (β-glycosidic linkages) and GT-B folds transfer hexose positions with retained stereochemistry (α-glycosidic linkages) (FIG. 1A). This is emphasized by the fact that the reactions containing the Cps7D TagF-like domain mutants (Cps7D(H612A) and Cps7D(H743A)) contain considerable amounts of UDP (FIG. 5C) presumably resulting from enzyme-facilitated hydrolysis of UDP-Gal. Thus, it is likely to speculate that this domain is responsible for the Gal transfer. Accordingly, the TagF-like domain needs to be responsible for the glycerol-phosphate transfer.

It was found that the TPR (tetratricopeptide repeat) domain predicted in the majority of TagF-like polymerases (FIG. 1C,D and FIG. 8) is not involved in the catalysis of the polymerase reaction of Cps1B (FIG. 3B). Thus, polymer synthesis and the transfer of both sugar positions catalyzed by Cps1B are solely catalyzed by the GT-A and the TagF-like domain. This is consistent with the fact that CslB and Cps12B are active polymerases, even though they do not contain a TPR domain. Of note, truncation of the predicted TPR domain in Cps1B changed the oligomerization status to a monomer, whereas full-length Cps1B protein assembled a di- to trimer (FIG. 3A). TPRs form superhelical structures that are known to mediate protein-protein interactions (42). As the assembly and translocation of the capsule polysaccharide of group II capsules occur in a complex pathway with a number of enzymes involved (1), it is likely that the TPR domain mediates protein-protein interactions and specific regulatory steps within this complex synthesis machinery. Unfortunately, attempts to truncate the N-terminal TPR domain in Cps7D resulted in badly expressed and non-purifiable proteins. Two reasons for this are likely: (i) the TPR domain stabilizes the Cps7D protein itself or is responsible for the formation of a specific oligomerization state required for Cps7D stability, (ii) the selected truncation point was not suitable and resulted in an unstable construct, independently of the TPR domain.

The CDP-glycerol used as substrate for the Cps3D and Cps7D reactions was a racemic mixture with regard to C2 of the glycerol. Interestingly, the NMR results clearly showed that both polymerases incorporate both enantiomers, although the natural capsule was reported to be enantiomerically pure (32, 33).

It is known that glycerol-phosphate resulting from CDP-glycerol has R-chirality (regarding C2 of glycerol) (sn-glycerol-3-phosphate), while phosphatidylglycerol is the source of sn-glycerol-1-phosphate (C2 of glycerol has S-chirality) in bacteria (49). It is thus tempting to speculate that the lacking pressure for the selection of sn-glycerol-3-phosphate allowed the polymerases to evolve a low specificity for enantiomerically pure glycerol-phosphate.

REFERENCES

1. Willis, L. M., and Whitfield, C. (2013) Structure, biosynthesis, and function of bacterial capsular polysaccharides synthesized by ABC transporter-dependent pathways. *Carbohydr. Res.* 378, 35-44.
2. Roberts, I. S. (1996) The biochemistry and genetics of capsular polysaccharide production in bacteria. *Annu. Rev. Microbiol.* 50, 285-315.
3. Geno, K. A., Gilbert, G. L., Song, J. Y., Skovsted, I. C., Klugman, K. P., Jones, C., Konradsen, H. B., and Nahm, M. H. (2015) Pneumococcal Capsules and Their Types: Past, Present, and Future. *Clin. Microbiol. Rev.* 28, 871-99.
4. Whitfield, C. (2006) Biosynthesis and assembly of capsular polysaccharides in *Escherichia coli*. *Annu. Rev. Biochem.* 75, 39-68.
5. Harrison, O. B., Claus, H., Jiang, Y., Bennett, J. S., Bratcher, H. B., Jolley, K. A., Corton, C., Care, R., Poolman, J. T., Zollinger, W. D., Frasch, C. E., Stephens, D. S., Feavers, I., Frosch, M., Parkhill, J., Vogel, U., Quail, M. A., Bentley, S. D., and Maiden, M. C. J. (2013) Description and Nomenclature of *Neisseria meningitidis* Capsule Locus. *Emerg. Infect. Dis.* 19, 566-573.
6. Jessing, S. G., Ahrens, P., Inzana, T. J., and Angen, O. (2008) The genetic organisation of the capsule biosynthesis region of *Actinobacillus pleuropneumoniae* serotypes 1, 6, 7, and 12. *Vet. Microbiol.* 129, 350-359.
7. Kroll, J. S., Zamze, S., Loynds, B., and Moxon, E. R. (1989) Common Organization of Chromosomal Loci for Production of Different Capsular Polysaccharides in *Haemophilus influenzae*. *J. Bacteriol.* 171, 3343-3347.
8. Guerry, P., Poly, F., Riddle, M., Maue, A. C., Chen, Y.-H., and Monteiro, M. A. (2012) *Campylobacter* polysaccharide capsules: virulence and vaccines. *Front. Cell. Infect. Microbiol.* 2, 7.
9. Lo, R. Y. C., McKerral, L. J., Hills, T. L., and Kostrzynska, M. (2001) Analysis of the capsule biosynthetic locus of Mannheimia (*Pasteurella*) *haemolytica* A1 and proposal of a nomenclature system. *Infect. Immun.* 69, 4458-4464.
10. Breton, C., Snajdrova, L., Jeanneau, C., Koca, J., and Imberty, A. (2006) Structures and mechanisms of glycosyltransferases. *Glycobiology.* 16, 29R-37R.
11. Lairson, L. L., Henrissat, B., Davies, G. J., and Withers, S. G. (2008) Glycosyltransferases: structures, functions, and mechanisms. *Annu. Rev. Biochem.* 77, 521-555
12. Gloster, T. M. (2014) Advances in understanding glycosyltransferases from a structural perspective. *Curr. Opin. Struct. Biol.* 28, 131-141.
13. Sperisen, P., Schmid, C. D., Bucher, P., and Zilian, O. (2005) Stealth proteins: in silico identification of a novel protein family rendering bacterial pathogens invisible to host immune defense. *PLoS Comput. Biol.* 1, e63.
14. Litschko, C., Romano, M. R., Pinto, V., Claus, H., Vogel, U., Berti, F., Gerardy-Schahn, R., and Fiebig, T. (2015) The Capsule Polymerase CslB of *Neisseria meningitidis* Serogroup L Catalyzes the Synthesis of a Complex Trimeric Repeating Unit Comprising Glycosidic and Phosphodiester Linkages. *J. Biol. Chem.* 290, 24355-24366.
15. Lovering, A. L., Lin, L. Y.-C., Sewell, E. W., Spreter, T., Brown, E. D., and Strynadka, N. C. J. (2010) Structure of the bacterial teichoic acid polymerase TagF provides insights into membrane association and catalysis. *Nat. Struct. Mol. Biol.* 17, 582-589.
16. Fiebig, T., Berti, F., Freiberger, F., Pinto, V., Claus, H., Romano, M. R., Proietti, D., Brogioni, B., Stummeyer, K., Berger, M., Vogel, U., Costantino, P., and Gerardy-Schahn, R. (2014) Functional expression of the capsule polymerase of *Neisseria meningitidis* serogroup X: A new perspective for vaccine development. *Glycobiology.* 24, 150-158.
17. Kavoosi, M., Creagh, A. L., Kilburn, D. G., and Haynes, C. A. (1996) Strategy for Selecting and Characterizing Linker Peptides for CBM9-Tagged Fusion Proteins Expressed in *Escherichia coli*. *Biotechnol. Bioeng.* 98, 599-610.
18. Min, H., and Cowman, M. K. (1986) Combined alcian blue and silver staining of glycosaminoglycans in polyacrylamide gels: application to electrophoretic analysis of molecular weight distribution. *Anal. Biochem.* 2, 275-285.
19. Kelley, L. A., and Sternberg, M. J. E. (2009) Protein structure prediction on the Web: a case study using the Phyre server. *Nat. Protoc.* 4, 363-71.
20. Sievers, F., Wilm, A., Dineen, D., Gibson, T. J., Karplus, K., Li, W., Lopez, R., Mcwilliam, H., Remmert, M., So Ding, J., Thompson, J. D., and Higgins, D. G. (2011) Fast, scalable generation of high-quality protein multiple sequence alignments using Clustal Omega. *Mol. Syst. Biol.* 10.1038/msb.2011.75.
21. Boutet, E., Lieberherr, D., Tognolli, M., Schneider, M., Bansal, P., Bridge, A. J., Poux, S., Bougueleret, L., and Xenarios, I. (2016) UniProtKB/Swiss-Prot, the Manually Annotated Section of the UniProt KnowledgeBase: How to Use the Entry View, pp. 23-54, 10.1007/978-1-4939-3167-5_2.

22. Beynon, L. M., Richards, J. C., and Perry, M. B. (1991) Structural studies of the capsular polysaccharide from *Actinobacillus pleuropneumoniae* serotype 12. *Carbohydr. Res.* 212, 21927.
23. Branefors-Helander, P., Classon, B., Kenne, L., and Lindberg, B. (1979) Structural studies of the capsular antigen of *Haemophilus infuenzae* type c. *Carbohydr. Res.* 76, 197-202.
24. Altman, E., Brisson, J., and Perry, M. B. (1986) Structural studies of the capsular polysaccharide from *Haemophilus pleuropneumoniae* serotype 1. *Biochem. Cell Biol.* 64, 707716.
25. Altman, E., Brisson, J.-R., and Perry, M. B. (1988) Structural studies of the capsular polysaccharide from *Actinobacillus (Haemophilus) pleuropneumoniae* serotype 4. *Biochem. Cell Biol.* 66, 998-1004.
26. Branefors-Helander, P., Kenne, L., and Lindqvist, B. (1980) Structural studies of the capsular antigen from *Haemophilus influenzae* type f. *Carbohydr. Res.* 79, 308-12.
27. Egan, W., Tsui, F. P., and Schneerson, R. (1980) Structural studies of the *Haemophilus influenzae* type f capsular polysaccharide. *Carbohydr. Res.* 79, 271-7.
28. Michon, F., Roy, R., Jennings, H. J., and Ashton, F. E. (1984) Structural elucidation of the capsular polysaccharide of *Neisseria meningitidis* group H'.
29. Jennpngs, H. J., Rosell, M.-G., and Paul K E N, D. C. Structural elucidation of the capsular polysaccharide antigen of Neisserk mmeningitidis sersgrcsup Z using I a 4: nuclear magnetic resonance.
30. Fischer, W., Schmidt, M. A., Jann, B., and Jann, K. (1982) Structure of the *Escherichia coli* K2 capsular antigen. Stereochemical configuration of the glycerophosphate and distribution of galactopyranosyl and galactofuranosyl positions. *Biochemistry.* 21, 1279-1784.
31. Altman, E., Brisson, J.-R., and Perry, M. B. (1987) Structural studies of the capsular polysaccharide from *Haemophilus pleuropneumoniae* serotype 2. *Biochem. Cell Biol.* 65, 414422.
32. Altman, E., Brisson, J. R., and Perry, M. B. (1987) Structure of the Capsular Polysaccharide of *Hemophilus-Pleuropneumoniae* Serotype 3. *Eur. J. Biochem.* 170, 185-192.
33. Beynon, L. M., Perry, M. B., and Richards, J. C. (1991) Structure of the capsular polyscchardie from *Actinobacillus pleuropneumoniae* serotype 7. *Carbohydr. Res.* 209, 211-223.
34. Beynon, L. M., Richards, J. C., and Perry, M. B. (1992) Nuclear-magnetic-resonance analysis of the capsular antigen of *Actinobacillus pleuropneumoniae* serotype 9. Its identity with the capsular antigen of *Escherichia coli* K62 (K2ab), *Neisseria meningitidis* serogroup H and *Pasteurella haemolytica* serotype T15. *Eur. J. Biochem.* 210, 119-124.
35. Perry, M. B., Altman, E., Brisson, J. R., Beynon, L. M., and Richards, J. C. (1990) Structural characteristics of the antigenic capsular polysaccharides and lipopolysaccharides involved in the serological classification of *Actinobacillus (Haemophilus) pleuropneumoniae* strains. *Serodiagn. Immunother. Infect. Dis.* 4, 299-308.
36. Richards, J. C., and Leitch, R. A. (1990) Determination of the structure and absolute configuration of the glycerolphosphate-containing capsular polysaccharide of *Pasteurella haemolytica* serotype T 3 by high-resolution nuclear magnetic resonance spectroscopyl. *Can. J. Chem.* 68, 1574-1584.
37. Adlam, C., Knights, J. M., Mugridge, A., Lindon, J. C., and WilliamsS, J. M. (1985) Purification, Characterization and Immunological Properties of the Serotype-specific Capsular Polysaccharide of *Pasteurella haemolytica* (Serotype T4) Organisms. *Microbiology.* 131, 387394.
38. Adlam, C., Knights, J. M., Mugridge, A., Lindon, J. C., Williams, J. M., and Beesley, J. E. (1985) Purification, Characterization and Immunological Properties of the Capsular Polysaccharide of *Pasteurella haemolytica* Serotype T15: Its Identity with the K62 (K2ab) Capsular Polysaccharide of *Escherichia coli* and the Capsular Polysaccharide of Neisser. *J. Gen. Microbiol.* 62, 1963-1972.
39. Blackall, P. J., Bojesen, A. M., Christensen, H., and Bisgaard, M. (2007) Reclassification of [*Pasteurella*] *trehalosi* as *Bibersteinia trehalosi* gen. nov., comb. nov. *Int. J. Syst. Evol. Microbiol.* 57, 666-674.
40. Osawa, T., Sugiura, N., Shimada, H., Hirooka, R., Tsuji, A., Shirakawa, T., Fukuyama, K., Kimura, M., Kimata, K., and Kakuta, Y. (2009) Crystal structure of chondroitin polymerase from *Escherichia coli* K4. *Biochem. Biophys. Res. Commun.* 378, 10-4.
41. Sobhanifar, S., Worrall, L. J., Gruninger, R. J., Wasney, G. A., Blaukopf, M., Baumann, L., Lameignere, E., Solomonson, M., Brown, E. D., Withers, S. G., and Strynadka, N. C. J. (2015) Structure and mechanism of *Staphylococcus aureus* TarM, the wall teichoic acid a-glycosyltransferase. *Proc. Natl. Acad. Sci. U.S.A.* 10.1073/pnas.1418084112.
42. D'Andrea, L. D., and Regan, L. (2003) TPR proteins: The versatile helix. *Trends Biochem. Sci.* 28, 655-662.
43. Jennings, H. J., Lugowsky, C. W., Ashton, F. E., and Ryan, J. A. (1983) The Structure of the Capsular Polysaccharide obtained from a new Serogroup (L) of *Neisseria meningitidis. Carbohydr. Res.* 112, 105-111.
44. Beynon, L. M., Richards, J. C., and Perry, M. B. (1991) Structural studies of the capsular polysaccharide *Actinobacillus* pleuropneumonias serotype 12. *Carbohydr. Res.* 212, 219-227.
45. van Der Kaaden, A., van Doorn-Van Wakeren, J. I. M., Kamerling, J. P., Vliegenthart, J. F., and Tiesjema, R. H. (1985) Structure of the capsular antigen of *Neisseria meningitidis* serogroup H. *Eur. J. Biochem.* 152, 663-668.
46. Blatch, G. L., and Lassie, M. (1999) The tetratricopeptide repeat: A structural motif mediating protein-protein interactions. *BioEssays.* 21, 932-939.
47. Schertzer, J. W., Bhaysar, A. P., and Brown, E. D. (2005) Two conserved histidine positions are critical to the function of the TagF-like family of enzymes. *J. Biol. Chem.* 280, 36683-36690.
48. Romanow, A., Haselhorst, T., Stummeyer, K., Claus, H., Bethe, A., Mühlenhoff, M., Vogel, U., Itzstein, M. Von, and Gerardy-Schahn, R. (2013) Biochemical and biophysical characterization of the sialyl-/hexosyltransferase synthesizing the meningococcal serogroup W135 heteropolysaccharide capsule. *J. Biol. Chem.* 288, 11718-11730.
49. van der Es, D., Hogendorf, W. F. J., Overkleeft, H. S., van der Marel, G. A., and Codee, J. D. C. (2017) Teichoic acids: synthesis and applications. Chem. Soc. Rev. 10.1039/C6CS00270F.
50. Kröncke, K. D., Golecki, J. R., Jann, K. & Kroncke, K.-D. Further Electron Microscopic Studies on the Expression of *Escherichia coli* Group II Capsules. *J. Bacteriol.* 172, 3469-3472 (1990).
51. Ophir, T. & Gutnick, D. L. A role for exopolysaccharides in the protection of microorganisms from desiccation. *Appl. Environ. Microbiol.* 60, 740-745 (1994).
52. Hill, D. J., Griffiths, N. J., Borodina, E. & Virji, M. Cellular and molecular biology of *Neisseria meningitidis* colonization and invasive disease. *Clin. Sci. (Lond).* 118, 547-64 (2010).

53. Costantino, P., Rappuoli, R. & Berti, F. The design of semi-synthetic and synthetic glycoconjugate vaccines. *Expert Opin. Drug Discov.* 6, 1045-66 (2011).
54. PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York (1983), pgs. 1-12; Seifter, *Meth. Enzymol.* 182 (1990); 626-646, Rattan, Ann. NY Acad. Sci. 663 (1992); 48-62.
55. Owens, Proc. Natl. Acad. Sci. USA 98 (2001), 1471-1476.

The invention claimed is:

1. A host cell, which comprises under the control of a heterologous promoter a polynucleotide comprising a nucleotide sequence encoding a polypeptide, wherein the nucleotide sequence is selected from the group consisting of:

a) a nucleotide sequence encoding a polypeptide comprising a TagF-like domain and a GT-B domain having the amino acid sequences shown in SEQ ID NO. 1 and 17, SEQ ID NO. 2 and 18, SEQ ID NO. 3 and 19, SEQ ID NO. 4 and 20, SEQ ID NO. 5 and 21, SEQ ID NO.

6 and 22, SEQ ID NO. 7 and 23, SEQ ID NO. 8 and 24, SEQ ID NO. 9 and 25, SEQ ID NO. 10 and 26, or SEQ ID NO. 11 and 27, wherein the polypeptide synthesizes a polysaccharide consisting of a dimeric repeating unit;

b) a nucleotide sequence encoding a polypeptide comprising a TagF-like domain and a GT-A domain having the amino acid sequences shown in SEQ ID NO. 12 and 28, SEQ ID NO. 13 and 29, SEQ ID NO. 14 and 30, SEQ ID NO. 15 and 31, or SEQ ID NO. 16 and 32, wherein the polypeptide synthesizes a polysaccharide consisting of a dimeric repeating unit;

c) a nucleotide sequence encoding a polypeptide having an amino acid sequence that is at least 18% identical to the amino acid sequence of residues 1 to 378 of SEQ ID NO. 3 and that is at least 40% identical to the amino acid sequence of residues 1 to 389 of SEQ ID NO. 23, wherein the polypeptide synthesizes a polysaccharide consisting of a dimeric repeating unit; and d) a nucleotide sequence encoding a polypeptide having an amino acid sequence that is at least 18% identical to the amino acid sequence of residues 1 to 378 of SEQ ID NO. 3 and that is at least 30% identical to the amino acid sequence of residues 1 to 256 of SEQ ID NO. 32, wherein the polypeptide synthesizes a polysaccharide consisting of a dimeric repeating unit, and wherein the nucleotide sequence of (a) to (d) encodes a polypeptide having a conserved tyrosine at a position corresponding to position 49 of SEQ ID NO. 3 or having a conserved aspartic acid at a position corresponding to position 49 of SEQ ID NO. 3.

2. The host cell of claim 1, wherein the host cell is a prokaryotic host cell or a eukaryotic host cell, optionally wherein the prokaryotic host cell is selected from the group consisting of *Escherichia coli, Actinobacillus pleuropneumoniae, Bibersteinia trehalosi, Actinobacillus suis, Haemophilus influenzae, Campylobacter jejuni, Campylobacter coli, Neisseria meningitidis, Mannheimia varigena, Neisseria mucosa, Moraxella lacunata, Neisseria elongate, Klebsiella* sp G5, *Cronobacter universalis, Cronobacter turicensis, Aeromonas veronii, Cronobacter sakazakii, Yersinia enterocolitica, Helicobacter pullorum* and *Bacillus cereus.*

3. The host cell of claim 1, wherein the host cell is cultured and the polynucleotide comprising the nucleotide sequence encoding the polypeptide is expressed.

4. The host cell of claim 1, wherein the heterologous promoter is a prokaryotic promoter,
optionally wherein the prokaryotic promoter is a tac promoter, lacUV5 promoter, T4 promoter, T7 promoter, araBAD ($P_{BAD}$) promoter, tet promoter or a T5 promoter.

5. The host cell of claim 1, wherein the nucleotide sequence encodes a polypeptide having a conserved aspartic acid at a position corresponding to position 364 of SEQ ID NO. 3.

6. The host cell of claim 1, wherein the polypeptide is selected from the group consisting of a polymerase, glycosyltransferase, hexose-phosphate transferase, and alditol-phosphate transferase.

7. The host cell of claim 1, wherein the polypeptide is fused to a N- and/or C-terminal tag.

8. The host cell of claim 7, wherein the N- and/or C-terminal tag is selected from the group consisting of a His tag, MBP tag, GFP tag, FLAG tag, Strep tag, StrepII tag, NusA tag, GST tag, thioredoxin and intein.

9. The host cell of claim 1, wherein the polysaccharide comprises a repeating unit of two different monosaccharides or one monosaccharide and one alditol.

10. The host cell of claim 9, wherein the repeating unit comprises one or more glycosidic and one or more phosphodiester linkage(s).

11. The host cell of claim 9, wherein the two different monosaccharides of the repeating unit are connected by a β-glycosidic linkage or wherein the monosaccharide and the alditol of the repeating unit are connected by an α-glycosidic linkage.

12. The host cell of claim 1, wherein the polysaccharide is a phosphate containing polysaccharide.

13. A method of producing a host cell of claim 1, the method comprising:
a) cloning a nucleotide sequence encoding a polypeptide expressed by the host cell of claim 1 into a vector;
b) transforming cells with said vector of (a) and growing the cells in medium.

14. A method of expressing a polypeptide in a host cell comprising:
a) culturing the host cell of claim 1;
b) expressing the polypeptide in the host cell.

15. A vaccine composition comprising the host cell of claim 1.

* * * * *

```
                              SEQUENCE LISTING

<160> NUMBER OF SEQ ID NOS: 83

<210> SEQ ID NO 1
<211> LENGTH: 388
<212> TYPE: PRT
<213> ORGANISM: Artificial sequence
<220> FEATURE:
<223> OTHER INFORMATION: TagF-like domain CshC

<400> SEQUENCE: 1

Ile Ala Pro Lys Asp Ala Ile Lys Asn Lys Glu Glu Glu Tyr Leu Ser
1               5                   10                  15

Tyr Tyr Thr Glu Tyr Tyr Glu Thr Leu Pro Leu Gln Asp Asn Leu Ile
                20                  25                  30

Met Phe Glu Ser Phe Phe Gly Ser Asn Ile Ser Cys Asn Pro Tyr Ala
            35                  40                  45

Ile Leu Ser Tyr Met Leu Glu His Gln Tyr Asn Tyr Ile Tyr Ile Val
        50                  55                  60

Val Ile Lys Glu Gly Thr Leu Ile Pro Asn Asn Leu Lys His Asn Glu
65                  70                  75                  80

Asn Ile Ile Phe Val Lys Arg Gly Ser Asp Leu Tyr Leu Arg Tyr Leu
                85                  90                  95

Cys Ser Ala Lys Tyr Leu Val Asn Asn Val Thr Phe Pro Tyr Tyr Phe
            100                 105                 110

Ile Arg Lys Glu Gly Gln Val Tyr Leu Asn Thr Trp His Gly Thr Pro
        115                 120                 125

Met Lys Thr Leu Gly Lys Asp Ile Lys Ser Pro Phe Gln Asp His Ala
    130                 135                 140

Asn Val Ser Arg Asn Phe Leu Gln Ala Thr His Ile Ile Ser Pro Asn
145                 150                 155                 160

Arg His Thr Thr Asp Ile Ile Leu Asp Lys Tyr Asp Ile Lys Pro Phe
                165                 170                 175

Phe Asn Gly Met Leu Ser Glu Thr Gly Tyr Pro Arg Ile Asp Leu Gly
            180                 185                 190

Leu Asn Leu Ser Ser Lys Arg Lys Gln Glu Ile Ala Asp Ile Leu Gly
        195                 200                 205

Ile Thr Leu Asn Lys Pro Ile Val Phe Tyr Ala Pro Thr Trp Arg Gly
    210                 215                 220

Thr Ser Gln Asp Lys Ser Phe Asp Val Ser Lys Leu Gln Asn Asp Leu
225                 230                 235                 240

Lys Phe Leu Asn Ser Asp Lys Tyr Gln Leu Ile Phe Arg Gly His His
                245                 250                 255

Leu Val Glu Asn Ile Leu Lys Asp Ile Asp Leu Asn Val Ile Val Ala
            260                 265                 270

Ala Lys Glu Ile Asp Ser Asn Glu Leu Leu Gly Leu Cys Asp Ile Leu
        275                 280                 285

Ile Thr Asp Tyr Ser Ser Ile Val Tyr Asp Phe Leu Ser Thr Gly Lys
    290                 295                 300

Asn Val Ile Ser Tyr Ile Tyr Asp Phe Thr Ala Tyr Asn Ala Glu Arg
305                 310                 315                 320
```

```
Gly Leu Tyr Phe Gln Lys His Glu Leu Ile Gly His Ile Cys Thr Thr
            325                 330                 335

Ile Lys Glu Val Lys Asn Ser Ile Leu Lys Gln Ile Ala Asp Glu Leu
            340                 345                 350

Lys Ser Asn Ile Ser Ser Asn Glu Ile Glu Lys Tyr Ala Ala Phe Asp
            355                 360                 365

Asp Gly Ser Ala Thr Lys Arg Thr Ile Asp Phe Met Phe Tyr Asn Asp
            370                 375                 380

Arg Ser Asn Leu
385

<210> SEQ ID NO 2
<211> LENGTH: 382
<212> TYPE: PRT
<213> ORGANISM: Artificial sequence
<220> FEATURE:
<223> OTHER INFORMATION: TagF-like domain Bt189

<400> SEQUENCE: 2

Asp Val Ile Lys Asn Lys Glu Glu Tyr Leu Thr Tyr Tyr Thr Glu
1               5                   10                  15

Tyr Tyr Glu Thr Leu Ala Val Asn Glu Lys Gln Val Leu Ile Glu Ser
                20                  25                  30

Phe Phe Gly Gly Asn Ile Ser Cys Asn Pro Tyr Ala Ile Leu Leu Tyr
            35                  40                  45

Met Leu Asp His Asn Tyr Asp Phe Thr Tyr Ile Val Val Val Lys Pro
        50                  55                  60

Glu Thr Val Ile Pro Asp Ser Leu Lys Phe Lys Gln Asn Ile Ile Phe
65                  70                  75                  80

Ile Asn Arg Gly Ser Asp Ala Tyr Leu Arg Tyr Leu Cys Thr Ala Lys
                85                  90                  95

Tyr Leu Ile Asn Asn Val Ser Phe Pro Tyr Tyr Phe Ile Arg Lys Ala
            100                 105                 110

Glu Gln Ile Tyr Leu Asn Thr Trp His Gly Thr Pro Met Lys Thr Leu
        115                 120                 125

Gly Lys Asp Ile Lys Ser Pro Phe Gln Asp His Ser Asn Val Ser Arg
    130                 135                 140

Asn Phe Leu Gln Ala Thr His Leu Ile Ser Pro Asn Arg His Thr Thr
145                 150                 155                 160

Asp Ile Met Leu Glu Lys Tyr Asp Ile Lys Asp Leu Phe Ser Gly Glu
                165                 170                 175

Ile Ala Glu Thr Gly Tyr Pro Arg Ile Asp Leu Ser Phe Leu Ser Glu
            180                 185                 190

Glu Arg Arg Asn Glu Ile Arg Lys Lys Leu Gly Phe Lys Asn Asn Lys
        195                 200                 205

Pro Val Val Phe Tyr Ala Pro Thr Trp Arg Gly Thr Ser Gln Ser Lys
    210                 215                 220

Asp Phe Asp Thr Gln Lys Leu Lys Asn Asp Leu Lys Arg Leu Lys Ser
225                 230                 235                 240

Asp Lys Tyr Asn Leu Val Phe Arg Gly His His Leu Val Glu Ser Leu
                245                 250                 255

Leu Ser Glu Ile Lys Leu Asp Val Val Val Ala Pro Lys Glu Ile Asp
            260                 265                 270

Ser Asn Glu Leu Leu Gly Tyr Cys Asp Leu Leu Ile Thr Asp Tyr Ser
        275                 280                 285
```

```
Ser Ile Ile Tyr Asp Phe Leu Ala Leu Asn Lys Pro Ala Ile Ser Tyr
            290                 295                 300

Val Tyr Asp Phe Asp Glu Tyr Lys Glu Glu Arg Gly Leu Tyr Phe Glu
305                 310                 315                 320

Lys Asp Glu Met Val Gly Ala Val Cys Ser Thr Ile Ser Glu Val Arg
                325                 330                 335

Gln Ala Ile Leu Glu Asn Leu Asn Thr Asn Lys Ser Asn Val Leu Glu
            340                 345                 350

Arg Asp Ile Glu Lys Tyr Ser Tyr Leu Asp Asp Gly Arg Ala Thr Gln
        355                 360                 365

Arg Thr Ile Asp Phe Ile Phe Asp Asn Asp Arg Ser Ser Ile
370                 375                 380

<210> SEQ ID NO 3
<211> LENGTH: 378
<212> TYPE: PRT
<213> ORGANISM: Artificial sequence
<220> FEATURE:
<223> OTHER INFORMATION: TagF-like domain Bt188

<400> SEQUENCE: 3

Lys Asp Val Ile Lys Asn Lys Glu Glu Glu Tyr Leu Thr Tyr Tyr Thr
1               5                   10                  15

Glu Tyr Tyr Glu Thr Leu Ala Val Asn Glu Lys Gln Val Leu Ile Glu
            20                  25                  30

Ser Phe Phe Gly Gly Asn Ile Ser Cys Asn Pro Tyr Ala Ile Leu Leu
        35                  40                  45

Tyr Met Leu Asp His Asn Tyr Asp Phe Thr Tyr Ile Val Val Val Lys
    50                  55                  60

Pro Glu Thr Val Ile Pro Asp Ser Leu Lys Phe Lys Gln Asn Ile Ile
65                  70                  75                  80

Phe Ile Asn Arg Gly Ser Asp Ala Tyr Leu Arg Tyr Leu Cys Thr Ala
                85                  90                  95

Lys Tyr Leu Ile Asn Asn Val Ser Phe Pro Tyr Tyr Phe Ile Arg Lys
            100                 105                 110

Ala Glu Gln Ile Tyr Leu Asn Thr Trp His Gly Thr Pro Met Lys Thr
        115                 120                 125

Leu Gly Lys Asp Ile Lys Ser Pro Phe Gln Asp His Ser Asn Val Ser
    130                 135                 140

Arg Asn Phe Leu Gln Ala Thr His Leu Ile Ser Pro Asn Arg His Thr
145                 150                 155                 160

Thr Asp Ile Met Leu Glu Lys Tyr Asp Ile Lys Asp Leu Phe Ser Gly
                165                 170                 175

Glu Ile Ala Glu Thr Gly Tyr Pro Arg Ile Asp Leu Ser Phe Leu Ser
            180                 185                 190

Glu Glu Arg Arg Asn Glu Ile Arg Lys Lys Leu Gly Phe Lys Asn Asn
        195                 200                 205

Lys Pro Val Val Phe Tyr Ala Pro Thr Trp Arg Gly Thr Ser Gln Ser
    210                 215                 220

Lys Asp Phe Asp Thr Gln Lys Leu Gln Asn Asp Leu Lys Arg Leu Lys
225                 230                 235                 240

Ser Asp Lys Tyr Asn Leu Val Phe Arg Gly His His Leu Val Glu Ser
                245                 250                 255

Leu Leu Ser Glu Ile Lys Leu Asp Val Val Val Ala Pro Lys Glu Ile
            260                 265                 270
```

Asp Ser Asn Glu Leu Leu Gly Tyr Cys Asp Leu Leu Ile Thr Asp Tyr
        275                 280                 285

Ser Ser Ile Ile Tyr Asp Phe Leu Ala Leu Asn Lys Pro Val Ile Ser
        290                 295                 300

Tyr Val Tyr Asp Phe Asp Glu Tyr Lys Glu Glu Arg Gly Leu Tyr Phe
305                 310                 315                 320

Glu Lys Asp Glu Met Val Gly Ala Val Cys Ser Thr Ile Ser Glu Val
                325                 330                 335

Arg Gln Ala Ile Leu Glu Asn Leu Asn Lys Asn Lys Ser Asn Val Leu
                340                 345                 350

Glu Arg Asp Ile Glu Lys Tyr Ser Tyr Leu Asp Asp Gly Arg Ala Thr
            355                 360                 365

Gln Arg Thr Val Asp Phe Ile Phe Lys Asn
        370                 375

<210> SEQ ID NO 4
<211> LENGTH: 383
<212> TYPE: PRT
<213> ORGANISM: Artificial sequence
<220> FEATURE:
<223> OTHER INFORMATION: TagF-like domain Bt192

<400> SEQUENCE: 4

Lys Asp Val Ile Lys Asn Lys Glu Glu Tyr Leu Thr Tyr Tyr Thr
1               5                   10                  15

Glu Tyr Tyr Glu Thr Leu Ala Val Asn Glu Lys Gln Val Leu Ile Glu
                20                  25                  30

Ser Phe Phe Gly Gly Asn Ile Ser Cys Asn Pro Tyr Ala Ile Leu Leu
            35                  40                  45

Tyr Met Leu Asp His Asn Tyr Asp Phe Thr Tyr Ile Val Val Val Lys
50                  55                  60

Pro Glu Thr Ile Ile Pro Asp Ser Leu Lys Phe Lys Gln Asn Ile Ile
65                  70                  75                  80

Phe Ile Asn Arg Gly Ser Asp Ala Tyr Leu Arg Tyr Leu Cys Thr Ala
                85                  90                  95

Lys Tyr Leu Ile Asn Asn Val Ser Phe Pro Tyr Tyr Phe Ile Arg Lys
            100                 105                 110

Ala Glu Gln Ile Tyr Leu Asn Thr Trp His Gly Thr Pro Met Lys Thr
        115                 120                 125

Leu Gly Lys Asp Ile Lys Ser Pro Phe Gln Asp His Ser Asn Val Ser
    130                 135                 140

Arg Asn Phe Leu Gln Ala Thr His Leu Ile Ser Pro Asn Arg His Thr
145                 150                 155                 160

Thr Asp Ile Met Leu Glu Lys Tyr Asp Ile Lys Asp Leu Phe Ser Gly
                165                 170                 175

Glu Ile Ala Glu Thr Gly Tyr Pro Arg Ile Asp Leu Ser Phe Leu Ser
            180                 185                 190

Glu Glu Arg Arg Asn Glu Ile Arg Lys Lys Leu Gly Phe Lys Asn Asn
        195                 200                 205

Lys Pro Val Val Phe Tyr Ala Pro Thr Trp Arg Gly Thr Ser Gln Ser
    210                 215                 220

Lys Asp Phe Asp Thr Gln Lys Leu Gln Asn Asp Leu Lys Arg Leu Lys
225                 230                 235                 240

Ser Asp Lys Tyr Asn Leu Val Phe Arg Gly His His Leu Val Glu Ser
                245                 250                 255

```
Leu Leu Ser Glu Ile Lys Leu Asp Val Val Ala Pro Lys Glu Ile
            260                 265                 270

Asp Ser Asn Glu Leu Leu Gly Tyr Cys Asp Leu Leu Ile Thr Asp Tyr
        275                 280                 285

Ser Ser Ile Ile Tyr Asp Phe Leu Ala Leu Asn Lys Pro Ala Ile Ser
290                 295                 300

Tyr Val Tyr Asp Phe Asp Glu Tyr Lys Glu Glu Arg Gly Leu Tyr Phe
305                 310                 315                 320

Glu Lys Asp Glu Met Val Gly Ala Val Cys Ser Thr Ile Ser Glu Val
                325                 330                 335

Arg Gln Ala Ile Leu Glu Asn Leu Asn Thr Asn Lys Ser Asn Val Leu
            340                 345                 350

Glu Arg Asp Ile Glu Lys Tyr Ser Tyr Leu Asp Asp Gly Arg Ala Thr
        355                 360                 365

Gln Arg Thr Val Asp Phe Ile Phe Lys Asn Asp Asn Arg Tyr Val
    370                 375                 380
```

<210> SEQ ID NO 5
<211> LENGTH: 378
<212> TYPE: PRT
<213> ORGANISM: Artificial sequence
<220> FEATURE:
<223> OTHER INFORMATION: TagF-like domain Cps3D

<400> SEQUENCE: 5

```
Asp Val Ile Lys His Lys Glu Glu Phe Leu Ser Tyr Tyr Thr Glu
1               5                   10                  15

Tyr Tyr Glu Thr Leu Glu Leu Asp Glu Lys Leu Val Leu Ile Glu Ser
            20                  25                  30

Phe Phe Gly Gly Asn Ile Ser Cys Asn Pro Tyr Ala Ile Leu Ser Tyr
        35                  40                  45

Met Leu Glu Asn Asn Tyr Asp Tyr Thr Tyr Val Val Ile Lys Asp
50                  55                  60

Gly Thr Val Ile Pro Asp Asn Leu Lys Phe Asn Arg Asn Ile Ile Phe
65                  70                  75                  80

Ile Lys Arg Gly Ser Asp Ala Tyr Leu Arg Tyr Leu Cys Thr Ala Lys
                85                  90                  95

Tyr Leu Ile Asn Asn Val Ser Phe Pro Tyr Tyr Phe Ile Arg Lys Glu
            100                 105                 110

Gly Gln Val Tyr Leu Asn Thr Trp His Gly Thr Pro Met Lys Thr Leu
        115                 120                 125

Gly Lys Asp Ile Lys Ser Pro Phe Met Asp His Ala Asn Val Ser Arg
130                 135                 140

Asn Phe Leu Gln Ala Thr His Ile Ile Ser Pro Asn Arg His Thr Thr
145                 150                 155                 160

Asp Val Ile Leu Glu Gln Tyr Asp Val Lys Asp Leu Phe Ser Gly Lys
                165                 170                 175

Leu Ala Glu Thr Gly Tyr Pro Arg Ile Asp Leu Ser Phe Asn Leu Thr
            180                 185                 190

Asp Lys Arg Arg Asn Glu Ile Ala Glu Lys Leu Gly Phe Ser Asn Asn
        195                 200                 205

Lys Pro Val Val Phe Tyr Ala Pro Thr Trp Arg Gly Thr Ser Gln Ser
210                 215                 220

Lys Asp Phe Asp Thr Ser Lys Leu Gln Tyr Asp Leu Arg Lys Leu Lys
225                 230                 235                 240
```

-continued

```
Ser Asn Lys Tyr Asn Leu Ile Phe Arg Gly His His Leu Val Glu Gln
            245                 250                 255

Leu Leu Glu Thr Ile Asn Leu Asp Val Thr Val Ala Pro Lys Asp Ile
        260                 265                 270

Asp Ser Asn Glu Leu Leu Gly Phe Cys Asp Leu Leu Ile Thr Asp Tyr
    275                 280                 285

Ser Ser Ile Ile Tyr Asp Phe Leu Ala Leu Ser Lys Pro Ala Ile Ser
290                 295                 300

Tyr Ile Tyr Asp Tyr Glu Glu Tyr Asp Ala Glu Arg Gly Leu Tyr Leu
305                 310                 315                 320

Lys Pro Thr Glu Met Ser Gly Thr Val Cys Thr Thr Ile Thr Asp Val
                325                 330                 335

Lys Lys Thr Ile Leu Glu His Ile Ser Ser Gly Lys Ser Asn Val Ser
            340                 345                 350

Glu Gln Asp Ile Gln Lys Tyr Ser Tyr Leu Asp Asp Gly Gln Ala Thr
        355                 360                 365

Lys Arg Thr Val Glu Phe Met Leu Asp Lys
    370                 375
```

```
<210> SEQ ID NO 6
<211> LENGTH: 381
<212> TYPE: PRT
<213> ORGANISM: Artificial sequence
<220> FEATURE:
<223> OTHER INFORMATION: TagF-like domain Cps9D

<400> SEQUENCE: 6

Ile Lys His Lys Glu Glu Tyr Leu Ser Tyr Tyr Thr Glu Tyr Tyr
1               5                   10                  15

Glu Thr Leu Glu Leu Asp Glu Lys Leu Val Leu Ile Glu Ser Phe Phe
            20                  25                  30

Gly Gly Asn Ile Ser Cys Asn Pro Tyr Ala Ile Leu Ser Tyr Met Leu
        35                  40                  45

Gly Asn Asn Tyr Asp Tyr Thr Tyr Val Val Ile Lys Asp Gly Thr
    50                  55                  60

Val Ile Pro Asp Asn Leu Lys Phe Asn Arg Lys Ile Ile Phe Ile Lys
65                  70                  75                  80

Arg Gly Ser Asp Ala Tyr Leu Arg Tyr Leu Cys Thr Ala Lys Tyr Leu
                85                  90                  95

Ile Asn Asn Val Ser Phe Pro Tyr Tyr Phe Ile Arg Lys Glu Gly Gln
            100                 105                 110

Ile Tyr Leu Asn Thr Trp His Gly Thr Pro Met Lys Thr Leu Gly Lys
        115                 120                 125

Asp Ile Lys Asn Pro Phe Met Asp His Ala Asn Val Ser Arg Asn Phe
    130                 135                 140

Leu Gln Ala Thr His Ile Ile Ser Pro Asn Arg His Thr Thr Asp Ile
145                 150                 155                 160

Ile Leu Glu Gln Tyr Asp Val Lys Asp Leu Phe Ser Gly Lys Leu Ala
                165                 170                 175

Glu Thr Gly Tyr Pro Arg Ile Asp Leu Ala Phe Asn Leu Thr Gly Lys
            180                 185                 190

Arg Arg Glu Glu Ile Lys Glu Lys Leu Gly Leu Ser Asn Lys Lys Pro
        195                 200                 205

Val Val Phe Tyr Ala Pro Thr Trp Arg Gly Thr Ser Gln Ser Lys Asp
    210                 215                 220
```

```
Phe Asp Thr Thr Lys Leu Gln Ser Asp Leu Lys Lys Leu Lys Ser Asp
225                 230                 235                 240

Lys Tyr Asn Leu Ile Phe Arg Gly His His Leu Val Glu Gln Leu Leu
            245                 250                 255

Glu Thr Ile Asn Leu Asp Val Ile Val Ala Pro Lys Asp Ile Asp Ser
        260                 265                 270

Asn Glu Leu Leu Gly Phe Cys Asp Leu Leu Ile Thr Asp Tyr Ser Ser
    275                 280                 285

Ile Ile Tyr Asp Phe Leu Ala Leu Asn Lys Pro Ala Ile Ser Tyr Ile
290                 295                 300

Tyr Asp Tyr Glu Glu Tyr Asp Ala Glu Arg Gly Leu Tyr Leu Lys Pro
305                 310                 315                 320

Glu Glu Met Ser Gly Thr Val Cys Thr Thr Ile Thr Asp Val Lys Asn
                325                 330                 335

Ala Ile Leu Glu Asn Ile Ala Leu Gly Lys Thr Asn Val Ser Glu Gln
            340                 345                 350

Asp Ile Asn Lys Tyr Ser Tyr Leu Asp Asp Gly Lys Ala Thr Lys Arg
        355                 360                 365

Thr Val Glu Phe Met Phe Asp Arg Asp Asp Ser Cys Val
    370                 375                 380
```

<210> SEQ ID NO 7
<211> LENGTH: 384
<212> TYPE: PRT
<213> ORGANISM: Artificial sequence
<220> FEATURE:
<223> OTHER INFORMATION: TagF-like domain Cps11D

<400> SEQUENCE: 7

```
Lys Asn Val Ile Lys His Lys Glu Glu Tyr Leu Ser Tyr Tyr Thr
1               5                   10                  15

Glu Tyr Tyr Glu Thr Leu Glu Leu Asp Glu Lys Leu Val Leu Ile Glu
            20                  25                  30

Ser Phe Phe Gly Gly Asn Ile Ser Cys Asn Pro Tyr Ala Ile Leu Ser
        35                  40                  45

Tyr Met Leu Gly Asn Asn Tyr Asp Tyr Thr Tyr Val Val Ile Lys
50                  55                  60

Asp Gly Thr Val Ile Pro Asp Asn Leu Lys Phe Asn Arg Lys Ile Ile
65                  70                  75                  80

Phe Ile Lys Arg Gly Ser Asp Ala Tyr Leu Arg Tyr Leu Cys Thr Ala
                85                  90                  95

Lys Tyr Leu Ile Asn Asn Val Ser Phe Pro Tyr Tyr Phe Ile Arg Lys
            100                 105                 110

Glu Gly Gln Ile Tyr Leu Asn Thr Trp His Gly Thr Pro Met Lys Thr
        115                 120                 125

Leu Gly Lys Asp Ile Lys Asn Pro Phe Met Asp His Ala Asn Val Ser
130                 135                 140

Arg Asn Phe Leu Gln Ala Thr His Ile Ile Ser Pro Asn Arg His Thr
145                 150                 155                 160

Thr Asp Ile Ile Leu Glu Gln Tyr Asp Val Lys Asp Leu Phe Ser Gly
                165                 170                 175

Lys Leu Ala Glu Thr Gly Tyr Pro Arg Ile Asp Leu Ala Phe Asn Leu
            180                 185                 190

Thr Gly Lys Arg Arg Glu Glu Ile Lys Glu Lys Leu Gly Leu Ser Asn
        195                 200                 205
```

```
Lys Lys Pro Val Val Phe Tyr Ala Pro Thr Trp Arg Gly Thr Ser Gln
    210             215                 220

Ser Lys Asp Phe Asp Thr Thr Lys Leu Gln Ser Asp Leu Lys Lys Leu
225             230                 235                 240

Lys Ser Asp Lys Tyr Asn Leu Ile Phe Arg Gly His His Leu Val Glu
            245                 250                 255

Gln Leu Leu Glu Thr Ile Asn Leu Asp Val Ile Val Ala Pro Lys Asp
        260                 265                 270

Ile Asp Ser Asn Glu Leu Leu Gly Phe Cys Asp Leu Leu Ile Thr Asp
        275                 280                 285

Tyr Ser Ser Ile Ile Tyr Asp Phe Leu Ala Leu Asn Lys Pro Ala Ile
290             295                 300

Ser Tyr Ile Tyr Asp Tyr Glu Glu Tyr Asp Ala Glu Arg Gly Leu Tyr
305             310                 315                 320

Leu Lys Pro Glu Glu Met Ser Gly Thr Val Cys Thr Thr Ile Thr Asp
            325                 330                 335

Val Lys Asn Ala Ile Leu Glu Asn Ile Ala Leu Gly Lys Thr Asn Val
            340                 345                 350

Ser Glu Gln Asp Ile Asn Lys Tyr Ser Tyr Leu Asp Asp Gly Lys Ala
        355                 360                 365

Thr Lys Arg Thr Val Glu Phe Met Phe Asp Arg Asp Asp Ser Cys Val
370                 375                 380
```

<210> SEQ ID NO 8
<211> LENGTH: 383
<212> TYPE: PRT
<213> ORGANISM: Artificial sequence
<220> FEATURE:
<223> OTHER INFORMATION: TagF-like domain C3694

<400> SEQUENCE: 8

```
Leu Thr Lys Asn Leu Thr Phe Arg Arg Asn Ala Thr Tyr Thr Glu Phe
1               5                   10                  15

Tyr Glu Thr Leu Ser Ile Glu Lys Asn Thr Ile Leu Tyr Glu Ser Phe
            20                  25                  30

His Gly Ala Ser Ile Ser Cys Asn Pro Tyr Ala Leu Phe Leu Asp Ile
        35                  40                  45

Ile Asp Asp Gln Arg Phe Asp Asn Phe Arg His Ile Trp Val Ile Asn
    50                  55                  60

Asn Glu Lys Lys Ile Pro Glu Gln Leu Lys Asn Lys Asn Val Tyr
65              70                  75                  80

Phe Val Ser Arg Gln Ser Asp Leu Tyr Met Gln Cys Leu Ala Ser Cys
                85                  90                  95

Glu Phe Leu Ile Asn Asn Val Ser Phe Pro Glu Tyr Phe Ile Arg Lys
            100                 105                 110

Lys Gly Gln Arg Tyr Leu Asn Thr Trp His Gly Thr Pro Ile Lys Phe
        115                 120                 125

Leu Gly Lys Asp Ile Lys Asp Glu Phe Leu Ala His Lys Asn Val Ala
    130                 135                 140

Arg Asn Phe Leu His Thr Thr His Leu Leu Ser Pro Asn Thr His Thr
145                 150                 155                 160

Thr Asn Ile Leu Leu Asp Arg Tyr Asp Ile Ser Asn Ile Phe Ser Gly
                165                 170                 175

Glu Ile Lys Glu Leu Gly Tyr Pro Arg Ile Asp Arg Thr Ile Asn Leu
            180                 185                 190
```

Ser Ser Glu Arg Lys Glu Tyr Ile Arg Arg Lys Ile Asn Ala Asn Val
            195                 200                 205

Tyr Asp Lys Val Val Leu Tyr Ala Pro Thr Trp Arg Gly Ile His Gly
210                 215                 220

Lys Ala Thr Leu Asp Ile Glu Lys Leu Lys Asn Asp Leu Glu Lys Leu
225                 230                 235                 240

Ala Asp Gln Asp Cys His Ile Val Phe Arg Gly His His Met Ile Glu
            245                 250                 255

Lys Leu Val Ser Glu Gln Asn Ile Ser Gly Ile Thr Ile Val Pro Ser
            260                 265                 270

Glu Ile Asp Thr Asn Glu Leu Leu Gly Ala Ile Asp Ile Leu Ile Thr
            275                 280                 285

Asp Tyr Ser Ser Ile Ala Phe Asp Phe Phe Val Met Asn Arg Pro Val
            290                 295                 300

Ile Tyr Tyr Ala Tyr Asp Ile Glu Gln Tyr Asn Asn Glu Arg Gly Leu
305                 310                 315                 320

Tyr Phe Pro Leu Asn Glu Leu Pro Gly Thr Val Cys Phe Asn Asp Val
            325                 330                 335

Glu Leu Leu Asn Thr Leu Ser Gly Tyr Leu Arg Asn Glu Ile Tyr Phe
            340                 345                 350

Asp Ala Ser Lys Gly Ile Asp Lys Phe Cys Lys Asn Asp Asp Gly Ser
            355                 360                 365

Val Cys Gly Lys Val Ile Glu Trp Phe Phe Phe Glu Glu Lys Ser
            370                 375                 380

<210> SEQ ID NO 9
<211> LENGTH: 372
<212> TYPE: PRT
<213> ORGANISM: Artificial sequence
<220> FEATURE:
<223> OTHER INFORMATION: TagF-like domain CszC

<400> SEQUENCE: 9

Ala Ile Tyr Ser Glu Tyr Tyr Ser Val Leu Asn Val Ile Asp Lys Thr
1               5                   10                  15

Ile Val Tyr Glu Ser Phe Ala Gly Gln Ser Met Ser Cys Ser Pro Tyr
            20                  25                  30

Ala Leu Phe Leu Tyr Met Phe Asn His Pro Asp Tyr Gln Asp Trp Thr
        35                  40                  45

His Ile Trp Val Ile Asn Asp Pro Ala Lys Ile Pro Glu Glu Tyr Lys
    50                  55                  60

Cys Tyr Lys Asn Val Ile Phe Val Ala Arg Gly Ser Asp Val Tyr Leu
65                  70                  75                  80

Arg Tyr Leu Ala Thr Ala Lys Val Leu Leu Asn Ser Asn Phe Pro
            85                  90                  95

Pro Cys Phe Ile Arg Lys Pro Glu Gln Lys Tyr Leu Ser Ala Trp His
            100                 105                 110

Gly Thr Pro Phe Lys Thr Leu Gly Arg Asp Met Glu Gly Arg Phe Phe
        115                 120                 125

Glu His Lys Asn Leu Thr Arg Asn Ile Phe Gln Ala Thr His Leu Leu
    130                 135                 140

Ser Pro Asn Pro His Thr Ser His Val Leu Tyr Lys Arg His Asp Ile
145                 150                 155                 160

His Glu Ile Tyr Thr Gly Lys Leu Ile Glu Ala Gly Tyr Pro Arg Ile
                165                 170                 175

Asp Leu Thr Leu Val Gln Thr Ser Glu Glu Lys Ala Tyr Leu Arg Glu
            180                 185                 190

Arg Leu Gly Leu Thr Asp Gln Glu Lys Leu Ile Phe Tyr Ala Pro Thr
        195                 200                 205

Trp Arg Gly Thr His Asp Asn Ile Asp Phe Asp Tyr Glu Lys Leu Gln
    210                 215                 220

Gln Asp Phe Asp Arg Leu Gly Arg Leu Lys Gly Ala Lys Leu Val Phe
225                 230                 235                 240

Arg Gly His Ala Leu Leu Gln Ala Ala Leu Ala Asp Met Asp Leu Asn
                245                 250                 255

Val Thr Val Ala Pro Asp Asp Leu Asp Thr Asn Arg Ile Leu Gly Val
            260                 265                 270

Thr Asp Ile Leu Ile Thr Asp Tyr Ser Ser Thr Leu Phe Asp Tyr Leu
        275                 280                 285

Pro Val Leu Lys Pro Leu Val Leu Tyr Met Tyr Asp Ile Glu Glu Tyr
    290                 295                 300

Thr Ala Glu Arg Gly Leu Tyr Phe Ser Ala Gly Glu Leu Pro Gly His
305                 310                 315                 320

Lys Cys Tyr Asn Ser Asn Glu Leu Ile Gln Thr Leu Gln Asp Ile Leu
                325                 330                 335

Asp Gln Gly Val Pro Ser Val Thr Ala Glu Glu His Gln Leu Ser Arg
            340                 345                 350

Phe Ala Pro Tyr Asp Asp Gly His Val Ser Glu Arg Val Met Asn Ala
        355                 360                 365

Ile Leu Tyr Asp
    370

<210> SEQ ID NO 10
<211> LENGTH: 384
<212> TYPE: PRT
<213> ORGANISM: Artificial sequence
<220> FEATURE:
<223> OTHER INFORMATION: TagF-like domain Cps7D

<400> SEQUENCE: 10

Asp Ile Leu Ser Lys Asp Ile Ser Tyr Ala Glu Val Ala Thr Tyr Asn
1               5                   10                  15

Glu Tyr Tyr Asn Ile Leu Asn Ile Lys Glu Gln Thr Val Leu Tyr Glu
            20                  25                  30

Ser Phe Ser Gly Gln Gly Met Ser Cys Asn Pro Leu Ala Leu Phe Leu
        35                  40                  45

Tyr Leu Phe Asn His Asn Glu Tyr Lys Asn Trp Thr His Ile Trp Val
    50                  55                  60

Ile Asn Asp Thr Ser Asn Ile Pro Glu Glu Tyr Arg Lys Tyr Asp Asn
65                  70                  75                  80

Val Ile Phe Ile Arg Arg Gly Ser Asp Ser Tyr Leu Arg Tyr Leu Ala
                85                  90                  95

Thr Thr Lys Ile Leu Ile Asn Asn Ser Asn Phe Pro Pro Tyr Phe Ile
            100                 105                 110

Arg Lys Pro Glu Gln Lys Phe Leu Ser Thr Trp His Gly Thr Pro Phe
        115                 120                 125

Lys Thr Leu Gly Arg Asp Met Glu Gly Arg Phe Phe Glu His Lys Asn
    130                 135                 140

Leu Thr Arg Asn Ile Phe Gln Ser Thr His Leu Leu Ser Pro Asn Ala
145                 150                 155                 160

His Thr Ser Lys Ile Leu Tyr Glu Arg His Asp Ile Lys Glu Ile Tyr
                165                 170                 175

Thr Gly Arg Leu Ile Glu Ser Gly Tyr Pro Arg Ile Asp Met Thr Leu
            180                 185                 190

Ser Leu Ala Lys Glu Glu Lys Ile Glu Leu Arg Glu Lys Leu Gly Val
        195                 200                 205

Leu Asn Asn Glu Lys Leu Val Phe Tyr Ala Pro Thr Trp Arg Gly Ile
    210                 215                 220

His Gly Asp Ile Glu Phe Asp Tyr Glu Lys Leu Gln Ser Asp Leu Asn
225                 230                 235                 240

Lys Leu Ser Lys Leu Glu Gly Ala Lys Val Val Phe Arg Gly His Ser
                245                 250                 255

Leu Leu Gln Glu Ala Leu Ser Lys Ile Asn Leu Gly Ile Thr Val Val
            260                 265                 270

Pro Asp Glu Leu Asp Thr Asn Lys Ile Leu Ser Val Thr Asp Ile Leu
        275                 280                 285

Ile Thr Asp Tyr Ser Ser Val Leu Phe Asp Tyr Leu Pro Thr Leu Lys
    290                 295                 300

Pro Leu Val Leu Tyr Met Tyr Asp Ile Lys Glu Tyr Thr Glu Glu Arg
305                 310                 315                 320

Gly Leu Tyr Phe Ser Glu Asn Glu Leu Pro Gly Glu Lys Cys Tyr Asn
                325                 330                 335

Ile Asn Glu Leu Val Lys Thr Leu Thr Tyr Leu Leu Glu Asn Asn Ile
            340                 345                 350

Thr Ser Val Ser Phe Glu Asp Ser Lys Val Ala Gln Phe Ala Pro His
        355                 360                 365

Asp Asp Gly Asn Val Ser Glu Lys Val Ile Asn Ala Leu Phe Leu Asp
    370                 375                 380

<210> SEQ ID NO 11
<211> LENGTH: 377
<212> TYPE: PRT
<213> ORGANISM: Artificial sequence
<220> FEATURE:
<223> OTHER INFORMATION: TagF-like domain Cps2D

<400> SEQUENCE: 11

Ile Gly Phe Ala Glu Ala Ala Ser Tyr Ser Glu Tyr Tyr Asn Val Leu
1               5                   10                  15

Lys Ile Lys Asp Lys Thr Ile Leu Tyr Glu Ser Phe Ser Gly Gln Gly
            20                  25                  30

Met Ser Cys Asn Pro Tyr Ala Leu Phe Leu Tyr Leu Leu Asn His Gln
        35                  40                  45

Glu Tyr Lys Ser Trp Thr His Ile Trp Val Val Asn Asn Ile Asp Asn
    50                  55                  60

Ile Ser Ser Glu Tyr Lys Lys Gln His Asn Ile Ile Phe Val Ser Arg
65                  70                  75                  80

Gly Ser Asp Ser Tyr Leu Arg Tyr Leu Ala Thr Ala Lys Val Leu Ile
                85                  90                  95

Asn Asn Ser Asn Phe Pro Pro Tyr Phe Ile Arg Lys Pro Glu Gln Lys
            100                 105                 110

Phe Leu Ser Thr Trp His Gly Thr Pro Phe Lys Thr Leu Gly Arg Asp
        115                 120                 125

Met Glu Gly Arg Phe Phe Glu His Lys Asn Leu Thr Arg Asn Ile Phe
    130                 135                 140

Gln Ser Thr His Leu Leu Ser Pro Asn Ala His Thr Ser Lys Ile Leu
145                 150                 155                 160

Tyr Asp Arg His Glu Ile Lys Glu Ile Tyr Thr Gly Lys Leu Ile Glu
                165                 170                 175

Ser Gly Tyr Pro Arg Ile Asp Met Thr Leu Ser Leu Thr Glu Glu Glu
            180                 185                 190

Lys Leu Glu Leu Arg Glu Lys Leu Gly Val Leu Asn Asn Glu Lys Leu
        195                 200                 205

Val Phe Tyr Ala Pro Thr Trp Arg Gly Thr His Gly Asp Ile Glu Phe
210                 215                 220

Asp Tyr Asp Lys Leu Lys Ser Asp Leu Asn Lys Leu Ser Lys Leu Lys
225                 230                 235                 240

Gly Ala Lys Val Ile Phe Arg Gly His Ser Leu Leu Gln Glu Ala Leu
                245                 250                 255

Ser Lys Ile Asn Leu Asp Ile Thr Val Ala Pro Asp Glu Leu Asp Thr
            260                 265                 270

Asn Lys Ile Leu Gly Val Thr Asp Ile Leu Ile Thr Asp Tyr Ser Ser
        275                 280                 285

Val Leu Phe Asp Tyr Leu Pro Thr Leu Lys Pro Leu Val Leu Tyr Met
290                 295                 300

Tyr Asp Ile Lys Glu Tyr Thr Glu Glu Arg Gly Leu Tyr Phe Ser Glu
305                 310                 315                 320

Asn Glu Leu Pro Gly Glu Lys Cys Tyr Asn Ile Asp Glu Leu Val Lys
                325                 330                 335

Thr Leu Thr Tyr Leu Leu Glu Asn Asn Ile Thr Ser Val Ser Val Glu
            340                 345                 350

Asp Asn Lys Val Ala Glu Phe Ala Pro His Asp Asp Gly Asn Val Ser
        355                 360                 365

Glu Lys Val Ile Asn Ala Leu Phe Ser
    370                 375

<210> SEQ ID NO 12
<211> LENGTH: 404
<212> TYPE: PRT
<213> ORGANISM: Artificial sequence
<220> FEATURE:
<223> OTHER INFORMATION: TagF-like domain Fcs2

<400> SEQUENCE: 12

Ser Thr Val Ile Asn Lys Ile Ser Asn Arg Ile Lys Ser Leu Phe Leu
1               5                   10                  15

Ile Arg Lys Arg His Lys Thr Trp Lys Trp Leu Arg Leu Leu Lys Leu
                20                  25                  30

Asn Lys Pro Lys Tyr Trp Leu Phe Asn Asp Arg Pro Ile Asn Ala Asn
            35                  40                  45

Asp Asn Ala Glu Ala Phe Phe Thr Tyr Ile Asn Lys Ser Val Pro His
        50                  55                  60

Ile Ala Lys Asn Ser Tyr Phe Val Leu Asp Lys Asn Ser Pro Asp Ile
65                  70                  75                  80

Ser Arg Ile Lys Lys Ile Gly Lys Val Ile Ile Gln Asn Ser Leu Lys
                85                  90                  95

His Lys Leu Leu Tyr Leu Asn Ser Lys Tyr Ile Phe Thr Ser His Leu
            100                 105                 110

Ala Thr Ser Phe Phe Lys Pro Ile Ser Phe Lys His Leu Lys Tyr Tyr
        115                 120                 125

Asn Asp Leu Ile Glu Thr Lys Ile Ile Trp Leu Gln His Gly Ile Thr
130                 135                 140

Met Asn Asn Ile Glu Ile Ala Ala Asn Lys Phe Asn Lys His Ile Tyr
145                 150                 155                 160

Lys Ile Val Thr Ala Ala Asn Phe Glu Asn Ser Ile Phe Lys Asn Lys
                165                 170                 175

Asn Phe Phe Phe Asn Lys Glu Asp Leu Phe Asn Val Gly Phe Pro Arg
            180                 185                 190

Tyr Asp Lys Leu Ile Lys Lys Asp Glu Asp Lys Ile Val Leu Ile
        195                 200                 205

Met Pro Thr Trp Arg Ser Tyr Leu Ser Gly Asn Ile Leu Lys Asn Gly
210                 215                 220

Leu His Ala Glu Leu Glu Ile Phe Lys Glu Ser Asp Tyr Tyr Lys Asn
225                 230                 235                 240

Phe Val Asp Leu Leu Ser Asn Lys Leu Leu Ile Asn Thr Leu Lys Glu
                245                 250                 255

Asn Asn Val Ile Ile Lys Phe Val Leu His Pro Gly Phe Lys Gln Tyr
            260                 265                 270

Ala Lys Tyr Phe Lys Gln Leu Glu Ser Asn Glu Ile Leu Ile Ile Asp
        275                 280                 285

Glu Leu Ser Leu Ser Tyr Lys Asp Leu Phe Asn Glu Ala Ser Leu Leu
290                 295                 300

Ile Thr Asp Tyr Ser Ser Val Phe Phe Asp Phe Ser Tyr Lys Glu Lys
305                 310                 315                 320

Pro Ser Ile Phe Phe Gln Phe Asp Glu Asp Phe Tyr Ser Lys His
                325                 330                 335

Tyr Lys Lys Gly Phe Phe Asp Phe Thr Ser Met Ala Pro Gly Lys Val
            340                 345                 350

Thr Tyr Asn Thr Asp Asp Leu Ile Ser Glu Ile Ile Lys Ser Ile Ile
        355                 360                 365

Ser Asn Phe Ser Ile Lys Asn Glu Tyr Leu Tyr Arg Ile Arg Asn Met
370                 375                 380

Tyr Lys Tyr Asn Asp Asn Lys Asn Cys Glu Arg Leu Leu Asn Glu Val
385                 390                 395                 400

Leu Lys Asn Glu

<210> SEQ ID NO 13
<211> LENGTH: 395
<212> TYPE: PRT
<213> ORGANISM: Artificial sequence
<220> FEATURE:
<223> OTHER INFORMATION: TagF-like domain Cps1B

<400> SEQUENCE: 13

Ile Ser Val Lys Gly Thr Leu Phe Ser Lys Gly Ile Ser Ile Asn Lys
1               5                   10                  15

Ile Leu Ser Ala Phe Thr Pro Gln Ala Lys Tyr Leu Thr Asp Gly Ser
            20                  25                  30

Trp Leu Leu Met Asp Arg Glu Thr Lys Ala Asp Asp Asn Ala Glu His
        35                  40                  45

Phe Tyr Arg Tyr Met Gln Thr His His Pro Glu Gln Arg Cys Tyr Phe
    50                  55                  60

Val Leu Asn Lys Ser Ser Ile Asp Trp Gln Arg Leu Lys Lys Asp Lys
65                  70                  75                  80

Phe Asn Leu Val Glu Phe Gly Ser Ile Glu Tyr Glu Arg Arg Leu Glu
                85                  90                  95

Lys Ala Ser Lys Ile Ile Ser Ser His Leu Glu Ala His Ile Asn Asn
            100                 105                 110

Tyr Phe Gly Asp Asn Tyr Asp Phe Ser Lys Lys Phe Ile Phe Leu Gln
        115                 120                 125

His Gly Ile Thr Lys Asp Asp Leu Ser Gln Trp Phe Asn Thr Lys Lys
    130                 135                 140

Asn Leu Ser Gly Val Ile Thr Ala Thr Ile Pro Glu Tyr Asn Ser Ile
145                 150                 155                 160

Val Glu Glu Leu Asn Lys Tyr Lys Ile Gly Lys Lys Glu Thr Phe Leu
                165                 170                 175

Thr Gly Phe Pro Arg His Asp Lys Leu Leu Ser Gly Asn Ile Lys Gly
            180                 185                 190

Ala Lys Thr Ile Leu Ile Val Pro Thr Trp Arg His Tyr Ile Met Gly
        195                 200                 205

Thr Gln Ile Gly Lys Gly Ala Asn Thr Arg Glu Leu Asn Lys Ala Phe
    210                 215                 220

Met Thr Thr Asn Tyr Ala Lys Ala Trp Tyr Asn Leu Leu His Ser Gln
225                 230                 235                 240

Glu Leu Lys Asn Leu Ile Lys Asn Leu Gly Tyr Lys Val Ile Phe Ala
                245                 250                 255

Pro His Pro Asn Ile Glu Pro Tyr Leu Asn Glu Phe Asn Ile Pro Gln
            260                 265                 270

Tyr Ile Asp Val Trp Lys Ser Ala Ile Ser Arg Glu Ser Met Gln Ser
        275                 280                 285

Leu Phe Gln Gln Ser Asn Leu Leu Ile Thr Asp Tyr Ser Ser Ile Ala
    290                 295                 300

Phe Glu Met Ala Phe Leu Gly Lys Gln Thr Ile Tyr Tyr Gln Phe Asp
305                 310                 315                 320

Lys Glu Glu Phe Arg Ser Gly Ile His Thr Tyr Gln Gln Gly Tyr Phe
                325                 330                 335

Glu Tyr Glu Lys Asp Gly Phe Gly Pro Val Ala Glu Thr Leu Asp Asp
            340                 345                 350

Leu Phe Ile His Leu Asp Lys Phe Val Asn Gly Glu Asn Asp Tyr Ile
        355                 360                 365

Asn Ile Tyr Gln Ser Arg Ile Gln Lys Thr Phe Lys Tyr Arg Asp Thr
    370                 375                 380

Asn Asn Cys Gln Arg Val Tyr Glu Ala Ile Ile
385                 390                 395

<210> SEQ ID NO 14
<211> LENGTH: 400
<212> TYPE: PRT
<213> ORGANISM: Artificial sequence
<220> FEATURE:
<223> OTHER INFORMATION: TagF-like domain BtY31

<400> SEQUENCE: 14

Gln Ile Ala Arg Leu Ser Leu Phe Gly Arg Gln Met Asn Gln Val Arg
1               5                   10                  15

Ile Arg Asp Ile Ile Ser Lys Tyr Gln Pro Ser Glu Lys Tyr Ile Thr
            20                  25                  30

Asp Gly Ser Trp Ile Ile Met Asp Arg Asp Ile Gln Ala Asp Asp Asn
        35                  40                  45

```
Ala Glu His Phe Tyr Arg Tyr Met Met Lys Asn His Pro Glu Gln Cys
 50                  55                  60

Cys Tyr Phe Ala Leu Asn Glu Asp Ser His Asp Trp Lys Arg Leu Glu
 65                  70                  75                  80

Gln Glu Gly Phe Asn Leu Leu Lys Tyr Lys Ser Ser Asn Phe Glu Met
                 85                  90                  95

Lys Leu Arg Lys Ala Ser Lys Val Ile Ser Ser His Phe Asp Asp Tyr
            100                 105                 110

Ile Tyr Asn Tyr Phe Gly Asp His Tyr Glu Asn Ser Lys Lys Phe Ile
            115                 120                 125

Phe Leu Gln His Gly Val Ile Gln Asn Asn Leu Ser Arg Trp Leu Asn
130                 135                 140

Tyr Lys Arg Tyr Leu Ser Leu Phe Val Thr Ser Thr Pro Ala Glu Tyr
145                 150                 155                 160

Lys Ser Ile Ala Gly Asp Asn Thr Ser Tyr Gln Val Gly Lys Lys Glu
                165                 170                 175

Val Val Leu Thr Gly Leu Ser Arg His Asp Ala Leu Leu Lys Val Ser
            180                 185                 190

Gln Ser Leu Ala Gln Asp Lys Met Ile Leu Ile Met Pro Thr Trp Arg
            195                 200                 205

Ala Ser Ile Leu Gly Lys Ala Ser Arg Val Gly Asn Glu Arg Glu Phe
210                 215                 220

Asn Pro Asp Phe Met Asn Thr Asn Tyr Ala Gln His Trp Ser Ser Leu
225                 230                 235                 240

Ile Asn Ser Pro Lys Leu Lys Asp Leu Ala Ser Asn Tyr Gly Tyr Gln
                245                 250                 255

Ile Ile Phe Ala Pro His Ala Asn Ile Glu Pro Tyr Leu Pro Met Phe
            260                 265                 270

Lys Val Pro Glu Tyr Ile Ser Val Trp Gly Ala Lys Asn Asn Gln Asp
            275                 280                 285

Gly Ile Gln Lys Leu Phe Ser Lys Ala Ala Leu Met Ile Thr Asp Tyr
290                 295                 300

Ser Ser Val Ala Phe Glu Met Ala Phe Leu Lys Lys Met Val Leu Tyr
305                 310                 315                 320

Tyr Gln Phe Asp Lys Asp Glu Val Phe Ser Gly Ser His Ile Val Gln
                325                 330                 335

Gln Gly Tyr Phe Ser Tyr Glu Asp Asp Gly Phe Gly Pro Val Ala Ile
            340                 345                 350

Ala Glu Glu Glu Leu Leu Leu Asn Leu Glu Lys Cys Leu Gln Val Asp
            355                 360                 365

Cys Val Ala Ile Glu Pro Tyr Lys Thr Arg Ile Glu Asn Thr Phe Pro
370                 375                 380

Phe Arg Asp Gly Lys Asn Cys Glu Arg Ile Tyr Gln Ser Ile Gln Ala
385                 390                 395                 400

<210> SEQ ID NO 15
<211> LENGTH: 379
<212> TYPE: PRT
<213> ORGANISM: Artificial sequence
<220> FEATURE:
<223> OTHER INFORMATION: TagF-like domain Ccs2

<400> SEQUENCE: 15

Cys Ser Thr Val Lys Asn Tyr Phe Val Lys Asn Ser Thr Lys Val Thr
  1               5                  10                  15
```

Gln Asp Trp Ile Phe Ile Asp Arg Asn Asn Gln Ala Asp Asn Ala
                 20                  25                  30

Glu His Leu Tyr Cys Tyr Val Met Lys Asn Asn Pro Ser Gln Ser Ile
             35                  40                  45

Tyr Phe Val Leu Asn Arg Asp Ser His Asp Trp Glu Arg Leu Glu Lys
 50                  55                  60

Glu Gly Phe Asn Leu Leu Glu Phe Gly Ser Lys Lys Phe Glu Asp Ile
 65                  70                  75                  80

Leu Arg Lys Cys Glu Lys Ile Ile Ser Ser His Ile Asp Gly Tyr Ile
                 85                  90                  95

Thr His Tyr Phe Lys Asp Asn Ser Leu Met Asp Lys Tyr Val Phe
             100                 105                 110

Leu Gln His Gly Ile Thr Lys Asp Asp Leu Ser Ser Trp Leu Asn Thr
             115                 120                 125

Lys Lys Asn Met Ser Leu Phe Val Thr Ala Thr Gln Asp Glu Tyr Asn
130                 135                 140

Ser Ile Arg Gly Asn His Ser Ala Tyr Lys Phe Thr Asp Lys Glu Val
145                 150                 155                 160

Ile Leu Ser Gly Phe Pro Arg His Asp Ala Leu Leu Ala Lys Asn Lys
                 165                 170                 175

His Asp Ser Lys Thr Ile Leu Ile Met Pro Thr Trp Arg Asn Asn Ile
             180                 185                 190

Val Gly Lys Ile Leu Glu Gly Asn Lys Arg Ala Tyr Asn Ser Gln Phe
             195                 200                 205

Met Glu Thr Glu Tyr Ala Ile His Trp Gln Ala Phe Leu Lys Arg Gln
210                 215                 220

Ser Val Lys Met Leu Ser Gln Lys Tyr Gly Tyr Lys Phe Ile Phe Ala
225                 230                 235                 240

Pro His Pro Asn Met Gln Glu Tyr Leu Lys Glu Phe Asp Ile Pro Glu
                 245                 250                 255

Tyr Ile Asp Ile Trp Lys Tyr Ser Asp Gly Asn Ile Gln Asn Leu Phe
             260                 265                 270

Gln Asn Ala Leu Val Leu Ile Thr Asp Tyr Ser Ser Ile Ala Phe Asp
             275                 280                 285

Phe Ala Tyr Leu Asp Lys Ser Val Ile Tyr Tyr Gln Phe Asp Ala Asp
290                 295                 300

Ala Val Phe Ser Gly Ser His Thr Tyr Lys Lys Gly Tyr Phe Ser Tyr
305                 310                 315                 320

Glu Glu Asn Gly Phe Gly Asp Val Val Lys Ser Leu Pro Glu Leu Glu
                 325                 330                 335

Leu Ser Leu Ser Tyr Leu Leu Ile Asn Ser Lys Gly Lys Pro His Thr
             340                 345                 350

Lys Tyr Leu Lys Arg Ile Asn Asp Thr Phe Pro Phe Arg Asp Gly Lys
             355                 360                 365

Asn Cys Gln Arg Val Tyr Glu Ala Ile Thr Asn
370                 375

<210> SEQ ID NO 16
<211> LENGTH: 401
<212> TYPE: PRT
<213> ORGANISM: Artificial sequence
<220> FEATURE:
<223> OTHER INFORMATION: TagF-like domain Cps4B

<400> SEQUENCE: 16

```
Phe Lys Ile Asn Gly Gln Glu Pro Arg Ile Ser Leu Ala Gly Lys Gln
1               5                   10                  15

His Lys Ser Gly Leu Pro Ile His Thr Phe Leu Arg Asp Met Pro Val
            20                  25                  30

Lys Lys Tyr Thr His Ile Glu Asp Phe Trp Ile Ile Met Asp Arg Asp
                35                  40                  45

Val Gln Ala Asp Asp Asn Gly Glu His Phe Tyr Arg Tyr Met Met Asn
    50                  55                  60

Asn His Pro Glu Gln Lys Ile Tyr Phe Ala Ile Asn Arg Asn Ser Asn
65                  70                  75                  80

Asp Trp Gly Arg Leu Lys Arg Glu Gly Phe Asn Leu Ile Asp Phe Lys
                85                  90                  95

Ser Asn Glu Phe Lys Thr Leu Val Ser Gln Cys Ser Arg Leu Ile Ser
            100                 105                 110

Ser His Ile Asp Glu Tyr Ile Ile Asn Pro Phe Lys Asp His Phe Glu
            115                 120                 125

Phe Thr Lys Lys Phe Ile Phe Leu Gln His Gly Val Thr His Asn Asp
    130                 135                 140

Leu Ser Asp Trp Leu Asn Ser Lys Lys Ile Leu Ser Cys Ile Ile Thr
145                 150                 155                 160

Ala Thr Pro Asp Glu Tyr Asn His Ile Ser Glu Asn Lys Ser Arg Tyr
                165                 170                 175

Lys Tyr Ser Thr Lys Glu Ala Ile Leu Thr Gly Phe Pro Arg His Asp
            180                 185                 190

Ala Leu Leu Arg Gly Asn Lys Thr Glu Thr Arg Thr Ile Leu Ile Met
            195                 200                 205

Pro Thr Trp Arg Asn Ser Ile Leu Gly Lys Asn Ala Lys Gly Asn Glu
    210                 215                 220

Arg Ser Ile Asn Ser Glu Phe Met Asn Thr Gln Tyr Ala Lys Ala Trp
225                 230                 235                 240

Gly Ala Ile Leu Ser Ser Pro Ile Leu Glu Lys Leu Ala Asn Gln Tyr
                245                 250                 255

Asp Phe Glu Val Ile Phe Ala Pro His Lys Asn Ile Glu Pro Tyr Leu
            260                 265                 270

Asp Leu Phe Asn Ile Pro Lys Tyr Ile Lys Gln Trp Lys Ala Ser Glu
            275                 280                 285

Gly Asn Ile Gln Lys Leu Phe Gln Asn Ser Lys Phe Met Ile Thr Asp
    290                 295                 300

Tyr Ser Ser Val Ala Phe Glu Met Gly Tyr Leu Asn Lys Thr Val Leu
305                 310                 315                 320

Tyr Tyr Gln Phe Asp Lys Asp Ser Phe Phe Ser Gly Gly His Ala Phe
                325                 330                 335

Lys Arg Gly Tyr Phe Ser Tyr Glu Gln His Gly Phe Gly Pro Val Val
            340                 345                 350

Tyr Thr Glu Glu Glu Phe Phe Ile Asn Leu Glu Asn Ile Leu Lys Asn
            355                 360                 365

Asn Gly Asn Pro Ser Glu Ile Tyr Lys Ser Arg Ile Ala Gln Thr Phe
    370                 375                 380

Pro Phe Gln Asp Gly Lys Cys Cys Glu Arg Val Tyr Phe Ala Ile Gln
385                 390                 395                 400

Asn

<210> SEQ ID NO 17
```

```
<211> LENGTH: 424
<212> TYPE: PRT
<213> ORGANISM: Artificial sequence
<220> FEATURE:
<223> OTHER INFORMATION: GT-B domain CshC

<400> SEQUENCE: 17
```

Ala Ala Phe Asp Asp Gly Ser Ala Thr Lys Arg Thr Ile Asp Phe Met
1               5                   10                  15

Phe Tyr Asn Asp Arg Ser Asn Leu Tyr Asn Tyr Glu Arg Gln Pro Cys
            20                  25                  30

Asn Ile Phe Phe Glu Gly Pro Phe Ile Pro Asn Gly Ile Ser Arg Ser
        35                  40                  45

Phe Ile Asn Leu Met Ser Ser Leu Lys Gly Ser Ser Ala His Ser Val
50                  55                  60

Leu Leu Ile Asn Gly Ala Asp Ile Ala Ser Asp Lys Lys Arg Leu Glu
65                  70                  75                  80

Glu Phe Lys Asn Leu Pro Asp Asn Ile Ser Val Leu Ser Arg Val Gly
            85                  90                  95

Arg Thr Pro Met Thr Leu Glu Glu Leu Trp Val Arg Asn Lys Phe Glu
            100                 105                 110

Asn Ile Phe Lys Phe Pro Ser Glu Ala Phe Lys Thr Thr Leu Ile Arg
        115                 120                 125

Ile Tyr Lys Arg Glu Ala Arg Arg Leu Leu Gly Glu Ser Asn Phe Leu
130                 135                 140

Asn Ala Ile His Phe Glu Gly Tyr Ser Leu Phe Trp Val Leu Leu Phe
145                 150                 155                 160

Ser Gln Ile Asn Ala Ser Lys His Leu Ile Tyr Gln His Asn Asp Lys
            165                 170                 175

Tyr Lys Glu Trp Val Gly Arg Phe Pro Tyr Leu Glu Gly Val Phe Asn
            180                 185                 190

Ser Tyr Glu Phe Phe Asp Lys Thr Ile Ser Val Ser Glu Lys Thr Met
        195                 200                 205

Glu Asn Asn Ile Leu Asn Leu Ser Thr Arg Phe Asn Ile Pro Ile Asp
210                 215                 220

Lys Phe Ala Phe Cys Asn Asn Thr Ile Asn Ile Ser Gln Ile Ile Asp
225                 230                 235                 240

Ser Ala Asp Gln Pro Ile Lys Met Ala Tyr Glu Phe Thr Gln Phe Thr
            245                 250                 255

Gly Thr Lys Phe Ile Asn Ile Gly Arg Met Ser His Glu Lys Asp Gln
            260                 265                 270

Ile Lys Leu Ile Lys Ala Phe Asn Ile Val His Lys Lys Asn Pro Asn
        275                 280                 285

Thr Arg Leu Phe Ile Leu Gly Asp Gly Pro Leu Arg His Asp Leu Glu
290                 295                 300

Leu Thr Ile Lys Glu Leu Gly Met Glu Lys Ile Val Tyr Leu Leu Gly
305                 310                 315                 320

Gln Gln Pro Asn Leu Phe Pro Tyr Leu Lys Asn Ser Asp Cys Phe Val
            325                 330                 335

Leu Ser Ser Asn His Glu Gly Gln Pro Met Val Leu Leu Glu Ser Leu
            340                 345                 350

Thr Leu Gly Val Pro Ile Ile Ala Thr Asp Ile Ile Gly Asn Arg Ser
        355                 360                 365

Ile Leu Gly Asn Lys Tyr Gly Thr Leu Val Glu Asn Ser Glu Asn Gly
370                 375                 380

Leu Ile Asn Gly Met Asn Ser Phe Leu Glu Gly Ala Leu Ser Gln Gly
385                 390                 395                 400

Asp Glu Asn Phe Asp Pro Tyr Lys Tyr Gln Thr Asp Ala Leu Asn Lys
                405                 410                 415

Phe Ile Thr Leu Thr Glu Glu Asn
            420

<210> SEQ ID NO 18
<211> LENGTH: 389
<212> TYPE: PRT
<213> ORGANISM: Artificial sequence
<220> FEATURE:
<223> OTHER INFORMATION: GT-B domain Bt189

<400> SEQUENCE: 18

Ser Asp Val Phe Phe Glu Gly Pro Phe Ile Pro Asn Gly Ile Ser Arg
1               5                   10                  15

Ser Phe Leu Asn Leu Met Ser Ser Leu Asn Asn His Lys Asn Asn Ile
            20                  25                  30

Thr Leu Leu Ile Asn Gly Ala Asp Ile Ala Gln Asp His Lys Arg Ile
        35                  40                  45

Asn Glu Phe Asn Asn Leu Pro Asp Asn Val Thr Val Leu Ser Arg Val
    50                  55                  60

Gly Arg Thr Pro Met Thr Leu Glu Glu Leu Trp Val Lys Thr Lys Phe
65              70                  75                  80

Glu Glu Thr Tyr Gln Phe Tyr Ser Lys Glu Phe Glu Glu Thr Leu Ile
            85                  90                  95

Arg Ile Tyr Lys Arg Glu Ser Arg Arg Leu Leu Gly Asp Ser Lys Phe
            100                 105                 110

Asn Asn Ala Ile His Phe Glu Gly Tyr Ala Leu Phe Trp Val Leu Leu
            115                 120                 125

Phe Ser Gln Ile Asn Ala Asn Gln His Ile Ile Tyr Gln His Asn Asp
        130                 135                 140

Lys Tyr Lys Glu Trp Lys Gly Arg Phe Pro Tyr Leu Glu Gly Val Phe
145                 150                 155                 160

Asn Ala Tyr Lys Phe Tyr Asp Lys Ile Val Ser Val Ser Glu Lys Thr
                165                 170                 175

Met Glu Asn Asn Ile Asn Asn Leu Ser Lys Glu Phe Asn Leu Ser Lys
            180                 185                 190

Asp Lys Phe Asp Phe Cys Asn Asn Ser Ile Asn Ile Asn Gln Val Ile
        195                 200                 205

Ser Ser Ala Lys Asp Gly Ile Glu Ile Glu Asp Glu Phe Ala Asn Phe
    210                 215                 220

Ala Gly Thr Lys Phe Ile Asn Ile Gly Arg Met Ser His Glu Lys Asp
225                 230                 235                 240

Gln Leu Lys Leu Ile Glu Ala Phe Ala Glu Val Asn Lys Lys His Lys
                245                 250                 255

Asp Thr Arg Leu Phe Ile Leu Gly Asp Gly Ala Leu Lys Gln Glu Leu
            260                 265                 270

Ile Thr Arg Ile Lys Glu Leu Ser Leu Glu Lys Asp Val Phe Leu Leu
        275                 280                 285

Gly Gln Lys Thr Asn Pro Phe Ala Tyr Leu Lys Gln Ala Asp Ile Phe
    290                 295                 300

Val Leu Ser Ser Asn His Glu Gly Gln Pro Met Val Leu Leu Glu Ser
305                 310                 315                 320

```
Leu Ile Leu Gly Thr Pro Ile Ile Ala Thr Asp Ile Val Gly Asn Arg
                325                 330                 335

Ser Ile Leu Gly Asn Lys Tyr Gly Leu Leu Val Glu Asn Ser Lys Gln
            340                 345                 350

Gly Leu Ile Asn Gly Met Asn Glu Tyr Leu Glu Asn Gly Ser Lys Gln
        355                 360                 365

Asp Asn Phe Asp Pro Ile Ala Tyr Gln Lys Asp Ala Met Asp Lys Phe
    370                 375                 380

Tyr Ala Leu Leu Asn
385

<210> SEQ ID NO 19
<211> LENGTH: 390
<212> TYPE: PRT
<213> ORGANISM: Artificial sequence
<220> FEATURE:
<223> OTHER INFORMATION: GT-B domain Bt188

<400> SEQUENCE: 19

Asp Thr Asp Val Phe Phe Val Gly Pro Phe Leu Gln Asn Gly Ile Thr
1               5                   10                  15

Arg Ser Phe Leu Asn Leu Met Ser Thr Ile Gly Arg Glu Lys Asn Ile
            20                  25                  30

Leu Val Leu Ile Asn Gly Asn Asp Leu Gln Ser Asp Asn Lys Arg Leu
        35                  40                  45

Glu Glu Phe Tyr Arg Leu Pro Lys Asp Ile Ser Val Phe Ser Arg Ser
    50                  55                  60

Gly Arg Met Leu Met Thr Leu Glu Glu Leu Trp Val Arg Asn Lys Phe
65                  70                  75                  80

Asp Glu Asn Phe Lys Phe Tyr Ser Glu Glu Phe Lys Arg Val Ile Glu
                85                  90                  95

Lys Ile Tyr Lys Arg Glu Ala Arg Arg Leu Phe Gly Asp Ser Lys Ile
            100                 105                 110

Arg Asn Ile Ile Asn Phe Glu Gly Tyr Ala Leu Phe Trp Val Leu Leu
        115                 120                 125

Ile Ser Gln Val Asn Ala Lys Gln His Ile Ile Tyr Gln His Asn Asp
    130                 135                 140

Lys Tyr Lys Glu Trp Lys Ser Lys Phe Pro Tyr Leu Glu Gly Val Phe
145                 150                 155                 160

Arg Thr Tyr Arg Tyr Tyr Asp Lys Ile Val Ser Val Ser Glu Lys Thr
                165                 170                 175

Met Glu Asn Asn Arg Asn Asn Ile Ser Tyr Glu Phe Gly Ile Ala Glu
            180                 185                 190

Lys Arg Phe Val Phe Cys Asn Asn Pro Ile Asn Ile Asp Gln Ile Ile
        195                 200                 205

Ser Asn Ala Lys Asp Asp Ile Glu Ile Glu Asp Glu Phe Asp Asn Phe
    210                 215                 220

Ala Gly Thr Lys Phe Ile Asn Ile Gly Arg Met Ser His Glu Lys Asp
225                 230                 235                 240

Gln Leu Lys Leu Ile Glu Ala Phe Ala Glu Val Asn Lys Lys His Lys
                245                 250                 255

Asp Thr Arg Leu Phe Ile Leu Gly Asp Gly Pro Leu Lys Gln Glu Leu
            260                 265                 270

Ile Thr Arg Ile Lys Lys Leu Ser Leu Glu Lys Asp Val Phe Leu Leu
        275                 280                 285
```

```
Gly Gln Lys Thr Asn Pro Phe Ala Tyr Leu Lys Gln Ala Asp Ile Phe
            290                 295                 300

Val Leu Ser Ser Asn His Glu Gly Gln Pro Met Val Leu Leu Glu Ser
305                 310                 315                 320

Leu Thr Leu Gly Thr Pro Ile Ile Ala Thr Asp Ile Val Gly Asn Arg
                325                 330                 335

Ser Ile Leu Gly Asp Lys Tyr Gly Leu Leu Val Glu Asn Ser Lys Gln
                340                 345                 350

Gly Leu Ile Asn Gly Met Asn Glu Tyr Leu Glu Asn Gly Ser Lys Gln
            355                 360                 365

Asp Asn Phe Asp Pro Ile Ala Tyr Gln Lys Asp Ala Met Asp Lys Phe
            370                 375                 380

Tyr Ala Leu Leu Asn Glu
385                 390

<210> SEQ ID NO 20
<211> LENGTH: 387
<212> TYPE: PRT
<213> ORGANISM: Artificial sequence
<220> FEATURE:
<223> OTHER INFORMATION: GT-B domain Bt192

<400> SEQUENCE: 20

Thr Asp Val Phe Phe Val Gly Pro Phe Leu Gln Asn Gly Ile Thr Arg
1               5                   10                  15

Ser Phe Leu Asn Leu Met Ser Thr Ile Gly Arg Glu Lys Asn Ile Leu
            20                  25                  30

Val Leu Ile Asn Gly Asn Asp Leu Gln Ser Asp Asn Lys Arg Leu Glu
        35                  40                  45

Glu Phe Tyr Arg Leu Pro Lys Asp Ile Ser Val Phe Ser Arg Ser Gly
    50                  55                  60

Arg Met Leu Met Thr Leu Glu Glu Leu Trp Val Arg Asn Lys Phe Asp
65                  70                  75                  80

Glu Asn Phe Lys Phe Tyr Ser Glu Glu Phe Lys Arg Val Ile Glu Lys
                85                  90                  95

Ile Tyr Lys Arg Glu Ala Arg Arg Leu Phe Gly Asp Ser Lys Ile Arg
            100                 105                 110

Asn Ile Ile Asn Phe Glu Gly Tyr Ala Leu Phe Trp Val Leu Leu Ile
        115                 120                 125

Ser Gln Val Asn Ala Lys Gln His Ile Ile Tyr Gln His Asn Asp Lys
130                 135                 140

Tyr Lys Glu Trp Lys Ser Lys Phe Pro Tyr Leu Glu Gly Val Phe Arg
145                 150                 155                 160

Thr Tyr Arg Tyr Tyr Asp Lys Ile Val Ser Val Ser Glu Lys Thr Met
                165                 170                 175

Glu Asn Asn Arg Asn Asn Ile Ser Tyr Glu Phe Gly Ile Ala Glu Lys
            180                 185                 190

Arg Phe Val Phe Cys Asn Asn Pro Ile Asn Ile Asp Gln Ile Ile Ser
        195                 200                 205

Asn Ala Lys Asp Asp Ile Glu Ile Glu Asp Glu Phe Asp Asn Phe Thr
210                 215                 220

Gly Thr Lys Phe Ile Asn Ile Gly Arg Met Ser His Glu Lys Asp Gln
225                 230                 235                 240

Leu Lys Leu Ile Glu Ala Phe Ala Glu Val Asn Lys Lys His Lys Asp
                245                 250                 255
```

```
Thr Arg Leu Phe Ile Leu Gly Asp Gly Pro Leu Lys Gln Glu Leu Ile
            260                 265                 270

Thr Arg Ile Lys Glu Leu Ser Leu Glu Lys Asp Val Phe Leu Leu Gly
            275                 280                 285

Gln Lys Thr Asn Pro Phe Ala Tyr Leu Lys Gln Ala Asp Ile Phe Val
            290                 295                 300

Leu Ser Ser Asn His Glu Gly Gln Pro Met Val Leu Leu Glu Ser Leu
305                 310                 315                 320

Thr Leu Gly Thr Pro Ile Ile Ala Thr Asp Ile Val Gly Asn Arg Ser
                325                 330                 335

Ile Leu Gly Asn Lys Tyr Gly Leu Leu Val Glu Asn Ser Lys Gln Gly
            340                 345                 350

Leu Ile Asn Gly Met Asn Glu Tyr Leu Glu Asn Gly Ser Arg Gln Asp
            355                 360                 365

Asn Phe Asp Pro Val Ala Tyr Gln Lys Asp Ala Met Asp Lys Phe Tyr
            370                 375                 380

Ala Leu Leu
385

<210> SEQ ID NO 21
<211> LENGTH: 390
<212> TYPE: PRT
<213> ORGANISM: Artificial sequence
<220> FEATURE:
<223> OTHER INFORMATION: GT-B domain Cps3D

<400> SEQUENCE: 21

Ser Asp Val Phe Phe Glu Gly Pro Phe Ile Pro Asn Gly Ile Ser Arg
1               5                   10                  15

Ser Phe Leu Asn Leu Met Ala Ser Ile Lys Asp Ser Gly Lys Asn Ile
            20                  25                  30

Thr Leu Leu Ile Asn Gly Ser Asp Ile Ala Gln Asp Gln Lys Arg Leu
        35                  40                  45

Glu Glu Phe Asn Asn Leu Pro Ser Asn Ile Thr Val Leu Ser Arg Val
50                  55                  60

Gly Arg Thr Pro Met Thr Leu Glu Glu Leu Trp Val Arg Asn Lys Phe
65                  70                  75                  80

Glu Glu Thr Tyr Gln Ile Tyr Ser Glu Ser Phe Thr Asn Thr Leu Leu
                85                  90                  95

Lys Val Tyr Lys Arg Glu Val Arg Arg Leu Leu Gly Asn Ser Ser Phe
            100                 105                 110

Asp Asn Ala Ile His Phe Glu Gly Tyr Ser Leu Phe Trp Val Leu Leu
        115                 120                 125

Phe Ser Gln Ile Asn Ala Lys Lys His Ile Ile Tyr Gln His Asn Asp
130                 135                 140

Lys Tyr Lys Glu Trp Lys Gly Arg Phe Pro Tyr Leu Glu Gly Val Phe
145                 150                 155                 160

Asn Ser Tyr Val Phe Phe Asp Gln Ile Val Ser Val Ser Glu Lys Thr
                165                 170                 175

Met Glu Asn Asn Ile Leu Asn Leu Ser Lys Glu Phe Asn Ile Pro Glu
            180                 185                 190

Ile Lys Phe Thr Phe Cys Asn Asn Pro Ile Asn Ile Gln Gln Ile Leu
        195                 200                 205

Ser Ser Ala Glu Glu Asn Ile Glu Met Glu Ser Glu Phe Thr Leu Phe
210                 215                 220
```

```
Asn Gly Gln Lys Phe Ile Asn Ile Gly Arg Met Ser His Glu Lys Asp
225                 230                 235                 240

Gln Leu Lys Leu Ile Glu Ala Phe Tyr Glu Ala Lys Lys Ala His Val
            245                 250                 255

Asn Ile Arg Leu Phe Ile Leu Gly Asp Gly Val Leu Lys Gln Asp Leu
        260                 265                 270

Ile Asn Lys Ile Lys Asp Leu Ser Leu Glu Asp Ser Val Tyr Leu Leu
    275                 280                 285

Gly Gln Lys Lys Asn Pro Phe Pro Tyr Leu Lys Gln Ala Asp Val Phe
290                 295                 300

Ile Leu Ser Ser Asn His Glu Gly Gln Pro Met Val Leu Leu Glu Ser
305                 310                 315                 320

Leu Thr Leu Gly Thr Pro Ile Ile Ala Thr Asp Ile Val Gly Asn Arg
            325                 330                 335

Ser Ile Leu Gly Glu Asn Tyr Gly Thr Leu Val Glu Asn Asn Lys Asp
        340                 345                 350

Gly Leu Val Gln Gly Ile Asn Ala Tyr Met Glu Lys Gly Gly Arg Lys
    355                 360                 365

Asp Lys Phe Asp Pro Tyr Glu Tyr Gln Asn Asp Ala Met Ala Lys Phe
370                 375                 380

Tyr Ser Leu Leu Ala Asn
385                 390

<210> SEQ ID NO 22
<211> LENGTH: 392
<212> TYPE: PRT
<213> ORGANISM: Artificial sequence
<220> FEATURE:
<223> OTHER INFORMATION: GT-B domain Cps9D

<400> SEQUENCE: 22

Arg Lys Lys Ser Asp Ile Phe Phe Glu Gly Pro Phe Ile Pro Asn Gly
1               5                   10                  15

Ile Ser Arg Ser Phe Leu Asn Leu Met Ala Ser Ile Lys Asp Ser Glu
            20                  25                  30

Lys Asn Ile Thr Leu Leu Ile Asn Gly Ala Asp Ile Ala Gln Asp Gln
        35                  40                  45

Lys Arg Leu Ala Glu Phe Asp Asn Leu Pro Ser Asn Val Thr Val Leu
50                  55                  60

Ser Arg Val Gly Arg Thr Pro Met Thr Leu Glu Glu Leu Trp Val Arg
65                  70                  75                  80

Asn Lys Phe Glu Glu Thr Tyr Gln Met Tyr Ser Glu Ser Phe Thr Glu
                85                  90                  95

Thr Leu Leu Lys Val Tyr Lys Arg Glu Val Arg Arg Leu Leu Gly Asp
            100                 105                 110

Ser Leu Phe Glu Asn Ala Ile His Phe Glu Gly Tyr Ser Leu Phe Trp
        115                 120                 125

Val Leu Leu Phe Ser Gln Ile Asn Ala Lys Lys His Ile Ile Tyr Gln
130                 135                 140

His Asn Asp Lys Tyr Lys Glu Trp Lys Gly Arg Phe Pro Tyr Leu Glu
145                 150                 155                 160

Gly Val Phe Asn Ser Tyr Val Phe Phe Asp Gln Ile Val Ser Val Ser
                165                 170                 175

Glu Lys Thr Met Glu Asn Asn Ile Leu Asn Leu Ser Lys Ser Phe Asn
            180                 185                 190
```

Ile Pro Lys Glu Lys Phe Thr Phe Cys Asn Asn Pro Ile Asn Ile Gln
            195                 200                 205

Gln Ile Leu Ser Ser Ala Glu Glu Asp Ile Glu Met Glu Ser Glu Phe
        210                 215                 220

Thr Ser Phe Asn Gly Gln Lys Phe Ile Asn Ile Gly Arg Met Ser His
225                 230                 235                 240

Glu Lys Asp Gln Leu Lys Leu Ile Glu Ala Phe Cys Glu Ala Lys Lys
                245                 250                 255

Val His Ala Asn Ile Arg Leu Phe Ile Leu Gly Asp Gly Val Leu Lys
            260                 265                 270

Gln Asp Leu Thr Asn Lys Ile Lys Glu Leu Ser Leu Glu Lys Asp Val
            275                 280                 285

Tyr Leu Leu Gly Gln Lys Lys Asn Pro Phe Pro Tyr Leu Lys Gln Ala
        290                 295                 300

Asp Val Phe Ile Leu Ser Ser Asn His Glu Gly Gln Pro Met Val Leu
305                 310                 315                 320

Leu Glu Ser Leu Thr Leu Gly Thr Pro Ile Ile Ala Thr Asp Ile Val
                325                 330                 335

Gly Asn Arg Ser Ile Leu Gly Asp Asn Tyr Gly Val Leu Val Glu Asn
            340                 345                 350

Ser Lys Asp Gly Leu Val Lys Gly Ile Asn Ile Tyr Met Glu Gln Gly
        355                 360                 365

Gly Arg Lys Asp Ser Phe Asp Pro Tyr Glu Tyr Gln Asn Asp Ala Met
    370                 375                 380

Ala Lys Phe Tyr Ser Leu Leu Thr
385                 390

<210> SEQ ID NO 23
<211> LENGTH: 389
<212> TYPE: PRT
<213> ORGANISM: Artificial sequence
<220> FEATURE:
<223> OTHER INFORMATION: GT-B domain Cps11D

<400> SEQUENCE: 23

Ser Asp Ile Phe Phe Glu Gly Pro Phe Ile Pro Asn Gly Ile Ser Arg
1               5                   10                  15

Ser Phe Leu Asn Leu Met Ala Ser Ile Lys Asp Ser Glu Lys Asn Ile
            20                  25                  30

Thr Leu Leu Ile Asn Gly Ala Asp Ile Ala Gln Asp Gln Lys Arg Leu
        35                  40                  45

Ala Glu Phe Asp Asn Leu Pro Ser Asn Val Thr Val Leu Ser Arg Val
50                  55                  60

Gly Arg Thr Pro Met Thr Leu Glu Glu Leu Trp Val Arg Asn Lys Phe
65                  70                  75                  80

Glu Glu Thr Tyr Gln Met Tyr Ser Glu Ser Phe Thr Glu Thr Leu Leu
                85                  90                  95

Lys Val Tyr Lys Arg Glu Val Arg Arg Leu Leu Gly Asp Ser Leu Phe
            100                 105                 110

Glu Asn Ala Ile His Phe Glu Gly Tyr Ser Leu Phe Trp Val Leu Leu
        115                 120                 125

Phe Ser Gln Ile Asn Ala Lys Lys His Ile Ile Tyr Gln His Asn Asp
    130                 135                 140

Lys Tyr Lys Glu Trp Lys Gly Arg Phe Pro Tyr Leu Glu Gly Val Phe
145                 150                 155                 160

```
Asn Ser Tyr Val Phe Phe Asp Gln Ile Val Ser Val Ser Glu Lys Thr
            165                 170                 175

Met Glu Asn Asn Ile Leu Asn Leu Ser Lys Ser Phe Asn Ile Pro Lys
        180                 185                 190

Glu Lys Phe Thr Phe Cys Asn Asn Pro Ile Asn Ile Gln Gln Ile Leu
            195                 200                 205

Ser Ser Ala Glu Glu Asp Ile Glu Met Glu Ser Glu Phe Thr Ser Phe
210                 215                 220

Asn Gly Gln Lys Phe Ile Asn Ile Gly Arg Met Ser His Glu Lys Asp
225                 230                 235                 240

Gln Leu Lys Leu Ile Glu Ala Phe Cys Glu Ala Lys Lys Val His Ala
                245                 250                 255

Asn Ile Arg Leu Phe Ile Leu Gly Asp Gly Val Leu Lys Gln Asp Leu
            260                 265                 270

Thr Asn Lys Ile Lys Glu Leu Ser Leu Glu Lys Asp Val Tyr Leu Leu
        275                 280                 285

Gly Gln Lys Lys Asn Pro Phe Pro Tyr Leu Lys Gln Ala Asp Val Phe
290                 295                 300

Ile Leu Ser Ser Asn His Glu Gly Gln Pro Met Val Leu Leu Glu Ser
305                 310                 315                 320

Leu Thr Leu Gly Thr Pro Ile Ile Ala Thr Asp Ile Val Gly Asn Arg
                325                 330                 335

Ser Ile Leu Gly Asp Asn Tyr Gly Val Leu Val Glu Asn Ser Lys Asp
            340                 345                 350

Gly Leu Val Lys Gly Ile Asn Ile Tyr Met Glu Gln Gly Gly Arg Lys
        355                 360                 365

Asp Ser Phe Asp Pro Tyr Glu Tyr Gln Asn Asp Ala Met Ala Lys Phe
370                 375                 380

Tyr Ser Leu Leu Thr
385

<210> SEQ ID NO 24
<211> LENGTH: 388
<212> TYPE: PRT
<213> ORGANISM: Artificial sequence
<220> FEATURE:
<223> OTHER INFORMATION: GT-B domain C3694

<400> SEQUENCE: 24

Asn Lys Asn Ile Leu Phe Tyr Ile Gly Pro Phe Ile Pro Asn Gly Ile
1               5                   10                  15

Leu Ser Ser Trp Leu Asn Leu Ile Ser Val Ile Asp Arg Asp Lys Tyr
            20                  25                  30

Asn Ile Ser Leu Val Val Asp Pro Lys Ser Ile His Gly Phe Gln Glu
        35                  40                  45

Arg Phe Glu Gln Phe Lys Arg Val Ser Pro Asp Ile Gln Val Ile Gly
    50                  55                  60

Thr Cys Gly Asn Met Leu Tyr Asn Ile Glu Glu Lys Trp Leu Asn Asp
65                  70                  75                  80

Lys Leu Asn Asn Gln Phe Thr Leu Ala Ser Lys Glu Met Tyr Asp Ile
                85                  90                  95

Leu Asp His Ala Tyr Gln Arg Glu Phe Leu Arg Leu Phe Gly Tyr Ser
            100                 105                 110

His Ile Asp His Leu Ile His Phe Glu Gly Tyr Asn Gln Ser Trp Val
        115                 120                 125
```

Ile Arg Phe Ala Asn Ala Pro Lys Asp Thr Val Arg Asn Lys Ile Ile
130                 135                 140

Phe Gln His Asn Asp Lys Leu Ser Glu Trp Arg Glu Arg Phe Pro Tyr
145                 150                 155                 160

Leu Arg Val Val Phe Asp Phe Tyr Lys Ser Tyr Asn Lys Ile Val Ser
                165                 170                 175

Val Ser Glu Lys Thr Met Glu Leu Asn Arg Asp Asn Leu Ser Glu Phe
            180                 185                 190

Phe Asn Ile Glu His Asp Lys Phe Ile Tyr Cys Asp Asn Val Gln Asn
        195                 200                 205

Pro Asp Glu Val Ile Lys Lys Ser Asp Asp Ile Asp Thr Ser Gly Phe
210                 215                 220

Ile Phe Glu Asn Asp Lys Ile Tyr Phe Ile Thr Leu Gly Arg Leu Ser
225                 230                 235                 240

Val Glu Lys Asp Gln Gln Lys Leu Ile Asn Ala Phe Cys Arg Leu Gln
                245                 250                 255

Lys Leu Tyr Pro Asn Ile Glu Leu Leu Ile Leu Gly Asp Gly Pro Leu
            260                 265                 270

Lys Ile Asp Leu Gln Arg Gln Ile Ile Thr Leu Gly Leu Glu Lys Ser
        275                 280                 285

Val His Leu Leu Gly Arg Ile Ser Asn Pro Phe Pro Leu Leu Lys Arg
290                 295                 300

Ala Asp Cys Phe Val Leu Ser Ser Asn His Glu Gly Gln Pro Met Val
305                 310                 315                 320

Leu Phe Glu Ala Met Ile Leu Asp Lys Pro Ile Ile Ser Thr Asp Ile
                325                 330                 335

Thr Gly Ser Arg Ser Ala Leu Glu Gly Arg Ser Gly Val Leu Val Glu
            340                 345                 350

Asn Ser Val Asp Gly Leu Phe Asn Gly Met Arg Asp Phe Ile Leu Gly
        355                 360                 365

Arg Leu Glu Phe Lys His Phe Asp Ile Glu Ser Tyr Gln Lys Asn Ala
370                 375                 380

Leu Ser Met Phe
385

<210> SEQ ID NO 25
<211> LENGTH: 442
<212> TYPE: PRT
<213> ORGANISM: Artificial sequence
<220> FEATURE:
<223> OTHER INFORMATION: GT-B domain CszC

<400> SEQUENCE: 25

Gln Gly Val Pro Ser Val Thr Ala Glu Glu His Gln Leu Ser Arg Phe
1               5                   10                  15

Ala Pro Tyr Asp Asp Gly His Val Ser Glu Arg Val Met Asn Ala Ile
                20                  25                  30

Leu Tyr Asp Asp Tyr Gln Gly Ile Lys Val Ile Asn Asp Val Pro Lys
            35                  40                  45

Asp Lys Gln Ser Leu Leu Ile Tyr Gly Gly Pro Phe Met Gly Asn Gly
        50                  55                  60

Ile Thr Thr Ala Thr Ile Asn Leu Ile Ala Asn Ile Asp Arg Ser Lys
65                  70                  75                  80

Tyr Thr Val Thr Leu Val Ile Asp Pro Gly Ser Ile Ile Asn Asp Glu
                85                  90                  95

Thr Arg Met Thr Gln Phe Glu Lys Leu Pro Gln Asp Ile Asn Val Ile
            100                 105                 110

Ala Arg Val Gly Arg Met Asp Met Thr Leu Glu Asp Arg Tyr Ile His
            115                 120                 125

Gly Leu Met Asn Gln Arg Tyr Glu Leu Asp Ser Pro Ala Ala Lys Lys
130                 135                 140

Ile Leu Lys Asp Ser Trp Lys Gln Glu Tyr Asp Arg Val Phe Gly Gln
145                 150                 155                 160

Ala Lys Phe Asp Ala Leu Ile His Phe Glu Gly Tyr Asn Arg Phe Trp
                165                 170                 175

Ala Gly Val Phe Thr Ser Val Asn Asp Gly Arg Lys Thr Ser Ile Tyr
            180                 185                 190

Met His Ser Ser Met Lys Glu Glu Tyr Gln Leu Lys Phe Pro Tyr Leu
            195                 200                 205

Lys Ala Met Phe Gly Tyr Gly Ala Gln Ala Asn Lys Tyr Ile Ser Val
            210                 215                 220

Ser Lys Ser Thr Met Gln Arg Asn Gln Ser Asn Leu Ala Gln Pro Phe
225                 230                 235                 240

Asn Ile Pro Leu Glu Lys Phe Asp Tyr Thr Asp Asn Leu Gln Gln Pro
                245                 250                 255

Glu Gln Thr Arg Ile Leu Ala Ala Glu Pro Leu Leu Pro Glu Asp Glu
            260                 265                 270

Gln Tyr Phe Gln Gly Thr Gly Lys Val Phe Ile Thr Ile Gly Arg Leu
            275                 280                 285

Ser Met Glu Lys Asp His Ala Lys Leu Ile Asn Ser Phe Ala Gln Ile
            290                 295                 300

Ala Ala Asp Tyr Pro Asp Ser Arg Leu Leu Ile Val Gly Asp Gly Ala
305                 310                 315                 320

Leu Arg His Ala Leu Ser Gln Gln Ile Ala Glu Leu Lys Leu Glu Asn
                325                 330                 335

Gln Val His Leu Leu Gly Leu Arg Ser Asn Pro Phe Pro Leu Leu Lys
            340                 345                 350

Lys Ala Asp Cys Phe Val Leu Ser Ser Asn His Glu Gly Gln Pro Met
            355                 360                 365

Thr Leu Phe Glu Ala Met Ile Leu Glu Lys Met Ile Ile Ala Thr Asp
            370                 375                 380

Ile Val Gly Ser Arg Gly Val Leu Glu Asn Arg Ser Gly Tyr Leu Val
385                 390                 395                 400

Glu Asn Ser Val Ala Gly Leu Ala Gln Gly Leu Ala Asp Phe Leu Ala
                405                 410                 415

Gly Lys Leu Thr Leu Thr Thr Tyr Asp Ile Glu Glu Tyr Gln Gln Gln
            420                 425                 430

Ala Ile Asn Arg Phe Tyr His Leu Ile Asn
            435                 440

<210> SEQ ID NO 26
<211> LENGTH: 391
<212> TYPE: PRT
<213> ORGANISM: Artificial sequence
<220> FEATURE:
<223> OTHER INFORMATION: GT-B domain Cps7D

<400> SEQUENCE: 26

Lys Lys Ser Leu Leu Ile Tyr Gly Gly Pro Phe Met Gly Asn Gly Ile
1               5                   10                  15

Thr Thr Ser Val Ile Asn Leu Ile Ser Asn Ile Asp Arg Ser Lys Tyr
            20                  25                  30

Thr Val Thr Leu Val Ile Asp Pro Gly Ser Ile Glu Lys Glu Ala Gly
        35                  40                  45

Arg Leu Arg Gln Phe Glu Lys Leu Pro Lys Asp Ile Asn Val Val Ala
50                  55                  60

Arg Val Gly Arg Met Asn Met Asp Leu Glu Glu Arg Tyr Ile His Gly
65                  70                  75                  80

Leu Asn Asn Gln His Tyr Glu Leu Gln Ser Ser Val Ala Arg Gly Ile
                85                  90                  95

Leu Gln Asp Ser Trp Glu Lys Glu Tyr Gln Arg Ile Phe Gly Asn Ala
            100                 105                 110

Lys Phe Asp Ser Leu Ile Gln Phe Glu Gly Tyr Asn Arg Phe Trp Ser
        115                 120                 125

Gly Val Phe Thr Ser Ile Gln Asn Lys Lys Ser Ser Ile Tyr Met His
130                 135                 140

Asn Ser Met Glu Glu Glu Tyr Arg Leu Lys Tyr Pro Tyr Leu Lys Ser
145                 150                 155                 160

Met Phe Tyr Tyr Cys Ser Leu Ala Asn Lys Val Ile Ser Val Ser Glu
                165                 170                 175

Leu Thr Met Glu Leu Asn Lys Asp Lys Leu Ala Asp Lys Phe Gly Ile
            180                 185                 190

Leu Ser Ser Lys Phe Asp Tyr Ser Asp Asn Leu Gln Gln Pro Glu Lys
        195                 200                 205

Ile Arg Lys Leu Ala Asp Glu Pro Leu Leu Leu Asp Asp Glu Ile Tyr
210                 215                 220

Phe Lys Thr Pro Gly Lys Val Phe Leu Thr Ile Gly Arg Leu Ser Ile
225                 230                 235                 240

Glu Lys Asp His Ala Lys Leu Ile Asn Ser Phe Ala Lys Leu Ile Lys
                245                 250                 255

Tyr Tyr Pro Asp Ser Lys Leu Leu Ile Ile Gly Asp Gly Ser Leu Lys
            260                 265                 270

Tyr Ala Leu Thr Gln Gln Ile Lys Glu Leu Lys Leu Asp Asn Asn Val
        275                 280                 285

Tyr Leu Leu Gly Leu Arg Thr Asn Pro Phe Pro Leu Leu Lys Asn Ala
290                 295                 300

Asp Cys Phe Ile Leu Pro Ser Asn His Glu Gly Gln Pro Met Thr Leu
305                 310                 315                 320

Phe Glu Ala Met Ile Leu Gly Lys Met Ile Ala Thr Asp Ile Val
                325                 330                 335

Gly Ser Arg Ser Ala Leu Glu Gly Arg Ser Gly Tyr Leu Val Glu Asn
            340                 345                 350

Ser Val Asp Gly Leu Lys Gly Met Ser Asp Phe Leu Glu Gly Lys
        355                 360                 365

Leu Ser Leu Ile Thr Phe Asp Ile Asn Glu Tyr Gln Glu Gln Ala Ile
370                 375                 380

Asn Arg Phe Tyr Asn Val Ile
385                 390

<210> SEQ ID NO 27
<211> LENGTH: 439
<212> TYPE: PRT
<213> ORGANISM: Artificial sequence
<220> FEATURE:

<223> OTHER INFORMATION: GT-B domain Cps2D

<400> SEQUENCE: 27

```
Asn Ile Thr Ser Val Ser Val Glu Asp Asn Lys Val Ala Glu Phe Ala
1               5                   10                  15

Pro His Asp Asp Gly Asn Val Ser Glu Lys Val Ile Asn Ala Leu Phe
            20                  25                  30

Ser Asp Asp Tyr Thr Asp Leu Lys Ile Ile Asn Asp Ile Pro Glu Asn
        35                  40                  45

Lys Arg Ser Leu Leu Ile Tyr Gly Gly Pro Phe Met Gly Asn Gly Ile
    50                  55                  60

Thr Thr Ser Val Ile Asn Leu Ile Ala Asn Ile Asp Arg Ser Lys Tyr
65                  70                  75                  80

Thr Ile Thr Leu Val Ile Asp Pro Gly Ser Ile Glu Lys Glu Val Gly
                85                  90                  95

Arg Leu Ile Gln Phe Glu Lys Leu Pro Gln Asp Ile Asn Val Val Ala
            100                 105                 110

Arg Val Gly Arg Met Asp Met Asp Leu Glu Glu Arg Tyr Ile His Gly
        115                 120                 125

Leu Asn Asn Gln His Tyr Glu Leu Gln Ser Ser Val Ala Gln Asp Ile
    130                 135                 140

Leu Trp Asn Ser Trp Glu Lys Glu Tyr Gln Arg Ile Phe Gly Asn Ala
145                 150                 155                 160

Lys Phe Asp Ser Leu Ile Gln Phe Glu Gly Tyr Asn Arg Phe Trp Ser
                165                 170                 175

Gly Val Phe Thr Ser Ile Lys Asn Lys Lys Ser Ser Ile Tyr Met His
            180                 185                 190

Asn Ser Met Glu Glu Glu Tyr Arg Leu Lys Tyr Pro Tyr Leu Lys Ser
        195                 200                 205

Ile Phe Tyr Tyr Cys Ser Leu Ala Asp Lys Val Ile Ser Val Ser Glu
    210                 215                 220

Leu Thr Met Lys Leu Asn Gln Asp Lys Leu Ser Asp Arg Phe Asn Ile
225                 230                 235                 240

Pro Leu Ser Lys Phe Asp Tyr Ser Asp Asn Leu Gln Gln Pro Glu Lys
                245                 250                 255

Ile Lys Val Leu Ala Arg Asp Glu Leu Leu Glu Gln Asp Lys Ala Tyr
            260                 265                 270

Phe Asn Thr Glu Asp Lys Val Phe Leu Thr Ile Gly Arg Leu Ser Ile
        275                 280                 285

Glu Lys Asp His Ala Lys Leu Ile Asn Ser Phe Ala Asn Val Val Lys
    290                 295                 300

Lys Tyr Pro Lys Thr Gln Leu Leu Ile Ile Gly Asp Gly Ser Leu Arg
305                 310                 315                 320

Tyr Pro Leu Val Gln Gln Ile Lys Gln Leu Gly Leu Glu Lys Asn Val
                325                 330                 335

His Leu Leu Gly Leu Arg Ala Asn Pro Phe Pro Leu Leu Lys Lys Ala
            340                 345                 350

Asp Cys Phe Ile Leu Pro Ser Asn His Glu Gly Gln Pro Met Thr Leu
        355                 360                 365

Phe Glu Ala Met Ile Leu Glu Lys Met Ile Ile Ala Thr Asp Ile Val
    370                 375                 380

Gly Ser Arg Ser Ala Leu Glu Gly Arg Ser Gly Tyr Leu Val Glu Asn
385                 390                 395                 400
```

```
Ser Val Ser Gly Leu Glu Lys Gly Met Leu Asp Tyr Ile Ser Gly Ser
            405                 410                 415

Leu Pro Leu Val Thr Tyr Asp Ile Asn Glu Tyr Gln Lys Gln Ala Ile
            420                 425                 430

Asn Lys Phe Tyr Ser Ile Val
            435
```

<210> SEQ ID NO 28
<211> LENGTH: 245
<212> TYPE: PRT
<213> ORGANISM: Artificial sequence
<220> FEATURE:
<223> OTHER INFORMATION: GT-A domain Fcs2

<400> SEQUENCE: 28

```
Met Lys Thr Asn Phe Ile Phe Ser Ile Ile Met Pro Ile Tyr Asn Val
1               5                   10                  15

Asp Gln Trp Leu Glu Glu Ala Ile Leu Ser Ile Ile Asn Gln Lys Lys
            20                  25                  30

Ile Asn Phe Glu Glu Asn Val Gln Leu Ile Leu Val Asn Asp Cys Ser
            35                  40                  45

Pro Asp Asn Ser Glu Glu Ile Cys Leu Lys Phe Arg Lys Lys Tyr Pro
        50                  55                  60

Asn Asn Ile Leu Tyr Tyr Lys Asn Glu Lys Asn Leu Gly Leu Ser Gly
65                  70                  75                  80

Thr Arg Asn Lys Gly Leu Thr Leu Ala Glu Gly Lys Tyr Ile Asn Phe
                85                  90                  95

Phe Asp Pro Asp Asp Thr Leu Ser Pro Ser Val Leu Tyr Glu Val Asn
            100                 105                 110

Lys Phe Phe Thr Gln Asn Ser Ser Gln Asn Leu Ala His Ile Ser Ile
        115                 120                 125

Pro Leu Val Phe Phe Glu Ala Ala Ser Gly Leu His Pro Lys Tyr Arg
    130                 135                 140

Leu Leu Gly Asn Lys Asn Arg Ile Ile Asp Leu Asp Lys Glu Gln His
145                 150                 155                 160

Asn Phe Ile Leu Ser Ser Ala Ser Ser Phe Tyr Pro Arg Asp Asn Ile
                165                 170                 175

Lys Lys Asn Lys Phe Asp Thr Ser Leu Phe Gly Glu Glu Asp Thr Leu
            180                 185                 190

Phe Asn Phe Asn Ile Tyr Ser Asn Ile Asn Lys Phe Gly Tyr Val Cys
        195                 200                 205

Glu Asn Gly Val Gln Tyr Asn Tyr Arg Arg Arg Gln Glu Gly Gly Ser
    210                 215                 220

Gln Val Asp Leu Ser Arg Val Lys Pro Gln Ala Phe Ile Thr Pro Ile
225                 230                 235                 240

Gln Ile Leu Glu Asn
            245
```

<210> SEQ ID NO 29
<211> LENGTH: 266
<212> TYPE: PRT
<213> ORGANISM: Artificial sequence
<220> FEATURE:
<223> OTHER INFORMATION: GT-A domain Cps1B

<400> SEQUENCE: 29

```
Ile Lys Lys His Leu Pro Val Lys Tyr Glu Gly Lys His Gln Phe Thr
1               5                   10                  15
```

Ile Val Ser Ala Val Tyr Asn Val Glu Lys Tyr Leu Asp Asp Phe Phe
            20                  25                  30

Asp Ser Ile Val Lys Gln Asn Leu Ser Phe Lys Lys His Ile Gln Ile
            35                  40                  45

Ile Leu Val Asp Asp Gly Ser Lys Asp Ser Ala Asn Ile Ile Lys
50                  55                  60

Lys Trp Gln Lys Lys Tyr Pro Asn Asn Ile His Tyr Tyr Lys Glu
65                  70                  75                  80

Asn Gly Gly Gln Ala Ser Ala Arg Asn Leu Gly Leu Lys Tyr Val Gln
            85                  90                  95

Thr Glu Trp Val Thr Phe Ile Asp Pro Asp Asp Phe Leu Ser Leu Asn
            100                 105                 110

Tyr Phe Leu Glu Val Asp Lys Lys Leu Ser Glu His Lys Asn Ile Ala
            115                 120                 125

Met Ile Val Cys Asn Leu Leu Phe Phe Met Glu Lys Lys Glu Ile Ile
            130                 135                 140

Thr Asp Lys His Pro Leu Lys Phe Arg Phe Glu Lys Asp Val Asn Cys
145                 150                 155                 160

Leu Ser Ile Lys Asp Leu Asn Asn Asn Leu Asn Leu Ser Val Ala Thr
            165                 170                 175

Ser Phe Phe Arg Thr Ser Val Ile Gln Gly Asn Gln Leu Leu Phe Asp
            180                 185                 190

Asn Arg Val Lys Pro Asn Phe Glu Asp Gly Lys Phe Ile Ser Asp Tyr
            195                 200                 205

Leu Phe Glu Leu Gln His Tyr Asn Ala Leu Phe Leu Lys Lys Pro Val
            210                 215                 220

Tyr Phe Tyr Arg Lys Arg Glu Asp Gly Thr Ser Thr Leu Asp Thr Ser
225                 230                 235                 240

Trp Gln Lys Pro Glu Lys Tyr Lys Asn Val Leu Glu Tyr Gly Phe Ile
            245                 250                 255

Pro Met Leu Gln Lys Tyr His Asn Lys Leu
            260                 265

<210> SEQ ID NO 30
<211> LENGTH: 247
<212> TYPE: PRT
<213> ORGANISM: Artificial sequence
<220> FEATURE:
<223> OTHER INFORMATION: GT-A domain BtY31

<400> SEQUENCE: 30

Tyr Thr Val Val Asn Asn Met Thr Gln Ile Ser Leu Leu Lys Leu Arg
1               5                   10                  15

Lys Tyr Leu Pro Ile Lys Lys Arg Gln Gly Asn His Gln Phe Thr Val
            20                  25                  30

Val Thr Ala Val Tyr Asn Val Ser Lys Tyr Leu Pro Asp Phe Phe Glu
            35                  40                  45

Ser Ile Val Asn Gln Ser Leu Asp Phe Glu Lys His Ile His Ile Ile
            50                  55                  60

Cys Val Asp Asp Gly Ser Thr Asp Ser Ser Glu Val Ile Lys Asn
65                  70                  75                  80

Trp Gln Arg Lys Tyr Pro Asn Asn Ile Thr Tyr Leu Tyr Lys Glu Asn
            85                  90                  95

Gly Gly Ile Ser Ser Ala Arg Asn Leu Gly Leu Gln Tyr Val Glu Thr
            100                 105                 110

```
Glu Trp Val Thr Phe Ile Asp Ser Asp Asp Phe Val His Tyr Asp Tyr
            115                 120                 125

Phe Arg Val Val Asp Asn Ala Val Ser Lys Asn Asn Asp Ile Lys Leu
130                 135                 140

Ala Val Gly Asn Leu Arg Phe Tyr Phe Glu Glu Asn Lys Leu Val Lys
145                 150                 155                 160

Asp Gly His Ser Leu Arg Tyr Arg Phe Thr Gln Lys Glu Val Asn Ile
            165                 170                 175

Val Pro Ile Asp Asn Leu Asp Lys Asn Ile Asn Leu Phe Val Thr Val
            180                 185                 190

Ser Phe Phe Lys Thr Lys Leu Leu His Asp Asn Lys Ile Ile Phe Asn
            195                 200                 205

Asp Lys Ile Lys Pro Asn Phe Glu Asp Gly Lys Phe Leu Ala Asp Tyr
            210                 215                 220

Phe Leu Cys Val Glu Thr Gly Asn Val Ala Tyr Leu Gln Lys Ala Ile
225                 230                 235                 240

Phe Phe Tyr Arg Lys Arg Gly
            245

<210> SEQ ID NO 31
<211> LENGTH: 249
<212> TYPE: PRT
<213> ORGANISM: Artificial sequence
<220> FEATURE:
<223> OTHER INFORMATION: GT-A domain Ccs2

<400> SEQUENCE: 31

Leu Lys Lys Tyr Ile Pro Ser Ser His Lys Gly Asn Asn Lys Phe Thr
1               5                   10                  15

Ile Ile Ser Ala Ile Tyr Asn Thr Glu Lys Tyr Leu Asp Glu Tyr Phe
            20                  25                  30

Ser Ser Ile Thr Thr Gln Leu Leu Asn Phe Lys Asn Asn Ile Phe Ile
            35                  40                  45

Ile Cys Val Asp Asp Gly Ser Val Asp Ser Ala Lys Ile Ile Lys
50                  55                  60

Lys Trp Gln Arg Lys Tyr Pro Lys Asn Ile Thr Tyr Ile Tyr Lys Glu
65                  70                  75                  80

Asn Gly Gly Gln Ala Ser Ala Arg Asn Val Gly Ile Glu His Val Gln
            85                  90                  95

Thr Glu Trp Val Thr Phe Ile Asp Pro Asp Asp Phe Val Ser Lys Asn
            100                 105                 110

Tyr Phe Ser Glu Val Asp Lys Gln Ile Ser Glu Ser Glu Asn Val Ser
            115                 120                 125

Leu Ile Ala Cys Pro Leu Val Phe Tyr Phe Glu Asp Lys Asp Met Phe
130                 135                 140

Lys Asp Thr His Pro Leu Lys Tyr Arg Phe Asn Lys Gly Asn Val Thr
145                 150                 155                 160

Leu Pro Ile Ser Asp Leu Lys Asp Lys Ile Gln Leu Ser Ala Ser Thr
            165                 170                 175

Ala Phe Phe Lys Ser Ser Asp Ile Gly Asn Val Arg Phe Asp Glu Lys
            180                 185                 190

Met Lys Pro Ser Phe Glu Asp Ala Lys Phe Val Ile Asp Tyr Leu Leu
            195                 200                 205

Ser Asn Lys Asn Lys Tyr Ala Ser Phe Val Ser Asn Ile Ser Tyr Tyr
            210                 215                 220
```

Tyr Arg Lys Arg Ala Asp Gly Ser Ser Thr Leu Asp Gly Ala Trp Phe
225                 230                 235                 240

Asn Thr Asn Leu Phe Thr Arg Val Leu
                245

<210> SEQ ID NO 32
<211> LENGTH: 256
<212> TYPE: PRT
<213> ORGANISM: Artificial sequence
<220> FEATURE:
<223> OTHER INFORMATION: GT-A domain Cps4B

<400> SEQUENCE: 32

Ser Ile Lys Leu Glu Lys Phe Leu Ser Ile Lys His Tyr Gly Asn Asn
1               5                   10                  15

Glu Phe Thr Ile Val Ser Ala Ile Tyr Asn Val Glu Lys Tyr Leu Asp
                20                  25                  30

Gln Tyr Phe Asn Ser Ile Phe Lys Gln Thr Leu Leu Phe Lys Asn Asn
            35                  40                  45

Ile Asn Ile Ile Cys Val Asp Asp Gly Ser Thr Asp Lys Ser Ala Glu
50                  55                  60

Ile Ile Glu Lys Tyr Arg Lys Lys Tyr Pro Gln Asn Ile Lys Tyr Ile
65                  70                  75                  80

Tyr Lys Glu Asn Gly Gly Gln Ala Ser Ala Arg Asn Leu Gly Ile Lys
                85                  90                  95

Tyr Val Thr Thr Lys Trp Val Thr Phe Ile Asp Pro Asp Asp Phe Ile
            100                 105                 110

Ser Arg Asn Tyr Phe Glu Leu Val Asp Asp Phe Ile Glu Lys Asn Thr
        115                 120                 125

Asn Leu Ser Leu Val Ser Cys Pro Phe Ile Phe Tyr Phe Glu Asp Lys
    130                 135                 140

Asn Ile Tyr Lys Asp Arg His Pro Leu Asn Phe Arg Phe Lys Asn Gly
145                 150                 155                 160

Glu Tyr Ile Ser Pro Ile Lys Ser Leu Asp Lys His Ile Gln Leu Ser
                165                 170                 175

Val Asn Ser Ala Phe Phe Arg Thr Ala Val Ile Lys Lys Asn Asn Ile
            180                 185                 190

Gln Phe Gly Glu Ile Arg Pro Asn Phe Glu Asp Ala Lys Phe Val Gly
        195                 200                 205

Asp Tyr Leu Leu Ser Val Asn Gln Glu Asn Leu Ile Gly Phe Met Lys
    210                 215                 220

Asp Val Ser Tyr Phe Tyr Arg Lys Arg Ser Asp Gln Ser Ser Thr Leu
225                 230                 235                 240

Asp Thr Ala Trp Lys Asn Pro Leu Leu Tyr Ser Gln Val Leu Glu Asn
                245                 250                 255

<210> SEQ ID NO 33
<211> LENGTH: 417
<212> TYPE: PRT
<213> ORGANISM: Artificial sequence
<220> FEATURE:
<223> OTHER INFORMATION: TagF-like domain CsIB

<400> SEQUENCE: 33

Asp Asn Asn Lys Ser Lys Ile Tyr Ser Asp Phe Lys Leu Leu Lys Asp
1               5                   10                  15

Asp Asp Ile Asp Phe Tyr Gln Pro Tyr Ile Ala Lys Lys Gly Gln Phe

```
                20                  25                  30
Lys Asn Phe Gly Ile Phe Val Asp Ser Gly Tyr Lys Ala Asp Asp Asn
                35                  40                  45

Ala Glu His Leu Tyr Arg Ser Trp Phe Ile Ser Thr Asp Asn Ser Pro
 50                  55                  60

Asp Ile Thr Pro Tyr Tyr Leu Leu Asp Lys Lys Ser Ser His Trp Pro
 65                  70                  75                  80

Lys Leu Lys Ala Glu Gly Phe Asn Leu Val Glu Ile Asn Ser Phe Arg
                85                  90                  95

Ala Val Gln Leu Leu Lys Ser Ser Thr Tyr Ile Phe Ser Ser Tyr Leu
                100                 105                 110

Pro Gly His Leu Gly Glu Trp Val Thr Gly His Asn Phe Lys Phe Gln
                115                 120                 125

Lys Phe Ile Phe Leu Gln His Gly Val Ile Ser Asn Leu Ser Lys
                130                 135                 140

Pro Phe Asn Ala Phe Phe Ser Gln Ile Phe Lys Met Val Val Ser Ser
145                 150                 155                 160

Pro Phe Glu Tyr Lys Glu Ile Thr Glu Ser Ser Tyr Asn Tyr Ile Tyr
                165                 170                 175

His Lys Gln Asp Ile Leu Met Ser Gly Ile Pro Arg Phe Asp Thr Leu
                180                 185                 190

Leu Lys Ala Lys Ser Ser Gln Ser Pro Ile His Thr Ile Lys His Arg
                195                 200                 205

Lys Asp Lys Leu Gln Lys Ile Leu Ile Cys Pro Thr Trp Arg Ser Lys
                210                 215                 220

Phe Asn Thr Leu Asn Leu Lys Ser Glu Thr Gln Leu Val Asn Phe Leu
225                 230                 235                 240

Asp Ser Asp Tyr Leu Lys Asn Trp Leu Gly Phe Leu Asn Ser Pro Lys
                245                 250                 255

Ile Leu Glu Lys Leu Glu Gln Gly Asn Leu Glu Ile Thr Phe Val Pro
                260                 265                 270

His Pro Asn Phe Tyr Ser Ile Leu Glu Glu Tyr Glu Leu Leu Asp Ile
                275                 280                 285

Val Phe Lys Asn Leu Asn Asp Ser Ile Lys Ile Lys Asn Pro Lys Asn
                290                 295                 300

Val Ser Tyr Gln Glu Leu Phe Leu Lys Asn His Ile Leu Ile Thr Asp
305                 310                 315                 320

Tyr Ser Ser Leu His Phe Asp Phe Ala Val Leu His Lys Pro Val Ile
                325                 330                 335

Tyr Tyr Gln Phe Asp Lys Glu Gln Phe Tyr Gly Gly Thr His Val Tyr
                340                 345                 350

Gln Lys Gly Ser Phe Glu Phe Ser Lys His Gly Phe Gly Pro Val Val
                355                 360                 365

Asp Asn Leu Glu Ala Leu Val Lys Val Thr Asn Thr Tyr Phe Asn Arg
                370                 375                 380

Gly Glu Gly Thr Phe Lys Lys Tyr Lys Arg Val Asp Glu Ile Phe
385                 390                 395                 400

Pro Thr Leu His Gln Lys Ser Ser Glu Ile Ile Lys Leu Glu Leu Phe
                405                 410                 415

Lys

<210> SEQ ID NO 34
<211> LENGTH: 414
```

<212> TYPE: PRT
<213> ORGANISM: Artificial sequence
<220> FEATURE:
<223> OTHER INFORMATION: TagF-like domain Cps12B

<400> SEQUENCE: 34

```
Lys Ala Lys Ile Tyr Thr Asp Phe Lys Ile Leu Ser Asp Lys Asp Thr
1               5                   10                  15

Asp Phe Tyr Lys Gly Tyr Ile Ser Lys Asn Asn Ser Leu Lys Asn Ile
            20                  25                  30

Ala Leu Phe Ile Asp Ser Gly Tyr Lys Ala Asp Asp Asn Ala Glu His
                35                  40                  45

Leu Tyr Glu Lys Leu Leu Lys Asn Lys Asn Leu Asp Asn Phe Ile Asp
50                  55                  60

Asp His Tyr Tyr Leu Leu Asp Lys Glu Ser Glu His Trp Asn Arg Leu
65                  70                  75                  80

Ile Leu Lys Gly Phe Asn Leu Val Asp Ile Lys Ser Met Lys Gly Val
                85                  90                  95

Trp Leu Met Lys Asn Ala Lys Tyr Ile Phe Cys Ser Tyr Leu Pro Gly
            100                 105                 110

His Leu Asn Glu Trp Ala Thr His His Ser Phe Lys Phe Gln Lys Phe
        115                 120                 125

Ile Phe Leu Gln His Gly Ile Ile Thr Ser Asn Leu Ser Lys Pro Phe
130                 135                 140

Asn Ala Ser Tyr Ser Gln Ile Tyr Lys Met Val Ile Ser Ser Lys Phe
145                 150                 155                 160

Glu Lys Ser Glu Ile Leu Asp Asp Lys Phe Asn Tyr Ile Phe His Ser
                165                 170                 175

Asn Asp Leu Ile Leu Ser Thr Ile Pro Arg Leu Asp Lys Leu Val Asn
            180                 185                 190

His Lys Arg Asn Gln Ser Asn Lys Val Lys Lys Ile Leu Val Cys Pro
        195                 200                 205

Thr Trp Arg Thr Ser Leu Gly Asn Ile Asn Phe Asn Lys Lys Asp Ala
210                 215                 220

Ile Ser Ser Phe Lys Glu Thr Ser Tyr Ile Lys Asn Trp Leu Gly Leu
225                 230                 235                 240

Leu Tyr Ser Asp Lys Leu Arg Asn Tyr Leu Glu Glu Gly Lys Ile Glu
                245                 250                 255

Ile Ser Phe Leu Pro His Gln Asn Phe His Gln Leu Leu Glu Glu Asn
            260                 265                 270

Ser Leu Asn Glu Lys Leu Phe Phe Asp Ile Asn Glu Asn Ile Arg Ile
        275                 280                 285

Leu Asn Pro Lys Lys Ser Ser Tyr Gln Glu Leu Phe Ile Asp His Asp
290                 295                 300

Ile Leu Ile Thr Asp Phe Ser Ser Leu His Phe Asp Phe Ala Thr Leu
305                 310                 315                 320

Gln Lys Asp Ile Leu Tyr Phe Gln Phe Asp Lys Asp Glu Phe Tyr Gly
                325                 330                 335

Ile Ser His Ala Tyr Gln Lys Gly Leu Phe Asn Phe Glu Lys Asp Gly
            340                 345                 350

Phe Gly Gln Val Thr Tyr Thr Leu Glu Glu Leu Leu Asp Gln Leu Val
        355                 360                 365

Ile Leu Ile Asn Ser Gln Asn Glu Lys Val Val Asn Gly Tyr Lys Lys
370                 375                 380
```

```
Arg Ile Ser Asn Val Phe Leu Pro Ser Leu Gly Asp Ser Cys Asn Tyr
385                 390                 395                 400

Ile Leu Lys Asn Val Phe Thr Asn Pro Lys Arg Asn Ile Asn
                405                 410
```

<210> SEQ ID NO 35
<211> LENGTH: 505
<212> TYPE: PRT
<213> ORGANISM: Artificial sequence
<220> FEATURE:
<223> OTHER INFORMATION: TagF-like domain Cps6D

<400> SEQUENCE: 35

```
Arg Lys Thr Val Leu Leu Ile Pro Ser Asp Tyr Asn His Arg Val Met
1               5                   10                  15

Ala Asp Ile Ser Ser Phe Ile Gln Tyr Tyr Lys Asp Lys Phe Asp Val
                20                  25                  30

Tyr Ile Ile Leu Arg Glu Leu Pro Glu Asp Ile Val Tyr Lys Asn Thr
            35                  40                  45

His Val Leu Val Lys Asn Gly Thr Ser Phe Gly Glu Tyr Leu Lys Phe
        50                  55                  60

Thr Ala Asp Tyr Val Ile Asp Ser Gly Thr Met Asn Tyr Ser Tyr Arg
65                  70                  75                  80

Ile Thr Asp Thr Asn Lys Trp Val Ser Val Trp His Gly Ile Pro Tyr
                85                  90                  95

Lys Lys Met Phe Val Asp Leu Asp Ile Lys His Ile Ser Thr Ala Ile
                100                 105                 110

Arg Tyr Asp Leu Ala Tyr Asp Ser Met Ile Ser Met Ser Asn Phe Tyr
            115                 120                 125

Thr Asp Thr Phe Leu Arg Lys Ala Met Arg Tyr Asp Gly Glu Ile Leu
130                 135                 140

Gln Leu Gly Cys Ala Lys Met Asp Asn Leu Phe Ser Ser Ile Ser Thr
145                 150                 155                 160

Ser Asn Ala Asp Lys Ala Asn Ala Leu Arg Asn Glu Leu Gly Leu Pro
                165                 170                 175

Asn Asn Lys Lys Val Ile Leu Tyr Ala Pro Glu Phe Arg Glu Val Gly
            180                 185                 190

Glu Leu Tyr Phe Pro Phe Asp Pro Asn Lys Leu Leu Ser His Leu Gly
        195                 200                 205

Glu Glu Tyr Cys Leu Leu Thr Leu Leu Pro Phe Lys Gly Tyr Ile Lys
210                 215                 220

Gln Ala Glu Asn Asn Ile Tyr Tyr Ile Ser Asp Leu Asp Asn Lys Asp
225                 230                 235                 240

Ala Leu Leu Ile Ala Asp Leu Leu Ile Ser Asp Tyr His Glu Leu Ile
                245                 250                 255

Tyr Thr Phe Asp Arg Tyr Asn Lys Pro Ala Val Leu Ile Gln Tyr Asp
            260                 265                 270

Tyr Glu Ser Phe Val Lys Gln His Thr Ser Arg Lys Gln Glu Leu Glu
        275                 280                 285

Ile Leu Ala Ser Arg Lys Tyr Val Ala Gln Glu Ala Glu Leu Tyr
290                 295                 300

Gln Phe Asn Trp Asn Leu Leu Lys Arg Tyr Ser Thr His Ala Thr Leu
305                 310                 315                 320

Pro Glu Tyr Leu Asp Ser Ser Tyr Ile Lys His Lys Leu Gly Ile Pro
                325                 330                 335
```

```
Phe Asp Lys Lys Ile Ile Leu Tyr Ala Pro Thr Tyr Arg Lys Ala Gly
            340                 345                 350

Ala Val Gln Leu Pro Phe Asp Pro Asn Thr Leu Leu Asn Tyr Leu Asp
        355                 360                 365

Asn Asp Tyr Val Leu Ile Thr Lys Met His Tyr Leu Asn Tyr Leu Ala
    370                 375                 380

Asn Thr Tyr Asn Asp Val Ile Asp Cys Thr Ser His Glu Asn Met Ala
385                 390                 395                 400

Glu Leu Met Lys Ile Ala Asp Ile Leu Ile Ser Asp Tyr Ser Ser Leu
                405                 410                 415

Val Leu Asp Phe Ala Val Leu Asn Lys Pro Ile Ile Leu Phe Gln Tyr
            420                 425                 430

Asp Tyr Asp Glu Tyr Met Lys Gln Arg Gly Val Tyr Phe Asn Phe Gly
        435                 440                 445

Asp Tyr Leu Pro Lys Glu Gln Ile Ile Arg Thr Glu Phe Glu Leu Tyr
    450                 455                 460

Thr Leu Asn Trp Asn Lys Leu Asn Ser Asp Asn Ser Lys Ile Ile Asn
465                 470                 475                 480

Glu Phe Tyr Pro Leu Glu Asp Gly Lys Ser Thr Gln Arg Ile Val Asp
                485                 490                 495

Lys Ile Asn Phe Asn Ala Asp Leu Arg
            500                 505

<210> SEQ ID NO 36
<211> LENGTH: 472
<212> TYPE: PRT
<213> ORGANISM: Artificial sequence
<220> FEATURE:
<223> OTHER INFORMATION: TagF-like domain Cps8D

<400> SEQUENCE: 36

Lys Leu Gly Asn Phe Ser Glu Ala His Ser Phe Ile Ala Lys Ala Leu
1               5                   10                  15

Glu Ile Ala Pro Tyr Asn Thr His Trp Arg Lys Gln Leu Gln Gln Ala
            20                  25                  30

Glu Arg His Phe Asn Asn Thr Tyr Ser Ser Pro His Lys Ile Thr Thr
        35                  40                  45

Val Val Thr Arg Met Lys Gln Ser Gly Ile Ser Gln Ser Ile Gly Thr
    50                  55                  60

Ala Ile Arg Lys Thr Val Leu Leu Ile Pro Ser Asp Tyr Asn His Arg
65                  70                  75                  80

Val Met Ala Asp Ile Ser Ser Phe Ile Gln Tyr Tyr Lys Asp Lys Phe
                85                  90                  95

Asp Val Tyr Ile Ile Leu Arg Glu Leu Pro Glu Asp Ile Val Tyr Lys
            100                 105                 110

Asn Thr His Val Leu Val Lys Asn Gly Thr Ser Phe Gly Glu Tyr Leu
        115                 120                 125

Lys Phe Thr Ala Asp Tyr Val Ile Asp Ser Gly Thr Met Asn Tyr Ser
    130                 135                 140

Tyr Arg Ile Thr Asp Thr Asn Lys Trp Val Ser Val Trp His Gly Ile
145                 150                 155                 160

Pro Tyr Lys Lys Met Phe Val Asp Phe Asp Ile Lys Asn Leu Ala Thr
                165                 170                 175

Ala Ile Arg Tyr Asp Leu Ala Tyr Asp Ser Met Val Ser Met Ser Asn
            180                 185                 190
```

```
Phe Tyr Thr Asp Thr Phe Leu Arg Lys Ala Met Arg Tyr Asp Gly Glu
            195                 200                 205

Ile Leu Gln Leu Gly Cys Ala Lys Ile Asp Asn Leu Phe Ser Ser Ile
210                 215                 220

Ser Thr Ser Asn Ala Asp Lys Val Asn Ala Leu Arg Asn Glu Leu Gly
225                 230                 235                 240

Leu Pro Asn Asn Lys Lys Val Ile Leu Tyr Ala Pro Glu Phe Arg Glu
                245                 250                 255

Val Gly Glu Leu Tyr Phe Pro Phe Asp Pro Asn Lys Leu Leu Ser His
            260                 265                 270

Leu Gly Glu Glu Tyr Cys Leu Leu Thr Leu Leu Pro Phe Lys Gly Tyr
        275                 280                 285

Ile Glu Gln Ala Glu Asn Asn Ile Tyr Tyr Ile Ser Asp Leu Asp Asn
    290                 295                 300

Lys Asp Ala Leu Leu Ile Ala Asp Leu Leu Ile Ser Asp Tyr His Glu
305                 310                 315                 320

Leu Ile Tyr Thr Phe Asp Arg Tyr Asn Lys Pro Ala Val Leu Ile Gln
                325                 330                 335

Tyr Asp Tyr Glu Ser Phe Val Lys Gln His Thr Ser Arg Lys Gln Glu
            340                 345                 350

Leu Glu Ile Leu Ala Ser Arg Lys Tyr Val Ala Lys Glu Ala Asn Glu
        355                 360                 365

Leu Tyr Gln Phe Asn Trp Asn Leu Leu Lys Arg Tyr Ser Lys Gln Ser
    370                 375                 380

Thr Leu Pro Glu Tyr Leu Asp Ser Ser Tyr Ile Lys His Lys Leu Gly
385                 390                 395                 400

Ile Pro Phe Asp Lys Lys Ile Val Leu Tyr Ala Pro Thr Phe Arg Lys
                405                 410                 415

Ala Gly Ala Val Gln Leu Pro Phe Asp Pro Asn Thr Leu Leu Asn Tyr
            420                 425                 430

Leu Asp Asn Asp Tyr Val Leu Ile Thr Lys Met His Tyr Leu Asn Tyr
        435                 440                 445

Leu Ala Asn Thr Tyr Asn Gly Val Ile Asp Cys Thr Ser His Glu Asn
450                 455                 460

Met Ala Glu Leu Met Lys Ile Ala
465                 470

<210> SEQ ID NO 37
<211> LENGTH: 150
<212> TYPE: PRT
<213> ORGANISM: Artificial sequence
<220> FEATURE:
<223> OTHER INFORMATION: TagF-like domain Cps5B

<400> SEQUENCE: 37

Lys Gln Gln Lys Pro Ile Ile Thr Ile Ile Gly Gln Val Ile Asn Asp
1               5                   10                  15

Phe Ser Val Leu Glu Tyr Lys Gly Arg Gly Leu Ser Thr Ile Lys Ile
                20                  25                  30

Tyr Lys Glu Leu Ile Ser Lys Leu Ser Glu Asn Gly Phe Asn Val Val
            35                  40                  45

Leu Lys Thr His Pro Trp Glu Glu Lys Asn Asn Ile Arg Thr Ser
        50                  55                  60

Leu Thr Lys Asn Ile Ile Glu Glu Phe Leu Lys Asn Leu Thr Glu Asn
65                  70                  75                  80
```

```
Gln Gln Glu Cys Ile Lys Ile Val Asp His Tyr Ser Ile Lys Lys Leu
                85                  90                  95

Phe Lys Gln Ser Asp Phe Ile Ile Ser Leu Asn Ser Gln Gly Leu Leu
            100                 105                 110

Glu Ala Ala Phe Asp Gly Ile Lys Pro Ile Gln Leu Gly Asn Ala Phe
        115                 120                 125

Tyr Gly Lys Lys Gly Phe Thr Tyr Asp Tyr Asp Phe Leu Asp Ile Asp
    130                 135                 140

Gln Leu Val Asn Asp Leu
145             150
```

<210> SEQ ID NO 38
<211> LENGTH: 191
<212> TYPE: PRT
<213> ORGANISM: Artificial sequence
<220> FEATURE:
<223> OTHER INFORMATION: TagF-like domain Cps10C

<400> SEQUENCE: 38

```
Tyr Val Asp Lys Leu Phe Ile Gln Lys Ala Ile Ser Asn Thr Ser Asp
1               5                   10                  15

Lys Ser Leu Leu Pro Glu Asn Ile Lys Gly Lys Arg Val Ile Phe Phe
            20                  25                  30

Pro Leu Gln Val Gln Leu Asp Thr Asn Ile Ile Met Tyr Cys Lys Tyr
        35                  40                  45

Asn Thr Met Arg Glu Val Phe Phe Glu Ile Tyr Ser His Leu Asn Asn
    50                  55                  60

Asp Asp Val Ile Phe Val Val Arg Pro His Pro Glu Glu Asp Val Glu
65                  70                  75                  80

Thr Leu Ser Asn Leu Pro Asn Trp Asp Asn Leu Ile Val Ser Thr Asp
                85                  90                  95

Leu Asp Leu Asn Phe Trp Leu Glu Asn Ser Asp Leu Ile Val Thr Ile
            100                 105                 110

Asn Ser Thr Val Gly Leu Glu Ala Leu Leu Lys Gly Lys Pro Val Ile
        115                 120                 125

Cys Leu Gly Lys Ser Ile Tyr Ser Ser Leu Pro Cys Leu Ser Lys Tyr
    130                 135                 140

Asn His Ile Leu Asp Asp Arg Gly Lys Ile Leu Cys Asn Val Ser Gly
145                 150                 155                 160

Tyr Leu Gly Tyr Leu Leu Thr His Asn Leu Ile Val Lys Asp Ser Ile
                165                 170                 175

Tyr Asn Thr Asn Val Ile Lys Ser Ile Phe Lys Phe Asn Asp Lys
            180                 185                 190
```

<210> SEQ ID NO 39
<211> LENGTH: 188
<212> TYPE: PRT
<213> ORGANISM: Artificial sequence
<220> FEATURE:
<223> OTHER INFORMATION: SiaTF domain Csw

<400> SEQUENCE: 39

```
Ile Lys Val Ser Asp Ile Gln Tyr Ala Ala Ile Thr Pro Tyr His Pro
1               5                   10                  15

Ala Tyr Phe Lys Ser Pro Lys Ser His Tyr Val Ala Asp Lys Leu Phe
            20                  25                  30

Leu Trp Ser Glu Tyr Trp Asn His Glu Leu Leu Pro Asn Pro Thr Arg
        35                  40                  45
```

```
Glu Ile Gly Ser Gly Ala Ala Tyr Trp Tyr Ala Leu Asp Asp Val Arg
        50                  55                  60

Phe Ser Glu Lys Leu Asn Tyr Asp Tyr Ile Phe Leu Ser Gln Ser Arg
 65                  70                  75                  80

Ile Ser Ser Arg Leu Leu Ser Phe Ala Ile Glu Phe Ala Leu Lys Asn
                 85                  90                  95

Pro Gln Leu Gln Leu Leu Phe Ser Lys His Pro Asp Glu Asn Ile Asp
                100                 105                 110

Leu Lys Asn Arg Ile Ile Pro Asp Asn Leu Ile Ile Ser Thr Glu Ser
            115                 120                 125

Ser Ile Gln Gly Ile Asn Glu Ser Arg Val Ala Val Gly Val Tyr Ser
        130                 135                 140

Thr Ser Leu Phe Glu Ala Leu Ala Cys Gly Lys Gln Thr Phe Val Val
145                 150                 155                 160

Lys Tyr Pro Gly Tyr Glu Ile Met Ser Asn Glu Ile Asp Ser Gly Leu
                165                 170                 175

Phe Phe Ala Val Glu Thr Pro Glu Glu Met Leu Glu
                180                 185
```

<210> SEQ ID NO 40
<211> LENGTH: 188
<212> TYPE: PRT
<213> ORGANISM: Artificial sequence
<220> FEATURE:
<223> OTHER INFORMATION: SiaTF domain Csy

<400> SEQUENCE: 40

```
Ile Lys Val Ser Asp Ile Gln Tyr Ala Ala Ile Thr Pro Tyr His Pro
 1               5                  10                  15

Ala Tyr Phe Lys Ser Pro Lys Ser His Tyr Val Ala Asp Lys Leu Phe
                20                  25                  30

Leu Trp Ser Glu Tyr Trp Asn His Glu Leu Leu Pro Asn Pro Thr Arg
            35                  40                  45

Glu Ile Gly Ser Gly Ala Ala Tyr Trp Tyr Ala Leu Asp Asp Val Arg
        50                  55                  60

Phe Ser Glu Lys Leu Asn Tyr Asp Tyr Ile Phe Leu Ser Gln Ser Arg
 65                  70                  75                  80

Ile Ser Ser Arg Leu Leu Ser Phe Ala Ile Glu Phe Ala Leu Lys Asn
                 85                  90                  95

Pro Gln Leu Gln Leu Leu Phe Ser Lys His Pro Asp Glu Asn Ile Asp
                100                 105                 110

Leu Lys Asn Arg Ile Ile Pro Asp Asn Leu Ile Ile Ser Thr Glu Ser
            115                 120                 125

Ser Ile Gln Gly Ile Asn Glu Ser Arg Val Ala Val Gly Val Tyr Ser
        130                 135                 140

Thr Ser Leu Phe Glu Ala Leu Ala Cys Gly Lys Gln Thr Phe Val Val
145                 150                 155                 160

Lys Tyr Pro Gly Tyr Glu Ile Met Ser Asn Glu Ile Asp Ser Gly Leu
                165                 170                 175

Phe Phe Ala Val Glu Thr Pro Glu Glu Met Leu Glu
                180                 185
```

<210> SEQ ID NO 41
<211> LENGTH: 229
<212> TYPE: PRT
<213> ORGANISM: Artificial sequence
<220> FEATURE:
<223> OTHER INFORMATION: GT-A domain CsIB

<400> SEQUENCE: 41

Pro Lys Leu Lys Ala Thr Ser Lys Lys Tyr Thr Ile Ile Ser Ala Ile
1               5                   10                  15

Tyr Asn Val Ala Pro Tyr Leu Asp Asp Tyr Phe Lys Ser Leu Glu Lys
            20                  25                  30

Gln Arg Leu Asp Phe Gln Ser Asn Ile Asn Val Ile Leu Val Asp Asp
        35                  40                  45

Gly Ser Pro Asp Asn Ser Arg Glu Ile Ile Met Lys Trp Val Asn Lys
50                  55                  60

Tyr Pro Asn Asn Ile Phe Tyr Ile Tyr Lys Lys Asn Gly Gly Gln Ser
65                  70                  75                  80

Ser Ala Arg Asn Leu Gly Leu Lys Tyr Val Ser Thr Glu Trp Val Thr
                85                  90                  95

Phe Ile Asp Pro Asp Asp Phe Leu Asp Ser Asn Tyr Phe Tyr Leu Ile
            100                 105                 110

Asp Lys Thr Ile Lys Asp Gln Lys Asn Ile Gly Gly Val Ile Thr Lys
        115                 120                 125

Phe Lys Leu Phe Lys Glu Lys Leu Gly Thr Tyr His Asp Gly Phe Gln
130                 135                 140

Thr Asp Phe Cys Phe Asn Lys Pro Val Arg Ile Val Thr Thr Ser Asn
145                 150                 155                 160

Phe Glu Asp Cys Val Gln Phe Ser Ser Ser Ser Ile Tyr Gln Thr
                165                 170                 175

Lys Ile Ile Lys Asp Asn Asn Ile Leu Phe Asp Glu Lys Leu Thr Ala
            180                 185                 190

Ser Phe Glu Asp Thr Lys Phe Phe Tyr Glu Tyr Leu Phe Tyr Leu Asp
        195                 200                 205

Ser Ser Lys Asn Thr Asn Ile Ala Tyr Val Arg Asp Ala Leu Tyr Tyr
    210                 215                 220

Tyr Arg Leu Arg Ala
225

<210> SEQ ID NO 42
<211> LENGTH: 272
<212> TYPE: PRT
<213> ORGANISM: Artificial sequence
<220> FEATURE:
<223> OTHER INFORMATION: GT-A domain Cps12B

<400> SEQUENCE: 42

Arg Leu Leu Gln Leu Arg Asn Phe Ile Tyr Leu Asn Ser Arg Lys Lys
1               5                   10                  15

Lys Leu Asn Ser Lys Lys Phe Thr Ile Ile Ser Ala Val Tyr Asn Val
            20                  25                  30

Ser Glu Tyr Leu Asp Asp Tyr Leu Glu Ser Leu Val Asn Gln Arg Leu
        35                  40                  45

Asp Phe Glu Thr Ser Ile Asp Val Ile Leu Val Asn Asp Gly Ser Pro
    50                  55                  60

Asp Asp Ser Glu Ile Ile Ile Lys Lys Trp Ile Lys Lys Tyr Pro Asn
65                  70                  75                  80

Asn Ile His Tyr Ile Lys Lys Lys Asn Gly Gly Gln Ser Ser Ala Arg
                85                  90                  95

Asn Leu Gly Leu Lys Phe Val Lys Thr Glu Trp Val Thr Phe Ile Asp

```
            100                 105                 110
Pro Asp Asp Phe Leu Asp Leu Asn Tyr Phe Tyr Leu Leu Asn Asp Thr
            115                 120                 125

Leu Glu Lys Tyr Asp His Ile Gly Ala Phe Val Thr Lys Phe Lys Leu
            130                 135                 140

Phe Lys Glu Lys Phe Gly Thr Tyr His Asp Gly Phe Gln Thr Asp Phe
145                 150                 155                 160

Cys Phe Thr Lys Pro Ile Arg Val Leu Lys Ala Asn Asp Met Glu Asp
            165                 170                 175

Cys Val Gln Phe Ser Ser Ser Ser Val Tyr Arg Thr Asp Val Ile
            180                 185                 190

His Lys Asn Lys Ile Leu Phe Asp Glu Lys Leu Thr Ala Ser Phe Glu
            195                 200                 205

Asp Thr Lys Phe Phe Tyr Asp Tyr Leu Tyr Asn Ile Lys Glu Ser Asn
            210                 215                 220

Ile Leu Tyr Ile Lys Asp Ala Ile Tyr Asn Tyr Arg Leu Arg Ser Asn
225                 230                 235                 240

Glu Ser Ser Ser Asn Ser Gln Trp Thr Lys Lys Ala Lys Tyr Gln
            245                 250                 255

Glu Phe Phe Gln Phe Gly Leu Leu Ser Val Ile Lys Lys Tyr Asn Glu
            260                 265                 270

<210> SEQ ID NO 43
<211> LENGTH: 292
<212> TYPE: PRT
<213> ORGANISM: Artificial sequence
<220> FEATURE:
<223> OTHER INFORMATION: GT-B domain Cps6D

<400> SEQUENCE: 43

Ile Asp Phe Lys Leu Ser Ser Gln Tyr Leu Asn Gly Ala Cys Ala Asn
1               5                   10                  15

Ile Leu Gln Asn Thr Asp Gly Ile Val Ile Ser Leu Gln Phe Ser Ala
            20                  25                  30

His Met Tyr Phe Gln Lys Tyr Leu Thr Asn Ala Lys Ser Val Leu Met
            35                  40                  45

Phe His Gly Asp Val Lys Asp Met Ile Ser Arg Glu Leu Tyr Gly Pro
        50                  55                  60

His Leu Asp Trp Leu Asn Lys Gly Lys Leu Tyr Asn Tyr Gln Lys Leu
65                  70                  75                  80

Leu Leu Leu Thr Gln Ser Ala Val Asp Leu Leu Lys Pro His Leu Asn
            85                  90                  95

Pro Glu Ile Gln Asp Lys Leu Gly Phe Met His Asn Ser Ile Asp Glu
            100                 105                 110

Glu Phe Ser Pro Ile Lys Gln Asn Lys Lys Tyr Gln Leu Asn Thr Ala
            115                 120                 125

Val Ile Ser Arg Leu Asp Ala Asp Lys Asn Ile Phe Ala Ile Ile Asp
            130                 135                 140

Leu Gly Lys Thr Ile Leu Thr Gln Asn Ser Asn Ile Val Val Asn Ile
145                 150                 155                 160

Tyr Gly Asp Gly Ala Leu Lys Asp Glu Phe Ile Ala Glu Ile Asn Arg
            165                 170                 175

His Gly Leu Glu His Ile Leu Lys Val Arg Gly Phe Glu Ser Asn Lys
            180                 185                 190

Ala Lys Ile Phe Ser Glu Asn Asn Ser Leu Leu Leu Met Ser Lys Ser
```

```
                195                 200                 205
Glu Gly Phe Gly Leu Val Ile Leu Glu Ala Tyr Ala Tyr Gly Lys Pro
            210                 215                 220
Val Ile Val Phe Asp Ser Phe Thr Ala Ala Lys Glu Val Val Lys His
225                 230                 235                 240
Asn Gln Ser Gly Phe Leu Leu Pro Tyr Gly Asp Tyr Glu Asn Val Val
                245                 250                 255
Lys Ala Ile Glu Asn Ser Lys Asn Ile Lys Leu Lys Asp Ile Glu Met
            260                 265                 270
Leu Phe Asn Asn Phe Ser Asn Pro Thr Val Phe Ala Lys Trp Asp Ser
        275                 280                 285
Leu Ile Leu Ser
        290

<210> SEQ ID NO 44
<211> LENGTH: 291
<212> TYPE: PRT
<213> ORGANISM: Artificial sequence
<220> FEATURE:
<223> OTHER INFORMATION: GT-B domain Cps8D

<400> SEQUENCE: 44

Ile Asp Phe Lys Leu Ser Ser Gln Tyr Leu Asn Gly Ala Cys Ala Asn
1               5                   10                  15
Ile Leu Gln Asn Thr Asp Gly Ile Val Ile Ser Leu Gln Phe Ser Ala
            20                  25                  30
His Met Tyr Phe Gln Lys Tyr Leu Thr Asn Ala Lys Ser Val Leu Met
        35                  40                  45
Phe His Gly Asp Val Lys Asp Met Ile Ser Arg Glu Leu Tyr Gly Pro
    50                  55                  60
His Leu Asp Trp Leu Asn Lys Gly Lys Leu Tyr Asn Tyr Gln Lys Leu
65                  70                  75                  80
Leu Leu Leu Thr Gln Ser Ala Leu Asp Leu Leu Lys Pro His Leu Asn
                85                  90                  95
Pro Glu Ile Gln Asp Lys Leu Gly Phe Met His Asn Ser Ile Asp Glu
            100                 105                 110
Glu Phe Ser Pro Ile Lys Gln Asn Lys Lys His Gln Leu Asn Thr Ala
        115                 120                 125
Val Ile Ser Arg Leu Asp Ala Asp Lys Asn Ile Phe Ala Met Ile Asp
    130                 135                 140
Leu Gly Lys Glu Ile Leu Ala Gln Asn Ser Asn Val Val Val Asn Ile
145                 150                 155                 160
Tyr Gly Asp Gly Ala Leu Lys Asp Glu Phe Ile Ala Glu Ile Thr Arg
                165                 170                 175
His Gly Leu Glu His Ile Leu Lys Val Arg Gly Phe Glu Ser Asn Lys
            180                 185                 190
Ser Lys Ile Phe Ser Glu Asn Asn Ser Leu Leu Leu Met Ser Lys Ser
        195                 200                 205
Glu Gly Phe Pro Leu Val Leu Leu Glu Ala Tyr Ala Tyr Gly Lys Pro
    210                 215                 220
Val Ile Val Phe Asp Ser Phe Thr Ala Ala Lys Glu Ile Val Lys His
225                 230                 235                 240
Asn Gln Ser Gly Phe Leu Leu Pro Tyr Gly Asp Tyr Gly Asn Val Val
                245                 250                 255
Lys Ala Ile Glu Asn Ser Lys Asn Ile Lys Leu Lys Asp Ile Glu Met
```

```
                    260                 265                 270
Ile Phe Asn Asn Phe Ser Asn Pro Thr Val Phe Ala Lys Trp Asp Ser
                275                 280                 285

Leu Ile Leu
    290

<210> SEQ ID NO 45
<211> LENGTH: 266
<212> TYPE: PRT
<213> ORGANISM: Artificial sequence
<220> FEATURE:
<223> OTHER INFORMATION: GT-B domain Cps5A

<400> SEQUENCE: 45

Lys Val Tyr His Tyr His Arg Pro His Leu Glu Glu Lys Leu Leu Pro
1               5                  10                  15

Asn Ser Val Cys Thr Val His His Asp Leu Asn Asp Pro Asp Pro Trp
            20                  25                  30

His Ala Lys Tyr Arg Phe Ile Pro Arg Tyr Met Glu Ala Gly Ala Ile
        35                  40                  45

Ile Cys Leu Asn Tyr Thr Gln Lys Glu Ile Leu Ile Ser Gln Gly Leu
    50                  55                  60

Pro Glu His Lys Leu Phe Val Ile Pro His Gly Tyr Asn Gln Lys Val
65                  70                  75                  80

Leu Phe Pro Lys Lys Ile Lys Glu Ile Ser Ser Thr Asp Lys Ile Thr
                85                  90                  95

Leu Gly Ile Ala Ser Arg Arg Tyr Gly Arg Arg Val Lys Gly Asp Ala
            100                 105                 110

Tyr Leu Phe Glu Leu Ala Lys Arg Leu Asn Pro Asp His Phe Lys Phe
        115                 120                 125

Ile Phe Val Gly Lys Asp Arg Gln Tyr Ser Ala Leu Glu Met Gln Asp
    130                 135                 140

Leu Gly Phe Glu Ala Gln Val Tyr Glu Arg Leu Pro Tyr Arg Met Phe
145                 150                 155                 160

Gln Ser Phe Tyr Asn Asn Ile Asp Val Leu Leu Met Cys Ser Ser His
                165                 170                 175

Glu Gly Gly Pro Ala Asn Ile Pro Glu Ala Leu Ala Thr Gly Thr Pro
            180                 185                 190

Ile Phe Ser Ser Asn Ile Gly Ile Pro Lys Asp Val Val Ile Asn Tyr
        195                 200                 205

Lys Asn Gly Leu Ile Leu Thr Leu Asp Pro Asp Ile Asp Ala Glu Gln
    210                 215                 220

Ile Asn Phe Ile Cys Leu Glu Lys Pro Asn Ile Phe Glu Asn Ile Leu
225                 230                 235                 240

Asp Phe Ser Leu Lys Gln Ser Pro Ser Leu Ala Ile Ser Trp Glu Lys
                245                 250                 255

Cys Ile Gln Gln Asn Ile Leu Val Tyr Lys
            260                 265

<210> SEQ ID NO 46
<211> LENGTH: 403
<212> TYPE: PRT
<213> ORGANISM: Artificial sequence
<220> FEATURE:
<223> OTHER INFORMATION: GT-B domain Cps10D

<400> SEQUENCE: 46
```

-continued

```
Asn Thr Leu Phe Ile Phe Pro Gly Ser Ile Ile Pro Leu Ser Met Gly
 1               5                  10                  15

Ser His Gln Arg Ala Phe Asn Phe Leu Tyr Asn Leu Ser Met Lys Gly
            20                  25                  30

Val Ile Phe Asp Val Leu Ile Pro Ser Asn Asn Lys Leu Asp Lys Val
         35                  40                  45

Ala Leu Lys Ser Ala Leu Lys Ser Val Ala Ser Asn Val Tyr Phe Tyr
 50                  55                  60

Arg Asn Lys Pro Lys Lys Phe Thr Lys Leu Asn Thr Leu Lys Arg Gly
 65                  70                  75                  80

Ile Glu Lys Arg Val Arg Thr Leu Ile Asn Lys Asp Ala Ser Leu Ser
                 85                  90                  95

Asp Leu Phe Ser Glu Arg Ala Tyr Arg Lys Pro Thr Glu Ser Leu Lys
            100                 105                 110

Arg Trp Val Asn Ser Leu Tyr Leu Ala Lys Asp Tyr Glu Asn Ile Ile
            115                 120                 125

Val Ser Tyr Ala Trp Leu Leu Asp Ser Ile Gln Tyr Ile Glu His Leu
        130                 135                 140

Arg Asp Asp Phe Asn Leu Ile Cys Asp Thr His Asp Val Gln Phe Tyr
145                 150                 155                 160

Arg Asn Gln Asn Ile Leu Ser Arg Lys Glu Arg Leu Phe Phe Asn Lys
                165                 170                 175

Asp Leu Glu Lys Gln Lys Glu Val Asn Leu Leu Asn Lys Cys Asp Tyr
            180                 185                 190

Val Ile Ser Ile Ser Asp Met Asp Lys Lys Leu Leu Glu Glu Asn Ile
        195                 200                 205

Asn Ser Lys Val Ile Pro Ile Tyr Pro Gly Phe Asp Tyr Ile Lys Val
210                 215                 220

Pro Val Lys Gln Arg Pro Val Gly Arg Pro Ile Tyr Phe Gly Phe Ile
225                 230                 235                 240

Gly Gly Ser Met Ser Ala Asn Val Ile Ala Leu Arg Tyr Val Ile Glu
                245                 250                 255

His Trp Trp Pro Val Ile Lys Lys His Ser Pro Asp Ser His Leu Tyr
            260                 265                 270

Ile Ala Gly Ser Ile Cys Asn Asp Pro Ser Ile Arg Glu Leu Cys Phe
        275                 280                 285

Phe Glu Lys Asn Ile Glu Leu Leu Gly Phe Val Lys Asp Ile Phe Ser
290                 295                 300

Phe Tyr Asn Lys Phe Glu Val Ser Leu Asn Pro Val Leu Val Ser Gly
305                 310                 315                 320

Gly Leu Asn Phe Lys Ser Val Glu Ala Val Cys Ala Gly Lys His Leu
                325                 330                 335

Phe Thr Asn Thr Leu Gly Lys Asp Cys Leu Ser Thr Asp Phe Pro Cys
            340                 345                 350

Ile Ile Ile Asp Asp Pro Ala Gln Ile Gln His Met Asn Gln Ile
        355                 360                 365

Glu Phe Asn Phe Ser Asp Asp Lys Lys Arg Arg Ile Ala Ser Gln Ala
370                 375                 380

Lys Ala Leu Glu Ile Phe Gly Asn Lys Asn His Gln Lys Ser Leu Ala
385                 390                 395                 400

Lys Leu Leu
```

<210> SEQ ID NO 47

<211> LENGTH: 396
<212> TYPE: PRT
<213> ORGANISM: Artificial sequence
<220> FEATURE:
<223> OTHER INFORMATION: GT-B domain Csw

<400> SEQUENCE: 47

```
Met Ala Val Ile Ile Phe Val Asn Gly Ile Arg Ala Val Asn Gly Leu
1               5                   10                  15

Val Lys Ser Ser Ile Asn Thr Ala Asn Ala Phe Ala Glu Glu Gly Leu
            20                  25                  30

Asp Val His Leu Ile Asn Phe Val Gly Asn Ile Thr Gly Ala Glu His
        35                  40                  45

Leu Tyr Pro Pro Phe His Leu His Pro Asn Val Lys Thr Ser Ser Ile
    50                  55                  60

Ile Asp Leu Phe Asn Asp Ile Pro Glu Asn Val Ser Cys Arg Asn Thr
65                  70                  75                  80

Pro Phe Tyr Ser Ile His Gln Gln Phe Lys Ala Glu Tyr Ser Ala
                85                  90                  95

His Tyr Lys His Val Leu Met Lys Ile Glu Ser Leu Leu Ser Ala Glu
            100                 105                 110

Asp Ser Ile Ile Phe Thr His Pro Leu Gln Leu Glu Met Tyr Arg Leu
        115                 120                 125

Ala Asn Asn Asp Ile Lys Ser Lys Ala Lys Leu Ile Val Gln Ile His
    130                 135                 140

Gly Asn Tyr Met Glu Glu Ile His Asn Tyr Glu Ile Leu Ala Arg Asn
145                 150                 155                 160

Ile Asp Tyr Val Asp Tyr Leu Gln Thr Val Ser Asp Glu Met Leu Glu
                165                 170                 175

Glu Met His Ser His Phe Lys Ile Lys Lys Asp Lys Leu Val Phe Ile
            180                 185                 190

Pro Asn Ile Thr Tyr Pro Ile Ser Leu Glu Lys Lys Glu Ala Asp Phe
        195                 200                 205

Phe Ile Lys Asp Asn Glu Asp Ile Asp Asn Ala Gln Lys Phe Lys Arg
    210                 215                 220

Ile Ser Ile Val Gly Ser Ile Gln Pro Arg Lys Asn Gln Leu Asp Ala
225                 230                 235                 240

Ile Lys Ile Ile Asn Lys Ile Lys Asn Glu Asn Tyr Ile Leu Gln Ile
                245                 250                 255

Tyr Gly Lys Ser Ile Asn Lys Asp Tyr Phe Glu Leu Ile Lys Lys Tyr
            260                 265                 270

Ile Lys Asp Asn Lys Leu Gln Asn Arg Ile Leu Phe Lys Gly Glu Ser
        275                 280                 285

Ser Glu Gln Glu Ile Tyr Glu Asn Thr Asp Ile Leu Ile Met Thr Ser
    290                 295                 300

Glu Ser Glu Gly Phe Pro Tyr Ile Phe Met Glu Gly Met Val Tyr Asp
305                 310                 315                 320

Ile Pro Ile Val Val Tyr Asp Phe Lys Tyr Gly Ala Asn Asp Tyr Ser
                325                 330                 335

Asn Tyr Asn Glu Asn Gly Cys Val Phe Lys Thr Gly Asp Ile Ser Gly
            340                 345                 350

Met Ala Lys Lys Ile Ile Glu Leu Leu Asn Asn Pro Glu Lys Tyr Lys
        355                 360                 365

Glu Leu Val Gln Tyr Asn His Asn Arg Phe Leu Lys Glu Tyr Ala Lys
    370                 375                 380
```

Asp Val Val Met Ala Lys Tyr Phe Thr Ile Leu Pro
385                 390                 395

<210> SEQ ID NO 48
<211> LENGTH: 396
<212> TYPE: PRT
<213> ORGANISM: Artificial sequence
<220> FEATURE:
<223> OTHER INFORMATION: GT-B domain Csy

<400> SEQUENCE: 48

Met Ala Val Ile Ile Phe Val Asn Gly Ile Arg Ala Val Asn Gly Leu
1               5                   10                  15

Val Lys Ser Ser Ile Asn Thr Ala Asn Ala Phe Ala Glu Glu Gly Leu
                20                  25                  30

Asp Val His Leu Ile Asn Phe Val Gly Asn Ile Thr Gly Ala Glu His
            35                  40                  45

Leu Ser Pro Pro Phe His Leu His Pro Asn Val Lys Thr Ser Ser Ile
        50                  55                  60

Ile Asp Leu Phe Asn Asp Ile Pro Glu Asn Val Ser Cys Arg Asn Ile
65                  70                  75                  80

Pro Phe Tyr Ser Ile His Gln Gln Phe Phe Lys Ala Glu Tyr Ser Ala
                85                  90                  95

His Tyr Lys His Val Leu Met Lys Ile Glu Ser Leu Leu Ser Glu Glu
            100                 105                 110

Asp Ser Ile Ile Phe Thr His Pro Leu Gln Leu Glu Met Tyr Arg Leu
        115                 120                 125

Ala Asn Asn Asn Ile Lys Ser Lys Ala Lys Leu Ile Val Gln Ile His
    130                 135                 140

Gly Asn Tyr Met Glu Glu Ile His Asn Tyr Glu Ile Leu Ala Arg Asn
145                 150                 155                 160

Ile Asp Tyr Val Asp Tyr Leu Gln Thr Val Ser Asp Glu Met Leu Glu
                165                 170                 175

Glu Met His Ser His Phe Lys Ile Lys Lys Asp Lys Leu Val Phe Ile
            180                 185                 190

Pro Asn Ile Thr Tyr Pro Ile Ser Leu Glu Lys Lys Glu Ala Asp Phe
        195                 200                 205

Phe Ile Lys Asp Asn Glu Asp Ile Asp Asn Ala Gln Lys Phe Lys Arg
    210                 215                 220

Ile Ser Ile Val Gly Ser Ile Gln Pro Arg Lys Asn Gln Leu Asp Ala
225                 230                 235                 240

Ile Lys Ile Ile Asn Lys Ile Lys Asn Glu Asn Tyr Ile Leu Gln Ile
                245                 250                 255

Tyr Gly Lys Ser Ile Asn Lys Asp Tyr Phe Glu Leu Ile Lys Lys Tyr
            260                 265                 270

Ile Lys Asp Asn Lys Leu Gln Asn Arg Ile Leu Phe Lys Gly Glu Ser
        275                 280                 285

Ser Glu Gln Glu Ile Tyr Glu Asn Thr Asp Ile Leu Ile Met Thr Ser
    290                 295                 300

Gln Ser Glu Gly Phe Gly Tyr Ile Phe Leu Gly Met Val Tyr Asp
305                 310                 315                 320

Ile Pro Ile Leu Ala Tyr Asn Phe Lys Tyr Gly Ala Asn Asp Phe Ser
                325                 330                 335

Asn Tyr Asn Glu Asn Ala Ser Val Phe Lys Thr Gly Asp Ile Ser Gly
            340                 345                 350

```
Met Ala Lys Lys Ile Ile Glu Leu Leu Asn Asn Pro Glu Lys Tyr Lys
        355                 360                 365

Glu Leu Val Gln Tyr Asn His Asn Arg Phe Leu Lys Glu Tyr Ala Lys
    370                 375                 380

Asp Val Val Met Ala Lys Tyr Phe Thr Ile Leu Pro
385                 390                 395

<210> SEQ ID NO 49
<211> LENGTH: 35
<212> TYPE: DNA
<213> ORGANISM: artificial
<220> FEATURE:
<223> OTHER INFORMATION: oligonucleotide primer CL57

<400> SEQUENCE: 49
ccatagggat ccaataaagt aaaacgtaaa tttag                              35

<210> SEQ ID NO 50
<211> LENGTH: 82
<212> TYPE: DNA
<213> ORGANISM: artificial
<220> FEATURE:
<223> OTHER INFORMATION: oligonucleotide primer CL59

<400> SEQUENCE: 50
cttttaccta ggaacgccca acttaattaa cattagtggt ggtggtggtg gtgctcgagg   60
atgaattttt caaaaaagat ag                                            82

<210> SEQ ID NO 51
<211> LENGTH: 31
<212> TYPE: DNA
<213> ORGANISM: artificial
<220> FEATURE:
<223> OTHER INFORMATION: oligonucleotide primer CL147

<400> SEQUENCE: 51
ccatagggat ccttaataaa caacgagaat g                                  31

<210> SEQ ID NO 52
<211> LENGTH: 31
<212> TYPE: DNA
<213> ORGANISM: artificial
<220> FEATURE:
<223> OTHER INFORMATION: oligonucleotide primer CL148

<400> SEQUENCE: 52
ggtgctcgag tttagtattt tcgttaaatt c                                  31

<210> SEQ ID NO 53
<211> LENGTH: 32
<212> TYPE: DNA
<213> ORGANISM: artificial
<220> FEATURE:
<223> OTHER INFORMATION: oligonucleotide primer CL74

<400> SEQUENCE: 53
ccatagggat ccaagaaaaa attttataaa gc                                 32

<210> SEQ ID NO 54
<211> LENGTH: 85
<212> TYPE: DNA
<213> ORGANISM: artificial
<220> FEATURE:
<223> OTHER INFORMATION: oligonucleotide primer CL94
```

<400> SEQUENCE: 54
cttttaccta ggaacgccca acttaattaa cattagtggt ggtggtggtg gtgctcgaga     60
ataacattat aaaatctatt aattg                                          85

<210> SEQ ID NO 55
<211> LENGTH: 25
<212> TYPE: DNA
<213> ORGANISM: artificial
<220> FEATURE:
<223> OTHER INFORMATION: oligonucleotide primer CL33

<400> SEQUENCE: 55
ccatagggat ccaataaaat tagta                                          25

<210> SEQ ID NO 56
<211> LENGTH: 28
<212> TYPE: DNA
<213> ORGANISM: artificial
<220> FEATURE:
<223> OTHER INFORMATION: oligonucleotide primer CL56

<400> SEQUENCE: 56
ggtgctcgag gtttatattt cttttgg                                        28

<210> SEQ ID NO 57
<211> LENGTH: 40
<212> TYPE: DNA
<213> ORGANISM: artificial
<220> FEATURE:
<223> OTHER INFORMATION: oligonucleotide primer CL40

<400> SEQUENCE: 57
gcatctcata tgagcaaaat caatagaaaa cttaagaaac                          40

<210> SEQ ID NO 58
<211> LENGTH: 37
<212> TYPE: DNA
<213> ORGANISM: artificial
<220> FEATURE:
<223> OTHER INFORMATION: oligonucleotide primer CL39

<400> SEQUENCE: 58
ggtgctcgag tgaaagtaaa tcggctaatt ttaattg                             37

<210> SEQ ID NO 59
<211> LENGTH: 25
<212> TYPE: DNA
<213> ORGANISM: artificial
<220> FEATURE:
<223> OTHER INFORMATION: oligonucleotide primer CL102

<400> SEQUENCE: 59
aaacatttac ctgttaaata tgaag                                          25

<210> SEQ ID NO 60
<211> LENGTH: 18
<212> TYPE: DNA
<213> ORGANISM: artificial
<220> FEATURE:
<223> OTHER INFORMATION: oligonucleotide primer CL104

<400> SEQUENCE: 60
catggactat ggtccttg                                                  18

<210> SEQ ID NO 61
<211> LENGTH: 26
<212> TYPE: DNA
<213> ORGANISM: artificial
<220> FEATURE:
<223> OTHER INFORMATION: oligonucleotide primer CL128

<400> SEQUENCE: 61
atccggcata tctaagttaa taatag                                    26

<210> SEQ ID NO 62
<211> LENGTH: 13
<212> TYPE: DNA
<213> ORGANISM: artificial
<220> FEATURE:
<223> OTHER INFORMATION: oligonucleotide primer CL129

<400> SEQUENCE: 62
ctcgagcacc acc                                                  13

<210> SEQ ID NO 63
<211> LENGTH: 31
<212> TYPE: DNA
<213> ORGANISM: artificial
<220> FEATURE:
<223> OTHER INFORMATION: oligonucleotide primer CL162

<400> SEQUENCE: 63
ttacctttat tgcgccagcg gattttctta g                              31

<210> SEQ ID NO 64
<211> LENGTH: 28
<212> TYPE: DNA
<213> ORGANISM: artificial
<220> FEATURE:
<223> OTHER INFORMATION: oligonucleotide primer CL163

<400> SEQUENCE: 64
cccattctgt ttgtacgtat tttagtcc                                  28

<210> SEQ ID NO 65
<211> LENGTH: 25
<212> TYPE: DNA
<213> ORGANISM: artificial
<220> FEATURE:
<223> OTHER INFORMATION: oligonucleotide primer CL137

<400> SEQUENCE: 65
taaagatgat ttatctcaat ggttc                                     25

<210> SEQ ID NO 66
<211> LENGTH: 18
<212> TYPE: DNA
<213> ORGANISM: artificial
<220> FEATURE:
<223> OTHER INFORMATION: oligonucleotide primer CL136

<400> SEQUENCE: 66
gttatacccg cctgtaaa                                             18

<210> SEQ ID NO 67
<211> LENGTH: 27
<212> TYPE: DNA
<213> ORGANISM: artificial
<220> FEATURE:
<223> OTHER INFORMATION: oligonucleotide primer CL164

```
<400> SEQUENCE: 67
ccatatttaa atgagtttaa catcccc                                          27

<210> SEQ ID NO 68
<211> LENGTH: 30
<212> TYPE: DNA
<213> ORGANISM: artificial
<220> FEATURE:
<223> OTHER INFORMATION: oligonucleotide primer CL165

<400> SEQUENCE: 68
ttcaatatta ggcgctggtg caaaaataac                                       30

<210> SEQ ID NO 69
<211> LENGTH: 26
<212> TYPE: DNA
<213> ORGANISM: artificial
<220> FEATURE:
<223> OTHER INFORMATION: oligonucleotide primer CL177

<400> SEQUENCE: 69
ttaaaacatt aggaagagat atggag                                           26

<210> SEQ ID NO 70
<211> LENGTH: 21
<212> TYPE: DNA
<213> ORGANISM: artificial
<220> FEATURE:
<223> OTHER INFORMATION: oligonucleotide primer CL176

<400> SEQUENCE: 70
atggagttcc cgcccatgta c                                                21

<210> SEQ ID NO 71
<211> LENGTH: 24
<212> TYPE: DNA
<213> ORGANISM: artificial
<220> FEATURE:
<223> OTHER INFORMATION: oligonucleotide primer CL179

<400> SEQUENCE: 71
aagcattatc caaaattaat ctag                                             24

<210> SEQ ID NO 72
<211> LENGTH: 24
<212> TYPE: DNA
<213> ORGANISM: artificial
<220> FEATURE:
<223> OTHER INFORMATION: oligonucleotide primer CL178

<400> SEQUENCE: 72
cctgaagtaa tgacgcccct ctaa                                             24

<210> SEQ ID NO 73
<211> LENGTH: 19
<212> TYPE: DNA
<213> ORGANISM: artificial
<220> FEATURE:
<223> OTHER INFORMATION: oligonucleotide primer CL181

<400> SEQUENCE: 73
gagaaggacc acgctaagt                                                   19

<210> SEQ ID NO 74
```

<211> LENGTH: 22
<212> TYPE: DNA
<213> ORGANISM: artificial
<220> FEATURE:
<223> OTHER INFORMATION: oligonucleotide primer CL180

<400> SEQUENCE: 74
tattgatagc gcacctattg tt 22

<210> SEQ ID NO 75
<211> LENGTH: 23
<212> TYPE: DNA
<213> ORGANISM: artificial
<220> FEATURE:
<223> OTHER INFORMATION: oligonucleotide primer CL160

<400> SEQUENCE: 75
gctaagttaa ttaatagttt tgc 23

<210> SEQ ID NO 76
<211> LENGTH: 16
<212> TYPE: DNA
<213> ORGANISM: artificial
<220> FEATURE:
<223> OTHER INFORMATION: oligonucleotide primer CL159

<400> SEQUENCE: 76
gtggtccgcc tctatt 16

<210> SEQ ID NO 77
<211> LENGTH: 3417
<212> TYPE: DNA
<213> ORGANISM: artificial sequence
<220> FEATURE:
<223> OTHER INFORMATION: Bt-188 protein sequence reverse translated into
DNA

<400> SEQUENCE: 77
catatgaagt acaaggtgaa actgagcctg attccgatgc tgctgaaagg cctgtatgcc 60
tataaacata aaaattataa cgaggccgag cgtatttttg cactgctgct ggataaacag 120
ggcgataatg cctatctgaa ttttcgctat ggcatggccc tgtataaaag taaaaaatgg 180
gatgaagcca actattatat ccagaaagca attaatatcg acccgagtaa aaaaagttgg 240
caggtgcagc tggcaaccag cgaacgttat aaacagaata gtgaaaaagt gaaggtggca 300
gaagcaaaaa aagcagcaat taaagatccg aatagtccgg aagttatttg ggaatatgca 360
attagtctgc tggaaaataa acagtattgg atggccaaac tgcagtttga aaaatatctg 420
attctgaaac cgaacagcga aaaagcattt gataatctgg gtaaagttag tgaaaagctg 480
agtgattatc cggaagccat taaatatttt gaaaaggcag caagtctgag cccgtttaat 540
agcaattata aatatcgcat cggctatagt tacgaatgtc tgggcgatct ggaaaatgcc 600
aatacctatt atgaactggt tagcagcttt gccaaaagca atgatgatgt ggcactgttt 660
ggcattggcg cactgcatgc aaaacgtggc ctgtgggata aagcactgaa tgcatataaa 720
cagtttctgg caaaaaccca gagtaataat ccggaactgt attatcgtat tggtgttgca 780
aatgaacgcc tgtatctgtg ggaagatgcc ggcaaagcat ttgaacaggc cgttaaactg 840
agtgaaatta ttaccgcacc gtggtgtttt aaatgtggcc aggcatacga acgcgccaaa 900
aattatgcca aagccgttga attttaccag aatgcagtgg cacgcagtaa taattataat 960
gattattggc tgtaccgcct ggcctatagt atggaaatga tgggtaattt tgagcaggcc 1020

-continued

```
gcaaaatatt atcagcagag tcgccgtcgc aaaattgccc atgcagttgc accgaaagat      1080
gtgattaaaa ataagaaga ggagtacctg acctattata ccgaatatta tgaaaccctg      1140
gccgtgaatg aaaaacaggt tctgattgaa agtttctttg gtggtaatat tagctgtaat      1200
ccgtatgcaa ttctgctgta tatgctggat cataattatg atttcaccta tatcgtggtt      1260
gttaaaccgg aaaccgttat tccggatagc ctgaaattta aacagaatat tatcttcatc      1320
aaccgcggca gtgatgccta tctgcgctat ctgtgtaccg caaaatatct gatcaataat      1380
gttagtttcc cgtattattt catccgcaaa gccgaacaga tttatctgaa tacctggcat      1440
ggtaccccga tgaaaaccct gggtaaagat attaaaagtc cgtttcagga tcatagtaat      1500
gttagtcgta atttttctgca ggcaacccat ctgattagcc cgaatcgcca taccaccgat      1560
attatgctgg aaaaatatga tatcaaggac ctgtttagtg gtgaaattgc agaaaccggt      1620
tatccgcgta ttgatctgag cttctctgagt gaagaacgcc gcaatgaaat tcgtaaaaaa      1680
ctgggtttta agaacaacaa accggtggtt ttttatgccc cgacctggcg tggcaccagc      1740
cagagtaaag attttgatac ccagaaactg cagaatgatc tgaaacgcct gaaaagcgat      1800
aaatataatc tggtgtttcg cggccatcat ctggtggaaa gcctgctgag cgaaattaaa      1860
ctggatgttg ttgttgcacc gaaggaaatt gatagcaatg aactgctggg ttattgcgat      1920
ctgctgatta ccgattatag tagcattatt tacgactttc tggcactgaa taaaccggtt      1980
attagctatg tttatgactt tgatgagtac aaagaggaac gtggtctgta ttttgaaaaa      2040
gatgaaatgg ttggcgccgt ttgtagcacc attagtgaag tgcgtcaggc cattctggaa      2100
aatctgaata aaaataagag caacgtgctg gaacgtgata ttgaaaaata tagttacctg      2160
gatgacggcc gtgcaaccca gcgcaccgtt gattttattt ttaaaaatga caaccgttac      2220
gtgtacgatt atattcgtaa agataccgat gttttcttcg tgggtccgtt tctgcagaat      2280
ggtattaccc gtagctttct gaatctgatg agcaccattg gtcgcgaaaa aaatatattctg      2340
gtgctgatta atggcaatga tctgcagagt gataataaac gtctggaaga atttaccgt      2400
ctgccgaaag atattagtgt ttttagccgc agtggccgca tgctgatgac cctggaagaa      2460
ctgtgggtgc gcaataaatt tgatgaaaat tttaagttct acagcgagga atttaagcgt      2520
gtgattgaaa aaatttacaa gcgcgaagca cgccgtctgt ttggtgatag taaaattcgt      2580
aatatcatca acttcgaggg ctatgcactg ttttgggttc tgctgattag tcaggtgaat      2640
gccaaacagc atattattta tcagcataat gacaagtaca aggaatggaa agtaaattt      2700
ccgtatctgg aaggtgtttt tcgcacctat cgttattatg ataaaatcgt tagcgtgagt      2760
gaaaaaacca tggaaaataa tcgcaataac atcagttacg aattcggtat tgcagaaaaaa      2820
cgctttgttt tttgcaataa tccgattaat atcgatcaga ttatcagcaa tgccaaagat      2880
gatattgaaa ttgaagacga attcgataac ttcgcaggta ccaaattta taatatcggc      2940
cgtatgagtc atgaaaaaga tcagctgaaa ctgattgaag catttgcaga agttaataaa      3000
aagcataagg acacccgcct gtttattctg ggcgatggtc cgctgaaaca ggaactgatt      3060
acccgtatta aaaaactgag cttagaaaaa gacgtgtttc tgctgggcca gaaaaccaat      3120
ccgtttgcat atctgaaaca ggcagatatt tttgtgctga gtagtaatca tgaaggccag      3180
ccgatggttc tgctggaaag cctgaccctg ggtaccccga ttattgcaac cgatattgtg      3240
ggcaatcgca gcattctggg cgacaaatat ggcctgctgg ttgaaaatag caaacagggt      3300
ctgattaatg gtatgaatga atatctggaa aacggcagta acaggataa ttttgatccg      3360
attgcatatc agaaagatgc aatggataaa ttttacgccc tgctgaatga actcgag      3417
```

```
<210> SEQ ID NO 78
<211> LENGTH: 49
<212> TYPE: DNA
<213> ORGANISM: artificial sequence
<220> FEATURE:
<223> OTHER INFORMATION: oligonucleotide primer TF156

<400> SEQUENCE: 78
gcatctggat ccttattaaa aagcgagaac tttaaaatga aacataatg          49

<210> SEQ ID NO 79
<211> LENGTH: 45
<212> TYPE: DNA
<213> ORGANISM: artificial sequence
<220> FEATURE:
<223> OTHER INFORMATION: oligonucleotide primer TF157

<400> SEQUENCE: 79
gcatctctcg agatttgtta ataatgaata aaacttcgcc atagc               45

<210> SEQ ID NO 80
<211> LENGTH: 82
<212> TYPE: DNA
<213> ORGANISM: artificial sequence
<220> FEATURE:
<223> OTHER INFORMATION: oligonucleotide primer IB 46

<400> SEQUENCE: 80
gctccaataa caataacaac aacaataaca ataacggatc caataaagta aaacgtaaat    60
ttagaaaatt actacgagat cc                                            82

<210> SEQ ID NO 81
<211> LENGTH: 50
<212> TYPE: DNA
<213> ORGANISM: artificial sequence
<220> FEATURE:
<223> OTHER INFORMATION: oligonucleotide primer IB 47

<400> SEQUENCE: 81
ggtggtggtg gtggtgctcg agggctttct ccgtgtatga ataaagtgtg          50

<210> SEQ ID NO 82
<211> LENGTH: 38
<212> TYPE: DNA
<213> ORGANISM: artificial sequence
<220> FEATURE:
<223> OTHER INFORMATION: oligonucleotide primer TF116

<400> SEQUENCE: 82
gcatctctcg agctcttttt cgtgaatttg ttttttgtc                      38

<210> SEQ ID NO 83
<211> LENGTH: 36
<212> TYPE: DNA
<213> ORGANISM: artificial sequence
<220> FEATURE:
<223> OTHER INFORMATION: oligonucleotide primer TF117

<400> SEQUENCE: 83
gcatctcata tgaaaaagt attaacctat ggaacc                          36
```